United States Patent
Braun et al.

(10) Patent No.: US 9,120,812 B2
(45) Date of Patent: Sep. 1, 2015

(54) PYRIMIDOOXAZOCINE DERIVATIVES AS MTOR-INHIBITORS

(71) Applicant: SANOFI, Paris (FR)

(72) Inventors: Alain Braun, Paris (FR); Olivier Crespin, Paris (FR); Yann Foricher, Paris (FR); Gilbert Marciniak, Paris (FR); Nicolas Muzet, Paris (FR); Eric Nicolai, Paris (FR); Cecile Pascal, Paris (FR); Bertrand Vivet, Paris (FR); Fabrice Viviani, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/374,838

(22) PCT Filed: Jan. 25, 2013

(86) PCT No.: PCT/IB2013/050656
§ 371 (c)(1),
(2) Date: Jul. 25, 2014

(87) PCT Pub. No.: WO2013/111106
PCT Pub. Date: Aug. 1, 2013

(65) Prior Publication Data
US 2014/0378433 A1 Dec. 25, 2014

(30) Foreign Application Priority Data
Jan. 26, 2012 (FR) .................................. 12 50768

(51) Int. Cl.
*C07D 498/04* (2006.01)
*C07D 519/00* (2006.01)

(52) U.S. Cl.
CPC ............ *C07D 498/04* (2013.01); *C07D 519/00* (2013.01)

(58) Field of Classification Search
CPC .................................................... C07D 498/04
USPC .......... 540/455, 490; 514/211.05, 218, 234.2, 514/254.11, 260.1
See application file for complete search history.

(56) References Cited

U.S. PATENT DOCUMENTS 6,995,153 B2 * 2/2006 Seto et al. ................ 514/211.05

FOREIGN PATENT DOCUMENTS

EP 1473295 B1 11/2004

OTHER PUBLICATIONS

Ashe, Karen M., et al., "Inhibition of glycogen biosynthesis via mTORC1 suppression as an adjunct therapy for Pompe disease" Molecular Genetics and Metabolism (2010), Elsevier, 309-315 (May 2010).

Benjamin, Don, et al. "Rapamycin passes the torch: a new generation of mTOR inhibitors" Reviews, vol. 10, pp. 868-880 (Nov. 2011).
Bhonde, Mandar R., et al. "A novel mTOR inhibitor is efficacious in a murine model of colitis" Am J Physiol Gastrointest Liver Physiol 295: G1237-G1245, 2008, First published (Oct. 2008).
Blumenkranz, Mark S. MD, "Tirolimus and mTOR Inhibition in Ocular Disease: An Update" Retina Today, http://retinatoday.com/2007/05/0507_07.html/, pp. 1-3, (Jun. 2014).
Bové, Jordi, et al., "Fighting neurodegeneration with rapamycin: mechanistic insights" Nature Reviews, Neuroscience, vol. 12, pp. 437-452 (Aug. 2011).
Dann, Stephen G. "mTOR Complex1—S6K1 signaling: at the crossroads of obesity, diabetes and cancer" Science Direct, Elsevier, TRENDS in Molecular Medicine vol. 13 No. 6, pp. 252-259 (Apr. 2007).
Feldman, Morris E. et al., "Active-Site Inhibitors of mTOR Target Rapamycin-Resistant Outputs of mTORC1 and mTORC2", PLoS Biology, www.plosbiology.org, vol. 7, Issue 2, pp. 371-383 (Feb. 2009).
Garcia-Echeverria, Carlos, "Blocking the mTOR pathway: a drug discovery perspective" mTOR Signalling in Health and Disease, Biochemical Society, vol. 39, part 2, 451-455, (Apr. 2011).
Guertin, David M., et al., "Defining the Role of mTOR in Cancer" Cancer Cell 12, Elsevier Inc., pp. 9-22 (Jul. 2007).
Hagenmueller, Marco, "Depletion of mammalian target of rapamycin (mTOR) via siRNA mediated knockdown leads to stabilization of b-catenin and elicits distinct features of cardiomyocyte hypertrophy" FEBS Letters by Elsevier, 584 74-80 (Jan. 4, 2010).
Harrison, David E., et al., "Rapamycin fed late in life extends lifespan in genetically heterogeneous mice" Letters, vol. 460, pp. 392-396, (Jul. 16, 2009).
Huang, Xiaoxing, et al., "Pharmacological inhibition of the mammalian target of rapamycin pathway suppresses acquired epilepsy" Neurobiology of Disease 40 193-199 (May 2010).
Mehrad, Borna, et al., "Fibrocyte CXCR4 regulation as a therapeutic target in pulmonary fibrosis", The International Journal of Biochemistry & Cell Biology vol. 41 pp. 1708-1718 (Aug. 2009).
Muci, Alex R., et al., "Practical Palladium Catalysts for C—N And C—O Bond Formation" Topics in Current Chemistry,vol. 219 pp. 133-209 (2002).
Richard, David J., et al. Recent advances in the development of selective, ATP-competitive inhibitors of mTOR, Thomson Reuters, Current Opinion in Drug Discovery & Development 13(4) pp. 428-440 (2010).
Rubinsztein, David C., et al., "Potential therapeutic applications of autophagy" Reviews, vol. 6 pp. 304-312 (Apr. 2007).

(Continued)

*Primary Examiner* — Bruck Kifle
(74) *Attorney, Agent, or Firm* — McDonnell Boehnen Hulbert & Berghoff LLP

(57) ABSTRACT

The invention relates to bicyclic heterocyclic derivatives of general formula (I) to a process for preparing them and to the therapeutic use thereof.

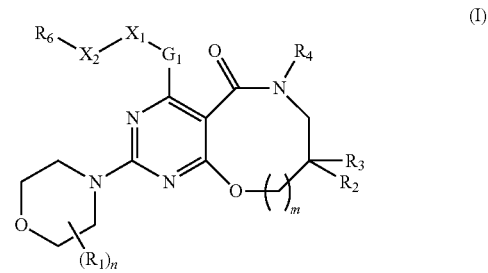

13 Claims, No Drawings

(56) References Cited

OTHER PUBLICATIONS

Seto, Shigeki, et al., "Design, synthesis, and evaluation of novel 2-substituted-4-aryl-6,7,8,9-tetrahydro-5H-pyrimido-[4,5-b][1,5]oxazocin-5-ones as NK1 antagonists" Science Direct, Elsevier, Bioorganic & Medicinal Chemistry 13 pp. 5717-5732 (Jun. 2005).

Sparks, CA et al., "Targeting mTOR: prospects for mTOR complex 2 inhibitors in cancer therapy" Oncogene 29, 3733-3744 (Feb. 2010).

Tsang, Kwan Chi, et al., "Targeting mammalian target of rapamycin (mTOR) for health and diseases" Reviews, Elsevier, Drug Discovery Today vol. 12, Nos. 3/4 pp. 112-124 (Feb. 2007).

Wang, Zhouxi et al., "Modeling trypanosomal TOR kinase domains: Implications for the design of anti-parasitic drugs" Chemistry and Chemical Biology, Northeastern University, Boston, MA, United States, p. 1 (2010).

Whittaker, S, et al., "The role of signaling pathways in the development and treatment of hepatocellular carcinoma" Oncogene 29, Macmillan Publishers Limited 4989-5005 (Jul. 2010).

Wullschleger, Stephan et al., "TOR Signaling in Growth and Metabolism" Cell 124 Elsevier pp. 471-484 (Feb. 10, 2006).

Yecies, Jessica et al., "mTOR links oncogenic signaling to tumor cell metabolism" Review, J Mol Med 89:221-228 (Feb. 2011).

Young, Deborah et al., "mTOR—beyond transplantation" Science Direct, Elsevier Current Opinion in Pharmacology 5:418-423 (Jun. 13, 2005).

Yuan, TL, et al., "PI3K pathway alterations in cancer: variations on a theme" Review Oncogene (2008) 27, 5497-5510 Macmillan Publishers Limited (Sep. 15, 2008).

Zoncu, Roberto, et al. "mTOR: from growth signal integration to cancer, diabetes and ageing" Nature Reviews Molecular cell Biology vol. 12 pp. 21-35 (Jan. 2011).

* cited by examiner

PYRIMIDOOXAZOCINE DERIVATIVES AS MTOR-INHIBITORS

This application is a national stage application under 35 U.S.C. §371 of International Application No. PCT/IB2013/050656, filed Jan. 25, 2013, the disclosure of which is explicitly incorporated by reference herein.

The present invention relates to bicyclic heterocyclic derivatives, and to the preparation and therapeutic use thereof.

mTOR (mammalian target of rapamycin), also known as FRAP (FKBP12 and rapamycin associated protein), is a 289-kDa serine/threonine kinase of the family of PIKKs (phosphoinositide 3-kinase-like kinases), although mTOR does not phosphorylate phospholipids.

The protein contains several domains, including a C-terminal kinase domain, an FKBP12-rapamycin binding domain, 20 N-terminal HEAT repetitions involved in protein-protein interactions, a FAT (FRAP-ATM-TRRAP) domain and a C-terminal FAT domain, which is also present in other PIKKs (Wullschleger et al. (2006) Cell, 124, 471-484).

The kinase mTOR is a central regulator of cell growth and proliferation, but also plays an important role in cell metabolism and angiogenesis. mTOR is activated by the PI3K/Akt axis and in turn phosphorylates the downstream effectors of the PI3K/Akt signalling pathway, in particular the ribosomal protein S6 kinase (S6K1) and the eukaryotic initiation factor 4E binding protein (4E-BP1), which are two main regulators of the cell protein translation machinery (the mTOR signalling pathway is described in Zoncu et al. (2011) Nature Rev. Mol. Cell Biol. 12, 21-35).

The mTOR signalling pathway is mutated and deregulated in a variety of human cancers. Mutations of the protein kinase Akt, of the lipid kinase PI3K and/or inactivation of the tumour suppressants PTEN and TSC2, but also amplifications and/or mutations affecting the growth factor receptors, are a few of the events upstream of mTOR that lead to constitutive inactivation of the PI3K/Akt/mTOR pathway and uncontrolled cell proliferation (for a review of the role of the protein mTOR in cancer, see Guertin and Sabatini (2007) Cancer Cell 12, 9-22).

Genetic mutations and amplifications affecting the mTOR pathway have been identified in the formation of glioblastomas, prostate cancers, tuberous sclerosis, lung cancers (NSCLC), breast cancer, ovarian cancer, endometrial cancer, bowel cancer, pancreatic cancer, cancer of the head and neck, skin cancer and hepatocellular carcinomas (Yuan and Cantley (2008) Oncogene 27, 5497-5510; Whittaker et al. (2010) Oncogene 29, 4989-5005).

mTOR recruits several partners to form two multi-protein complexes that are essential for tumour growth. By phosphorylating the proteins s6K and 4E-BP1, the mTORC1 complex makes the connection between oncogene signalling and protein synthesis, glycolysis and lipid biosynthesis (Yecies and Manning (2011) J. Mol. Med. 89, 221-228). The mTORC2 complex has recently been identified as the kinase that phosphorylates Akt on the Ser-473 residue, thus acting as an essential activator of the kinase Akt. The role of the complex mTORC2 has recently been specifically linked to cell transformation (Sparks and Guertin (2010) Oncogene 29, 3733-3744).

Rapamycin and analogues thereof, the rapalogues, via their association with the protein FKBP12, are allosteric inhibitors of the mTORC1 complex. Several of them are in clinical development for the treatment of certain cancers. Everolimus (Novartis) and Temsirolimus (Wyeth) have recently been approved for the treatment of kidney cancer (renal cell carcinoma or RCC). However, the efficacy of the rapalogues in cancer treatment has remained below expectations, despite certain promising results, and appears to be limited to a subset of cancers. These limitations have been attributed to the fact that rapalogues do not interact with the mTORC2 complex, and that certain aspects of the activity of the mTORC1 complex, and in particular the phosphorylating of 4E-BP1, are resistant to rapamycin and analogues thereof (Benjamin et al. (2011) Nature Reviews Drug Discovery 10, 868-880).

On the other hand, inhibitors of the kinase site of mTOR do not suffer from this drawback (Feldman et al. (2009) PLoS Biology 7, 371-383) and are considered as a novel generation of modulators of the mTOR pathway with, as advantages, a potential increase in antitumour efficacy and a broadened field of therapeutic applications. Several of them have now entered into clinical phases (Garcia-Echeverria (2011) Biochem. Soc. Trans. 39, 451-455; Richard et al. (2010) Curr. Drug Opinion Disc. Dev. 13, 428-440).

Other potential therapeutic indications have been proposed for mTOR inhibitors (Tsang et al. (2007) Drug Discovery Today 12, 112-124). mTOR inhibitors may have a neuroprotective role in neurodegenerative diseases such as Alzheimer's disease, Parkinson's disease and Huntington's disease (Bove et al. (2011) Nature Reviews Neuroscience 12, 437-452). Moreover, mTOR hyperactivity has been correlated with age-related pathologies (Harrison et al. (2009) Nature 460, 392). Other applications include kidney, lung and liver fibrosis (Mehrad et al. (2009) Int. J. Biochem. Cell Biol. 41, 1708-1718; Lieberthal and Levine (2009); Shouval (2011)), inflammation and autoimmune disorders (Bhonde et al. (2008) Am. J. Physiol. Gastrointest. Liver Physiol. 295, G1237-G1245; Young and Nickerson-Nutter (2005) Curr. Opinion Pharmacol. 5, 418-423), diabetes, obesity (Dann et al. (2007) Trends Mol. Medicine 13, 252-259), Pompe's disease (Ashe et al. (2010) Molecular Genetics and Metabolism 100, 309-315), cardiovascular diseases (Hagenmueller et al. (2010). FEBS Lett. 584, 74-80), ocular diseases (Blumenkranz (2007) Retina Today 24-26), epilepsy (Huang et al. (2010) Neurobiology of Disease 40, 193-199), and parasitic diseases (Wang et al. (2010) 240th ACS National Meeting Boston, MEDI-152).

mTOR inhibition also activates autophagocytosis and a certain number of diseases should be sensitive to its inhibition, in particular proteinopathies, bacterial and viral infections and cancer (review in Rubinsztein et al. (2007) Nature 6, 304-312).

The development of compounds targeting the mTOR kinase site and inhibiting the activity of the two compounds mTORC1 and mTORC2 is thus important.

[Compounds]

According to a first aspect, a subject of the present invention is the compounds corresponding to formula (I):

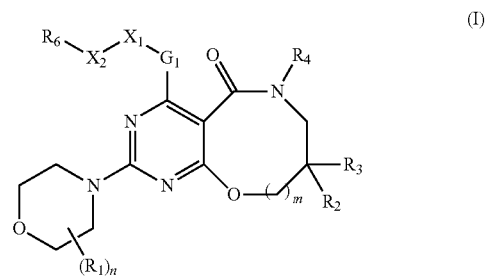

in which:
- each of the radicals $R_1$ independently represents a group $(C_1-C_6)$-alkyl, it being understood that two groups $R_1$ borne by two different carbon atoms of the morpholinyl ring may be linked together to form, with the morpholinyl ring, a bicyclic heterocyclic structure,
- $R_2$ and $R_3$ independently represent:
  - H, or
  - a group $(C_1-C_6)$-alkyl,
- $R_4$ represents:
  - H,
  - a group $(C_1-C_6)$-alkyl, optionally substituted with a hydroxyl group,
  - a group $(C_1-C_6)$-alkoxy,
  - a group $-L_1-R_{10}$, in which:
    - $L_1$ represents a group $(C_1-C_6)$-alkylene,
    - $R_{10}$ represents a group chosen from $—COOR_{11}$, $—CO—R_{12}$, $—OR_{13}$, $—CONR_{14}R_{15}$ and a 5- or 6-atom heterocycle optionally substituted with a group $—R_{16}$, $—COOR_{17}$, $—CO—R_{18}$, $—OR_{19}$ or $—NR_{20}R_{21}$, or
  - a 5- or 6-atom heterocycle optionally substituted with a group $—R_{22}$, $—COOR_{23}$, $—CO—R_{24}$, $—OR_{25}$ or $—CONR_{26}R_{27}$,
- $G_1$ represents a divalent phenyl or 5- to 6-atom heteroaryl radical, optionally substituted with 1 to 4 groups $R_5$ independently chosen from a halogen atom, a group $—OR_{30}$ and a group $—(C_1-C_6)$-alkyl optionally substituted with a hydroxyl,
- $X_1$ represents a group $—O—$ or $—NR_{40}—$,
- $X_2$ represents a single bond or a group $—CONR_{50}—$, $—CONR_{51}—O—$, $—COO—$, $—CO—$ or $—SO_2—$,
- $R_6$ represents:
  - H,
  - a group $-L_2-R_7$, in which:
    - $-L_2-$ represents a group $(C_1-C_6)$-alkylene or $(C_3-C_6)$-cycloalkylene,
    - $R_7$ represents a group chosen from:
      - H,
      - $OR_{60}$,
      - a halogen atom,
      - a group $(C_1-C_6)$-haloalkyl,
      - a 5- to 6-atom heterocycle optionally substituted with one or more groups chosen from a group $(C_1-C_6)$-alkyl, a group $(C_1-C_6)$-alkoxy and a group $=O$, or
  - a group $-G_2-X_3-G_3$, in which:
    - $X_3$ represents a single bond or a group $—O—$, $—CO—$ or $—CH_2—$,
    - $G_2$ represents a single bond or a 5- to 6-atom divalent cyclic radical optionally substituted with one or more groups $R_{80}$,
    - $G_3$ represents a 4- to 8-atom ring optionally substituted with one or more groups $R_{81}$,
    - or $-G_2-X_3-G_3$ together form a 7- to 10-atom fused bicycle,
  - each radical $R_{80}$ and each radical $R_{81}$ is independently chosen from:
    - a halogen atom,
    - a group $—COOR_{70}$, $—CO—R_{71}$, $—OR_{72}$, $—NR_{73}R_{74}$, $—CONR_{75}R_{76}$, $—CN$ or $—S(O)_p—R_{77}$,
    - a group $(C_1-C_6)$-alkyl optionally substituted with one or more groups $R_{100}$ and/or optionally interrupted with one or more oxygen atoms,
    - a group $(C_1-C_6)$-alkoxy optionally substituted with one or more groups $R_{101}$ and/or optionally interrupted with one or more oxygen atoms,
  - n represents 0, 1 or 2,
  - m represents 0 or 1,
  - p represents 0, 1 or 2,
  - $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{30}$, $R_{40}$, $R_{50}$, $R_{51}$, $R_{60}$, $R_{70}$, $R_{71}$, $R_{72}$, $R_{73}$, $R_{74}$, $R_{75}$, $R_{76}$ and $R_{77}$ independently represent H or a group $(C_1-C_6)$-alkyl optionally substituted with a group $R_{90}$ and/or optionally interrupted with one or more oxygen atoms,
  - $R_{90}$ represents a group $—OR_{91}$ or $—NR_{92}R_{93}$,
  - $R_{91}$, $R_{92}$ and $R_{93}$ independently represent H or a group $(C_1-C_6)$-alkyl,
  - $R_{100}$ and $R_{101}$ are independently chosen from a halogen atom and a hydroxyl in the form of the base or of an acid-addition salt.

The compounds of formula (I) can comprise one or more asymmetric carbon atoms. They may therefore exist in the form of enantiomers or diastereoisomers. These enantiomers, diastereoisomers, and also mixtures thereof, including racemic mixtures, form part of the invention.

The pure enantiomers of the compounds of the invention may be obtained from enantiomerically pure precursors or alternatively by chromatography on chiral phases or alternatively, when the compounds comprise acid or amine functions, by selective crystallization of diastereoisomeric salts obtained by reacting the compounds (I) with, respectively, chiral amines or acids.

The compounds of formula (I) may exist in the form of tautomers. These tautomeric forms form part of the invention.

By virtue of their structure, the compounds of general formula (I) may also exist in the form of enantiomers of rotamer or atropoisomer type.

The compounds of formula (I) may exist in the form of bases or acid-addition salts. Such addition salts form part of the invention.

These salts may be advantageously prepared with pharmaceutically acceptable acids, but salts of other acids that are of use, for example, for purifying or isolating the compounds of formula (I) also form part of the invention.

In the context of the present invention, the following definitions apply:
- a halogen atom: a fluorine atom, a chlorine atom, a bromine atom or an iodine atom, especially a fluorine atom;
- an alkyl group: a saturated, linear or branched hydrocarbon-based aliphatic group comprising, unless otherwise mentioned, from 1 to 6, especially from 1 to 4 and in particular from 1 to 2 carbon atoms, or a cyclic hydrocarbon-based aliphatic group, also be noted as cycloalkyl and defined hereinbelow. Examples that may be mentioned include methyl, ethyl, propyl, isopropyl, butyl, isobutyl, tert-butyl, pentyl, etc. groups;
- a cycloalkyl group: a cyclic alkyl group comprising, unless otherwise mentioned, from 3 to 6 carbon atoms. Examples that may be mentioned include cyclopropyl, cyclobutyl, cyclopentyl, cyclohexyl, etc. groups;
- an alkylene group: a linear or branched saturated hydrocarbon-based divalent aliphatic group, comprising, unless otherwise mentioned, from 1 to 6 carbon atoms;
- a cycloalkylene group: a cyclic or carbocyclic hydrocarbon-based divalent aliphatic group, comprising, unless otherwise mentioned, from 3 to 6 carbon atoms;
- an alkoxy group: a radical —O-alkyl in which the alkyl group is as defined previously. Examples that may be mentioned include the groups $—O—(C_1-C_6)$alkyl or $—(C_1-C_6)$-alkoxy, and in particular as (i) group $—O—C_1$alkyl, the group $—O$-methyl, as (ii) group $—O—C_2$alkyl, the group $—O$-ethyl, as (iii) group $—O—C_3$alkyl, the group $—O$-propyl, $—O—$isopropyl, as (iv) group —O—$C_4$alkyl, the group —O-butyl, —O-isobutyl, —O-tert-butyl, as (v) group —O—$C_5$alkyl, the group —O-pentyl, —O-isopentyl; as (vi) group —O—$C_6$alkyl, the group —O-hexyl;

a ring: a saturated, unsaturated or aromatic (aryl or heteroaryl) carbocycle or heterocycle;

a carbocycle: a ring composed of carbon atoms, which is saturated (the saturated carbocycles especially being a cycloalkyl, such as a cyclopropyl, a cyclopentyl, cyclohexyl or an adamantyl (example of a bridge tricycle)), unsaturated (for example a cyclohexene) or aromatic (i.e. an aryl). When the carbocycle comprises several substituents, they may be borne by the same atom or different atoms, an aryl: a monocyclic or bicyclic aromatic hydrocarbon-based group comprising, unless otherwise mentioned, between 5 and 10 carbon atoms. Examples of aryl groups that may be mentioned include phenyl and naphthyl, in particular phenyl, a heterocycle: a monocyclic or bicyclic group comprising, unless otherwise mentioned, from 3 to 10 atoms, and comprising one or more heteroatoms chosen from O, N and/or S. The said heterocycle may be saturated or partially unsaturated and may comprise one or more double bonds. It is then referred to as a heterocycloalkyl group. It may also be aromatic, comprising, unless otherwise mentioned, from 5 to 10 atoms and then represent a heteroaryl group. When the heterocycle is substituted, the substitution(s) may be on one (or more) carbon atom(s) and/or on the heteroatom(s). When the heterocycle comprises several substituents, they may be borne by the same atom or different atoms.

Non-aromatic heterocycles or heterocycloalkyls that may be mentioned include epoxyethyl, oxiranyl, aziridinyl, tetrahydrofuryl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, dithianyl, thiomorpholinyl, dihydrofuryl, 2-imidazolinyl, 2,3-pyrrolinyl, pyrazolinyl, dihydrothiophenyl, dihydropyranyl, pyranyl, tetrahydropyridyl, dihydropyridyl, tetrahydropyrinidinyl, dihydrothiopyranyl, isoxazolidinyl and the corresponding groups derived from fusion with a phenyl nucleus, and more particularly morpholinyl, dioxalanyl, benzothiazolidinyl, pyrrolidinyl and benzopyrrolidinyl rings.

Bridged heterocycles that may be mentioned include rings of bridged morpholinyl type such as:

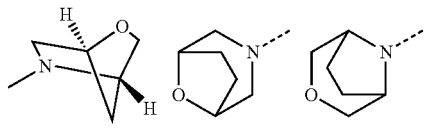

Heteroaryls that may especially be mentioned include the following representative groups: benzimidazolyl, benzothiazolyl, furyl, furazanyl, imidazolyl, indolyl, indolizinyl, isoxazolyl, isoquinolinyl, isothiazolyl, oxadiazolyl, 1,2,4-oxadiazolyl, 1,3,4-oxadiazolyl, pyrazinyl, pyridazinyl, pyrazolyl, pyridyl, pyrimidinyl, pyrrolyl, quinazolinyl, quinolinyl, 1,3,4-thiadiazolyl, 1,2,3-thiadiazolyl, thiazolyl, thienyl, triazolyl, 1,2,3-triazolyl and 1,2,4-triazolyl;

a fused bicycle comprises two rings as defined above, the fusion of the two rings possibly taking place by the sharing of a sequence of atoms (branch and bridgehead) (for example norbornane) or by sharing a bond between two atoms (for example isoquinoline or quinoline);

the ring of a cyclic divalent radical is as defined above. The ring of the cyclic divalent radical may be a carbocycle or a heterocycle and it may be saturated, unsaturated or aromatic, especially aromatic. In particular, the ring of a cyclic divalent radical may be an aryl, such as a phenyl, or a heteroaryl, in which the heteroatom(s) are especially nitrogen atoms. An example of a cyclic divalent radical of 5 atoms that may be mentioned is a divalent triazole radical, and examples of cyclic divalent radicals of 6 atoms that may be mentioned are divalent radicals of phenyl (phenylene), of pyridine and of pyrazine. For example, a cyclic divalent radical of 5 or 6 atoms may have one of the following formulae, it being understood that the atoms of the rings may be substituted (with one or more groups $R_{80}$):

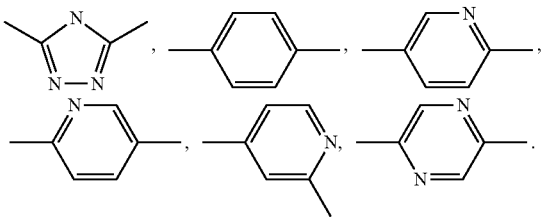

In one embodiment, a subject of the present invention is the compounds corresponding to formula (I) in which:

each of the radicals $R_1$ independently represents a group ($C_1$-$C_6$)-alkyl, advantageously a group ($C_1$-$C_3$)-alkyl, it being understood that two groups $R_1$ borne by two different carbon atoms of the morpholinyl ring may be linked together to form, with the morpholinyl ring, a bicyclic heterocyclic structure, $R_2$ and $R_3$ independently represent H or a group ($C_1$-$C_2$)-alkyl, $R_4$ represents:
H,
a group ($C_1$-$C_6$)-alkyl, advantageously a group ($C_1$-$C_3$)-alkyl optionally substituted with a hydroxyl group,
a group -$L_1$-$R_{10}$, in which:
$L_1$ represents a group ($C_1$-$C_2$)-alkylene,
$R_{10}$ represents a group chosen from —$COOR_{11}$, —$OR_{13}$, —$CONR_{14}R_{15}$ or a heterocycle of 5 atoms optionally substituted with a group —$COOR_{17}$, —CO—$R_{18}$, or
a heterocycle of 6 atoms optionally substituted with a group —$R_{22}$, $G_1$ represents a divalent phenyl or a 6-atom heteroaryl radical, optionally substituted with 1 to 4 groups $R_5$ independently chosen from a halogen atom and a group —($C_1$-$C_6$)-alkyl optionally substituted with a hydroxyl, $X_1$ represents a group —O— or —$NR_{40}$—, $X_2$ represents a single bond or a group —$CONR_{50}$—, —$CONR_{51}$—O—, —COO—, —CO— or —$SO_2$—, $R_6$ represents:
H,
a group -$L_2$-$R_7$, in which:
-$L_2$- represents a group ($C_1$-$C_4$)-alkylene or ($C_3$-$C_6$)-cycloalkylene, —$R_7$ represents a group chosen from:
H,
$OR_{60}$,
a halogen atom,
a 5- to 6-atom heterocycle optionally substituted with one or more groups chosen from a group $(C_1-C_6)$-alkyl and a group =O, or
a group $-G_2-X_3-G_3$, in which:
$X_3$ represents a single bond or a group —O—, —CO— or —CH$_2$—,
$G_2$ represents a single bond or a cyclic divalent radical of 5 to 6 atoms,
$G_3$ represents a 4- to 8-atom ring optionally substituted with one or more groups $R_{81}$,
or $-G_2-X_3-G_3$ together form a 7- to 10-atom fused bicycle,
each radical $R_{81}$ is independently chosen from:
a halogen atom,
a group —$COOR_{70}$, —$OR_{72}$, —$NR_{73}R_{74}$, —$CONR_{75}R_{76}$, —CN or —$S(O)_p$—$R_{77}$,
a group $(C_1-C_2)$-alkyl optionally substituted with one or more groups $R_{100}$,
a group $(C_1-C_2)$-alkoxy optionally substituted with one or more groups $R_{101}$,
n represents 0, 1 or 2,
m represents 0 or 1,
p represents 2,
$R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{30}$, $R_{40}$, $R_{50}$, $R_{51}$, $R_{60}$, $R_{70}$, $R_{71}$, $R_{72}$, $R_{73}$, $R_{74}$, $R_{75}$, $R_{76}$ and $R_{77}$ independently represent H or a group $(C_1-C_2)$-alkyl optionally substituted with a group $R_{90}$,
$R_{90}$ represents a group —$OR_{91}$ or —$NR_{92}R_{93}$,
$R_{91}$, $R_{92}$ and $R_{93}$ represent a group $(C_1-C_2)$-alkyl,
$R_{100}$ and $R_{101}$ represent a halogen atom,
in the form of the base or of an acid-addition salt.

In one embodiment, in formula (I) above, m represents 0 and $R_2$ and $R_3$ represent a methyl, the compounds then having the formula (II) below:

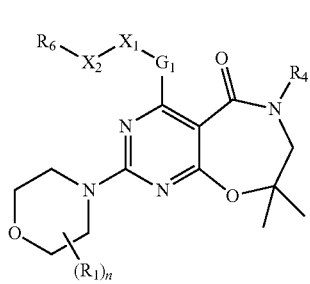

(II)

in which n, $R_1$, $R_4$, $G_1$, $X_1$, $X_2$ and $R_6$ are as defined above, in the form of the base or of an acid-addition salt.

In one embodiment, in formula (II) above, $G_1$ represents an optionally substituted phenyl group, $X_1$ represents —NH— and the compounds have the formula (III) below:

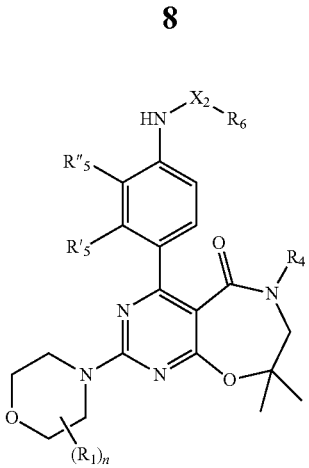

(III)

in which:
$R_4$ represents a group $(C_1-C_6)$-alkyl, in particular an ethyl group or a methyl group,
$R'_5$ and $R''_5$ represent —H or —F, it being understood that when one of the radicals $R'_5$ and $R''_5$ represents —F, then the other represents —H,
$X_2$ represents —$CONR_{50}$— or —COO—, especially —CONH— or —COO—, in particular —CONH—,
$R_6$ represents:
a group $-L_2-R_7$, in which:
$-L_2-$ represents a group $(C_1-C_6)$-alkylene or $(C_3-C_6)$-cycloalkylene,
$R_7$ represents a group chosen from:
H, or
$OR_{60}$,
a group $-G_2-X_3-G_3$, in which:
$X_3$ represents a single bond or a group —O—,
$G_2$ represents a single bond or a cyclic divalent radical of 6 atoms,
$G_3$ represents a 4- to 8-atom ring optionally substituted with one or more (especially 1 or 2) groups $R_{81}$,
n, $R_1$, $R_{50}$, $R_{60}$ and $R_{81}$ are as defined above, in the form of the base or of an acid-addition salt.

In the abovementioned formulae, the following embodiments may be used and independently combined with each other:
m represents 0,
the group

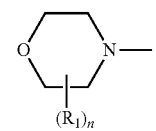

is especially chosen from the following groups:

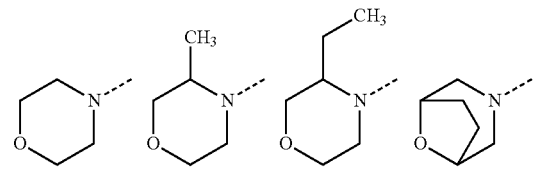

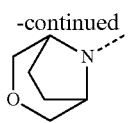

$R_2$ and $R_3$ represent a methyl group,
$R_4$ represents:
H,
a group $(C_1-C_6)$-alkyl, (especially $(C_1-C_2)$-alkyl), optionally substituted with a hydroxyl group,
a group $-L_1-R_{10}$, in which:
$L_1$ represents a group $(C_1-C_6)$-alkylene,
$R_{10}$ represents a group chosen from —$COOR_{11}$, —$OR_{13}$, —$CONR_{14}R_{15}$ and a 5- or 6-atom heterocycle optionally substituted with a group —$COOR_{17}$ or —CO—$R_{18}$, or
a 5- or 6-atom heterocycle optionally substituted with a group —$R_{22}$,
$R_4$ especially represents a group $(C_1-C_6)$-alkyl, such as a methyl group or an ethyl group,
$G_1$ represents a divalent phenyl or pyridyl radical optionally substituted with a group $R_5$ chosen from halogen atoms, especially fluorine,
$G_1$ represents a divalent pyridyl radical or a divalent phenyl radical optionally substituted with a group $R_5$ chosen from halogen atoms, especially fluorine,
$G_1$ especially represents a divalent phenyl radical optionally substituted with a fluorine group,
when $X_1$ represents O, $X_2$ represents a single bond and $R_6$ represents a group $(C_1-C_6)$-alkyl (i.e. a group $-L_2-R_7$ in which $-L_2-$ represents a $(C_1-C_6)$-alkylene and $R_7$ represents —H),
$X_1$ represents a group —$NR_{40}$—, especially —NH—,
$X_2$ represents a single bond or a group —CONH—, —COO—, —CO— or —$SO_2$—, especially —CONH— or —COO—,
$X_2$ represents —$CONR_{50}$— or —COO—, especially —CONH— or —COO—,
When $R_7$ represents a 5- to 6-atom heterocycle optionally substituted with one or more groups =O, the said heterocycle is typically a heterocycle bearing an oxidized sulfur atom, such as tetramethylene sulfone,
when $-G_2-X_3-G_3$ together form a 7- to 10-atom fused bicycle, the said ring is a benzimidazolyl or a 7-azaindolyl,
$G_2$ is a 6-atom cyclic divalent radical,
$G_2$ is a 6-atom cyclic divalent radical and the groups $X_2$ and $X_3$ are in the para position on this ring,
$G_2$ is optionally substituted with a group $R_{80}$,
$G_3$ is optionally substituted with 1, 2 or 3, especially 1 or 2, groups $R_{80}$,
$G_2$ is an aromatic ring,
$G_2$ is an aromatic ring and $G_3$ is a saturated ring,
each radical $R_{80}$ and each radical $R_{81}$ is independently chosen from:
a halogen atom, especially fluorine,
a group —$COOR_{70}$, —$OR_{72}$, —$NR_{73}R_{74}$, —$CONR_{75}R_{76}$, —CN or —$S(O)_p$—$R_{77}$,
a group $(C_1-C_6)$-alkyl substituted with one or more groups $R_{100}$,
a group $(C_1-C_6)$-alkoxy optionally substituted with one or more groups $R_{101}$ and/or optionally interrupted with one or more oxygen atoms,
in the form of the base or of an acid-addition salt.

Among the compounds of formula (I) that are subjects of the invention, mention may be made especially of the compounds in Table 1 below:

TABLE 1

| | Compounds according to the invention - IUPAC nomenclature |
|---|---|
| 1 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-methylurea |
| 2 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-methylurea |
| 3 | 1-Ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea |
| 4 | 1-{4-[8,8-Dimethyl-2-(8-oxa-3-azabicyclo[3.2.1]oct-3-yl)-5-oxo-6-(S)-1-pyrrolidin-2-ylmethyl-5,6,7,8-tetrahydro-9-oxa-1,3,6-triazabenzocyclohepten-4-yl]-2-fluorophenyl}-3-ethylurea |
| 5 | (S)-2-[4-[4-(3-Ethylureido)-3-fluorophenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-ylmethyl]pyrrolidine-1-carboxylic acid ethyl ester |
| 6 | 1-{4-[6-((S)-1-Acetylpyrrolidin-2-ylmethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-ethylurea |
| 7 | 3-[4-[4-(3-Ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid |
| 8 | 3-[4-[4-(3-Ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]-N,N-dimethylpropionamide |
| 9 | 1-Ethyl-3-{4-[6-(3-hydroxypropyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 10 | 1-Ethyl-3-{4-[6-ethyl-8,8-dimethyl-2-(8-oxa-3-azabicyclo[3.2.1]oct-3-yl)-5-oxo-6,7,8,9-tetrahydro-5H-10-oxa-1,3,6-triazabenzocycloocten-4-yl]phenyl}urea |
| 11 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-methylurea |
| 12 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-pyridin-4-ylurea |
| 13 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methylpiperazin-1-yl)phenyl]urea |

TABLE 1-continued

Compounds according to the invention - IUPAC nomenclature 14 1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-ethylurea
15 1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(5-methylisoxazol-3-yl)urea
16 1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(1-methyl-1H-pyrazol-3-yl)urea
17 1-Ethyl-3-{5-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]pyridin-2-yl}urea
18 1-(3-Difluoromethoxyphenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
19 1-(2,4-Difluorophenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
20 {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid (S)-2-hydroxypropyl ester
21 1-(4-Methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
22 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(1-methylpiperidin-4-yloxy)pyridin-3-yl]urea
23 1-[4-(4-Dimethylaminopiperidine-1-carbonyl)phenyl]-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea
24 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-hydroxy-2-methylpropyl)urea
25 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-pyrrolidin-1-ylpyridin-2-yl)urea
26 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-methylphenyl}-3-isoxazol-3-ylurea
27 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-((R)-2-hydroxy-1-methylethyl)urea
28 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyrazin-2-yl)urea
29 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((S)-3-methylmorpholin-4-yl)pyridin-3-yl]urea
30 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((R)-3-methylmorpholin-4-yl)pyridin-3-yl]urea
31 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(3,4,5,6-tetrahydro-2H-[1,2']bipyridinyl-5'-yl)urea
32 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-pyrrolidin-1-ylpyridin-3-yl)urea
33 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-2-ylurea
34 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-methylpyridin-2-yl)urea
35 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(4-methoxypyridin-2-yl)urea
36 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(6-methylpyridin-2-yl)urea
37 1-{4-[6-Ethyl-2-((S)-3-ethylmorpholin-4-yl)-8,8-dimethyl-5-oxo-5,6,7,8-tetrahydro-9-oxa-1,3,6-triazabenzocyclohepten-4-yl]-2-fluorophenyl}-3-(6-methylpyridin-3-yl)urea
38 1-Methyl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
39 1-Pyridin-2-yl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
40 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(2-methoxyethoxy)pyridin-2-yl]urea
41 1-Pyridin-2-yl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea TABLE 1-continued Compounds according to the invention - IUPAC nomenclature

| | |
|---|---|
| 42 | 1-(5-Methylpyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 43 | 1-Methyl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 44 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-methoxypyridin-2-yl)urea |
| 45 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-methylurea |
| 46 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-methylurea |
| 47 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-3-fluorophenyl}-3-methylurea |
| 48 | 1-(5-Methylpyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 49 | 1-(5-Methoxypyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 50 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-pyridin-3-ylurea |
| 51 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-pyridin-4-ylurea |
| 52 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-4-ylurea |
| 53 | {4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}carbamic acid (1S,2R)-2-hydroxycyclopentyl ester |
| 54 | 1-(5-Methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 55 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-(2-methylpyridin-4-yl)urea |
| 56 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-methylpyridin-4-yl)urea |
| 57 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-((S)-2-hydroxy-1-methylethyl)urea |
| 58 | 1-(2,6-Dimethylpyridin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 59 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(2-methylpyridin-4-yl)urea |
| 60 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-methylpyridin-4-yl)urea |
| 61 | {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid (S)-2-hydroxy-1-methylethyl ester |
| 62 | {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid (R)-2-hydroxy-1-methylethyl ester |
| 63 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-pyridin-2-ylurea |
| 64 | 1-(5-Dimethylaminopyridin-2-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 65 | {4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}carbamic acid 2-hydroxyethyl ester |
| 66 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methylpyridin-3-yl)urea |
| 67 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(6-methylpyridin-3-yl)urea |
| 68 | 1-Pyridin-4-yl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 69 | 1-Pyridin-4-yl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 70 | 1-(4-Methoxypyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |

TABLE 1-continued

Compounds according to the invention - IUPAC nomenclature

| | |
|---|---|
| 71 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-3-fluorophenyl}-3-pyridin-4-ylurea |
| 72 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(3-hydroxypyrrolidin-1-yl)pyridin-2-yl]urea |
| 73 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-((S)-3-methylmorpholin-4-yl)pyridin-3-yl]urea |
| 74 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-[6-((S)-3-methylmorpholin-4-yl)pyridin-3-yl]urea |
| 75 | 1-[4-((1S,5R)-6-Ethyl-8,8-dimethyl-2-3-oxa-8-azabicyclo[3.2.1]oct-8-yl-5-oxo-5,6,7,8-tetrahydro-9-oxa-1,3,6-triazabenzocyclohepten-4-yl)phenyl]-3-(3-fluoropyridin-4-yl)urea |
| 76 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(3-fluoropyridin-4-yl)urea |
| 77 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(tetrahydrofuran-3-yloxy)phenyl]urea |
| 78 | 1-(2-Dimethylaminopyridin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 79 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(4-methoxypyridin-2-yl)urea |
| 80 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[2-(4-methanesulfonylpiperazin-1-yl)pyridin-4-yl]urea |
| 81 | 4-[5-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}ureido)pyridin-2-yl]piperazine-1-carboxylic acid methyl ester |
| 82 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-pyridin-4-ylurea |
| 83 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-4-ylurea |
| 84 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-3-fluorophenyl}-3-pyridin-2-ylurea |
| 85 | 1-(3-Fluoropyridin-4-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 86 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(1H-pyrrolo[2,3-b]pyridin-4-yl)urea |
| 87 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-((R)-3-methylmorpholin-4-yl)pyridin-3-yl]urea |
| 88 | {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}carbamic acid (S)-2-hydroxypropyl ester |
| 89 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-3-fluorophenyl}-3-(4-methoxypyridin-2-yl)urea |
| 90 | 1-(2,6-Dimethylpyrimidin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 91 | 1-(2,6-Dimethylpyrimidin-4-yl)-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea |
| 92 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-pyrimidin-4-ylurea |
| 93 | 1-(2,6-Dimethylpyrimidin-4-yl)-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 94 | 1-[4-(8,8-Dimethyl-2-morpholin-4-yl-5-oxo-5,6,7,8-tetrahydro-9-oxa-1,3,6-triazabenzocyclohepten-4-yl)phenyl]-3-ethylurea |
| 95 | 4-(6-Aminopyridin-3-yl)-8,8-dimethyl-2-morpholin-4-yl-7,8-dihydro-6H-9-oxa-1,3,6-triazabenzocyclohepten-5-one |
| 96 | 1-Ethyl-3-[4-(6-ethyl-8,8-dimethyl-2-morpholin-4-yl-5-oxo-5,6,7,8-tetrahydro-9-oxa-1,3,6-triazabenzocyclohepten-4-yl)phenyl]urea |
| 97 | 1-Ethyl-3-[4-(6-ethyl-2-morpholin-4-yl-5-oxo-5,6,7,8-tetrahydro-9-oxa-1,3,6-triazabenzocyclohepten-4-yl)phenyl]urea |
| 98 | 1-Ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea |
| 99 | 1-Ethyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |

TABLE 1-continued

Compounds according to the invention - IUPAC nomenclature

| | |
|---|---|
| 100 | 6-Ethyl-4-(3-hydroxymethyl-4-methoxyphenyl)-8,8-dimethyl-2-morpholin-4-yl-7,8-dihydro-6H-9-oxa-1,3,6-triazabenzocyclohepten-5-one |
| 101 | 6-Ethyl-4-(3-hydroxymethyl-4-methoxyphenyl)-8,8-dimethyl-2-(8-oxa-3-azabicyclo[3.2.1]oct-3-yl)-7,8-dihydro-6H-9-oxa-1,3,6-triazabenzocyclohepten-5-one |
| 102 | 4-(4-Aminophenyl)-6-ethyl-8,8-dimethyl-2-morpholin-4-yl-7,8-dihydro-6H-9-oxa-1,3,6-triazabenzocyclohepten-5-one |
| 103 | [4-(6-Ethyl-8,8-dimethyl-2-morpholin-4-yl-5-oxo-5,6,7,8-tetrahydro-9-oxa-1,3,6-triazabenzocyclohepten-4-yl)phenyl]carbamic acid methyl ester |
| 104 | 1-Methoxy-3-[4-(6-ethyl-8,8-dimethyl-2-morpholin-4-yl-5-oxo-5,6,7,8-tetrahydro-9-oxa-1,3,6-triazabenzocyclohepten-4-yl)phenyl]urea |
| 105 | {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}carbamic acid methyl ester |
| 106 | {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}carbamic acid ethyl ester |
| 107 | 4-(6-Aminopyridin-3-yl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one |
| 108 | N-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}propionamide |
| 109 | 1-{4-[2-((2S,6R)-2,6-Dimethylmorpholin-4-yl)-6-ethyl-8,8-dimethyl-5-oxo-6,7,8,9-tetrahydro-5H-10-oxa-1,3,6-triazabenzocycloocten-4-yl]phenyl}-3-ethylurea |
| 110 | 1-Ethyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 111 | Ethanesulfonic acid {4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}amide |
| 112 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-3-ylurea |
| 113 | 1-Ethyl-3-{4-[6-ethyl-8,8-dimethyl-2-(8-oxa-3-azabicyclo[3.2.1]oct-3-yl)-5,6,7,8-tetrahydro-9-oxa-1,3,6-triazabenzocyclohepten-4-yl]phenyl}urea |
| 114 | 1-{4-[2-((2S,6R)-2,6-Dimethylmorpholin-4-yl)-6-ethyl-8,8-dimethyl-5-oxo-5,6,7,8-tetrahydro-9-oxa-1,3,6-triazabenzocyclohepten-4-yl]phenyl}-3-ethylurea |
| 115 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-methyl-2H-pyrazol-3-yl)urea |
| 116 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-methylisoxazol-3-yl)urea |
| 117 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-hydroxyethyl)urea |
| 118 | 4-[4-(1H-Benzimidazol-2-ylamino)phenyl]-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one |
| 119 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(3-hydroxypropyl)urea |
| 120 | 3-[4-[4-(3-Ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid tert-butyl ester |
| 121 | 6-Ethyl-8,8-dimethyl-4-[4-(5-methyl-[1,3,4]thiadiazol-2-ylamino)phenyl]-2-(8-oxa-3-azabicyclo[3.2.1]oct-3-yl)-7,8-dihydro-6H-9-oxa-1,3,6-triazabenzocyclohepten-5-one |
| 122 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(1-methyl-1H-pyrazol-3-yl)urea |
| 123 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-fluoroethyl)urea |
| 124 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-yl)urea |
| 125 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyrazin-2-ylurea |
| 126 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(1-methyl-1H-pyrazol-4-yl)urea |
| 127 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(3-methoxyphenyl)urea |
| 128 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(tetrahydrofuran-2-ylmethyl)urea |
| 129 | 1-(1,1-Dioxotetrahydro-1λ6-thiophen-3-ylmethyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |

TABLE 1-continued

Compounds according to the invention - IUPAC nomenclature

| | |
|---|---|
| 130 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(1-methylpiperidin-4-ylmethyl)urea |
| 131 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-methoxyethyl)urea |
| 132 | 1-{4-[8,8-Dimethyl-6-(1-methylpiperidin-4-yl)-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-ethylurea |
| 133 | 1-Cyclopropyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 134 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(tetrahydropyran-4-ylmethyl)urea |
| 135 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-isoxazol-3-ylurea |
| 136 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-methoxypyrimidin-5-yl)urea |
| 137 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-oxetan-3-ylurea |
| 138 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(4-fluoro-3-methoxyphenyl)urea |
| 139 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyrazin-2-yl)urea |
| 140 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridazin-3-yl)urea |
| 141 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-methoxypyridin-3-yl)urea |
| 142 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-2-yl)urea |
| 143 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(1-methyl-1H-pyrazol-4-yl)urea |
| 144 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-methoxypyrimidin-4-yl)urea |
| 145 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-ylmethyl)urea |
| 146 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyridazin-3-yl)urea |
| 147 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(3-trifluoromethylphenyl)urea |
| 148 | 1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(6-methoxypyridin-3-yl)urea |
| 149 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(2,2,2-trifluoroethyl)urea |
| 150 | 1-Cyclopropyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea |
| 151 | 1-Ethyl-3-{4-[6-ethyl-2-((S)-3-ethylmorpholin-4-yl)-8,8-dimethyl-5-oxo-5,6,7,8-tetrahydro-9-oxa-1,3,6-triazabenzocyclohepten-4-yl]-2-fluorophenyl}urea |
| 152 | 6-Ethyl-4-[3-fluoro-4-(5-methyl-4H-[1,2,4]triazol-3-ylamino)phenyl]-8,8-dimethyl-2-(8-oxa-3-azabicyclo[3.2.1]oct-3-yl)-7,8-dihydro-6H-9-oxa-1,3,6-triazabenzocyclohepten-5-one |
| 153 | 1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]-2-fluorophenyl}-3-isoxazol-3-ylurea |
| 154 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-fluoro-4-trifluoromethylphenyl)urea |
| 155 | 1-(2,4-Difluoro-5-methoxyphenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |

TABLE 1-continued

Compounds according to the invention - IUPAC nomenclature 156 1-{4-[8,8-Dimethyl-2-((S)-3-methylmorpholin-4-yl)-5-oxo-6-(tetrahydropyran-4-yl)-5,6,7,8-tetrahydro-9-oxa-1,3,6-triazabenzocyclohepten-4-yl]-2-fluorophenyl}-3-isoxazol-3-ylurea
157 1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-isoxazol-3-ylurea
158 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-2-ylurea
159 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-isoxazol-3-ylurea
160 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-pyrazin-2-ylurea
161 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-methylpyridin-3-yl)urea
162 1-(2,4-Difluorophenyl)-3-{4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
163 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(5-methoxypyridin-2-yl)urea
164 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(5-methylpyridin-2-yl)urea
165 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-methylphenyl}-3-isoxazol-3-ylurea
166 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(1-methyl-1H-pyrazol-3-yl)urea
167 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(5-methylpyrazin-2-yl)urea
168 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(5-methylpyridin-2-yl)urea
169 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(5-methylpyridin-2-yl)urea
170 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(5-methyl-[1,3,4]oxadiazol-2-yl)urea
171 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-(4-methylpiperazin-1-yl)pyridin-3-yl]urea
172 1-Isoxazol-3-yl-3-{4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
173 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(5-methoxypyridin-2-yl)urea
174 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-[6-(4-methylpiperazin-1-yl)pyridin-3-yl]urea
175 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-methylphenyl}-3-(6-methoxypyridin-3-yl)urea
176 N-(2-Dimethylaminoethyl)-4-(3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}ureido)-N-methylbenzamide
177 1-[4-(4-Dimethylaminopiperidine-1-carbonyl)phenyl]-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea
178 1-{2-Fluoro-4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyridin-3-yl)urea
179 1-{2-Fluoro-4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-isoxazol-3-ylurea
180 1-Isoxazol-3-yl-3-{4-[6-(2-methoxyethyl)-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea
181 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(4-methoxypyridin-2-yl)urea TABLE 1-continued Compounds according to the invention - IUPAC nomenclature 182  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(1-methyl-1H-imidazol-4-yl)urea 183  6-Ethyl-4-{3-fluoro-4-[5-(6-methoxypyridin-3-yl)-4H-[1,2,4]triazol-3-ylamino]phenyl}-8,8-dimethyl-2-(8-oxa-3-azabicyclo[3.2.1]oct-3-yl)-7,8-dihydro-6H-9-oxa-1,3,6-triazabenzocyclohepten-5-one 184  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(4-methoxypyridin-2-yl)urea 185  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methylpyridin-3-yl)urea 186  {4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}carbamic acid 2-hydroxyethyl ester 187  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-morpholin-4-ylpyridin-3-yl)urea 188  1-(2,4-Difluorophenyl)-3-{4-[6-(2-methoxyethyl)-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea 189  1-{4-[8,8-Dimethyl-2-((S)-3-methylmorpholin-4-yl)-5-oxo-6-(tetrahydropyran-4-yl)-5,6,7,8-tetrahydro-9-oxa-1,3,6-triazabenzocyclohepten-4-yl]-2-fluorophenyl}-3-(6-methoxypyridin-3-yl)urea 190  4-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}ureido)-N-(2-hydroxy-2-methylpropyl)benzamide 191  1-(2,4-Difluorophenyl)-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea 192  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-pyridin-2-ylurea 193  {4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}carbamic acid 3-methoxyphenyl ester 194  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(1-methyl-1H-imidazol-4-yl)urea 195  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(4-methylpiperazin-1-yl)pyridin-3-yl]urea 196  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-methylphenyl}-3-(6-methoxypyridin-3-yl)urea 197  1-{4-[6-(2-Methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyridin-3-yl)urea 198  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-methoxypyrazin-2-yl)urea 199  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(2-methylpyridin-4-yl)urea 200  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-morpholin-4-ylpyridin-3-yl)urea 201  1-{4-[6-(2-Methoxyethyl)-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(1-methyl-1H-pyrazol-4-yl)urea 202  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(2-fluorophenyl)urea 203  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(4-piperidin-1-ylmethylphenyl)urea 204  1-(3-Difluoromethoxyphenyl)-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea 205  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[4-(4-methylpiperazin-1-yl)phenyl]urea 206  1-[4-((1S,4S)-6-Ethyl-8,8-dimethyl-2-2-oxa-5-azabicyclo[2.2.1]hept-5-yl-5-oxo-5,6,7,8-tetrahydro-9-oxa-1,3,6-triazabenzocyclohepten-4-yl)-2-fluorophenyl]-3-methylurea 207  1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-methylurea TABLE 1-continued Compounds according to the invention - IUPAC nomenclature 208 1-(2,4-Difluoro-5-methoxyphenyl)-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea 209 {4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}carbamic acid 2-hydroxyethyl ester 210 1-{2-Fluoro-4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-methylurea 211 1-Ethyl-3-{2-fluoro-4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea 212 1-(3-Difluoromethoxyphenyl)-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea 213 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(2-fluoro-5-methoxyphenyl)urea 214 {4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}carbamic acid 2-hydroxy-2-methylpropyl ester 215 N-(2-Dimethylamino-ethyl)-4-(3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}ureido)-N-methylbenzamide 216 1-(3-Difluoromethoxyphenyl)-3-{4-[6-(2-methoxyethyl)-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea 217 1-Ethyl-3-{4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea 218 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-[5-(4-methylpiperazin-1-yl)pyridin-2-yl]urea 219 4-(3-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}ureido)-N-(2-hydroxy-2-methylpropyl)benzamide 220 1-(3-Difluoromethoxyphenyl)-3-{2-fluoro-4-[6-(2-methoxyethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea 221 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-pyridin-2-ylurea 222 {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid 2-hydroxyethyl ester 223 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-3-ylurea 224 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-hydroxy-1,1-dimethylethyl)urea 225 1-{2-Fluoro-4-[6-(2-methoxyethyl)-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-methylurea 226 1-{2-Fluoro-4-[6-(2-methoxyethyl)-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(2-hydroxy-2-methylpropyl)urea 227 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(4-morpholin-4-ylphenyl)urea 228 1-{4-[6-Ethyl-2-((S)-3-ethylmorpholin-4-yl)-8,8-dimethyl-5-oxo-5,6,7,8-tetrahydro-9-oxa-1,3,6-triazabenzocyclohepten-4-yl]-2-fluorophenyl}-3-methylurea 229 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-(6-methylpyridin-3-yl)urea 230 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-trifluoromethylpyridin-3-yl)urea 231 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-pyridin-4-ylurea 232 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(5-morpholin-4-ylpyrazin-2-yl)urea 233 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(5-morpholin-4-ylpyrazin-2-yl)urea 234 1-(5-Dimethylaminopyrazin-2-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea TABLE 1-continued Compounds according to the invention - IUPAC nomenclature 235 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methanesulfonylpiperazin-1-yl)phenyl]urea
236 4-[4-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}ureido)phenyl]piperazine-1-carboxylic acid methyl ester
237 1-[4-(1,1-Dioxo-1λ6-thiomorpholin-4-yl)phenyl]-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea
238 {4-[6,8,8-Trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}carbamic acid (S)-2-hydroxy-1-methylethyl ester
239 {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid (R)-2-hydroxypropyl ester
240 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-yl)urea
241 1-(2,6-Dimethylpyridin-4-yl)-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea
242 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-(4-methoxypyridin-2-yl)urea
243 {4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-3-fluorophenyl}carbamic acid 2-hydroxyethyl ester
244 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-(8-oxa-3-azabicyclo[3.2.1]oct-3-yl)pyridin-3-yl]urea
245 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-(3-oxa-8-azabicyclo[3.2.1]oct-8-yl)pyridin-3-yl]urea
246 {4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-3-fluorophenyl}carbamic acid 2-hydroxyethyl ester
247 1-(6-Cyanopyridin-3-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea
248 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-((S)-3-ethylmorpholin-4-yl)pyridin-3-yl]urea
249 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[6-((S)-3-ethylmorpholin-4-yl)pyridin-3-yl]urea
250 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-morpholin-4-ylpyridin-2-yl)urea
251 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(8-oxa-3-azabicyclo[3.2.1]oct-3-yl)pyridin-2-yl]urea
252 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[(1S,4S)-6-(2-oxa-5-azabicyclo[2.2.1]hept-5-yl)pyridin-3-yl]urea
253 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[(1S,4S)-6-(2-oxa-5-azabicyclo[2.2.1]hept-5-yl)pyridin-3-yl]urea
254 1-Cyclopropyl-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea
255 1-Ethyl-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea
256 1-[6-(3,3-Dimethylmorpholin-4-yl)pyridin-3-yl]-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea
257 1-[6-(3,3-Dimethylmorpholin-4-yl)pyridin-3-yl]-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea
258 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-(8-oxa-3-azabicyclo[3.2.1]oct-3-yl)pyridin-3-yl]urea
259 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[6-(8-oxa-3-azabicyclo[3.2.1]oct-3-yl)pyridin-3-yl]urea
260 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[2-(8-oxa-3-azabicyclo[3.2.1]oct-3-yl)pyridin-4-yl]urea TABLE 1-continued Compounds according to the invention - IUPAC nomenclature 261  1-(4,4-Difluoro-3,4,5,6-tetrahydro-2H-[1,2']bipyridinyl-4'-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea in the form of the base or of an acid-addition salt.

It should be noted that the numbers attributed to the compounds correspond to those of the examples and remain the same throughout the patent application.

Among the compounds of formula (III) that are subjects of the invention, mention may be made especially of the compounds of Table 2 below:

TABLE 2

Compounds according to the invention - IUPAC nomenclature 1  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-methylurea 2  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-methylurea 3  1-Ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea 12  1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-pyridin-4-ylurea 13  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methylpiperazin-1-yl)phenyl]urea 21  1-(4-Methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea 22  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(1-methylpiperidin-4-yloxy)pyridin-3-yl]urea 29  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((S)-3-methylmorpholin-4-yl)pyridin-3-yl]urea 30  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((R)-3-methylmorpholin-4-yl)pyridin-3-yl]urea 31  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(3,4,5,6-tetrahydro-2H-[1,2']bipyridinyl-5'-yl)urea 32  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-pyrrolidin-1-ylpyridin-3-yl)urea 37  1-{4-[6-Ethyl-2-((S)-3-ethylmorpholin-4-yl)-8,8-dimethyl-5-oxo-5,6,7,8-tetrahydro-9-oxa-1,3,6-triazabenzocyclohepten-4-yl]-2-fluorophenyl}-3-(6-methylpyridin-3-yl)urea 38  1-Methyl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea 40  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(2-methoxyethoxy)pyridin-2-yl]urea 43  1-Methyl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea 45  1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-methylurea 46  1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-methylurea 49  1-(5-Methoxypyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea 50  1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-pyridin-3-ylurea 51  1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-pyridin-4-ylurea 52  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-4-ylurea 54  1-(5-Methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea 55  1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-(2-methylpyridin-4-yl)urea 56  1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-methylpyridin-4-yl)urea TABLE 2-continued

| | Compounds according to the invention - IUPAC nomenclature |
|---|---|
| 58 | 1-(2,6-Dimethylpyridin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 59 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(2-methylpyridin-4-yl)urea |
| 60 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-methylpyridin-4-yl)urea |
| 64 | 1-(5-Dimethylaminopyridin-2-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 66 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methylpyridin-3-yl)urea |
| 67 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(6-methylpyridin-3-yl)urea |
| 68 | 1-Pyridin-4-yl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 69 | 1-Pyridin-4-yl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 70 | 1-(4-Methoxypyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea |
| 71 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-3-fluorophenyl}-3-pyridin-4-ylurea |
| 73 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-((S)-3-methylmorpholin-4-yl)pyridin-3-yl]urea |
| 74 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-[6-((S)-3-methylmorpholin-4-yl)pyridin-3-yl]urea |
| 75 | 1-[4-((1S,5R)-6-Ethyl-8,8-dimethyl-2-3-oxa-8-azabicyclo[3.2.1]oct-8-yl-5-oxo-5,6,7,8-tetrahydro-9-oxa-1,3,6-triazabenzocyclohepten-4-yl)phenyl]-3-(3-fluoropyridin-4-yl)urea |
| 76 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(3-fluoropyridin-4-yl)urea |
| 77 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(tetrahydrofuran-3-yloxy)phenyl]urea |
| 78 | 1-(2-Dimethylaminopyridin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 79 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(4-methoxypyridin-2-yl)urea |
| 80 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[2-(4-methanesulfonylpiperazin-1-yl)pyridin-4-yl]urea |
| 81 | 4-[5-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}ureido)pyridin-2-yl]piperazine-1-carboxylic acid methyl ester |
| 82 | 1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-pyridin-4-ylurea |
| 83 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-4-ylurea |
| 87 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-((R)-3-methylmorpholin-4-yl)pyridin-3-yl]urea |
| 98 | 1-Ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea |
| 99 | 1-Ethyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea |
| 110 | 1-Ethyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 112 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-3-ylurea |
| 116 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-methylisoxazol-3-yl)urea |
| 124 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-yl)urea |

TABLE 2-continued

Compounds according to the invention - IUPAC nomenclature

| | |
|---|---|
| 133 | 1-Cyclopropyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 135 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-isoxazol-3-ylurea |
| 141 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-methoxypyridin-3-yl)urea |
| 150 | 1-Cyclopropyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea |
| 159 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-isoxazol-3-ylurea |
| 161 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-methylpyridin-3-yl)urea |
| 168 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(5-methylpyridin-2-yl)urea |
| 171 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-(4-methylpiperazin-1-yl)pyridin-3-yl]urea |
| 174 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-[6-(4-methylpiperazin-1-yl)pyridin-3-yl]urea |
| 184 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(4-methoxypyridin-2-yl)urea |
| 185 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methylpyridin-3-yl)urea |
| 186 | {4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}carbamic acid 2-hydroxyethyl ester |
| 187 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-morpholin-4-ylpyridin-3-yl)urea |
| 195 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(4-methylpiperazin-1-yl)pyridin-3-yl]urea |
| 199 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(2-methylpyridin-4-yl)urea |
| 200 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-morpholin-4-ylpyridin-3-yl)urea |
| 202 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(2-fluorophenyl)urea |
| 205 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[4-(4-methylpiperazin-1-yl)phenyl]urea |
| 207 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-methylurea |
| 218 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-[5-(4-methylpiperazin-1-yl)pyridin-2-yl]urea |
| 221 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-pyridin-2-ylurea |
| 223 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-3-ylurea |
| 227 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(4-morpholin-4-ylphenyl)urea |
| 229 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-(6-methylpyridin-3-yl)urea |
| 231 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-pyridin-4-ylurea |
| 235 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methanesulfonylpiperazin-1-yl)phenyl]urea |
| 236 | 4-[4-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}ureido)phenyl]piperazine-1-carboxylic acid methyl ester |
| 237 | 1-[4-(1,1-Dioxo-1λ6-thiomorpholin-4-yl)phenyl]-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 240 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-yl)urea |
| 241 | 1-(2,6-Dimethylpyridin-4-yl)-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea |

TABLE 2-continued

Compounds according to the invention - IUPAC nomenclature

| | |
|---|---|
| 243 | {4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-3-fluorophenyl}carbamic acid 2-hydroxyethyl ester |
| 244 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-(8-oxa-3-azabicyclo[3.2.1]oct-3-yl)pyridin-3-yl]urea |
| 245 | 1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-(3-oxa-8-azabicyclo[3.2.1]oct-8-yl)pyridin-3-yl]urea |
| 247 | 1-(6-Cyanopyridin-3-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea |
| 248 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-((S)-3-ethylmorpholin-4-yl)pyridin-3-yl]urea |
| 249 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[6-((S)-3-ethylmorpholin-4-yl)pyridin-3-yl]urea |
| 250 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-morpholin-4-ylpyridin-2-yl)urea |
| 251 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(8-oxa-3-azabicyclo[3.2.1]oct-3-yl)pyridin-2-yl]urea |
| 252 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[(1S,4S)-6-(2-oxa-5-azabicyclo[2.2.1]hept-5-yl)pyridin-3-yl]urea |
| 253 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[(1S,4S)-6-(2-oxa-5-azabicyclo[2.2.1]hept-5-yl)pyridin-3-yl]urea |
| 254 | 1-Cyclopropyl-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea |
| 255 | 1-Ethyl-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea |
| 256 | 1-[6-(3,3-Dimethylmorpholin-4-yl)pyridin-3-yl]-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea |
| 257 | 1-[6-(3,3-Dimethylmorpholin-4-yl)pyridin-3-yl]-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea |
| 258 | 1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-(8-oxa-3-azabicyclo[3.2.1]oct-3-yl)pyridin-3-yl]urea |
| 259 | 1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[6-(8-oxa-3-azabicyclo[3.2.1]oct-3-yl)pyridin-3-yl]urea |
| 260 | 1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[2-(8-oxa-3-azabicyclo[3.2.1]oct-3-yl)pyridin-4-yl]urea |
| 261 | 1-(4,4-Difluoro-3,4,5,6-tetrahydro-2H-[1,2']bipyridinyl-4'-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea | in the form of the base or of an acid-addition salt.

Combinations of the groups of compounds according to the invention also form part of the invention as an embodiment.

[Preparation Process]

In the text hereinbelow, the term "PG" (protecting group) means a group that can, firstly, protect a reactive function such as a hydroxyl or an amine during the synthesis and, secondly, regenerate the intact reactive function at the end of the synthesis. Examples of protecting groups and of protection and deprotection methods are given in Protective Groups in Organic Chemistry, J. F. W. McOmie, Plenum Press, 1973, in Greene's Protective Groups in Organic Synthesis, by Theodora W. Greene published by John Wiley & Sons Inc., 2006 or in Protecting Groups, Kocienski P. J., 1994, Georg Thieme Verlag. Examples that may be mentioned, as temporary protecting groups for amines: benzyls, carbamates (such as tert-butyloxycarbonyl, which may be cleaved in acidic medium, or benzyloxycarbonyl, which may be cleaved by hydrogenolysis), as temporary protecting groups for carboxylic acids: alkyl esters (such as methyl, ethyl or tert-butyl, which may be hydrolysed in basic or acidic medium) and benzyl esters, which may be hydrogenolysed, temporary protecting groups for alcohols or phenols such as tetrahydropyranyl, methyloxymethyl, methylethoxymethyl, tert-butyl, benzyl and tert-butyldimethylsilyl ethers, temporary protecting groups for carbonyl derivatives such as linear or cyclic acetals, for instance 1,3-dioxan-2-yl or 1,3-dioxolan-2-yl; and reference may be made to the well-known general methods described in these publications.

The processes for protecting and deprotecting the protecting groups are typically those described in these publications.

Protection/deprotection steps for the various groups present on the compounds and reaction intermediates may be added before or after each of the steps mentioned below (or between two steps). Determining whether or not it is necessary to protect the groups, and the nature of the protecting groups to be used, are standard approaches for a person skilled in the art, who knows, in the light of his general knowledge, whether a group is liable to react during subsequent steps and whether or not it should be protected.

In the text hereinbelow, the term "LG" (leaving group) means a group that can be readily cleaved from a molecule by breaking a heterolytic bond, with loss of an electron pair. This group may thus be readily replaced with another group, for example during a substitution reaction. Such leaving groups are, for example, halogen atoms or an activated hydroxyl group such as a methanesulfonate, benzenesulfonate, p-toluenesulfonate, triflate, acetate, etc. Examples of leaving groups and also references for their preparation are given in *Advances in Organic Chemistry*, J. March, $3^{rd}$ Edition, Wiley Interscience, pp. 310-316.

The intermediates described below may comprise groups that are precursors of other functions which are generated subsequently in one or more other steps.

In accordance with the invention, the compounds of general formula (I) may be prepared according to the processes that follow.

In a first embodiment, the process for preparing the compound of formula (I) may comprise step m) below:

m) grafting a group —$X_2$—$R_6$ onto a compound of formula (XLII) below:

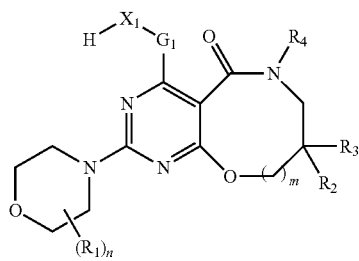

(XLII)

in which $R_1$, n, m, $R_2$, $R_3$, $R_4$, $G_1$ and $X_1$ are as defined above, to obtain the compound of formula (I).

The reaction scheme for the preparation of the compound of formula (I) via step m) is represented in scheme 1 below.

Scheme 1: reaction scheme for preparing the compound of formula (I) from the compound of formula (XLII).

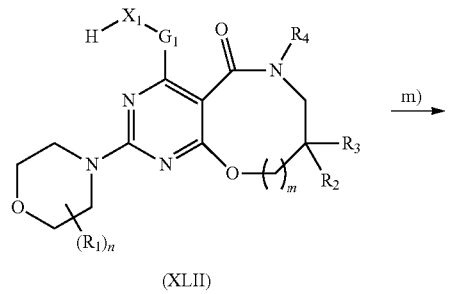

(XLII)

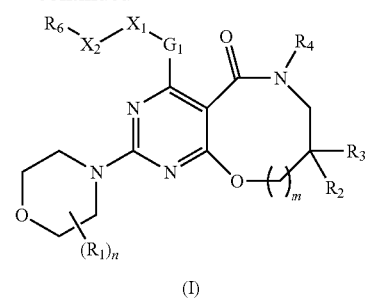

(I)

When the process performed requires the protection of $X_1$ (more precisely of the hydroxyl function when $X_1$ represents —O— or of the amine function when $X_1$ represents —$NR_{40}$—), the process for preparing the compound of formula (XLII) used in the abovementioned step m) generally comprises step l) below:

l) deprotection of a compound of formula (XLI) below:

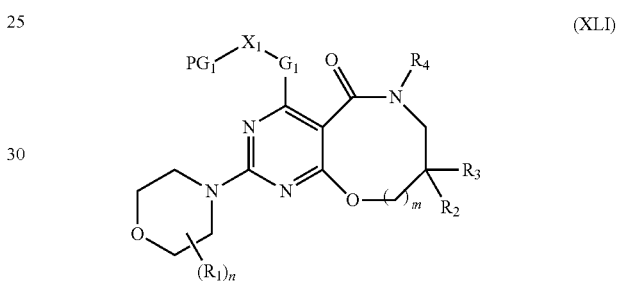

(XLI)

in which:

$R_1$, n, m, $R_2$, $R_3$, $R_4$, $G_1$ and $X_1$ are as defined above, and $PG_1$ is a protecting group for $X_1$ (protecting group for a hydroxyl function when $X_1$ represents —O— or for an amine when $X_1$ represents —$NR_{40}$—), to obtain the compound of formula (XLII).

The reaction scheme for the preparation of the compound of formula (XLII) via step l) is represented in scheme 2 below.

Scheme 2: Reaction scheme for the preparation of the compound of formula (XLII) from the compound of formula (XLI), when $PG_1$ is a protecting group for $X_1$.

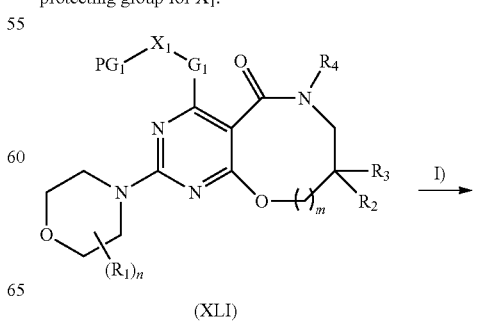

(XLI)

39

-continued

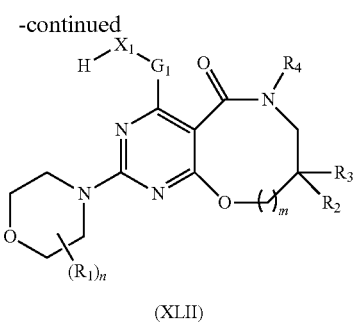

(XLII)

Step l) is not necessary when the process performed does not require protection of $X_1$. In this case, in the steps that follow, $PG_1$ represents H and the compound of formula (XLII) corresponds to the compound of formula (XLI) in which $PG_1$ represents H.

Thus, in the steps described below (for preparing the compounds of formula (I), (XLI) or (XLII)), $PG_1$ represents H or a protecting group for $X_1$.

Two alternative embodiments have been developed for preparing the abovementioned compounds of formula (XLI).

In a first alternative, the process for preparing the compound of formula (XLI) may comprise the following steps:

c) Suzuki reaction of a compound of formula (XIII) below:

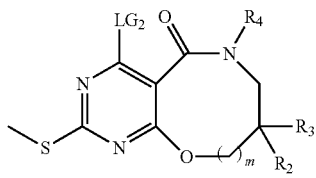

(XIII)

in which m, $R_2$, $R_3$ and $R_4$ are as defined above and $LG_2$ is a leaving group, for example a halogen atom such as chlorine, with a compound of formula $PG_1$-$X_1$-$G_1$-$R_{300}$, in which $X_1$, and $G_1$ are as defined above, $PG_1$ is H or a protecting group for $X_1$ and $R_{300}$ is a boronic acid or ester radical, typically with a compound of formula (CII) below:

(CII)

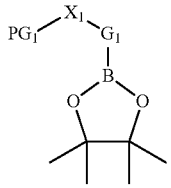

in which $X_1$, $PG_1$ and $G_1$ are as defined above,
to obtain a compound of formula (XXI) below:

(XXI)

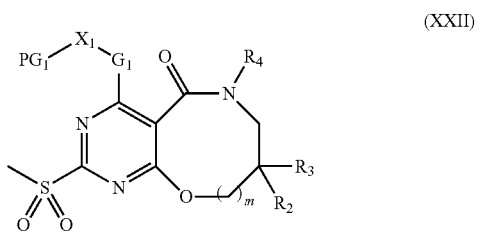

in which m, $R_2$, $R_3$, $R_4$, $X_1$, $PG_1$ and $G_1$ are as defined above,

40 d) oxidation of the compound of formula (XXI) obtained in step c) to obtain a compound of formula (XXII) below:

(XXII)

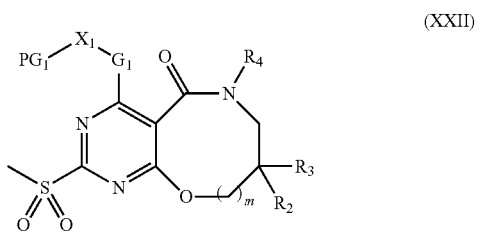

in which m, $R_2$, $R_3$, $R_4$, $X_1$, $PG_1$ and $G_1$ are as defined above, e) nucleophilic attack of a compound of formula (CI) below:

(CI)

in which n and $R_1$ are as defined above,
on the compound of formula (XXII) obtained in step d),
to obtain the compound of formula (XLI).

When $PG_1$ represents H, the compound of formula (XLI) obtained at the end of step e) corresponds to the compound of formula (XLII), which may be engaged directly in step m), without the deprotection step l) being necessary.

The reaction scheme for the preparation of the compound of formula (XLI) via steps c) to e) is represented in scheme 3 below (in the embodiment in which step c) uses the compound of formula (CII)).

Scheme 3: reaction scheme for the preparation of the compound of formula (XLI) starting with the compound of formula (XIII) via steps c) to e).

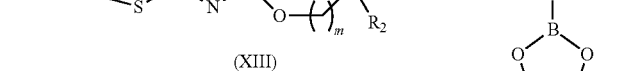

-continued

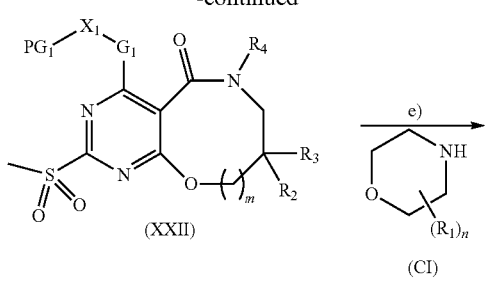

(XXII)

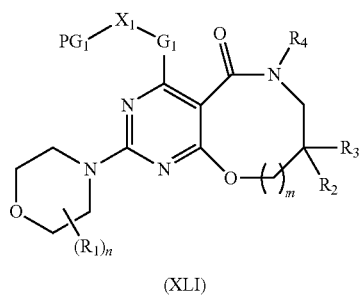

(XLI)

According to a second alternative, the process for preparing the compound of formula (XLI) may comprise the following steps:

f) nucleophilic attack of a compound of formula PG$_2$-OH, in which PG$_2$ is a protecting group for the hydroxyl function, for example a benzyl, on a compound of formula (XIII) below:

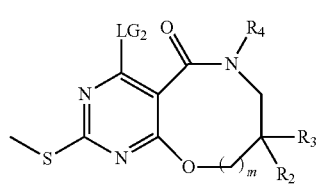

(XIII)

in which m, R$_2$, R$_3$ and R$_4$ are as defined above and LG$_2$ is a leaving group, for example a halogen atom such as chlorine, to obtain a compound of formula (XXXI) below:

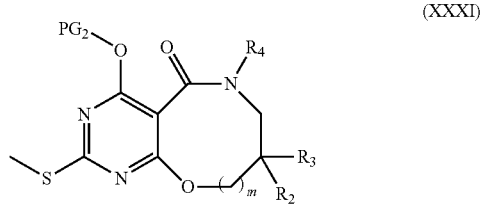

(XXXI)

in which PG$_2$, m, R$_2$, R$_3$ and R$_4$ are as defined above, g) oxidation of the compound of formula (XXXI) obtained in step f), to obtain a compound of formula (XXXII) below:

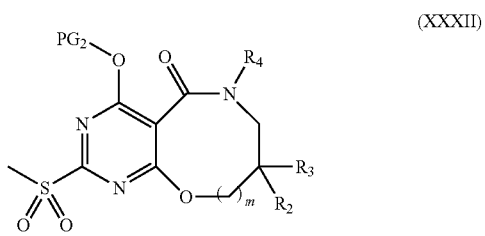

(XXXII)

in which m, R$_2$, R$_3$, R$_4$ and PG$_2$ are as defined above, h) nucleophilic attack of a compound of formula (CI) below:

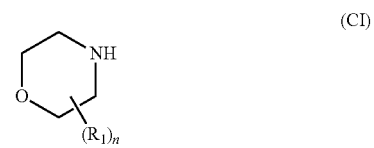

(CI)

in which n and R$_1$ are as defined above, on the compound of formula (XXXII) obtained in step g), to obtain the compound of formula (XXXIII) below:

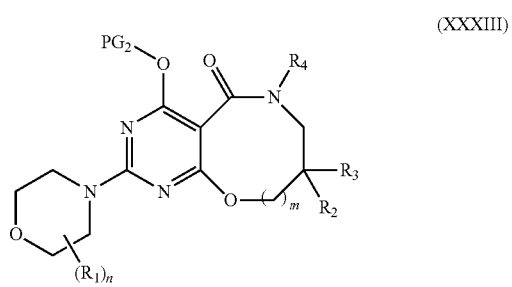

(XXXIII)

in which n, R$_1$, m, R$_2$, R$_3$, R$_4$ and PG$_2$ are as defined above, i) deprotection of the compound of formula (XXXIII) obtained in step h), to obtain a compound of formula (XXXIV) below:

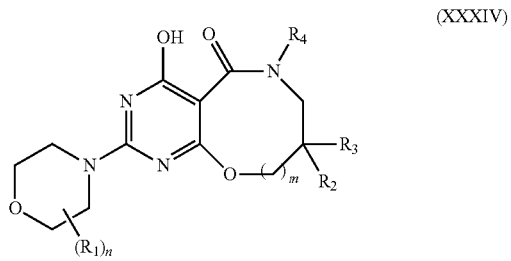

(XXXIV)

in which n, R$_1$, m, R$_2$, R$_3$ and R$_4$ are as defined above, j) grafting of a leaving group $LG_5$ onto the compound of formula (XXXIV) obtained in step i), to obtain the compound of formula (XXXV) below:

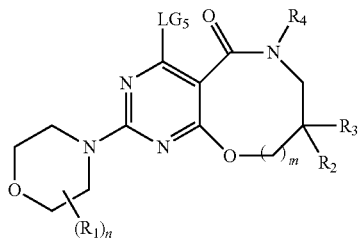
(XXXV)

in which n, $R_1$, m, $R_2$, $R_3$ and $R_4$ are as defined above and $LG_5$ is a leaving group, for example a halogen atom or a triflate, k) Suzuki reaction of the compound of formula (XXXV) obtained in step j) with a compound of formula $PG_1$-$X_1$-$G_1$-$R_{300}$, in which $X_1$ and $G_1$ are as defined above, $PG_1$ is H or a protecting group for $X_1$ and $R_{300}$ is a boronic acid or ester radical, typically with a compound of formula (CII) below:

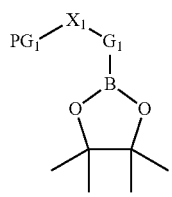
(CII)

in which $X_1$, $PG_1$ and $G_1$ are as defined above, to obtain the compound of formula (XLI).

When $PG_1$ represents H, the compound of formula (XLI) obtained at the end of step k) corresponds to the compound of formula (XLII), which may be engaged directly in step m), without the deprotection step l) being necessary.

The reaction scheme for the preparation of the compound of formula (XLI) via steps f) to k) is represented in scheme 4 below (in the embodiment in which step k) uses the compound of formula (CII)).

Scheme 4: reaction scheme for the preparation of the compound of formula (XLI) starting with the compound of formula (XIII) via steps f) to k).

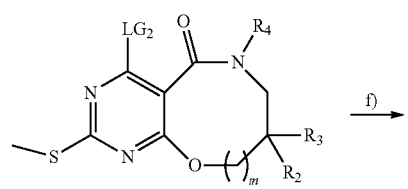

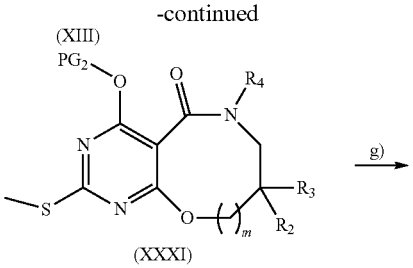
(XXXI)

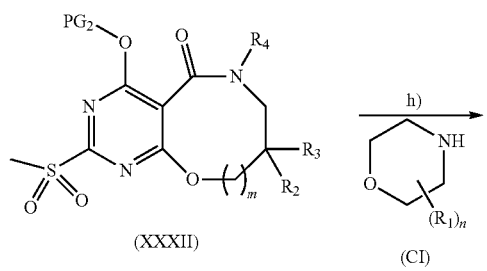
(XXXII)

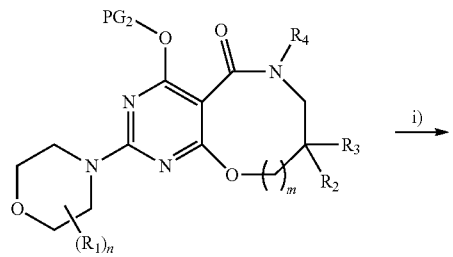
(XXXIII)

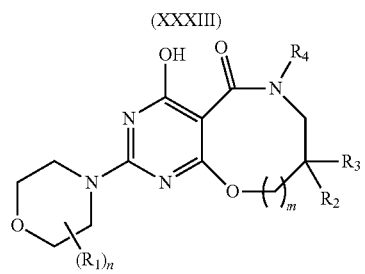
(XXXIV)

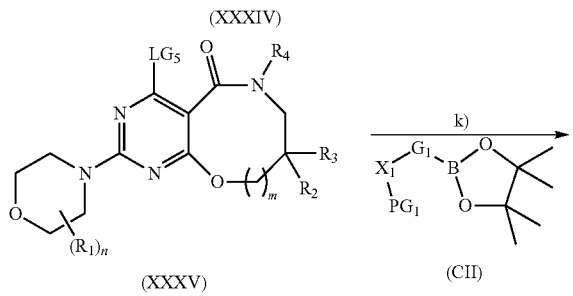
(XXXV)

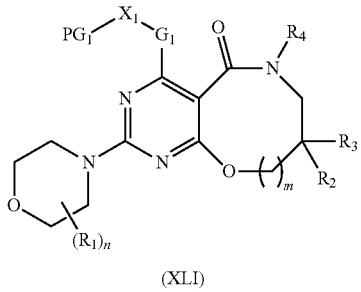
(XLI)

The process for the preparation of the abovementioned compound of formula (XIII), performed in steps c) or f) described above, typically comprises the following steps:

a) nucleophilic attack of a compound of formula (XI) below:

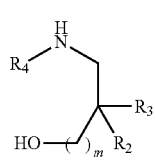

(XI)

in which m, $R_2$, $R_3$ and $R_4$ are as defined above,
on a compound of formula (X) below:

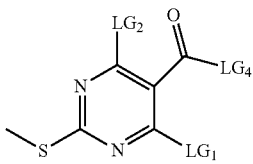

(X)

in which $LG_2$ is as defined above and $LG_1$ and $LG_4$ are independently leaving groups, for example halogen atoms such as chlorine atoms, to obtain a compound of formula (XII) below:

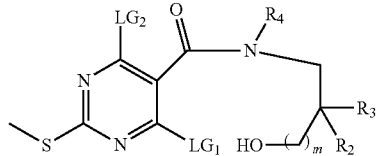

(XII)

in which m, $R_2$, $R_3$, $R_4$, $LG_1$ and $LG_2$ are as defined above, b) cyclization of the compound of formula (XII) obtained in step a), to obtain the compound of formula (XIII).

The reaction scheme for the preparation of the compound of formula (XIII) via steps a) and b) is represented in scheme 5 below.

Scheme 5: reaction scheme for the preparation of the compound of formula (XIII) starting with the compound of formula (X) via steps a) and b).

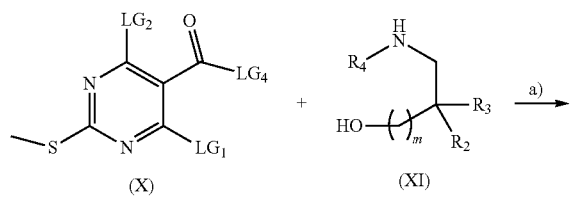

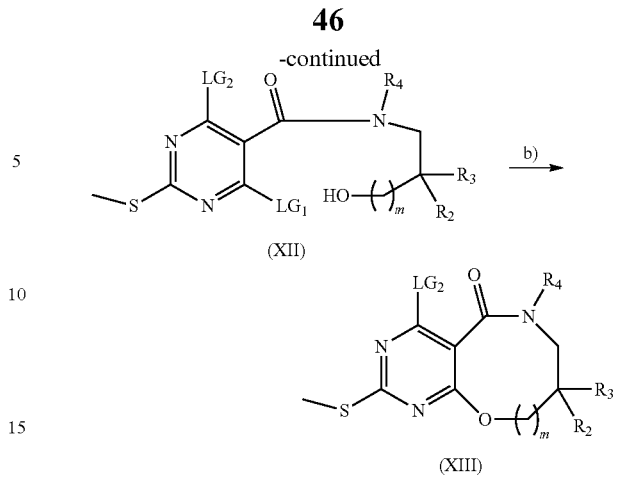

(XII)

(XIII)

In a second embodiment, when, in formula (I), $X_1$ represents —$NR_{40}$— and $X_2$ represents —$CONR_{50}$—, the process for preparing the compound of formula (I) may comprise the following step:

n) Suzuki reaction of the compound of formula (XXXV):

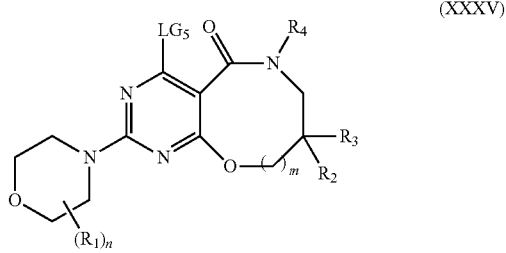

(XXXV)

in which n, $R_1$, m, $R_2$, $R_3$ and $R_4$ are as defined above and $LG_5$ is a leaving group, for example a halogen atom or a triflate, with a compound of formula $R_6R_{50}N$—(C=O)—$NR_{40}$-$G_1$-$R_{300}$, in which $G_1$, $R_6$, $R_{50}$ and $R_{40}$ are as defined above and $R_{300}$ is a boronic acid or ester radical, typically with a compound of formula (CIII) below:

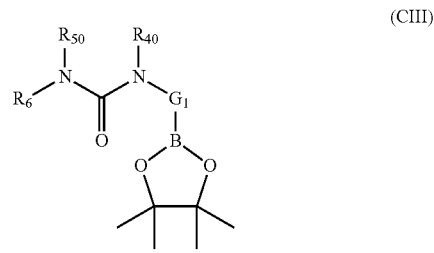

(CIII)

in which $G_1$, $R_6$, $R_{50}$ and $R_{40}$ are as defined above, to obtain the compound of formula (I) in which $X_1$ represents —$NR_{40}$— and $X_2$ represents —$CONR_{50}$—.

The process for the preparation of the compound of formula (XXXV) performed in step n) typically comprises the abovementioned steps f), g), h), i) and j).

The reaction scheme for the preparation of the compound of formula (I) via step n) is represented in scheme 6 below (in the embodiment in which step n) uses the compound of formula (CIII)).

Scheme 6: reaction scheme for preparing the compound of formula (I) from the compound of formula (XXXV) via a step n).

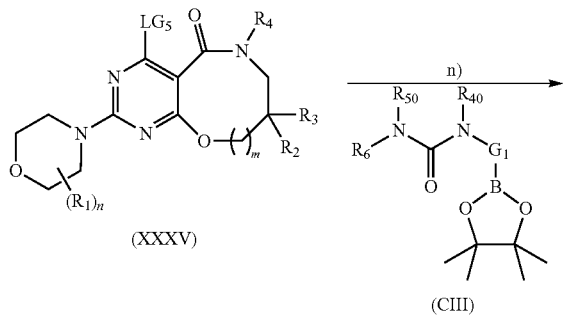

The reaction scheme for the preparation of the compound of formula (I) via step q) is represented in scheme 7 below:

Scheme 7: reaction scheme for preparing the compound of formula (I) from the compound of formula (LII) via step q).

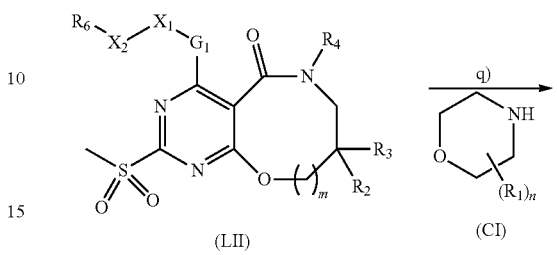

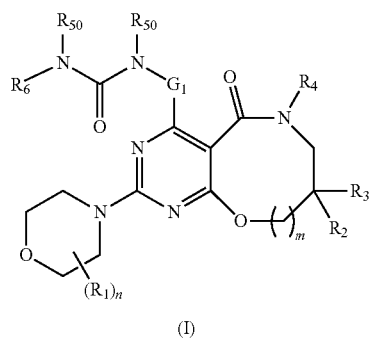

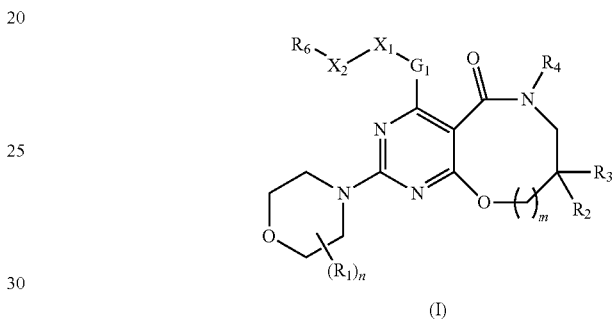

In a third embodiment, the process for preparing the compound of formula (I) may comprise step q) below:

q) nucleophilic attack of a compound of formula (CI) below:

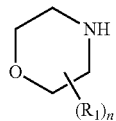

(CI)

in which n and $R_1$ are as defined above,
on a compound of formula (LII) below:

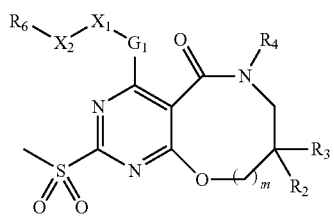

(LII)

in which m, $R_2$, $R_3$, $R_4$, $G_1$, $X_1$, $X_2$ and $R_6$ are as defined above, to obtain the compound of formula (I).

The process for the preparation of the compound of formula (LII) performed in the abovementioned step q) typically comprises the following steps:

o) Suzuki reaction of the compound of formula (XIII) below:

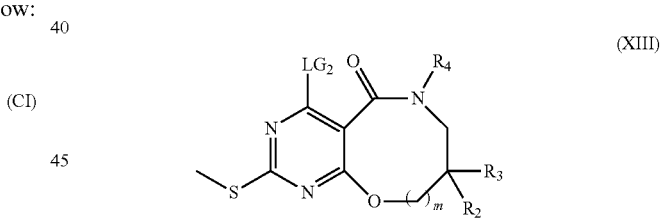

(XIII)

in which m, $R_2$, $R_3$, $R_4$ and $LG_2$ are as defined above, with a compound of formula $R_6$—$X_2$—$X_1$-$G_1$-$R_{300}$, in which $R_6$, $X_2$, $X_1$ and $G_1$ are as defined above and $R_{300}$ is a boronic acid or ester radical, typically with a compound of formula (CIV) below:

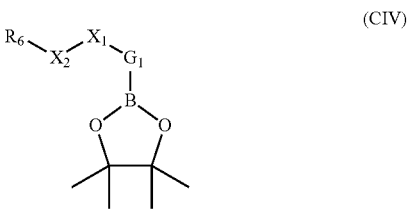

(CIV)

in which $R_6$, $X_2$, $X_1$ and $G_1$ are as defined above, to obtain the compound of formula (LI) below:

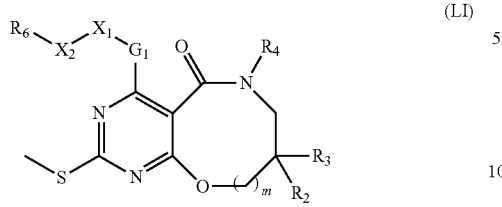

(LI)

in which $R_6$, $X_2$, $X_1$, $G_1$, m, $R_2$, $R_3$ and $R_4$ are as defined above, p) oxidation of the compound of formula (LI) obtained in step o), to obtain the compound of formula (LII).

The process for the preparation of the compound of formula (XIII) performed in step o) typically comprises the abovementioned steps a) and b).

The reaction scheme for the preparation of the compound of formula (LII) via steps o) and p) is represented in scheme 8 below (in the embodiment in which step o) uses the compound of formula (CIV)):

Scheme 8: reaction scheme for the preparation of the compound of formula (LII) starting with the compound of formula (XIII) via steps o) and p).

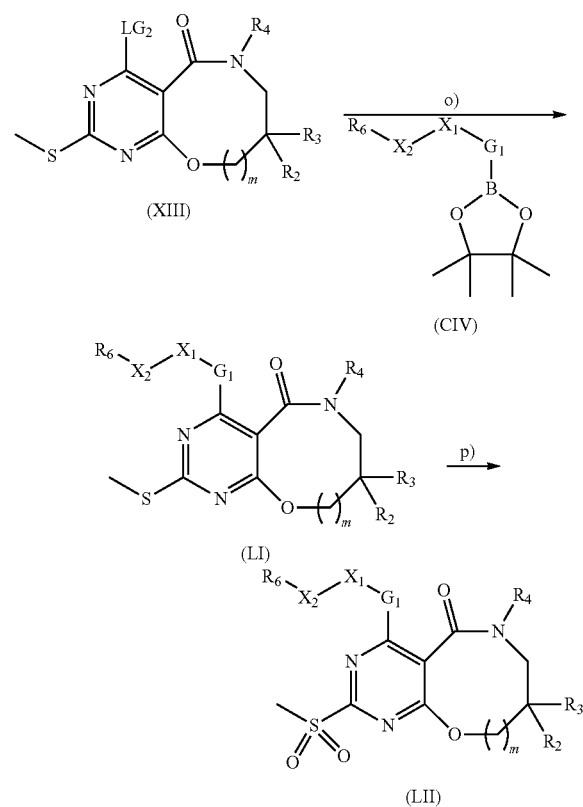

Embodiments for the abovementioned steps a) to q) are described below.

Step m) may be performed according to the procedures described in *Advanced Organic Chemistry*, J. March, 3$^{rd}$ Edition, Wiley Interscience, and the references cited therein.

For example, when $X_2$ represents a single bond and $R_6$ represents a group —$G_2$-$X_3$-$G_3$ in which:
- $G_2$ represents a divalent heteroaryl radical optionally substituted with one or more groups $R_{80}$, $X_3$ and $G_3$ being as defined above, or
- $G_2$ and $X_3$ represent single bonds and $G_3$ represents heteroaryl optionally substituted with one or more groups $R_{81}$, step m) may consist of a Buchwald-Hartwig reaction, as described in Topics in Current Chemistry Chemical Review 2002, 219, 131-209, by reaction of the compound of formula (XLII) with a compound of formula $LG_7$-$G_2$-$X_3$-$G_3$ in which:
- $G_2$ represents a divalent heteroaryl radical optionally substituted with one or more groups $R_{80}$, or
- $G_2$ and $X_3$ represent single bonds and $G_3$ represents heteroaryl optionally substituted with one or more groups $R_{81}$, and
- $LG_7$ represents a leaving group, for example a halogen atom, in the presence of a palladium catalyst, a base such as potassium carbonate, potassium fluoride, potassium tert-butoxide or potassium phosphate, and optionally a phosphine, in a solvent typically chosen from dimethylformamide, dioxane, ethylene glycol dimethyl ether, toluene, tert-butanol, tetrahydrofuran and water, or a mixture thereof, at a temperature generally ranging from room temperature to 150° C.

Four embodiments were developed for performing step m) when $X_2$ represents —$CONR_{50}$—, —$CONR_{51}$—O— or —COO—.

In a first embodiment, step m) comprises the following steps:
m1-1) reaction of the compound of formula (XLII) with phosgene or triphosgene in the presence of a base,
m1-2) reaction of a compound of formula $HNR_{50}R_6$, $HNR_{51}$—O—$R_6$ or HO—$R_6$ in which $R_6$, $R_{50}$ and $R_{51}$ are as defined above with the compound obtained in step m1-1), to obtain the compound of formula (I),
reactions m1-1) and m1-2) possibly being performed as a one-pot reaction.

In a second embodiment, step m) comprises the following steps:
m2-1) reaction of a compound of formula $HNR_{50}R_6$, $HNR_{51}$—O—$R_6$ or HO—$R_6$ in which $R_6$, $R_{50}$ and $R_{51}$ are as defined above with phosgene or triphosgene in the presence of a base,
m2-2) reaction of the compound of formula (XLII) with the compound obtained in step m2-1), to obtain the compound of formula (I),
reactions m2-1) and m2-2) possibly being performed as a one-pot reaction.

Steps m1-1), m1-2), m2-1) and m2-2) are typically performed in dichloromethane, dioxane or a mixture of the two. Steps m1-1) and m2-2) are generally performed in the presence of an amine base such as triethylamine or diisopropylethylamine.

In a third embodiment, step m) comprises the following steps:
m3-1) reaction of the compound of formula (XLII) with an alkyl or aryl chloroformate in the presence of a base,
m3-2) reaction of a compound of formula $HNR_{50}R_6$, $HNR_{51}$—O—$R_6$ or HO—$R_6$ in which $R_6$, $R_{50}$ and $R_{51}$ are as defined above with the compound obtained in step m3-1), to obtain the compound of formula (I),
reactions m3-1) and m3-2) possibly being performed as a one-pot reaction.

In a fourth embodiment, step m) comprises the following steps:

m4-1) reaction of a compound of formula $HNR_{50}R_6$, $HNR_{51}$—O—$R_6$ or HO—$R_6$ in which $R_6$, $R_{50}$ and $R_{51}$ are as defined above with an alkyl or aryl chloroformate in the presence of a base, m4-2) reaction of the compound of formula (XLII) with the compound obtained in step m4-1), to obtain the compound of formula (I), reactions m4-1) and m4-2) possibly being performed as a one-pot reaction.

Steps m3-1), m3-2), m4-1) and m4-2) are typically performed in a polar aprotic solvent such as dimethylformamide, tetrahydrofuran or a mixture of the two. Steps m3-1) and m4-1) are typically performed with phenyl chloroformate, generally at room temperature. Steps m3-2) and m4-2) are typically performed between 80 and 120° C. and may be performed by microwave.

Step a) is typically performed in the presence of a base, especially an amine base such as triethylamine, generally in a polar aprotic solvent such as tetrahydrofuran, at a temperature especially of −78° C.

Step b) is typically performed in the presence of a base, especially an amine base such as 1,8-diazabicyclo[5.4.0]undec-7-ene, generally in a polar aprotic solvent such as dimethyl sulfoxide, at a temperature especially between room temperature (25° C.) and 60° C.

Steps c), n) and o), which correspond to Suzuki coupling reactions, are typically performed in the presence of a mineral base such as sodium or potassium carbonate, potassium fluoride, potassium tert-butoxide or tripotassium phosphate and of a palladium complex such as tetrakis(triphenylphosphine)palladium or bis(triphenylphosphine)palladium (II) chloride, generally in a solvent chosen from dimethylformamide, dioxane, ethylene glycol dimethyl ether, toluene, tetrahydrofuran and water or a mixture thereof, typically in a dioxane/water mixture, typically at a temperature from room temperature to 150° C. The conditions described in Chemical Review 2007, 107, 133-173 may especially be followed. These steps may be performed by microwave.

Steps d), g) and p) are typically performed in the presence of an oxidizing agent such as magnesium monoperoxyphthalate hexahydrate, generally in an acetonitrile/alcohol mixture such as ethanol, typically a 3/1 to 3/2 mixture, generally at a temperature from room temperature to 70° C.

Steps e), h) and q) are generally performed in the presence of a base, especially an amine base such as triethylamine, typically in a polar aprotic solvent such as dimethyl sulfoxide or dioxane, at a temperature of between 70 and 110° C. These steps may be performed by microwave.

The conditions of step l) vary as a function of the nature of the protecting group $PG_1$. $PG_1$ is especially a Boc group. When $PG_1$ is a Boc group, step l) is typically performed in a solvent generally chosen from dichloromethane, diethyl ether, tetrahydrofuran and dioxane, or a mixture thereof, typically dichloromethane, in the presence of an acid such as trifluoroacetic acid or hydrochloric acid, generally at room temperature.

The conditions of step f) vary according to the nature of the protecting group $PG_2$. $PG_2$ is especially a benzyl group. When $PG_2$ is a benzyl group, step f) is typically performed by placing the compound of formula (XIII) in contact with benzoxide (generally obtained by reacting benzyl alcohol and a base such as sodium hydride), typically in an anhydrous polar aprotic solvent, such as anhydrous tetrahydrofuran, generally at a temperature of between −10 and 10° C.

The conditions of step i) vary according to the nature of the protecting group $PG_2$. $PG_2$ is especially a benzyl group. When $PG_2$ is a benzyl group, step i) may be performed:

by hydrogenolysis, for example in the presence of hydrogen and palladium-on-charcoal, or by reaction with ammonium formate in the presence of a palladium catalyst, especially in methanol at a temperature between room temperature and the reflux point.

The conditions of step j) vary according to the nature of the protecting group $LG_5$. $LG_5$ is especially a triflate group. When $LG_5$ is a triflate group, step i) may be performed by reacting the compound of formula (XXXIV) with triflic anhydride, typically in the presence of a base, especially an amine base such as triethylamine, for example dichloromethane, at a temperature generally between −10 and 10° C.

In the abovementioned reaction schemes, the starting compounds and the reagents, when their preparation method is not described, are commercially available or described in the literature, or alternatively may be prepared according to methods that are described therein or that are known to those skilled in the art.

The examples that follow describe the preparation of certain compounds in accordance with the invention. These examples are not limiting and serve merely to illustrate the present invention. The numbers of the compounds exemplified refer to those given in Table 3 below, which illustrates the chemical structures and physical properties of a number of compounds according to the invention.

A person skilled in the art can adapt without difficulty the teaching below to the compounds of general formula (I). He will be capable of selecting, in the light of his knowledge and of the literature, the appropriate protecting groups enabling the introduction of all the groups or functions described in the present invention.

In the procedures and examples below:

the proton magnetic resonance spectra CH NMR), as described below, are recorded at a temperature of 300 K (exchangeable protons not recorded) at 300, 400 or 600 MHz in DMSO-$d_6$, using the DMSO-$d_6$ peak as reference. The chemical shifts δ are expressed in parts per million (ppm). The signals observed are expressed as follows: s=singlet, d=doublet, m=multiplet, bs=broad signal, t=triplet, q=quartet.

The LC/MS characteristics as described below indicate successively the high-performance liquid chromatography analytical method used and detailed below, the peak M+H$^+$ identified by mass spectrometry and the retention time (Tr) of the compound expressed in minutes.

Method A

Instrument: Acquity UPLC chain (Waters); LCT mass spectrometer (Waters)

Column: BEH C18 50×2.1 mm 1.7 μm, T°=40° C.

Solvent A: $H_2O$+0.05% TFA; Solvent B: acetonitrile+ 0.035% TFA

Flow rate: 1.0 ml/min

Gradient A/B: t 0 min 2% B, t 1.6 min 100% B, t 2.1 min 100% B, t 2.5 min 2% B, t 3.0 min 2% B Detection: UV 220 nm Ionization: electrospray positive mode Method B Instrument: Alliance HPLC chain (Waters); ZQ mass spectrometer (Waters)

Column: Kromasil C18 50×2.1 mm, 3.5 μm, T°=40° C.

Solvent A: Ammonium acetate 5 mM+3% acetonitrile; Solvent B: acetonitrile

Flow rate: 0.8 ml/min

Gradient A/B: t 0 min 0% B, t 5.5 min 100% B, t 7.0 min 100% B, t 7.1 min 0% B, t 10.0 min 0% B
Detection: UV 220 nm
Ionization: electrospray positive mode
Method C
Instrument: Acquity UPLC type HPLC chain (Waters); SQD mass spectrometer (Waters)
Column: Ascentis Express C18 50×2.1 mm 2.7 μm, T°=55° C.
Solvent A: $H_2O$+0.02% TFA; Solvent B: acetonitrile+ 0.014% TFA
Flow rate: 1 ml/min
Gradient A/B: t 0 min 2% B, t 1.2 min 98% B, t 1.5 min 2% B
Detection: UV 220 nm
Ionization: electrospray positive mode
Method D
Instrument: Acquity UPLC type HPLC chain (Waters); SQD mass spectrometer (Waters)
Column: BEH C18 100×2.1 mm 1.7 μm, T°=70° C.
Solvent A: $H_2O$+0.02% TFA; Solvent B: acetonitrile+ 0.014% TFA
Flow rate: 0.8 ml/min
Gradient A/B: t 0 min 2% B, t 5.0 min 98% B, t 5.3 min 98% B, t 5.33 min 2% B
Detection: UV 220 nm
Ionization: electrospray positive mode
Method E
Instrument: Alliance HPLC chain (Waters); ZQ mass spectrometer (Waters)
Column: Xbridge C18 30×2.1 mm 2.5 μm, T°=55° C.
Solvent A: $H_2O$+0.02% TFA; Solvent B: MeOH
Flow rate: 0.7 ml/min
Gradient A/B: t 0 min 2% B, t 3.0 min 100% B, t 3.5 min 100% B, t 3.6 min 2% B
Detection: UV 220 nm
Ionization: electrospray positive mode
Method F
Instrument: Alliance HPLC chain (Waters); ZQ mass spectrometer (Waters)
Column: Waters Select CSH C18 30×7.5 mm, 3.5 μm, T°=60° C.
Solvent A: $H_2O$+0.1% formic acid; Solvent B: acetonitrile+ 0.1% formic acid
Flow rate: 1.1 ml/min
Gradient A/B: t 0 min 6% B, t 0.8 min 6% B, t 4.7 min 100% B, t 4.8 min 100% B, t 5.0 min 6% B, t 6.0 min 6% B
Detection: UV 220 nm
Ionization: electrospray positive mode The solvent mixtures are quantified in volumetric ratios.
The NMR spectra and mass spectra confirm the structures of the compounds obtained according to the examples below.
In the examples that follow, the following abbreviations and empirical formulae are used:
DBU: 1,8-diazabicyclo[5.4.0]undec-7-ene
DCM: dichloromethane
DIEA: N,N-diisopropylethylamine
DMF: N,N-dimethylformamide
DMSO: dimethyl sulfoxide
$Et_2O$: diethyl ether
EtOH: ethanol
HPLC: high performance liquid chromatography
$K_2CO_3$: potassium carbonate
LC/MS: liquid chromatography/mass spectrometry
MeOH: methanol
$MgSO_4$: magnesium sulfate
MHz: MegaHertz
Min: minute(s)
Mmol: milimoles
$Na_2CO_3$: sodium carbonate
NaCl: sodium chloride
$NaHCO_3$: sodium hydrogen carbonate
$Na_2SO_4$: sodium sulfate
Psi: pounds per square inch, with 1 psi=0.069 bar
TFA: trifluoroacetic acid
THF: tetrahydrofuran
° C.: degrees Celsius
Tr: retention time

EXAMPLE 1

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-methylurea

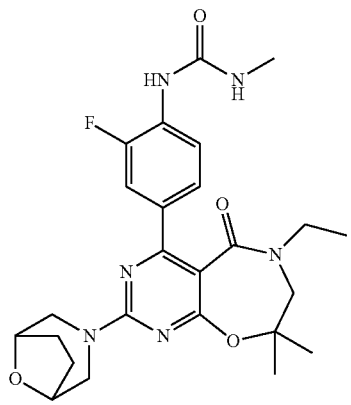 [SMILES: CCN1CC(C)(C)Oc2nc(N3CC4CCC(C3)O4)nc(-c3ccc(NC(=O)NC)c(F)c3)c2C1=O]

Step 1.1: (Preparation of a Compound of Formula (X))

4,6-Dichloro-2-methylsulfanylpyrimidine-5-carbonyl chloride

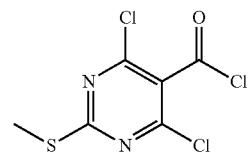

10 g of 4,6-dichloro-2-methylsulfanylpyrimidine-5-carboxylic acid (41.83 mmol) are placed in 61 ml of thionyl chloride (836.54 mmol) with stirring. After 18 hours at 80° C., the thionyl chloride is evaporated off and the residue is taken up twice with 15 ml of toluene and concentrated to give 10.77 g of 4,6-dichloro-2-methylsulfanylpyrimidine-5-carbonyl chloride.

Step 1.2: (Which Corresponds to Step a))

4,6-Dichloro-2-methylsulfanylpyrimidine-5-carboxylic acid ethyl-(2-hydroxy-2-methylpropyl)amide

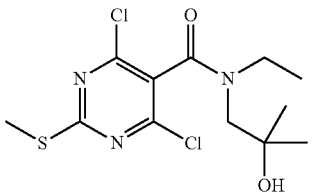 [SMILES: CCN(CC(C)(C)O)C(=O)c1c(Cl)nc(SC)nc1Cl]

4.9 g of 1-(ethylamino)-2-methylpropan-2-ol (41.82 mmol) and 17.5 ml of triethylamine (125.46 mmol) are placed in 30 ml of anhydrous THF with stirring. After cooling the reaction medium with a bath of cardice in acetone to −70° C., 10.77 g and (41.82 mmol) of the compound described in step 1.1 diluted in 80 ml of THF are added dropwise. After stirring for 4 hours at −70° C., the reaction medium is poured into ice-water and then extracted twice with DCM. The organic phase is washed with brine, dried over $Na_2SO_4$, filtered and evaporated to dryness. 13.54 g of 4,6-dichloro-2-methylsulfanylpyrimidine-5-carboxylic acid ethyl-(2-hydroxy-2-methylpropyl)amide are obtained.

LC/MS (method F): $M+H^+$=338; Tr=3.70 and 3.80 min (conformers)

Step 1.3: (which Corresponds to Step b))

4-Chloro-6-ethyl-8,8-dimethyl-2-methylsulfanyl-7,8-dihydro-6H-9-oxa-1,3,6-triazabenzocyclohepten-5-one

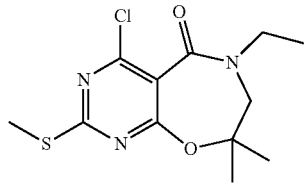 [SMILES: CCN1CC(C)(C)Oc2nc(SC)nc(Cl)c2C1=O]

13 g (38.43 mmol) of the compound described in step 1.2 are placed in 200 ml of DMSO, with stirring. 6.3 ml of DBU (42.28 mmol) are added. The reaction medium is stirred for 5 hours at 55° C., and 500 ml of ice-water are then added. A white precipitate forms, which is filtered off and rinsed twice with water. The solid is then taken up in acetonitrile and filtered off to give 3.6 g of 4-chloro-6-ethyl-8,8-dimethyl-2-methylsulfanyl-7,8-dihydro-6H-9-oxa-1,3,6-triazabenzocyclohepten-5-one.

The mother liquors are recovered and extracted with 3 times 300 ml of DCM. The organic phases are combined, washed with brine, dried over $Na_2SO_4$ and then filtered. The solution is evaporated to dryness. The residue is then chromatographed on silica gel with a gradient of ethyl acetate in DCM ranging from 0% to 10%. 3 g of 4-chloro-6-ethyl-8,8-dimethyl-2-methylsulfanyl-7,8-dihydro-6H-9-oxa-1,3,6-triazabenzocyclohepten-5-one are obtained.

LC/MS (method F): $M+H^+$=302; Tr=3.68 min

Step 1.4: (Which Corresponds to Step c))

[4-(6-Ethyl-8,8-dimethyl-2-methylsulfanyl-5-oxo-5,6,7,8-tetrahydro-9-oxa-1,3,6-triazabenzocyclohepten-4-yl)-2-fluorophenyl]carbamic acid tert-butyl ester

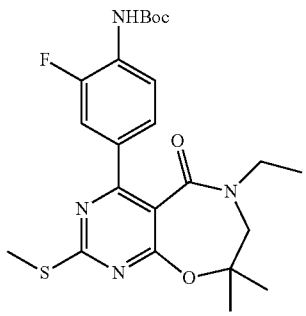 [SMILES: CCN1CC(C)(C)Oc2nc(SC)nc(-c3ccc(NC(=O)OC(C)(C)C)c(F)c3)c2C1=O]

8 g (26.51 mmol) of the compound described in step 1.3 are placed in 150 ml of dioxane. 7.67 g (29.16 mmol) of 4-N-Boc-amino-3-fluorophenylboronic acid, 66.27 ml (132.5 mmol) of aqueous 1N $Na_2CO_3$ solution and 1.53 g (1.33 mmol) of tetrakis(triphenylphosphine)palladium are successively added, with stirring. The mixture is stirred at 85° C. for 2 hours and is then poured into water. The precipitate obtained is then filtered off and rinsed with water. The solid obtained is taken up in MeOH, filtered off and rinsed with pentane. 11.2 g of [4-(6-ethyl-8,8-dimethyl-2-methylsulfanyl-5-oxo-5,6,7,8-tetrahydro-9-oxa-1,3,6-triazabenzocyclohepten-4-yl)-2-fluorophenyl]carbamic acid tert-butyl ester are obtained.

LC/MS (method F): $M+H^+$=477; Tr=4.55 min

Step 1.5: (which Corresponds to Step d))

[4-(6-Ethyl-2-methanesulfonyl-8,8-dimethyl-5-oxo-5,6,7,8-tetrahydro-9-oxa-1,3,6-triazabenzocyclohepten-4-yl)-2-fluorophenyl]carbamic acid tert-butyl ester

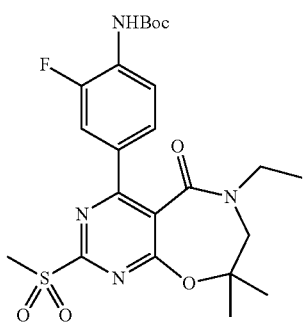 [SMILES: CCN1CC(C)(C)Oc2nc(S(C)(=O)=O)nc(-c3ccc(NC(=O)OC(C)(C)C)c(F)c3)c2C1=O]

21 g (44.06 mmol) of the compound described in step 1.4 and 34.1 g of magnesium monoperoxyphthalate hexahydrate (88.13 mmol) are placed in 300 ml of a 2/1 acetonitrile/EtOH mixture. After stirring for 18 hours at room temperature, the solvents are evaporated off. The residue is taken up in 500 ml of water. The product obtained is filtered off and rinsed twice with EtOH to give 22 g of [4-(6-ethyl-2-methanesulfonyl-8,8-dimethyl-5-oxo-5,6,7,8-tetrahydro-9-oxa-1,3,6-triazabenzocyclohepten-4-yl)-2-fluorophenyl]carbamic acid tert-butyl ester.

LC/MS (method F): M+H$^+$=509; Tr=4.08 min

Step 1.6: (Which Corresponds to Step e))

{4-[6-Ethyl-8,8-dimethyl-2-(8-oxa-3-azabicyclo [3.2.1]oct-3-yl)-5-oxo-5,6,7,8-tetrahydro-9-oxa-1,3,6-triazabenzocyclohepten-4-yl]-2-fluorophenyl}carbamic acid tert-butyl ester

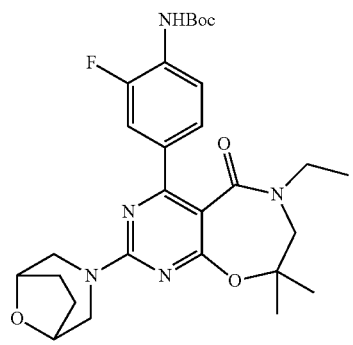 [SMILES: CCN1CC(C)(C)Oc2nc(N3CC4CCC(C3)O4)nc(-c3ccc(NC(=O)OC(C)(C)C)c(F)c3)c2C1=O]

5 g (9.83 mmol) of the compound described in step 1.5 are placed in 100 ml of DMSO. 5.67 ml of triethylamine (39.33 mmol) and 2.94 g of 8-oxa-3-azabicyclo[3.2.1]octane hydrochloride (19.66 mmol) are successively added. After stirring for 1 hour 30 minutes at 90° C., the DMSO is evaporated off. The residue is taken up in 200 ml of water and the solid formed is filtered off, rinsed with water, with acetonitrile and then with pentane to give 5 g of {4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid tert-butyl ester.

LC/MS (method F): M+H$^+$=542; Tr=4.49 min

Step 1.7: (Which Corresponds to Step l))

4-(4-Amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one

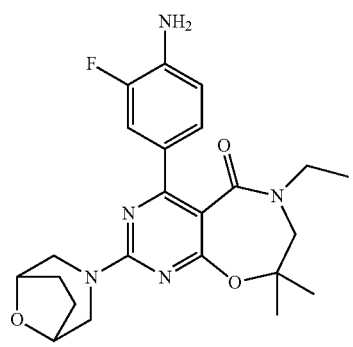 [SMILES: CCN1CC(C)(C)Oc2nc(N3CC4CCC(C3)O4)nc(-c3ccc(N)c(F)c3)c2C1=O]

5 g (9.23 mmol) of the compound described in step 1.6 are placed in 90 ml of DCM. 21.3 ml of TFA are added dropwise and the reaction medium is stirred at room temperature for 3 hours. Saturated aqueous NaHCO$_3$ solution is added to pH=10, and the reaction medium is extracted twice with DCM. The organic phase is dried over Na$_2$SO$_4$, filtered and evaporated. The solid is taken up in acetonitrile and filtered off to give 3.25 g of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one.

LC/MS (method F): M+H$^+$=442; Tr=3.71 min

Step 1.8: (Which Corresponds to Step m) (Steps m1-1) and m1-2))

1-{4-[6-Ethyl-8,8-dimethyl-2-(8-oxa-3-azabicyclo [3.2.1]oct-3-yl)-5-oxo-5,6,7,8-tetrahydro-9-oxa-1,3,6-triazabenzocyclohepten-4-yl]-2-fluorophenyl}-3-methylurea

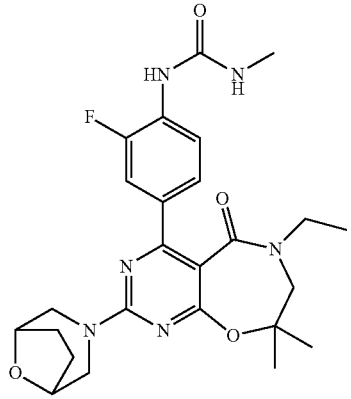 [SMILES: CCN1CC(C)(C)Oc2nc(N3CC4CCC(C3)O4)nc(-c3ccc(NC(=O)NC)c(F)c3)c2C1=O]

400 mg (0.91 mmol) of the compound described in step 1.7 and 0.24 ml of DIEA (1.36 mmol) are placed in 10 ml of dioxane. 0.715 ml of 1.9 N phosgene in toluene (1.6 mmol) is then added. After stirring for 30 minutes at 50° C., 3.17 ml of 2 N methylamine in THF (6.34 mmol) are added. After stirring for 1 hour at room temperature, the reaction mixture is filtered. The solid is rinsed with water, with ethyl acetate and then with pentane. 343 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-methylurea are obtained.

LC/MS (method A): M+H$^+$=499; Tr=0.90 min $^1$H NMR (400 MHz, DMSO-d$_6$) δ ppm 8.48 (m, 1H); 8.14 (dd, 1H); 7.35 (dd; 1H); 7.24 (dd, 1H); 6.53 (q, 1H); 4.41 (m, 2H); 4.22 (m, 2H); 3.66 (s, 2H); 3.51 (m, 2H); 3.10 (d, 2H); 2.67 (d, 3H); 1.81 (m, 2H); 1.64 (m, 2H); 1.34 (s, 6H); 1.14 (t, 3H)

EXAMPLE 2

Synthesis of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-methylurea

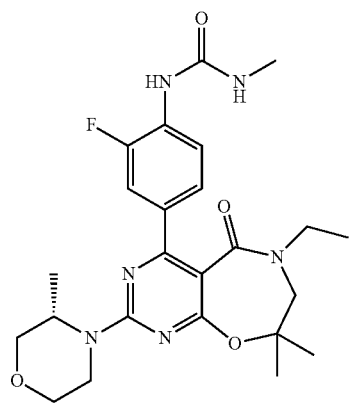 [SMILES: CCN1CC(C)(C)Oc2nc(N3CCOC[C@@H]3C)nc(-c3ccc(NC(=O)NC)c(F)c3)c2C1=O]

Step 2.1: (Which Corresponds to Step e))

{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}carbamic acid tert-butyl ester

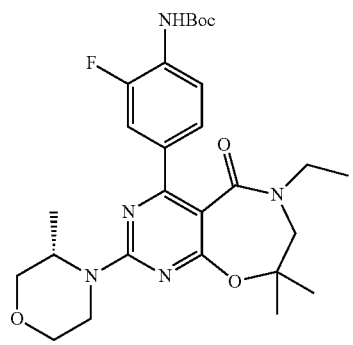 [SMILES: CCN1CC(C)(C)Oc2nc(N3CCOC[C@@H]3C)nc(-c3ccc(NC(=O)OC(C)(C)C)c(F)c3)c2C1=O]

2.5 g of [4-(6-ethyl-2-methanesulfonyl-8,8-dimethyl-5-oxo-5,6,7,8-tetrahydro-9-oxa-1,3,6-triazabenzocyclohepten-4-yl)-2-fluorophenyl]carbamic acid tert-butyl ester (19.66 mmol) in 20 ml of dioxane are placed in 4 microwave tubes, respectively. One quarter of (S)-3-methylmorpholine (98.32 mmol) is added to each tube, respectively. The tubes are heated for 2 hours at 100° C. in a Biotage microwave machine. The reaction media are filtered and rinsed with MeOH. The solid is washed with water, with acetonitrile and then with pentane. 3.7 g of {4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}carbamic acid tert-butyl ester are obtained. The DMSO/MeOH phase is evaporated to dryness. The residue is taken up in water and filtered, rinsed with acetonitrile and then with pentane. This product is chromatographed on silica gel with a gradient of MeOH in DCM ranging from 0 to 5%. 1.7 g of {4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}carbamic acid tert-butyl ester are obtained.

LC/MS (method F): M+H$^+$=530; Tr=4.52 min

Step 2.2: (Which Corresponds to Step l))

4-(4-Amino-3-fluorophenyl)-6-ethyl-8,8-dimethyl-2-((S)-3-methylmorpholin-4-yl)-7,8-dihydro-6H-9-oxa-1,3,6-triazabenzocyclohepten-5-one

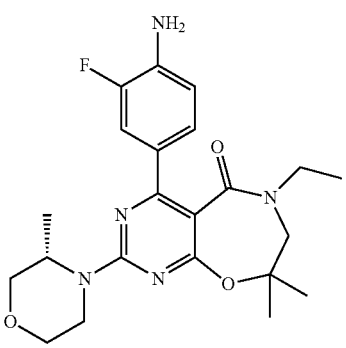 [SMILES: CCN1CC(C)(C)Oc2nc(N3CCOC[C@@H]3C)nc(-c3ccc(N)c(F)c3)c2C1=O]

5.4 g (10.2 mmol) of the compound described in step 2.1 are placed in 100 ml of DCM. 23.57 ml of TFA (305.89 mmol) are added dropwise. After stirring for 2 hours at room temperature, the medium is concentrated, taken up in water and basified with saturated NaHCO$_3$ solution. The aqueous phase is extracted with DCM and the organic phase is washed with brine, dried over Na$_2$SO$_4$ and then concentrated. 4.2 g of 4-(4-amino-3-fluorophenyl)-6-ethyl-8,8-dimethyl-2-((S)-3-methylmorpholin-4-yl)-7,8-dihydro-6H-9-oxa-1,3,6-triazabenzocyclohepten-5-one are obtained.

LC/MS (method F): M+H$^+$=430; Tr=3.75 min

Step 2.3: (Which Corresponds to Step m) (Steps m1-1) and m1-2))

1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-methylurea

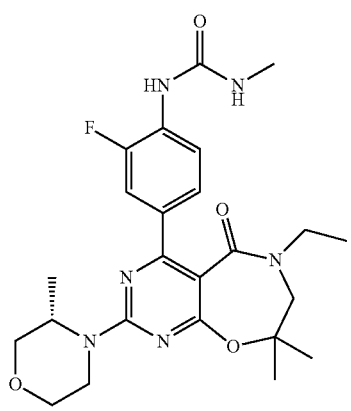 [SMILES: CCN1CC(C)(C)Oc2nc(N3CCOC[C@@H]3C)nc(-c3ccc(NC(=O)NC)c(F)c3)c2C1=O]

400 mg (0.93 μmol) of the compound described in step 2.2 and 0.23 ml of DIEA (1.30 mmol) are placed in 20 ml of dioxane. 0.686 ml of 1.9 N phosgene in toluene (1.3 mmol) is added. After stirring for 30 minutes at 50° C., 2.33 ml of 2 N methylamine in THF (4.66 mmol) are added. After stirring for 1 hour at room temperature, the reaction mixture is washed with water, dried over Na$_2$SO$_4$, filtered and concentrated. The residue is chromatographed on silica gel with a gradient of a 95/5 ethyl acetate/MeOH mixture in DCM ranging from 0% to 100%. 268 mg of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-methylurea are obtained.

LC/MS (method A): M+H$^+$=487; Tr=0.91 min $^1$H NMR (400 MHz, DMSO-d$_6$) δ ppm 8.48 (m, 1H); 8.14 (dd, 1H); 7.34 (dd, 1H); 7.25 (dd, 1H); 6.54 (q, 1H); 4.65 (m, 1H); 4.34 (m, 1H); 3.91 (m, 1H); 3.72-3.67 (m, 3H); 3.59-3.51 (m, 3H); 3.45-3.36 (m, 1H); 3.22-3.15 (m, 1H); 2.67 (d, 3H); 1.35 (s, 6H); 1.21 (d, 3H); 1.15 (t, 3H)

EXAMPLE 3

Synthesis of 1-ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea

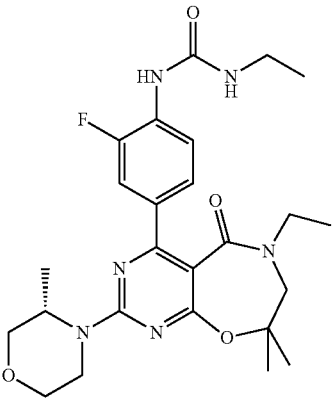 [SMILES: CCNC(=O)Nc1ccc(-c2nc(N3CCOC[C@@H]3C)nc3c2C(=O)N(CC)CC(C)(C)O3)cc1F]

Step 3.1: (Which Corresponds to Step f))

4-Benzyloxy-6-ethyl-8,8-dimethyl-2-methylsulfanyl-7,8-dihydro-6H-9-oxa-1,3,6-triazabenzocyclohepten-5-one

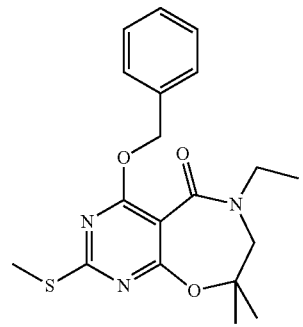 [SMILES: CCN1CC(C)(C)Oc2nc(SC)nc(OCc3ccccc3)c2C1=O]

6.20 ml of benzyl alcohol (59.64 mmol) are placed in 400 ml of anhydrous THF. The solution is cooled to 4° C. in an ice bath and 2.39 g of 60% sodium hydride (59.64 mmol) are added portionwise. The reaction mixture is stirred at 4° C. for 15 minutes. 15 g of 4-chloro-6-ethyl-8,8-dimethyl-2-methylsulfanyl-7,8-dihydro-6H-9-oxa-1,3,6-triazabenzo cyclohepten-5-one (49.70 mmol) dissolved in 400 ml of anhydrous THF are added dropwise. After stirring for 2 hours at 4° C., 400 ml of water are added and the THF is evaporated off. The aqueous phase is extracted twice with 300 ml of DCM, and the organic phases are combined and washed with 400 ml of water and then 400 ml of brine. The organic phase is dried over Na$_2$SO$_4$, filtered and concentrated. The residue is chromatographed on silica gel with a gradient of ethyl acetate in heptane ranging from 30% to 50%. 18.6 g of 4-benzyloxy-6-ethyl-8,8-dimethyl-2-methylsulfanyl-7,8-dihydro-6H-9-oxa-1,3,6-triazabenzocyclohepten-5-one are obtained.

LC/MS (method F): M+H$^+$=374; Tr=4.21 min

Step 3.2: (Which Corresponds to Step g))

4-Benzyloxy-6-ethyl-2-methanesulfonyl-8,8-dimethyl-7,8-dihydro-6H-9-oxa-1,3,6-triazabenzocyclohepten-5-one

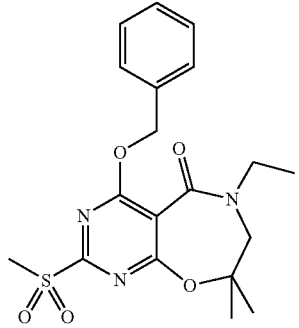 [SMILES: CCN1CC(C)(C)Oc2nc(S(C)(=O)=O)nc(OCc3ccccc3)c2C1=O]

18.6 g (49.80 mmol) of the compound described in step 3.1 and 49.27 g of magnesium monoperoxyphthalate hexahydrate (99.61 mmol) are placed in 375 ml of a 2/1 acetonitrile/EtOH mixture. After stirring for 2 hours at room temperature, the solvents are evaporated off. The residue is taken up in 400 ml of water. The mixture is filtered and rinsed twice with water. The solid obtained is taken up in DCM, dried over Na$_2$SO$_4$, filtered and evaporated to give 15.9 g of 4-benzyloxy-6-ethyl-2-methanesulfonyl-8,8-dimethyl-7,8-dihydro-6H-9-oxa-1,3,6-triazabenzocyclohepten-5-one.

LC/MS (method F): M+H$^+$=406; Tr=3.70 min

Step 3.3: (Which Corresponds to Step h))

4-Benzyloxy-6-ethyl-8,8-dimethyl-2-((S)-3-methylmorpholin-4-yl)-7,8-dihydro-6H-9-oxa-1,3,6-triazabenzocyclohepten-5-one

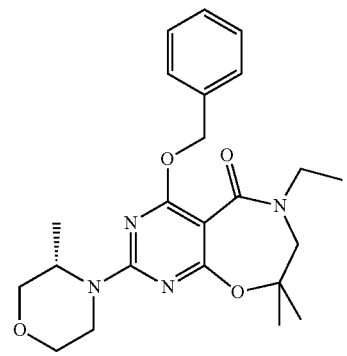 [SMILES: CCN1CC(C)(C)Oc2nc(N3CCOC[C@@H]3C)nc(OCc3ccccc3)c2C1=O]

11.23 g (27.7 mmol) of the compound described in step 3.2 are placed in 120 ml of DMSO. 5.79 ml of triethylamine (41.54 mmol) and 8.4 g of (S)-3-methylmorpholine (83.09 mmol) are successively added. The medium is dried with anhydrous MgSO₄ with stirring for 30 minutes. The mixture is filtered and divided among six 20 ml microwave tubes. The tubes are heated for 30 minutes at 100° C. in a Biotage microwave machine.

The reaction media are poured into water and extracted three times with ethyl acetate. The organic phase is washed three times with water, dried over Na₂SO₄, filtered and concentrated. The residue is chromatographed on silica gel with a gradient of ethyl acetate in DCM to give 6.91 g of 4-benzyloxy-6-ethyl-8,8-dimethyl-2-((S)-3-methyl morpholin-4-yl)-7,8-dihydro-6H-9-oxa-1,3,6-triazabenzocyclohepten-5-one.

LC/MS (method F): M+H⁺=427; Tr=4.16 min

Step 3.4: (Which Corresponds to Step i))

6-Ethyl-4-hydroxy-8,8-dimethyl-2-((S)-3-methyl-morpholin-4-yl)-7,8-dihydro-6H-9-oxa-1,3,6-triaza-benzocyclohepten-5-one

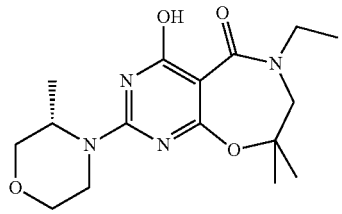 [SMILES: CCN1CC(C)(C)Oc2nc(N3CCOC[C@@H]3C)nc(O)c2C1=O]

6.9 g (16.18 mmol) of the compound described in step 3.3 and 160 ml of EtOH are placed in a Parr bottle. 0.17 g of 50% hydrated 10% palladium-on-charcoal (1.62 mmol) is added and the reaction medium is stirred at 40 psi of hydrogen for 1 hour at 25° C. The reaction medium is filtered and concentrated to give 4.81 g of 6-ethyl-4-hydroxy-8,8-dimethyl-2-((S)-3-methylmorpholin-4-yl)-7,8-dihydro-6H-9-oxa-1,3,6-triazabenzocyclohepten-5-one.

LC/MS (method F): M+H⁺=337; Tr=3.40 min

Step 3.5: (Which Corresponds to Step j))

Trifluoromethanesulfonic acid 6-ethyl-8,8-dimethyl-2-((S)-3-methylmorpholin-4-yl)-5-oxo-5,6,7,8-tetrahydro-9-oxa-1,3,6-triazabenzocyclohepten-4-yl ester

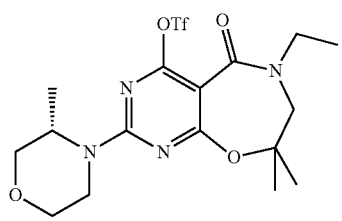 [SMILES: CCN1CC(C)(C)Oc2nc(N3CCOC[C@@H]3C)nc(OS(=O)(=O)C(F)(F)F)c2C1=O]

4.6 g (13.67 mmol) of the compound described in step 3.4 are placed in 140 ml of DCM. 2.86 ml of triethylamine (20.51 mmol) are added. The solution is cooled to 4° C. in an ice bath and 3.47 ml of trifluoromethanesulfonic anhydride (20.51 mmol) are then added. After stirring the mixture at 4° C. for 3 hours, 300 ml of water are added. The organic phase is extracted and washed with saturated aqueous NaHCO₃ solution, dried over Na₂SO₄, filtered and concentrated. The residue is chromatographed on silica gel with a gradient of from 20% to 50% of ethyl acetate in heptane to give 5.27 g of trifluoromethanesulfonic acid 6-ethyl-8,8-dimethyl-2-((S)-3-methylmorpholin-4-yl)-5-oxo-5,6,7,8-tetrahydro-9-oxa-1,3,6-triazabenzocyclohepten-4-yl ester.

LC/MS (method F): M+H⁺=469; Tr=4.35 min

Step 3.6: (Preparation of a Compound of Formula (CIII))

1-Ethyl-3-[2-fluoro-4-(4,4,5,5-tetramethyl-[1,3,2]dioxaborolan-2-yl)phenyl]urea

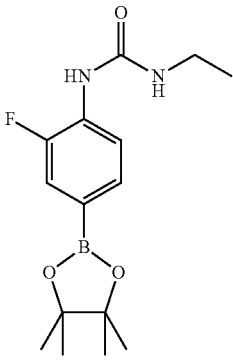 [SMILES: CCNC(=O)Nc1ccc(B2OC(C)(C)C(C)(C)O2)cc1F]

5 g of 4-amino-3-fluorophenylboronic acid pinacol ester (21.08 mmol) are placed in 100 ml of DCM. 3.23 ml of triethylamine (23.20 mmol) are added. The reaction mixture is cooled in an ice bath to 4° C. After stirring for 5 minutes, 2.21 g of triphosgene (7.38 mmol) are added portionwise, and the ice bath is then removed. After stirring for 1 hour 30 minutes at room temperature, 8.77 g of ethylamine hydrochloride (105.45 mmol) and then 14.57 g of K₂CO₃ (105.45 mmol) are added portionwise. After 2 hours, the medium is cooled in an ice bath and then acidified with 1 N hydrochloric acid solution. The aqueous phase is extracted 3 times with DCM. The organic phases are combined, washed with brine, dried over MgSO₄, filtered and concentrated. The residue is chromatographed on silica gel with a gradient of from 0% to 5% MeOH in DCM to give 4.65 g of 1-ethyl-3-[2-fluoro-4-(4,4,5,5-tetramethyl-[1,3,2]dioxaborolan-2-yl)phenyl]urea.

LC/MS (method F): M+H⁺=309; Tr=4.11 min

Step 3.7: (Which Corresponds to Step n))

1-Ethyl-3-{4-[6-ethyl-8,8-dimethyl-2-((S)-3-methyl-morpholin-4-yl)-5-oxo-5,6,7,8-tetrahydro-9-oxa-1,3,6-triazabenzocyclohepten-4-yl]-2-fluorophenyl}urea

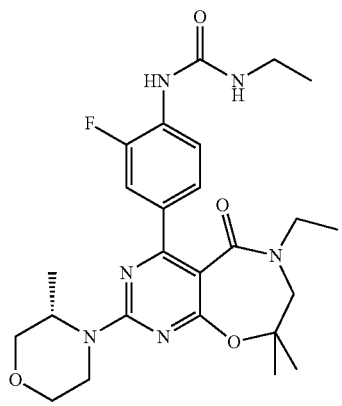 [SMILES: CCNC(=O)Nc1ccc(-c2nc(N3CCOC[C@@H]3C)nc3c2C(=O)N(CC)CC(C)(C)O3)cc1F]

420 mg (0.89 mmol) of the compound described in step 3.5 are placed in 10 ml of dioxane in a 20 ml microwave tube. 276 mg (0.89 mmol) of the compound described in step 3.6, 380 mg of tribasic potassium phosphate (1.79 mmol) and 0.5 ml of water are successively added. The solution is degassed with argon, and 63 mg of bis(triphenylphosphine)palladium (II) chloride (0.09 mmol) are then added. The tube is heated at 100° C. for 20 minutes in a Biotage microwave machine. The reaction medium is diluted in DCM, and washed twice with water and once with brine. The organic phase is dried over $Na_2SO_4$, filtered and concentrated. The residue is chromatographed on silica gel with a gradient of a 5/1 ethyl acetate/MeOH mixture in DCM ranging from 0% to 30%. The product is taken up in $Et_2O$ and then filtered off to give 222 mg of 1-ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea.

LC/MS (method A): $M+H^+$=501; Tr=1.02 min $^1$H NMR (400 MHz, DMSO-$d_6$) δ ppm 8.42 (m, 1H); 8.15 (dd, 1H); 7.34 (dd, 1H); 7.24 (dd, 1H); 6.66 (q, 1H); 4.65 (m, 1H); 4.32 (m, 1H); 3.91 (m, 1H); 3.72-3.67 (m, 3H); 3.59-3.37 (m, 4H); 3.21-3.09 (m, 3H); 1.35 (s, 6H); 1.21 (d, 3H); 1.15 (t, 3H); 1.07 (t, 3H)

EXAMPLE 4

Synthesis of 1-{4-[8,8-dimethyl-2-(8-oxa-3-azabicyclo[3.2.1]oct-3-yl)-5-oxo-6-(S)-1-pyrrolidin-2-ylmethyl-5,6,7,8-tetrahydro-9-oxa-1,3,6-triazabenzocyclohepten-4-yl]-2-fluorophenyl}-3-ethylurea

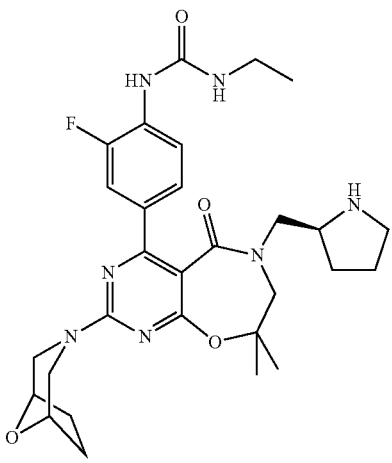 [SMILES: CCNC(=O)Nc1ccc(-c2nc(N3CC4CCC(C3)O4)nc3c2C(=O)N(C[C@@H]2CCCN2)CC(C)(C)O3)cc1F]

Step 4.1: (Preparation of a Compound of Formula (XI))

(S)-2-[(2-Hydroxy-2-methylpropylamino)methyl]pyrrolidine-1-carboxylic acid tert-butyl ester

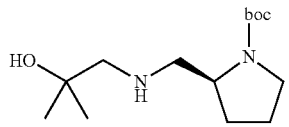

4.34 g of 1-amino-2-methylpropan-2-ol (48.68 mmol) are placed in 50 ml of MeOH. 2.79 ml of acetic acid (48.68 mmol) and then 4.72 ml of N-Boc-L-prolinal (24.34 mmol), diluted beforehand in 20 ml of MeOH, are successively added dropwise. The reaction mixture is stirred at room temperature for 30 minutes and 3.22 g of sodium cyanoborohydride (48.68 mmol) are then added portionwise. After stirring at room temperature for 18 hours, the medium is poured into 400 ml of saturated aqueous $NaHCO_3$ solution. The aqueous phase is extracted with 3 times 150 ml of DCM. The organic phases are combined, washed with 200 ml of water, with 200 ml of brine, dried over $MgSO_4$, filtered and evaporated. 7.19 g of (S)-2-[(2-hydroxy-2-methyl propylamino)methyl]pyrrolidine-1-carboxylic acid tert-butyl ester are obtained.

LC/MS (method F): $M+H^+$=273; Tr=2.55 min

Step 4.2: (Which Corresponds to Step a))

(S)-2-{[(4,6-Dichloro-2-methylsulfanylpyrimidine-5-carbonyl)-(2-hydroxy-2-methylpropyl)amino]methyl}pyrrolidine-1-carboxylic acid tert-butyl ester

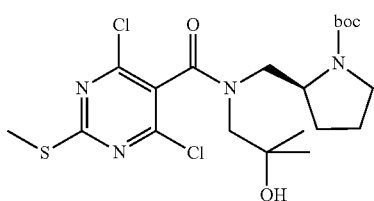

6.63 g (24.34 mmol) of the compound described in step 4.1 are placed in 17 ml of anhydrous THF. The reaction mixture is cooled in a bath of cardice in acetone at −70° C., followed by successive dropwise addition of 10.18 ml of triethylamine (73.02 mmol) and 6.46 g of 4,6-dichloro-2-methylsulfanylpyrimidine-5-carbonyl chloride (25.08 mmol) predissolved in 50 ml of THF. After stirring for 3 hours at −70° C., the reaction mixture is poured into ice-water and then extracted 4 times with 150 ml of DCM. The organic phases are combined and washed with 200 ml of water and then with 200 ml of brine. The organic phase is dried over $Na_2SO_4$, filtered and evaporated. The residue is chromatographed on silica gel with a gradient of from 6% to 60% ethyl acetate in heptane to give 10.56 g of (S)-2-{[(4,6-dichloro-2-methylsulfanylpyrimidine-5-carbonyl)-(2-hydroxy-2-methylpropyl)amino]methyl}pyrrolidine-1-carboxylic acid tert-butyl ester.

LC/MS (method F): $M+H^+$=493; Tr=4.57 min

Step 4.3: (Which Corresponds to Step b))

(S)-2-(4-Chloro-8,8-dimethyl-2-methylsulfanyl-5-oxo-7,8-dihydro-5H-9-oxa-1,3,6-triazabenzocyclohepten-6-ylmethyl)pyrrolidine-1-carboxylic acid tert-butyl ester

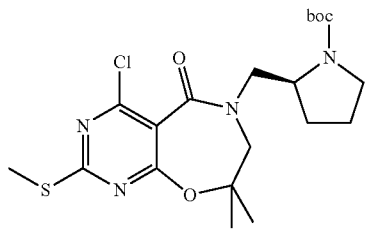

10.56 g (21.40 mmol) of the compound described in step 4.2 are placed in 107 ml of DMSO. 3.55 ml of DBU (23.54 mmol) are added dropwise and the reaction mixture is stirred at 55° C. for 5 hours. The medium is then poured into water and extracted with DCM. The organic phase is washed with brine, dried over MgSO$_4$, filtered and evaporated. The residue is chromatographed on silica gel with a gradient of from 5% to 50% ethyl acetate in heptane to give 3.55 g of (S)-2-(4-chloro-8,8-dimethyl-2-methylsulfanyl-5-oxo-7,8-dihydro-5H-9-oxa-1,3,6-triazabenzocyclohepten-6-ylmethyl)pyrrolidine-1-carboxylic acid tert-butyl ester.

LC/MS (method F): M+H$^+$=457; Tr=4.47 min

Step 4.4: (Which Corresponds to Step o))

(S)-2-{4-[4-(3-Ethylureido)-3-fluorophenyl]-8,8-dimethyl-2-methylsulfanyl-5-oxo-7,8-dihydro-5H-9-oxa-1,3,6-triazabenzocyclohepten-6-ylmethyl}pyrrolidine-1-carboxylic acid tert-butyl ester

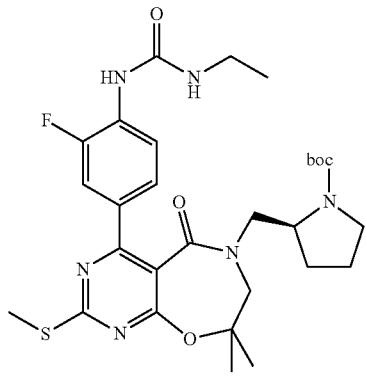

1 g (2.19 mmol) of the compound described in step 4.3 is placed in 10 ml of dioxane in a 20 ml microwave tube. 809 mg (2.63 mmol) of 1-ethyl-3[2-fluoro-4-(4,4,5,5-tetramethyl-[1,3,2]dioxaborolan-2-yl)phenyl]urea and 6.02 ml of 2 N Na$_2$CO$_3$ solution (12.04 mmol) are successively added. The solution is degassed with argon, followed by addition of 126 mg of tetrakis(triphenylphosphine)palladium (109.41 µmol). The tube is heated at 110° C. for 30 minutes in a Biotage microwave machine. The medium is poured into 300 ml of water and extracted twice with 300 ml of ethyl acetate. The organic phases are combined, washed with water and then with brine, dried over MgSO4, filtered and evaporated. The residue is chromatographed on silica gel with a gradient of ethyl acetate in heptane ranging from 7% to 70% to give 1.9 g of (S)-2-{4-[4-(3-ethylureido)-3-fluorophenyl]-8,8-dimethyl-2-methylsulfanyl-5-oxo-7,8-dihydro-5H-9-oxa-1,3,6-triazabenzocyclohepten-6-ylmethyl}pyrrolidine-1-carboxylic acid tert-butyl ester.

LC/MS (method F): M+H$^+$=603; Tr=4.42 min

Step 4.5: (Which Corresponds to Step p))

(S)-2-{4-[4-(3-Ethylureido)-3-fluorophenyl]-2-methanesulfonyl-8,8-dimethyl-5-oxo-7,8-dihydro-5H-9-oxa-1,3,6-triazabenzocyclohepten-6-ylmethyl}pyrrolidine-1-carboxylic acid tert-butyl ester

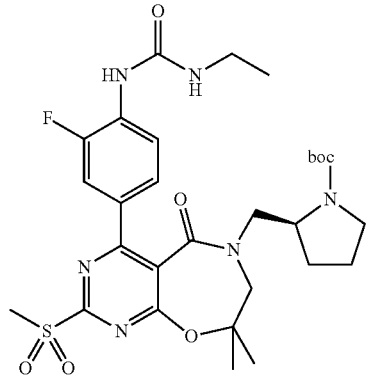

1.9 g (3.15 mmol) of the compound described in step 4.4 and 3.9 g of magnesium monoperoxyphthalate hexahydrate (6.3 mmol) are placed in 25 ml of a 3/2 acetonitrile/EtOH mixture. After stirring for 3 hours at room temperature, the medium is poured into water and extracted 3 times with DCM. The organic phases are combined, washed with water and then with brine, dried over MgSO4, filtered and evaporated. 2.5 g of (S)-2-{4-[4-(3-ethylureido)-3-fluorophenyl]-2-methanesulfonyl-8,8-dimethyl-5-oxo-7,8-dihydro-5H-9-oxa-1,3,6-triazabenzocyclohepten-6-ylmethyl}pyrrolidine-1-carboxylic acid tert-butyl ester are obtained.

LC/MS (method F): M+H$^+$=635; Tr=4.08 min

Step 4.6: (Which Corresponds to Step q))

(S)-2-[4-[4-(3-Ethylureido)-3-fluorophenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-ylmethyl]pyrrolidine-1-carboxylic acid tert-butyl ester

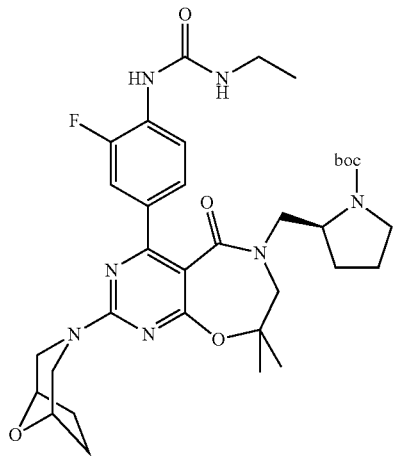

Half of 1.93 g (3.04 mmol) of the compound described in step 4.5 is placed in half of 26 ml of DMSO in two 20 ml microwave tubes, respectively. Half of each amount of reagents of the 1 g of 8-oxa-3-azadicyclo[3.2.1]octane hydrochloride (6.35 mmol) and 1.78 ml of triethylamine (12.68 mmol) are successively and respectively added. The tubes are heated for 30 minutes at 80° C. in a Biotage microwave machine. The media are poured into water and extracted 3 times with DCM. The organic phases are combined, washed with brine, dried over MgSO₄, filtered and evaporated. The residue is chromatographed on silica gel with a gradient of MeOH in DCM ranging from 1% to 10% to give 1.46 g of (S)-2-[4-[4-(3-ethylureido)-3-fluorophenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-ylmethyl]pyrrolidine-1-carboxylic acid tert-butyl ester.

LC/MS (method F): M+H⁺=668; Tr=4.37 min

Step 4.7: (Deprotection)

1-{4-[8,8-Dimethyl-2-(8-oxa-3-azabicyclo[3.2.1]oct-3-yl)-5-oxo-6-(S)-1-pyrrolidin-2-ylmethyl-5,6,7,8-tetrahydro-9-oxa-1,3,6-triazabenzocyclohepten-4-yl]-2-fluorophenyl}-3-ethylurea

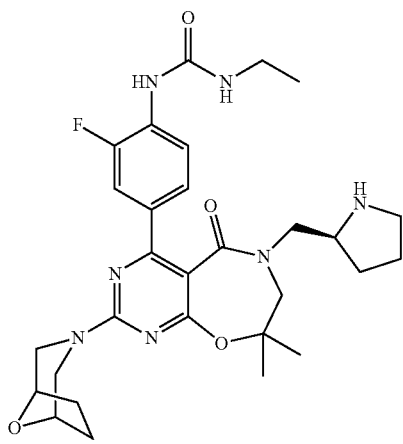 [SMILES: CCNC(=O)Nc1ccc(-c2nc(N3CC4CCC(C3)O4)nc3c2C(=O)N(C[C@@H]2CCCN2)CC(C)(C)O3)cc1F]

1.17 g (1.75 mmol) of the compound described in step 4.6 are placed in 20 ml of DCM. 4 ml of TFA (51.92 mmol) are added dropwise. After stirring for 30 minutes at room temperature, the reaction medium is concentrated to dryness. The residue is diluted in DCM and washed with saturated aqueous NaHCO₃ solution and then with brine. The organic phase is dried over MgSO₄, filtered and evaporated to give 1.15 g of 1-{4-[8,8-dimethyl-2-(8-oxa-3-azabicyclo[3.2.1]oct-3-yl)-5-oxo-6-(S)-1-pyrrolidin-2-ylmethyl-5,6,7,8-tetrahydro-9-oxa-1,3,6-triazabenzocyclohepten-4-yl]-2-fluorophenyl}-3-ethylurea.

LC/MS (method A): M+H⁺=568; Tr=0.76 min

¹H NMR (400 MHz, DMSO-d₆) δ ppm 8.43 (m, 1H); 8.14 (dd, 1H); 7.43 (dd, 1H); 7.35 (dd, 1H); 6.64 (t, 1H); 4.41 (m, 2H); 4.29 (d, 2H); 3.75 (d, 2H); 3.69-3.43 (m, 3H); 3.21-3.12 (m, 4H); 3.17-3.08 (m, 2H); 1.95-1.69 (m, 8H); 1.51 (m, 1H); 1.39 (d, 6H); 1.11 (t, 3H)

EXAMPLE 5

Synthesis of (S)-2-[4-[4-(3-ethylureido)-3-fluorophenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-ylmethyl]pyrrolidine-1-carboxylic acid ethyl ester

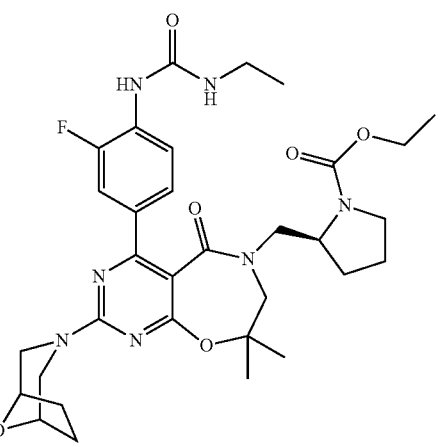

400 mg (704.65 μmol) of 1-{4-[8,8-dimethyl-2-(8-oxa-3-azabicyclo[3.2.1]oct-3-yl)-5-oxo-6-(S)-1-pyrrolidin-2-ylmethyl-5,6,7,8-tetrahydro-9-oxa-1,3,6-triazabenzocyclohepten-4-yl]-2-fluorophenyl}-3-ethylurea are placed in 5 ml of DCM. 0.15 ml of triethylamine (1.06 mmol) and 5 mg of 4-dimethylaminopyridine (40.93 μmol) are successively added. The reaction mixture is cooled in an ice bath to 4° C. and 89 μL of ethyl chloroformate (916.05 μmol) are added dropwise. The ice bath is removed and, after 4 hours, the reaction medium is poured into 100 ml of saturated aqueous NaHCO₃ solution. The organic phase is extracted, washed with water, with brine, dried over MgSO₄, filtered and evaporated. The residue is chromatographed on silica gel with a gradient of a 5/1 ethyl acetate/MeOH mixture in DCM ranging from 0% to 45%. The solid obtained is taken up in Et₂O and filtered off to give 310 mg of (S)-2-[4-[4-(3-ethylureido)-3-fluorophenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-ylmethyl]pyrrolidine-1-carboxylic acid ethyl ester.

LC/MS (method A): M+H⁺=640; Tr=1.08 min

¹H NMR (400 MHz, DMSO-d₆) δ ppm 8.43 (m, 1H); 8.15 (m, 1H); 7.39 (dd, 2H); 7.30 (dd, 1H); 6.63 (q, 1H); 4.40 (m, 2H); 4.08-3.99 (m, 4H); 3.77-3.59 (m, 3H); 3.41-3.31 (m, 3H); 3.17-3.08 (m, 4H); 1.90-1.81 (m, 6H); 1.65 (m, 2H); 1.35 (d, 6H); 1.19 (t, 3H); 1.06 (t, 3H)

EXAMPLE 6

Synthesis of 1-{4-[6-((S)-1-acetylpyrrolidin-2-ylmethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-ethylurea

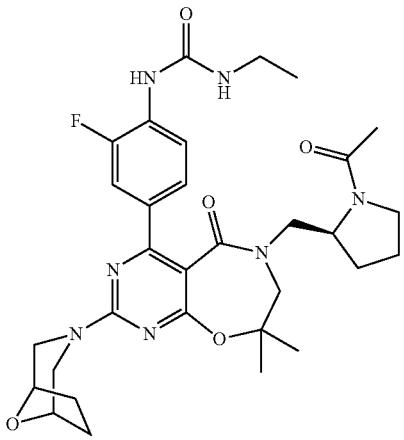 [SMILES: CCNC(=O)Nc1ccc(-c2nc(N3CC4CCC(C3)O4)nc3c2C(=O)N(C[C@@H]2CCCN2C(C)=O)CC(C)(C)O3)cc1F]

400 mg (704.65 µmol) of 1-{4-[8,8-dimethyl-2-(8-oxa-3-azabicyclo[3.2.1]oct-3-yl)-5-oxo-6-(S)-1-pyrrolidin-2-ylmethyl-5,6,7,8-tetrahydro-9-oxa-1,3,6-triazabenzocyclohepten-4-yl]-2-fluorophenyl}-3-ethylurea are placed in 5 ml of DCM. 0.19 ml of triethylamine (1.41 mmol) and 0.1 ml of acetic anhydride (1.06 mmol) are successively added dropwise. After stirring for 3 hours at room temperature, the reaction medium is poured into saturated aqueous NaHCO₃ solution and extracted twice with DCM. The organic phases are combined, washed with water and then with brine, dried over MgSO₄, filtered and evaporated. The residue is chromatographed on silica gel with a gradient of a 5/1 ethyl acetate/MeOH mixture in DCM ranging from 0% to 45%. The solid obtained is taken up in Et₂O and filtered off to give 277 mg of 1-{4-[6-((S)-1-acetylpyrrolidin-2-ylmethyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-ethyl urea.

LC/MS (method A): M+H⁺=610; Tr=0.91 min
¹H NMR (400 MHz, DMSO-d₆) δ ppm 8.10-8.04 (m, 2H); 7.41-7.30 (m, 2H); 6.46 (m, 1H); 4.38 (m, 2H); 4.29-4.22 (m, 2H); 3.38 (m, 3H); 3.43 (m, 3H); 3.14-3.10 (m, 5H); 1.97-1.81 (m, 9H); 1.68 (m, 2H); 1.36 (d, 6H); 1.08 (t, 3H)

EXAMPLE 7

Synthesis of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzo cyclohepten-6-yl]propionic acid

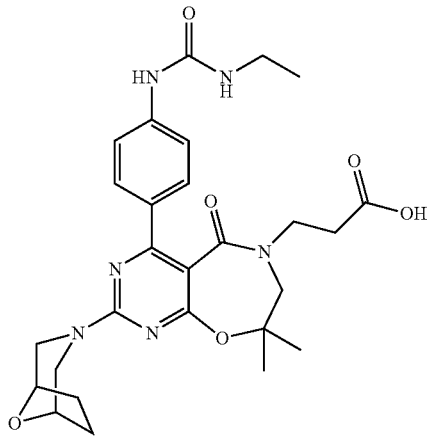 [SMILES: CCNC(=O)Nc1ccc(-c2nc(N3CC4CCC(C3)O4)nc3c2C(=O)N(CCC(=O)O)CC(C)(C)O3)cc1]

Step 7.1: (Preparation of a Compound of Formula (XI))

3-(2-Hydroxy-2-methylpropylamino)propionic acid tert-butyl ester

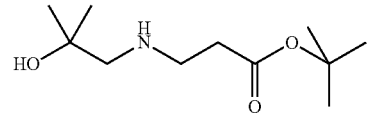

1 g of 1-aminomethylpropan-2-ol (11.22 mmol) is placed in 10 ml of DMF. 1.58 ml of triethylamine (11.22 mmol) and 1.87 ml of tert-butyl 3-bromopropionate (11.22 mmol) prediluted in 5 ml of DMF are successively added dropwise. After stirring for 18 hours at room temperature, the solvent is evaporated off. The residue is chromatographed on silica gel with a gradient of from 0% to 20% MeOH in DCM to give 2 g of 3-(2-hydroxy-2-methylpropylamino)propionic acid tert-butyl ester.

Step 7.2: (Which Corresponds to Step a))

3-[(4,6-Dichloro-2-methylsulfanylpyrimidine-5-carbonyl)-(2-hydroxy-2-methylpropyl)amino]propionic acid tert-butyl ester

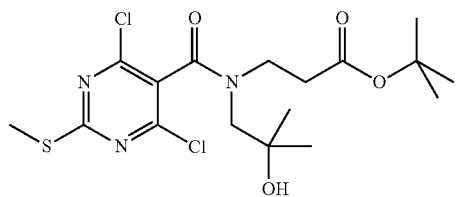 [SMILES: CSc1nc(Cl)c(C(=O)N(CCC(=O)OC(C)(C)C)CC(C)(C)O)c(Cl)n1]

1 g (4.58 mmol) of the compound described in step 7.1 is placed in 5 ml of anhydrous THF. 0.35 ml of triethylamine (4.58 mmol) is added and the mixture is cooled to −70° C. in a bath of cardice in acetone. 1.18 g of 4,6-dichloro-2-methylsulfanylpyrimidine-5-carbonyl chloride (4.58 mmol) prediluted in 10 ml of anhydrous THF are then added dropwise. After stirring for 2 hours at −70° C., 10 ml of water are added and the reaction medium is extracted with DCM. The organic phase is washed with brine, dried and concentrated to dryness. The residue is chromatographed on silica gel with a gradient of ethyl acetate in DCM ranging from 0% to 10% to give 1.3 g of 3-[(4,6-dichloro-2-methylsulfanylpyrimidine-5-carbonyl)-(2-hydroxy-2-methylpropyl) amino]propionic acid tert-butyl ester.

LC/MS (method F): M+H⁺=438; Tr=4.34 min

Step 7.3: (Which Corresponds to Step b))

3-(4-Chloro-8,8-dimethyl-2-methylsulfanyl-5-oxo-7,8-dihydro-5H-9-oxa-1,3,6-triazabenzocyclohepten-6-yl)propionic acid tert-butyl ester

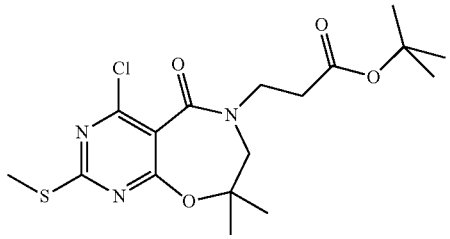 [SMILES: CSc1nc(Cl)c2c(n1)OC(C)(C)CN(CCC(=O)OC(C)(C)C)C2=O]

800 mg (1.82 mmol) of the compound described in step 7.2 are placed in 10 ml of DMSO. 0.3 ml of DBU (2.01 mmol) is added and the reaction mixture is stirred at 55° C. for 2 hours. The reaction medium is poured into water and extracted with ethyl acetate. The organic phase is washed with brine, dried over MgSO$_4$, filtered and evaporated. The residue is chromatographed on silica gel with a gradient of ethyl acetate in DCM ranging from 0% to 10% to give 460 mg of 3-(4-chloro-8,8-dimethyl-2-methylsulfanyl-5-oxo-7,8-dihydro-5H-9-oxa-1,3,6-triazabenzocyclohepten-6-yl)propionic acid tert-butyl ester.

LC/MS (method F): M+H$^+$=402 m; Tr=4.32 min

Step 7.4: (Which Corresponds to Step o))

3-{4-[4-(3-Ethylureido)phenyl]-8,8-dimethyl-2-methylsulfanyl-5-oxo-7,8-dihydro-5H-9-oxa-1,3,6-triazabenzocyclohepten-6-yl}propionic acid tert-butyl ester

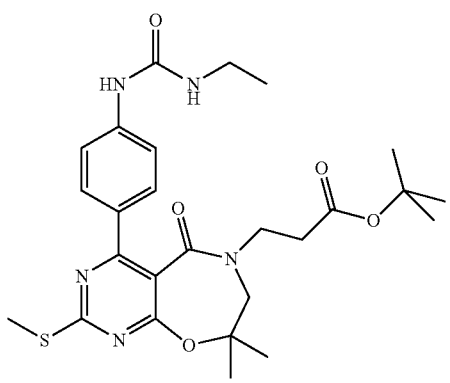 [SMILES: CCNC(=O)Nc1ccc(-c2nc(SC)nc3c2C(=O)N(CCC(=O)OC(C)(C)C)CC(C)(C)O3)cc1]

410 mg (1.02 mmol) of the compound described in step 7.3 are placed in 15 ml of dioxane in a 20 ml microwave tube. 350 mg (1.22 mmol) of 1-ethyl-3-[4-(4,4,5,5-tetramethyl-[1,3,2]dioxaborolan-2-yl)phenyl]urea and 2.8 ml of 2N Na$_2$CO$_3$ solution (5.61 mmol) are successively added. The solution is degassed with argon, followed by addition of 60 mg of tetrakis(triphenylphosphine)palladium (51 µmol). The tube is heated at 110° C. for 30 minutes in a Biotage microwave machine. The medium is poured into 75 ml of water and the solution is filtered. The solid is rinsed with acetonitrile and then with pentane to give 500 mg of 3-{4-[4-(3-ethylureido)phenyl]-8,8-dimethyl-2-methylsulfanyl-5-oxo-7,8-dihydro-5H-9-oxa-1,3,6-triazabenzocyclohepten-6-yl}propionic acid tert-butyl ester.

LC/MS (method F): M+H$^+$=603; Tr=4.42 min

Step 7.5: (Which Corresponds to Step p))

3-{4-[4-(3-Ethylureido)phenyl]-2-methanesulfonyl-8,8-dimethyl-5-oxo-7,8-dihydro-5H-9-oxa-1,3,6-triazabenzocyclohepten-6-yl}propionic acid tert-butyl ester

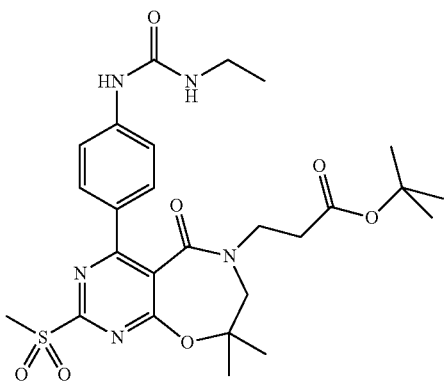 [SMILES: CCNC(=O)Nc1ccc(-c2nc(S(C)(=O)=O)nc3c2C(=O)N(CCC(=O)OC(C)(C)C)CC(C)(C)O3)cc1]

450 mg (0.85 mmol) of the compound described in step 7.4 and 1.05 g of magnesium monoperoxyphthalate hexahydrate (1.7 mmol) are placed in 6 ml of a 2/1 acetonitrile/EtOH mixture. After stirring for 18 hours at room temperature, the solvents are evaporated off. The residue is taken up in 20 ml of water. The product obtained is filtered off and rinsed with acetonitrile, with pentane and then with Et$_2$O to give 410 mg of 3-{4-[4-(3-ethylureido)phenyl]-2-methanesulfonyl-8,8-dimethyl-5-oxo-7,8-dihydro-5H-9-oxa-1,3,6-triazabenzocyclohepten-6-yl}propionic acid tert-butyl ester.

LC/MS (method F): M+H$^+$=562; Tr=3.81 min

Step 7.6: (Which Corresponds to Step q))

3-[4-[4-(3-Ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid tert-butyl ester

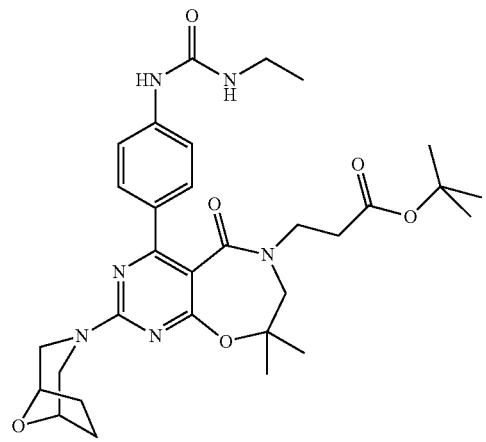 [SMILES: CCNC(=O)Nc1ccc(-c2nc(N3CC4CCC(C3)O4)nc3c2C(=O)N(CCC(=O)OC(C)(C)C)CC(C)(C)O3)cc1]

410 mg (0.73 mmol) of the compound described in step 7.5 are placed in 10 ml of DMSO in a 20 ml microwave tube. 345 mg of 8-oxa-3-azabicyclo[3.2.1]octane hydrochloride (2.19 mmol) and 0.6 ml of triethylamine (4.38 mmol) are successively added. The tube is heated at 80° C. for 45 minutes in a Biotage microwave machine. The medium is poured into water and extracted twice with DCM. The organic phases are combined, washed with brine, dried over MgSO$_4$, filtered and evaporated. The solid is rinsed with acetonitrile and with pentane to give 420 mg of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid tert-butyl ester.

LC/MS (method A): M+H$^+$=595; Tr=1.14 min

Step 7.7: (Deprotection))

3-[4-[4-(3-Ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid

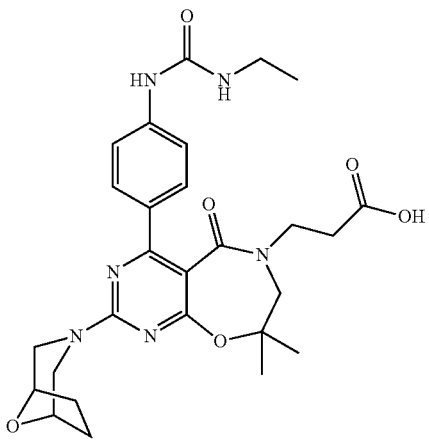 [SMILES: CCNC(=O)Nc1ccc(-c2nc(N3CC4CCC(C3)O4)nc3c2C(=O)N(CCC(=O)O)CC(C)(C)O3)cc1]

300 mg (0.5 mmol) of the compound described in step 7.6 are placed in 5 ml of DCM. 0.5 ml of a 4M solution of hydrogen chloride in dioxane (2 mmol) is added slowly to the medium. After stirring for 3 hours at room temperature, the solvent is evaporated off and the residue is chromatographed on silica gel with a gradient of MeOH containing 10% aqueous ammonia in DCM ranging from 0% to 10%. 130 mg of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid are obtained.

LC/MS (method A): M+H$^+$=539; Tr=0.86 min $^1$H NMR (400 MHz, DMSO-d$_6$) δ ppm 9.48 (m, 1H); 8.53 (m, 1H); 7.45-7.35 (m, 4H); 6.15 (t, 1H); 4.38 (m, 2H); 4.26 (m, 2H); 3.75-3.63 (m, 4H); 3.15-3.03 (m, 4H); 2.55 (t, 2H); 1.81 (m, 2H); 1.66 (m, 2H); 1.35 (s, 6H); 1.06 (t, 3H)

EXAMPLE 8

Synthesis of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]-N,N-dimethylpropionamide 70 mg (0.13 mmol) of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid are placed in 3 ml of DCM. 0.66 ml of DIEA (0.39 mmol), 12 mg of dimethylamine hydrochloride (0.14 mmol), 21 mg of hydroxybenzotriazole (0.14 mmol) and 27 mg of 1-ethyl-3-(dimethylaminopropyl)carbodiimide hydrochloride (0.14 mmol) are successively added, with stirring. After stirring for 3 days at room temperature, the DCM is evaporated off. The residue is taken up in water and extracted with ethyl acetate. The organic phase is washed with saturated aqueous NaHCO$_3$ solution and then with brine, dried over MgSO$_4$, filtered and evaporated. The solid obtained is taken up in acetonitrile, filtered off and rinsed with pentane to give 34 mg of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]-N,N-dimethylpropionamide.

LC/MS (method A): M+H$^+$=566; Tr=0.86 min $^1$H NMR (400 MHz, DMSO-d$_6$) δ ppm 8.64 (m, 1H); 7.38 (m, 4H); 6.15 (t, 1H); 4.40 (m, 2H); 4.23 (m, 2H); 3.72 (s, 2H); 3.66 (m, 2H); 3.15-3.05 (m, 4H); 3.01 (s, 3H); 2.88 (s, 3H); 2.68 (m, 2H); 1.81 (m, 2H); 1.65 (m, 2H); 1.34 (s, 6H); 1.05 (t, 3H)

EXAMPLE 9

Synthesis of 1-ethyl-3-{4-[6-(3-hydroxypropyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea

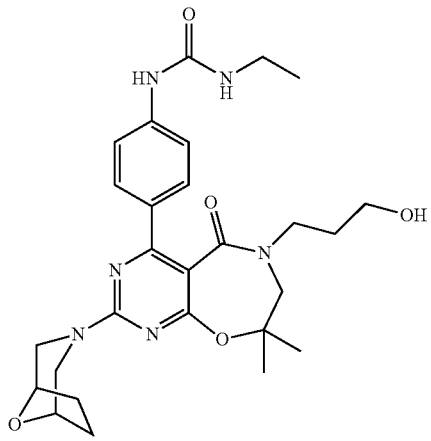 [SMILES: CCNC(=O)Nc1ccc(-c2nc(N3CC4CCC(C3)O4)nc3c2C(=O)N(CCCO)CC(C)(C)O3)cc1]

13 mg of lithium aluminium hydride (0.34 mmol) are placed in 5 ml of anhydrous THF. A solution containing 90 mg (0.17 mmol) of 3-[4-[4-(3-ethylureido)phenyl]-8,8-dimethyl-2-(8-oxa-3-azabicyclo[3.2.1]oct-3-yl)-5-oxo-7,8-dihydro-5H-9-oxa-1,3,6-triazabenzocyclohepten-6-yl]propionic acid in 10 ml of THF is added dropwise. The reaction mixture is heated at 66° C. for 18 hours. 72 mg of lithium aluminium hydride (1.89 mmol) are added and the mixture is heated for a further 24 hours at 66° C. The medium is then cooled in an ice-water bath to 4° C. and basified with saturated aqueous Na$_2$SO$_4$ solution. Ethyl acetate is added and the mixture is filtered through Celite, rinsed with ethyl acetate and concentrated. The residue is chromatographed on silica gel with a gradient of MeOH containing 10% aqueous ammonia DCM ranging from 0% to 10%. The solid is rinsed with acetonitrile and then with pentane to give 22 mg of 1-ethyl-3-{4-[6-(3-hydroxypropyl)-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea.

LC/MS (method A): M+H$^+$=525; Tr=0.82 min $^1$H NMR (400 MHz, DMSO-d$_6$) δ ppm 8.29 (m, 1H); 7.44-7.34 (m, 4H); 5.95 (t, 1H); 4.38 (m, 2H); 4.27 (d, 2H); 3.62 (s, 2H); 3.58-3.52 (m, 4H); 3.15-3.09 (m, 5H); 1.83-1.66 (m, 6H); 1.36 (s, 6H); 1.07 (t, 3H)

EXAMPLE 10

Synthesis of 1-ethyl-3-{4-[6-ethyl-8,8-dimethyl-2-(8-oxa-3-azabicyclo[3.2.1]oct-3-yl)-5-oxo-6,7,8,9-tetrahydro-5H-10-oxa-1,3,6-triazabenzocycloocten-4-yl]phenyl}urea

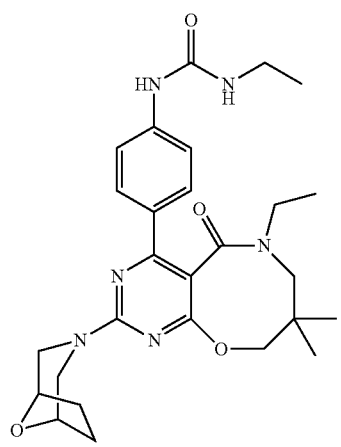 [SMILES: CCNC(=O)Nc1ccc(-c2nc(N3CC4CCC(C3)O4)nc3c2C(=O)N(CC)CC(C)(C)CO3)cc1]

Step 10.1

3-(tert-Butyldimethylsilanyloxy)-2,2-dimethylpropylamine

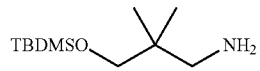

2 g of 3-amino2,2-dimethylpropan-1-ol (19.39 mmol) are placed in 40 ml of DCM. 2.56 g of imidazole (38.77 mmol) are added and the solution is cooled to +4° C. in an ice bath, followed by dropwise addition of 3.36 ml of tert-butyl(chloro)dimethylsilane (19.39 mmol). The medium is stirred for 30 minutes at +4° C., and the ice bath is then removed and the mixture is stirred at room temperature for 18 hours. The medium is then washed with water, and then with brine. The organic phase is dried over Na$_2$SO$_4$, filtered and concentrated to give 4.02 g of 3-(tert-butyldimethylsilanyloxy)-2,2-dimethylpropylamine.

Step 10.2: (Preparation of a Compound of Formula (XI) whose Hydroxyl Function is Protected)

[3-(tert-Butyldimethylsilanyloxy)-2,2-dimethylpropyl]ethylamine

4.02 g (18.49 mmol) of the compound described in step 10.1 are placed in 40 ml of anhydrous THF. 0.81 g of sodium hydride (20.34 mmol) is added portionwise. After 30 minutes, 1.63 ml of iodoethane (20.34 mmol) are added and the mixture is heated at 55° C. for 18 hours. The reaction medium is poured into water and extracted with ethyl acetate. The organic phase is washed with brine, dried over Na$_2$SO$_4$, filtered and concentrated to give 4.47 g of [3-(tert-butyldimethylsilanyloxy)-2,2-dimethylpropyl]ethylamine.

Step 10.3: (Which Corresponds to Step a), with the Hydroxyl Function Protected)

4,6-Dichloro-2-methylsulfanylpyrimidine-5-carboxylic acid [3-(tert-butyldimethylsilanyloxy)-2,2-dimethylpropyl]ethylamide

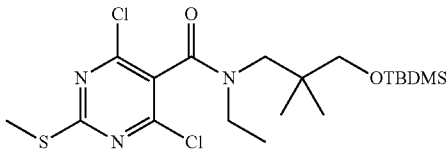 [SMILES: CCN(CC(C)(C)CO[Si](C)(C)C(C)(C)C)C(=O)c1c(Cl)nc(SC)nc1Cl]

4.47 g (18.21 mmol) of the compound described in step 10.2 are placed in 400 ml of THF. 7.57 ml of triethylamine (5.53 mmol) are added and the mixture is cooled to −70° C. in a bath of cardice in acetone. 4.69 g of 4,6-dichloro-2-methylsulfanylpyrimidine-5-carbonyl chloride (18.21 mmol) prediluted in 20 ml of anhydrous THF are then added dropwise. After stirring for 4 hours at −70° C., aqueous 1N hydrochloric acid solution is added and the reaction medium is extracted with ethyl acetate, dried over Na$_2$SO$_4$ and concentrated to dryness. The residue is taken up in acetonitrile and filtered. The filtrate is evaporated to give 4.1 g of 4,6-dichloro-2-methylsulfanylpyrimidine-5-carboxylic acid [3-(tert-butyldimethylsilanyloxy)-2,2-dimethylpropyl]ethylamide.

LC/MS (method F): M+H$^+$=466; Tr=5.77 min

Step 10.4: (Deprotection of the Alcohol Function)

4,6-Dichloro-2-methylsulfanylpyrimidine-5-carboxylic acid ethyl(3-hydroxy-2,2-dimethylpropyl)amide

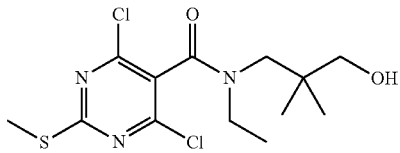 [SMILES: CCN(CC(C)(C)CO)C(=O)c1c(Cl)nc(SC)nc1Cl]

4.1 g (8.79 mmol) of the compound described in step 10.3 are placed in 40 ml of MeOH. 1.83 ml of 12N hydrochloric acid (21.98 mmol) are added. After 18 hours, the MeOH is evaporated off. The residue is taken up in ethyl acetate and washed with saturated NaHCO$_3$ solution. The organic phase is dried over Na$_2$SO$_4$, filtered and concentrated to give 3.1 g of 4,6-dichloro-2-methylsulfanylpyrimidine-5-carboxylic acid ethyl(3-hydroxy-2,2-dimethylpropyl)amide.

LC/MS (method F): M+H$^+$=352; Tr=4.08 min

Step 10.5: (Which Corresponds to Step b))

4-Chloro-6-ethyl-8,8-dimethyl-2-methylsulfanyl-6,7,8,9-tetrahydro-10-oxa-1,3,6-triazabenzocycloocten-5-one

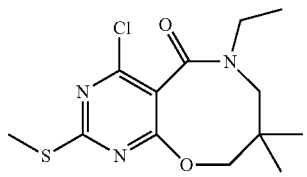

2.95 g (8.37 mmol) of the compound described in step 10.4 are placed in 55 ml of DMSO with stirring. 1.38 ml of DBU (9.21 mmol) are added. The reaction medium is stirred for 3 hours at 55° C., and 40 ml of ice-water are then added. The medium is extracted with ethyl acetate, washed with brine, dried over Na$_2$SO$_4$ and then filtered. The solution is evaporated to dryness. The residue is then chromatographed on silica gel with a gradient of ethyl acetate in DCM ranging from 0% to 10%. 1.18 g of 4-chloro-6-ethyl-8,8-dimethyl-2-methylsulfanyl-6,7,8,9-tetrahydro-10-oxa-1,3,6-triazabenzocycloocten-5-one are obtained.

LC/MS (method F): M+H$^+$=316; Tr=3.91 min

Step 10.6: (Which Corresponds to Step o))

1-Ethyl-3-[4-(6-ethyl-8,8-dimethyl-2-methylsulfanyl-5-oxo-6,7,8,9-tetrahydro-5H-10-oxa-1,3,6-triazabenzocycloocten-4-yl)phenyl]urea

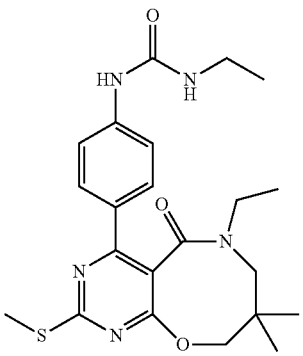

0.3 g (0.95 mmol) of the compound described in step 10.5 is placed in 8 ml of dioxane in a 20 ml microwave tube. 330 mg (1.14 mmol) of 1-ethyl-3-[4-(4,4,5,5-tetramethyl-[1,3,2]dioxaborolan-2-yl)phenyl]urea and 2.61 ml of 2N Na$_2$CO$_3$ solution (5.22 mmol) are successively added. The solution is degassed with argon, followed by addition of 55 mg of tetrakis(triphenylphosphine)palladium (50 μmol). The tube is heated at 110° C. for 30 minutes in a Biotage microwave machine. The medium is poured into water and filtered to give 330 mg of 1-ethyl-3-[4-(6-ethyl-8,8-dimethyl-2-methylsulfanyl-5-oxo-6,7,8,9-tetrahydro-5H-10-oxa-1,3,6-triazabenzocycloocten-4-yl)phenyl]urea.

LC/MS (method F): M+H$^+$=444; Tr=3.70 min

Step 10.7: (Which Corresponds to Step p))

1-Ethyl-3-[4-(6-ethyl-2-methanesulfonyl-8,8-dimethyl-5-oxo-6,7,8,9-tetrahydro-5H-10-oxa-1,3,6-triazabenzocycloocten-4-yl)phenyl]urea

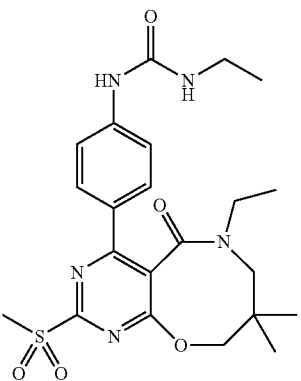

0.292 g (0.66 mmol) of the compound described in step 10.6 and 0.65 g of magnesium monoperoxyphthalate hexahydrate (1.32 mmol) are placed in 20 ml of a 2/1 acetonitrile/EtOH mixture. After stirring for 4 hours at room temperature, the solvents are evaporated off. The residue is taken up in water. The product obtained is filtered off and rinsed twice with water to give 0.25 g of 1-ethyl-3-[4-(6-ethyl-2-methanesulfonyl-8,8-dimethyl-5-oxo-6,7,8,9-tetrahydro-5H-10-oxa-1,3,6-triazabenzocycloocten-4-yl)phenyl]urea.

LC/MS (method F): M+H$^+$=476; Tr=3.34 min

Step 10.8: (Which Corresponds to Step q))

1-Ethyl-3-{4-[6-ethyl-8,8-dimethyl-2-(8-oxa-3-azabicyclo[3.2.1]oct-3-yl)-5-oxo-6,7,8,9-tetrahydro-5H-10-oxa-1,3,6-triazabenzocycloocten-4-yl]phenyl}urea

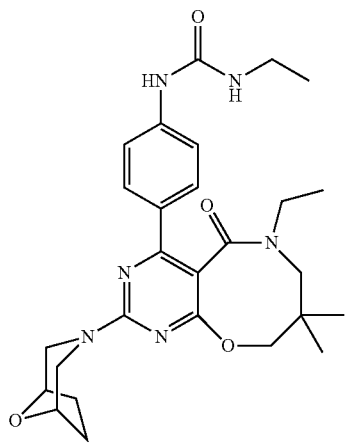 [SMILES: CCNC(=O)Nc1ccc(-c2nc(N3CC4CCC(C3)O4)nc3c2C(=O)N(CC)CC(C)(C)CO3)cc1]

410 mg (0.26 mmol) of the compound described in step 10.7 are placed in 7 ml of DMSO in a 20 ml microwave tube. 118 mg of 8-oxa-3-azabicyclo[3.2.1]octane hydrochloride (0.79 mmol) and 0.22 ml of triethylamine (1.58 mmol) are successively added. The tube is heated at 100° C. for 1 hour 30 minutes in a Biotage microwave machine. The medium is poured into water and extracted twice with ethyl acetate. The organic phases are combined, washed with brine, dried over MgSO$_4$, filtered and evaporated. The residue is chromatographed on silica gel with a gradient of MeOH containing 10% aqueous ammonia in DCM to give 48 mg of 1-ethyl-3-{4-[6-ethyl-8,8-dimethyl-2-(8-oxa-3-azabicyclo[3.2.1]oct-3-yl)-5-oxo-6,7,8,9-tetrahydro-5H-10-oxa-1,3,6-triazabenzocycloocten-4-yl]phenyl}urea.

LC/MS (method A): M+H$^+$=509; Tr=0.96 min $^1$H NMR (400 MHz, DMSO-d$_6$) δ ppm 8.60 (m, 1H); 7.36 (m, 4H); 6.13 (t, 1H); 4.39-3.92 (m, 5H); 3.72-3.62 (m, 2H); 3.14-3.03 (m, 5H); 2.93 (m, 1H); 1.81-1.61 (m, 5H); 1.1-1.03 (m, 9H); 0.93 (m, 3H)

EXAMPLE 11

Synthesis of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-methylurea

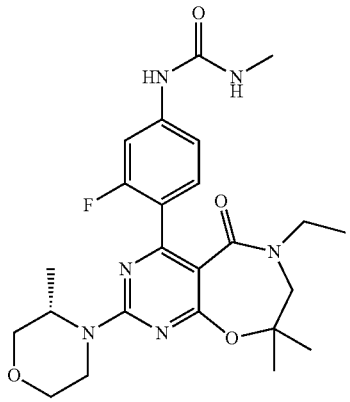 [SMILES: CCN1CC(C)(C)Oc2nc(N3CCOC[C@@H]3C)nc(-c3ccc(NC(=O)NC)cc3F)c2C1=O]

Step 11.1: (Which Corresponds to Step c))

[4-(6-Ethyl-8,8-dimethyl-2-methylsulfanyl-5-oxo-5,6,7,8-tetrahydro-9-oxa-1,3,6-triazabenzocyclohepten-4-yl)-3-fluorophenyl]carbamic acid tert-butyl ester

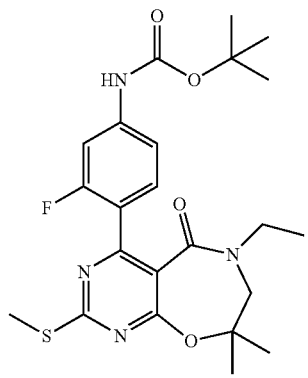 [SMILES: CCN1CC(C)(C)Oc2nc(SC)nc(-c3ccc(NC(=O)OC(C)(C)C)cc3F)c2C1=O]

1.77 g (5.85 mmol) of 4-chloro-6-ethyl-8,8-dimethyl-2-methylsulfanyl-7,8-dihydro-6H-9-oxa-1,3,6-triazabenzocyclohepten-5-one, 2.27 g (6.73 mmol) of [3-fluoro-4-(4,4,5,5-tetramethyl[1,3,2]dioxaborolan-2-yl)phenyl]carbamic acid tert-butyl ester and 14.63 ml of a 2 M solution of Na$_2$CO$_3$ in 35 ml dioxane are mixed together, followed by degassing 5 times with argon. 339 mg (293 μmol) of tetrakis(triphenylphosphine)palladium (0) are added and the mixture is degassed a further 3 times with argon and then heated at 90° C. for 2 hours 30 minutes. The resulting mixture is allowed to cool. It is poured into water. The product is filtered off, washed with water, dissolved in DCM, dried and concentrated. It is taken up in Et$_2$O, and the mixture is stirred, filtered and dried. 2.94 g of [4-(6-ethyl-8,8-dimethyl-2-methylsulfanyl-5-oxo-5,6,7,8-tetrahydro-9-oxa-1,3,6-triazabenzocyclohepten-4-yl)-3-fluorophenyl]carbamic acid tert-butyl ester are recovered.

LC/MS (method E): M+H$^+$=477; Tr=2.60 min

Step 11.2: (Which Corresponds to Step d))

[4-(6-Ethyl-2-methanesulfonyl-8,8-dimethyl-5-oxo-5,6,7,8-tetrahydro-9-oxa-1,3,6-triazabenzocyclohepten-4-yl)-3-fluorophenyl]carbamic acid tert-butyl ester

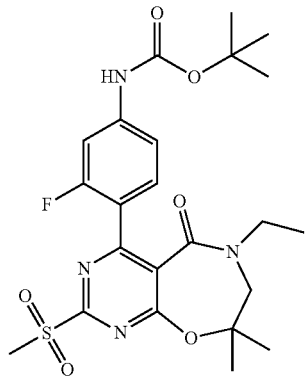 [SMILES: CCN1CC(C)(C)Oc2nc(S(C)(=O)=O)nc(-c3ccc(NC(=O)OC(C)(C)C)cc3F)c2C1=O]

2.79 g (5.85 mmol) of the compound described in step 11.1 are suspended in 30 ml of acetonitrile and 10 ml of EtOH, followed by addition of 7.23 g of magnesium monoperoxyphthalate hexahydrate (11.70 mmol). The mixture is stirred at 60° C. for 2 hours and is then stirred at room temperature overnight. 1 equivalent of magnesium monoperoxyphthalate hexahydrate is added. The mixture is heated at 60° C. for 2 hours. It is allowed to cool, diluted with water, stirred for 10 minutes and then filtered. The product is washed with water, dissolved in DCM, dried and concentrated to give 3.05 g of [4-(6-ethyl-2-methanesulfonyl-8,8-dimethyl-5-oxo-5,6,7,8-tetrahydro-9-oxa-1,3,6-triazabenzo cyclohepten-4-yl)-3-fluorophenyl]carbamic acid tert-butyl ester.

LC/MS (method E): M+H$^+$=509; Tr=2.20 min

Step 11.3: (Which Corresponds to Step e))

{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}carbamic acid tert-butyl ester

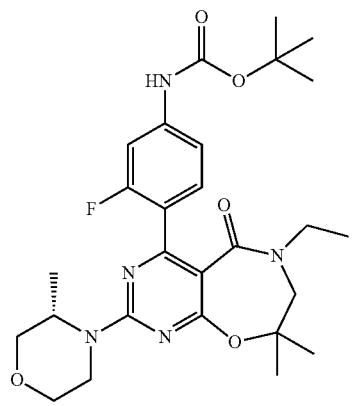 [SMILES: CCN1CC(C)(C)Oc2nc(N3CCOC[C@@H]3C)nc(-c3ccc(NC(=O)OC(C)(C)C)cc3F)c2C1=O]

To 1.02 g (2.0 mmol) of the compound described in step 11.2 suspended in 5 ml of anhydrous dioxane under argon are added 2.02 g (20 mmol) of (S)-3-methylmorpholine, followed by heating at 95° C. for 3 hours. The mixture is allowed to cool and is partly concentrated, water is added and the resulting mixture is then filtered. The residue is taken up in DCM and the solution is dried and concentrated. The solid obtained (1 g) is used without purification in the following step.

LC/MS (method E): M+H$^+$=530; Tr=2.64 min

Step 11.4: (Which Corresponds to Step l))

4-(4-Amino-2-fluorophenyl)-6-ethyl-8,8-dimethyl-2-((S)-3-methylmorpholin-4-yl)-7,8-dihydro-6H-9-oxa-1,3,6-triazabenzocyclohepten-5-one

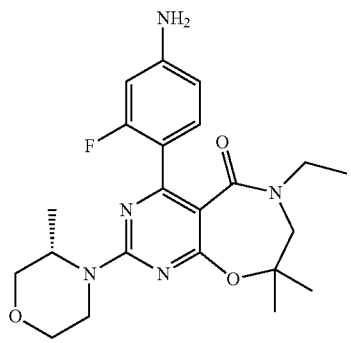 [SMILES: CCN1CC(C)(C)Oc2nc(N3CCOC[C@@H]3C)nc(-c3ccc(N)cc3F)c2C1=O]

The compound described in step 11.3 is suspended in 5 ml of DCM and 500 µL of water. 10 ml of TFA are added. The mixture is reacted at room temperature for 2 hours. The resulting mixture is concentrated, taken up in a DCM/water mixture and basified with K$_2$CO$_3$. The phases are separated by settling and the organic phase is dried and concentrated. The solid is taken up in Et$_2$O. The product is stirred, filtered off and air-dried to give 690 mg of 4-(4-amino-2-fluorophenyl)-6-ethyl-8,8-dimethyl-2-((S)-3-methylmorpholin-4-yl)-7,8-dihydro-6H-9-oxa-1,3,6-triazabenzocyclohepten-5-one.

LC/MS (method E): M+H$^+$=430; Tr=2.04 min

Step 11.5: (Which Corresponds to Step m) (Steps m1-1) and m1-2))

1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-methylurea

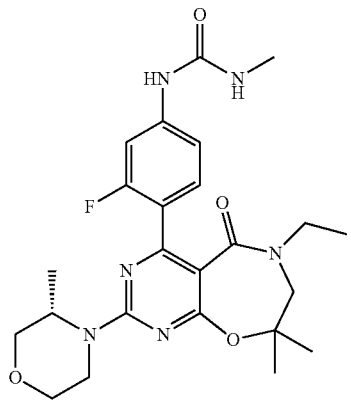 [SMILES: CCN1CC(C)(C)Oc2nc(N3CCOC[C@@H]3C)nc(-c3ccc(NC(=O)NC)cc3F)c2C1=O]

200 mg (466 µmol) of the compound described in step 11.4 are suspended in 5 ml of anhydrous dioxane under argon. The mixture is heated to dissolve the suspension. The resulting mixture is allowed to cool and 123 µl (699 µmol) of DIEA are added, followed by 368 µl (699 µmol) of a 1.9M solution of phosgene in toluene, after which the mixture is heated at 50° C. for 30 minutes. It is allowed to cool and 1.63 ml of 2M methylamine in THF (3.26 mmol) are added. The resulting mixture is reacted overnight. It is poured into water and filtered. The product is dissolved in DCM, dried over Na₂SO₄ and then concentrated under reduced pressure. The resulting product is taken up in Et₂O, stirred, filtered off and dried to give 191 mg of 1-{4-[6-ethyl-8,8-dimethyl-2-((S)-3-methyl-morpholin-4-yl)-5-oxo-5,6,7,8-tetrahydro-9-oxa-1,3,6-tri-azabenzocyclohepten-4-yl]-3-fluorophenyl}-3-methylurea.

LC/MS (method C): M+H⁺=487; Tr=0.64 min

¹H NMR (600 MHz, DMSO-d₆) δ ppm 8.95 (s, 1H); 7.49 (d, 1H); 7.45 (d, 1H); 7.05 (d, 1H); 6.17 (s, 1H); 4.63 (s, 1H); 4.29 (d, 1H); 3.90 (dd, 1H); 3.70 (d, 1H); 3.57 (dd, 1H); 3.52 (s, 2H); 3.36-3.50 (bs, 3H); 3.18 (bs, 1H); 2.65 (d, 3H); 1.35 (d, 6H); 1.21 (d, 3H); 1.08 (t, 3H)

EXAMPLE 12

Synthesis of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-pyridin-4-ylurea (Which Corresponds to Step m) (Steps m1-1) and m1-2))

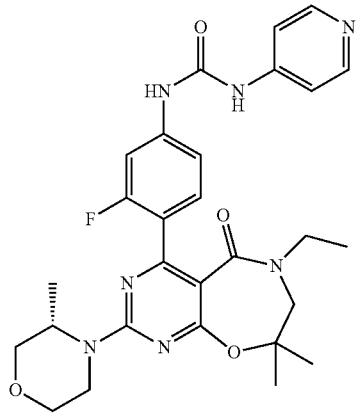 [SMILES: CCN1CC(C)(C)Oc2nc(N3CCOC[C@@H]3C)nc(-c3ccc(NC(=O)Nc4ccncc4)cc3F)c2C1=O]

150 mg (394 µmol) of 4-(4-amino-2-fluorophenyl)-6-ethyl-8,8-dimethyl-2-((S)-3-methylmorpholin-4-yl)-7,8-di-hydro-6H-9-oxa-1,3,6-triazabenzocyclohepten-5-one are suspended in 4 ml anhydrous dioxane under argon. 92 µl (524 µmol) of DIEA are added, followed by 276 µl of a 1.9M solution of phosgene in toluene, after which the mixture is heated at 50° C. for 30 minutes. The resulting mixture is allowed to cool, followed by addition of 202 mg (2.10 mmol) of 4-aminopyridine dissolved in 2 ml of anhydrous DMF. The resulting mixture is reacted for 3 hours. It is poured into water, stirred, filtered and washed with water. The product is dissolved in DCM, dried over Na₂SO₄ and then concentrated under reduced pressure. It is taken up in Et₂O, and the mixture is stirred and filtered. The product is dissolved in 5 ml of DCM with a small amount of MeOH, and 20 ml of ethyl acetate are added. The product is placed in a refrigerator and the solid is then filtered off to give 146 mg of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-pyridin-4-ylurea.

LC/MS (method C): M+H⁺=550; Tr=0.57 min

¹H NMR (600 MHz, DMSO-d₆) δ ppm 9.30 (s, 2H); 8.38 (d, 2H); 7.57 (t, 1H); 7.48 (dd, 1H); 7.45 (d, 2H); 7.17 (dd, 1H); 4.64 (s, 1H); 4.30 (d, 1H); 3.91 (dd, 1H); 3.71 (d, 1H); 3.58 (dd, 1H); 3.54 (s, 2H); 3.39-3.53 (m, 3H); 3.19 (dt, 1H); 1.36 (d, 6H); 1.22 (d, 3H); 1.09 (t, 3H)

EXAMPLE 13

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methylpiperazin-1-yl)phenyl]urea (Which Corresponds to Step m) (Steps m2-1) and m2-2))

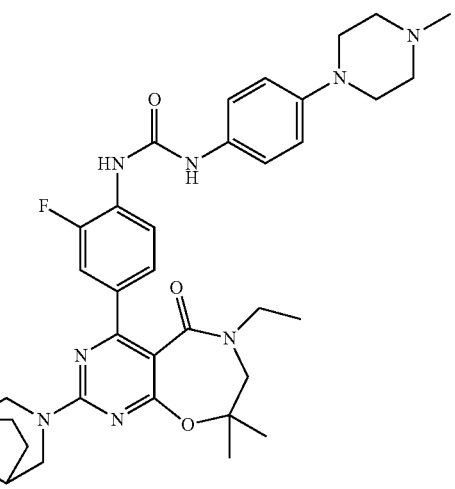

136.5 mg (460 µmol) of trisphosgene are dissolved in 2 ml of DCM. A mixture of 90.7 mg (460 µmol) of 4-(4-methylpip-erazin-1-yl)phenylamine and 389 µl (2.76 mmol) of triethy-lamine in 3 ml of DCM is added in a single portion. The resulting mixture is stirred for 30 minutes at room temperature. 100 mg (226.5 µmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one are added. The resulting mixture is reacted for 15 hours at room temperature. The reaction mixture is diluted in 50 ml of DCM and the organic phase is washed with twice 20 ml of saturated NaHCO₃ solution. The organic phase is dried over Na₂SO₄, filtered and evaporated. The residue is chromato-graphed on silica gel, eluting with an MeOH/DCM mixture (0/100 v/v) up to (10/90 v/v) to give 75 mg of a white powder. The powder obtained is washed again with 2 ml of MeOH and then 2 ml of ethyl acetate. The resulting product is dried. 68 mg of 1-{4-[6-ethyl-8,8-dimethyl-2-(8-oxa-3-azabicyclo [3.2.1]oct-3-yl)-5-oxo-5,6,7,8-tetrahydro-9-oxa-1,3,6-tri-azabenzocyclohepten-4-yl]-2-fluorophenyl}-3-[4-(4-meth-ylpiperazin-1-yl)phenyl]urea are recovered.

LC/MS (method C): M+H⁺=659; Tr=0.53 min

¹H NMR (600 MHz, DMSO-d₆) δ ppm 8.91 (1H); 8.67 (s, 1H); 8.19 (t, 1H); 7.42 (d, 1H); 7.30 (t, 3H); 6.91 (d, 2H); 4.43 (s, 2H); 4.1-4.3 (bs, 2H); 3.70 (s, 2H); 3.4-3.6 (bs, 2H); 3.11

(d, 2H); 3.06 (t, 4H); 2.46 (t, 4H); 2.22 (s, 3H); 1.8-1.9 (bs, 2H); 1.6-1.7 (bs, 2H); 1.36 (s, 6H); 1.17 (t, 3H)

EXAMPLE 14

Synthesis of 1-{4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-ethylurea

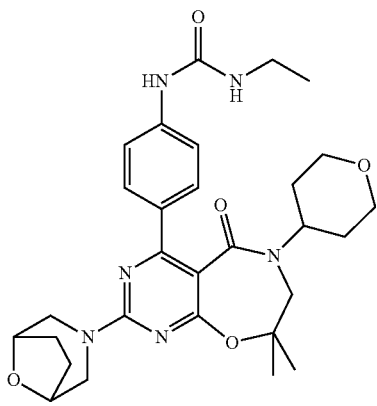 [SMILES: CCNC(=O)Nc1ccc(-c2nc(N3CC4CCC(C3)O4)nc3c2C(=O)N(C2CCOCC2)CC(C)(C)O3)cc1]

Step 14.1: (Preparation of a Compound of Formula (XI))

2-Methyl-1-(((tetrahydro-2H-pyran-4-yl)amino)propan-2-ol

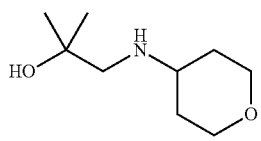

2.75 g of 1-amino-2-methylpropan-2-ol are dissolved in 20 ml of MeOH. 1.71 ml of glacial acetic acid are added dropwise under an inert atmosphere. 2 g of tetrahydropyran-4-one in 10 ml of MeOH are added, the mixture is stirred for 30 minutes at room temperature and 1.98 g of sodium cyanoborohydride are added. The resulting mixture is stirred under an inert atmosphere for 15 hours. The reaction medium is poured into saturated aqueous NaHCO$_3$ solution (100 ml). The resulting mixture is stirred for 30 minutes and then extracted with 4 times 100 ml of DCM. The organic phase is dried over Na$_2$SO$_4$, filtered and evaporated without heating. The MeOH contained in the aqueous phase is evaporated off and the extraction, drying, filtration and evaporation operation is repeated 3 times. 2.8 g of 2-methyl-1-((tetrahydro-2H-pyran-4-yl)amino)propan-2-ol are recovered in total.

Step 14.2 (Which Corresponds to Step a))

4,6-Dichloro-2-methylsulfanylpyrimidine-5-carboxylic acid (2-hydroxy-2-methylpropyl)(tetrahydropyran-4-yl)amide

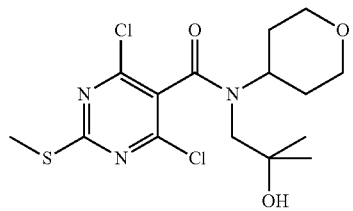 [SMILES: CSc1nc(Cl)c(C(=O)N(CC(C)(C)O)C2CCOCC2)c(Cl)n1]

This compound is prepared according to the procedure described in step 1.2 starting with 4,6-dichloro-2-methylsulfanylpyrimidine-5-carbonyl chloride and the compound described in step 14.1.
LC/MS (method E): M+H$^+$=395; Tr=2.13 min Step 14.3: (Which Corresponds to Step b))

4-Chloro-8,8-dimethyl-2-methylsulfanyl-6-(tetrahydropyran-4-yl)-7,8-dihydro-6H-9-oxa-1,3,6-triazabenzocyclohepten-5-one

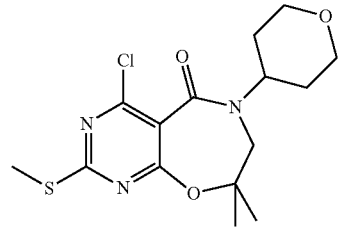 [SMILES: CSc1nc(Cl)c2c(n1)OC(C)(C)CN(C1CCOCC1)C2=O]

This compound is prepared according to the procedure described in step 1.3 starting with the compound described in step 14.2.
LC/MS (method E): M+H$^+$=360; Tr=1.90 min Step 14.4: (Which Corresponds to Step c))

{4-[8,8-Dimethyl-2-methylsulfanyl-5-oxo-6-(tetrahydropyran-4-yl)-5,6,7,8-tetrahydro-9-oxa-1,3,6-triazabenzocyclohepten-4-yl]phenyl}carbamic acid tert-butyl ester

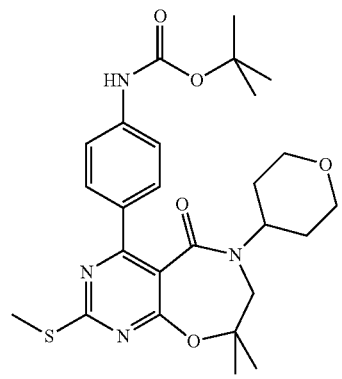 [SMILES: CSc1nc2c(c(-c3ccc(NC(=O)OC(C)(C)C)cc3)n1)C(=O)N(C1CCOCC1)CC(C)(C)O2]

This compound is prepared according to the procedure described in step 1.4 starting with the compound described in step 14.3 and [4-(4,4,5,5-tetramethyl-[1,3,2]dioxaborolan-2-yl)phenyl]carbamic acid tert-butyl ester.

LC/MS (method E): M+H$^+$=515; Tr=2.44 min

Step 14.5: (Which Corresponds to Step d))

{4-[2-Methanesulfonyl-8,8-dimethyl-5-oxo-6-(tetrahydropyran-4-yl)-5,6,7,8-tetrahydro-9-oxa-1,3,6-triazabenzocyclohepten-4-yl]phenyl}carbamic acid tert-butyl ester

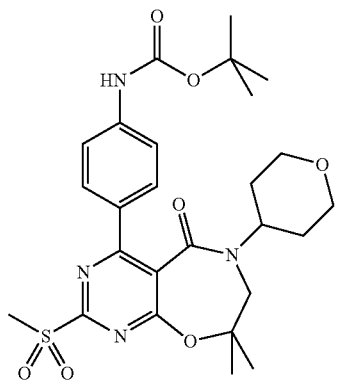 [SMILES: CC(C)(C)OC(=O)Nc1ccc(-c2nc(S(C)(=O)=O)nc3c2C(=O)N(C2CCOCC2)CC(C)(C)O3)cc1]

This compound is prepared according to the procedure described in step 1.5 starting with the compound described in step 14.4.

LC/MS (method E): M+H$^+$=547; Tr=2.03 min

Step 14.6: (Which Corresponds to Step e))

{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}carbamic acid tert-butyl ester

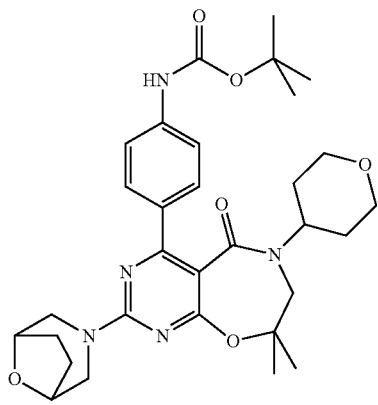 [SMILES: CC(C)(C)OC(=O)Nc1ccc(-c2nc(N3CC4CCC(C3)O4)nc3c2C(=O)N(C2CCOCC2)CC(C)(C)O3)cc1]

This compound is prepared according to the procedure described in step 1.6 starting with the compound described in step 14.5 and 8-oxa-3-azabicyclo[3.2.1]octane.

LC/MS (method E): M+H$^+$=580; Tr=2.43 min

Step 14.7: (Which Corresponds to Step l))

4-(4-Aminophenyl)-8,8-dimethyl-2-(8-oxa-3-azabicyclo[3.2.1]oct-3-yl)-6-(tetrahydropyran-4-yl)-7,8-dihydro-6H-9-oxa-1,3,6-triazabenzocyclohepten-5-one

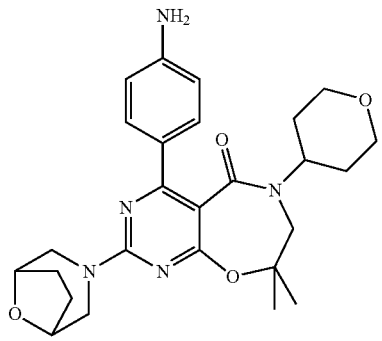 [SMILES: CC1(C)CN(C2CCOCC2)C(=O)c2c(nc(N3CC4CCC(C3)O4)nc2-c2ccc(N)cc2)O1]

This compound is prepared according to the procedure described in step 1.7 starting with the compound described in step 14.6.

LC/MS (method E): M+H$^+$=480; Tr=1.74 min

Step 14.8: (Which Corresponds to Step m) (Step m3-1))

{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}carbamic acid phenyl ester

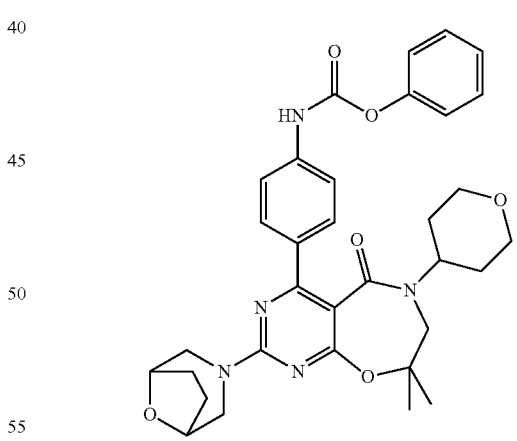

200 mg (417 µmol) of the compound described in step 14.7 are suspended in THF, and 152 µl (917.5 µmol) of DIEA are added, followed by addition of 66 mg (417 µmol) of phenyl chloroformate. The mixture is stirred at room temperature for 10 minutes. The solid is filtered off, rinsed with MeOH and dried. 171 mg of {4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}carbamic acid phenyl ester are recovered.

LC/MS (method E): M+H$^+$=600; Tr=2.40 min

Step 14.9: (Which Corresponds to Step m) (Step m3-2))

1-{4-[8,8-Dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-ethylurea

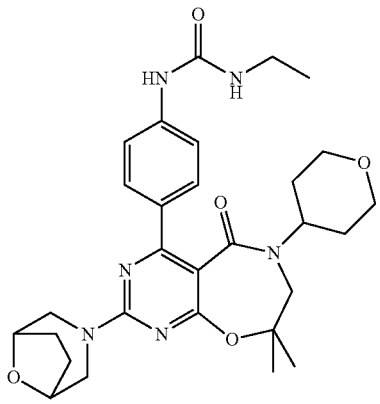 [SMILES: CCNC(=O)Nc1ccc(-c2nc(N3CC4CCC(C3)O4)nc3c2C(=O)N(C2CCOCC2)CC(C)(C)O3)cc1]

100 mg (166.8 μmol) of the compound described in step 14.8 suspended in 2 ml of DMF are placed in a microwave reactor, and 1 ml of a 2M solution of ethylamine (2.0 mmol) in THF is added. The mixture is heated in a Biotage microwave machine for 1 hour at 100° C. The solvents and the excess ethylamine are evaporated off. The residue is chromatographed on silica gel, eluting with an MeOH/DCM mixture from (0/100 v/v) up to (5/95 v/v) to give 66 mg of 1-{4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-ethylurea.

LC/MS (method C): M+H$^+$=551; Tr=0.61 min
$^1$H NMR (600 MHz, DMSO-d$_6$) δ ppm 8.61 (s, 1H); 7.38 (dd, 4H); 6.14 (t, 1H); 4.41 (m, 4H); 4.0-4.3 (bs, 1H); 3.95 (dd, 2H); 3.61 (s, 2H); 3.38 (t, 2H); 3.09-3.14 (m, 4H); 1.85-1.94 (m, 2H); 1.78-1.84 (m, 2H); 1.60-1.70 (m, 4H); 1.34 (s, 6H); 1.07 (t, 3H)

EXAMPLE 15

(Which Corresponds to Step m) (Step m3-2))

Synthesis of 1-{4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(5-methylisoxazol-3-yl)urea

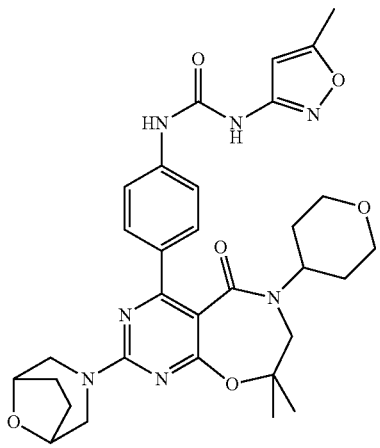 [SMILES: Cc1cc(NC(=O)Nc2ccc(-c3nc(N4CC5CCC(C4)O5)nc4c3C(=O)N(C3CCOCC3)CC(C)(C)O4)cc2)no1]

50 mg (83.38 μmol) of {4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}carbamic acid phenyl ester are placed in a microwave reactor and 25 mg (0.25 mmol) of 5-methylisoxazol-3-ylamine are added. 2 ml of DMF and 1 ml of THF are added. The reaction mixture is heated in a Biotage microwave machine for 30 minutes at 100° C. 100 mg (1.0 mmol) of 5-methylisoxazol-3-ylamine are added and the mixture is heated for 2 hours at 110° C. A further 300 mg (3 mmol) of 5-methylisoxazol-3-ylamine are added and the mixture is heated for 2 hours at 110° C. The solvents are evaporated off. The residue is taken up in water and the insoluble material is filtered off, washed three times with water, taken up in MeOH/DCM and dried. The residue is chromatographed on silica gel, eluting with an MeOH/DCM mixture from (0/100 v/v) up to (5/95 v/v) to give 6 mg of 1-{4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(5-methylisoxazol-3-yl)urea.

LC/MS (method C): M+H$^+$=604; Tr=0.68 min
$^1$H NMR (600 MHz, DMSO-d$_6$) δ ppm 9.52 (s, 1H); 9.03 (s, 1H); 7.44 (dd, 4H); 6.55 (s, 1H); 4.41 (m, 4H); 4.0-4.3 (bs, 1H); 3.95 (dd, 2H); 3.61 (s, 2H); 3.38 (t, 2H); 3.11 (d, 2H); 2.36 (s, 3H); 1.85-1.94 (m, 2H); 1.78-1.84 (m, 2H); 1.60-1.70 (m, 4H); 1.36 (s, 6H)

EXAMPLE 16

(Which Corresponds to Step m) (Step m3-2))

Synthesis of 1-{4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(1-methyl-1H-pyrazol-3-yl)urea

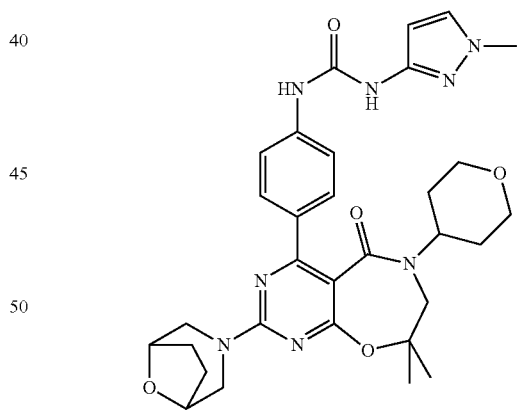

50 mg (83.4 μmol) of {4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}carbamic acid phenyl ester are placed in a microwave reactor and 25 mg (26 μmol) of 1-methyl-1H-pyrazol-3-ylamine are added. 1 ml of DMF and 2 ml of THF are added. The reactor is heated in a Biotage microwave machine for 30 minutes at 100° C. 100 mg (100 μmol) of 1-methyl-1H-pyrazol-3-ylamine are added and the mixture is heated for 2 hours at 110° C. The solvents are evaporated off. The residue is chromatographed on silica gel, eluting with an MeOH/DCM mixture from (0/100 v/v) up to (5/95 v/v) to give a solid, which is then washed with water and dried. 23 mg of 1-{4-[8,8-dimethyl-2-(8-oxa-3-azabicyclo[3.2.1]oct-3-yl)-5-oxo-6-(tetrahydropyran-4-yl)-5,6,7,8-tetrahydro-9-oxa-1,3,6-triazabenzocyclohepten-4-yl]phenyl}-3-(1-methyl-1H-pyrazol-3-yl)urea are recovered.

LC/MS (method C): M+H$^+$=603; Tr=0.63 min $^1$H NMR (600 MHz, DMSO-d$_6$) δ ppm 9.12 (s, 1H); 8.93 (s, 1H); 7.54 (s, 1H); 7.44 (dd, 4H); 6.24 (s, 1H); 4.41 (m, 4H); 4.0-4.3 (bs, 1H); 3.95 (dd, 2H); 3.74 (s, 3H); 3.61 (s, 2H); 3.38 (t, 2H); 3.11 (d, 2H); 1.85-1.94 (m, 2H); 1.78-1.84 (m, 2H); 1.60-1.70 (m, 4H); 1.36 (s, 6H)

EXAMPLE 17

Synthesis of 1-ethyl-3-{5-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]pyridin-2-yl}urea

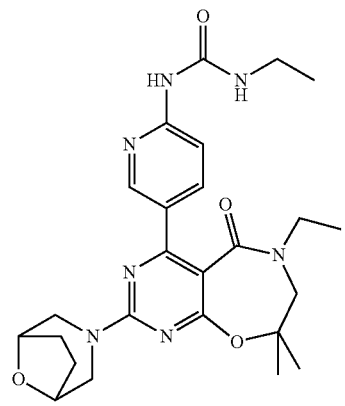 [SMILES: CCNC(=O)Nc1ccc(-c2nc(N3CC4CCC(C3)O4)nc3c2C(=O)N(CC)CC(C)(C)O3)cn1]

Step 17.1: (Which Corresponds to Step k))

4-(6-Aminopyridin-3-yl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one

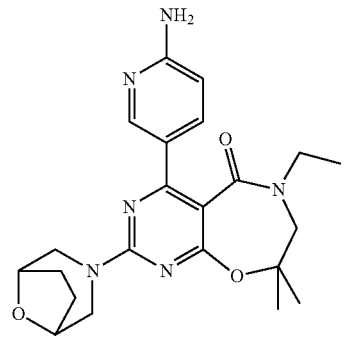 [SMILES: CCN1CC(C)(C)Oc2nc(N3CC4CCC(C3)O4)nc(-c3ccc(N)nc3)c2C1=O]

170 mg (353.83 μmol) of trifluoromethanesulfonic acid 6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl ester and 90.16 mg (389.21 μmol) of 5-(4,4,5,5-tetramethyl-[1,3,2]dioxaborolan-2-yl)pyridin-2-ylamine are dissolved in 3 ml of dioxane in a microwave tube. 150.21 mg (707.66 μmol) of tripotassium phosphate and 1 ml of water are added The solution is purged with argon. Finally, 24.84 mg (35.38 μmol) of bis(triphenylphosphine)palladium(II) chloride are added and the mixture is heated in a Biotage microwave machine for 15 minutes at 100° C. The reaction mixture is diluted in ethyl acetate and washed with water and then with saturated NaCl solution. The precipitate present in the organic phase is filtered off to give 120 mg of 4-(6-aminopyridin-3-yl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one.

$^1$H NMR (300 MHz, DMSO-d$_6$) δ ppm 8.08 (d, 1H); 7.58 (dd, 1H); 6.37-6.45 (m, 3H); 6.37-6.45 (m, 3H); 4.06-4.46 (bs, 4H); (bs, 4H); 3.42-3.68 (bs, 4H); 3.03-3.13 (bs, 2H); 1.73-1.86 (bs, 2H); 1.60-1.69 (bs, 2H); 1.33 (bs, 6H); 1.14 (t, 3H)

Step 17.2: (Which Corresponds to Step m) (Steps m3-1) and m3-2))

1-Ethyl-3-{5-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]pyridin-2-yl}urea

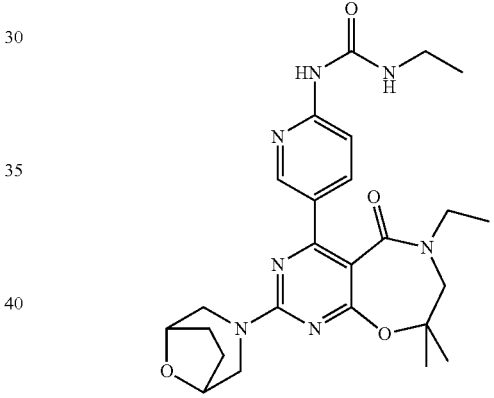

100 mg (235.57 μmol) of the compound described in step 17.1, 30.52 μl (235.57 μmol) of phenyl choroformate and 90.52 μl (518.26 μmol) of DIEA are placed in 2.5 ml of THF in a microwave tube. The resulting mixture is stirred for 30 minutes at room temperature. 235.57 μl (471.15 μmol) of 2N ethylamine are added in THF and the mixture is heated for 1 hour at 100° C. in a Biotage microwave machine. The reaction medium is evaporated under reduced pressure. The residue is chromatographed on silica gel, eluting with a DCM/MeOH mixture from (100/0 v/v) up to (95/5 v/v) to give 56 mg of 1-ethyl-3-{5-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]pyridin-2-yl}urea.

LC/MS (method C): M+H$^+$=496; Tr=0.59 min $^1$H NMR (300 MHz, DMSO-d6) ☐ ppm 9.39 (s, 1H); 8.34 (d, 1H); 7.92 (bs, 1H); 7.79 (dd, 1H); 7.41 (d, 1H); 4.05-4.46 (bs, 4H); 3.69 (bs, 2H); 3.51 (bs, 2H); 3.20 (m, 2H); 3.10 (bs, 2H); 1.82 (bs, 2H); 1.65 (bs, 2 H); 1.35 (bs, 6 H); 1.05-1.18 (m, 6 H)

EXAMPLE 18

(Which Corresponds to Step m) (Steps m4-1) and m4-2))

Synthesis of 1-(3-difluoromethoxyphenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triaza-benzocyclohepten-4-yl]phenyl}urea

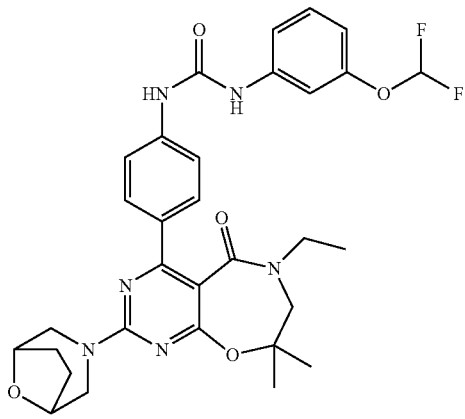 [SMILES: CCN1CC(C)(C)Oc2nc(N3CC4CCC(C3)O4)nc(-c3ccc(NC(=O)Nc4cccc(OC(F)F)c4)cc3)c2C1=O]

96.84 mg of 3-difluoromethoxyphenylamine (590.31 µmol), 206.20 µl of DIEA (1.18 mmol) and 30.81 µl of phenyl choroformate (237.83 µmol) are added to 4 ml of THF in a microwave tube. The mixture is stirred at room temperature for 20 minutes. 250 mg of 4-(4-aminophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one (590.31 µmol) are added and the resulting mixture is heated for 1 hour at 120° C. in a Biotage microwave machine. The reaction medium is evaporated under reduced pressure. The residue is chromatographed on silica gel, eluting with a DCM/MeOH mixture from (100/0 v/v) up to (98/2 v/v) to give 180 mg of 1-(3-difluoromethoxyphenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea.

LC/MS (method C): M+H$^+$=609; Tr=0.81 min $^1$H NMR (300 MHz, DMSO-d$_6$) δ ppm 9.23 (bs, 2H); 7.44-7.52 (bs, 5H); 7.27-7.36 (m, 1H); 6.92-7.25 (m, 2H); 6.73-6.81 (m, 1H); 4.41 (bs, 2H); 3.95-4.36 (bs, 2H); 3.67 (s, 2H); 3.37-3.63 (bs, 2H); 3.10 (m, 2H); 1.82 (bs, 2H); 1.65 (bs, 2H); 1.35 (bs, 6H); 1.15 (t, 3H)

EXAMPLE 19

(Which Corresponds to Step m) (Steps m1-1) and m1-2))

Synthesis of 1-(2,4-difluorophenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea

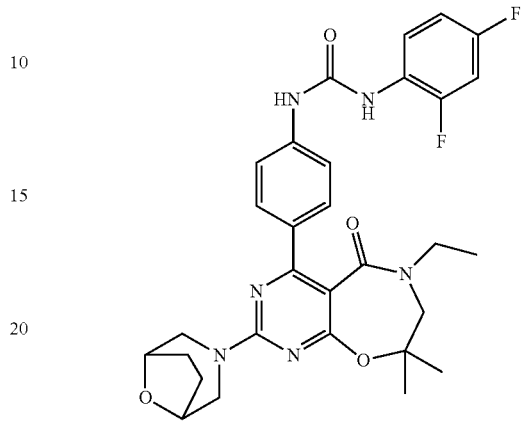

To a solution of 350.35 mg (1.18 mmol) of triphosgene in 6 ml of DCM is added in a single portion a suspension of 500 mg (1.18 mmol) of 4-(4-aminophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one and 987.33 µl (7.08 mmol) of triethylamine in 6 ml of DCM. The resulting mixture is stirred for 20 minutes at room temperature. 607.12 µl (5.90 mmol) of 2,4-difluoroaniline are added. The precipitate obtained is filtered off, rinsed twice with MeOH and dried under reduced pressure to give 575 mg of 1-(2,4-difluorophenyl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea.

LC/MS (method C): M+H$^+$=579; Tr=0.80 min $^1$H NMR (300 MHz, DMSO-d$_6$) δ ppm 9.22 (bs, 1H); 8.56 (bs, 1H); 8.08 (dt, 1H); 7.42-7.52 (m, 4H); 7.33 (m, 1H); 7.06 (m, 1H); 4.41 (bs, 2H); 4.11 (q, 2H); 3.67 (bs, 2H); 3.40-3.62 (bs, 2H); 3.10 (bs, 2H); 1.82 (bs, 2H); 1.65 (bs, 2H); 1.35 (bs, 6H); 1.15 (t, 3H)

EXAMPLE 20

(Which Corresponds to Step m) (Steps m1-1) and m1-2))

{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid (S)-2-hydroxypropyl ester

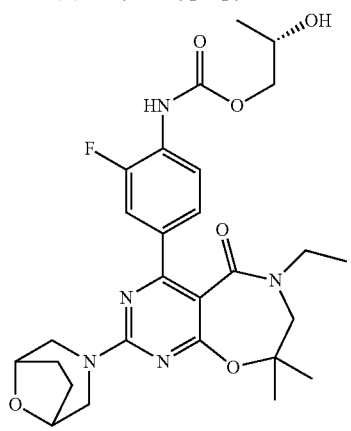 [SMILES: CCN1CC(C)(C)Oc2nc(N3CC4CCC(C3)O4)nc(-c3ccc(NC(=O)OC[C@H](C)O)c(F)c3)c2C1=O]

A mixture of 134.43 mg (0.45 mmol) of triphosgene, 200 mg (0.45 mmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one and 275.04 mg (2.72 mmol) of triethylamine in 50 ml of DCM is stirred at room temperature for 30 minutes. 134 mg (1.81 mmol) of (S)-propane-1,2-diol are added and the mixture is stirred for 2 hours at room temperature. The resulting mixture is hydrolysed with 5 ml of water and then evaporated under reduced pressure. The product is precipitated by addition of ethyl acetate/water. The product is filtered off and dried under vacuum to give 120 mg {4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}carbamic acid (S)-2-hydroxypropyl ester.

LC/MS (method C): M+H$^+$=544; Tr=0.64 min $^1$H NMR (600 MHz, DMSO-d$_6$) δ ppm 9.45 (bs, 1H); 7.7 (t, 1H); 7.32 (t, 2H); 4.8 (d, 1H); 4.42 (bs, 2H); 4.3 (m, 2H); 3.95 (m, 2H); 3.87 (m, 1H); 3.7 (bs, 2H); 3.5 (bs, 2H); 3.09 (bs, 1H); 1.82 (bs, 1H); 1.66 (bs, 1H); 1.35 (bs, 6H); 1.12 (t, 3H); 1.1 (t, 3H)

EXAMPLE 21

(Which Corresponds to Step m) (Steps m1-1) and m1-2))

Synthesis of 1-(4-methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzo cyclohepten-4-yl]phenyl}urea

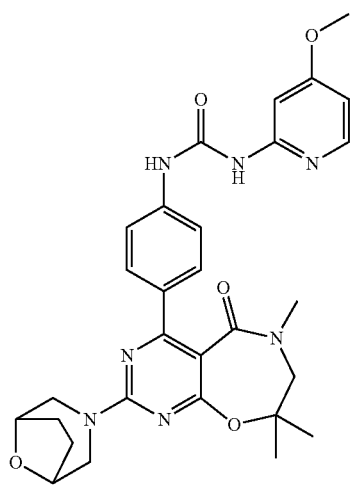 [SMILES: COc1ccnc(NC(=O)Nc2ccc(-c3nc(N4CC5CCC(C4)O5)nc4c3C(=O)N(C)CC(C)(C)O4)cc2)c1]

210 mg (0.51 mmol) of 4-(4-aminophenyl)-6,8,8-trimethyl-2-(8-oxa-3-azabicyclo[3.2.1]oct-3-yl)-7,8-dihydro-6H-9-oxa-1,3,6-triazabenzocyclohepten-5-one and 314.5 mg (3 mmol) of triethylamine are added to 3 ml of DCM. This mixture is then added under nitrogen to a solution containing 152.2 mg (0.51 mmol) of triphosgene in 3 ml of DCM. The mixture is stirred at room temperature for 30 minutes, and 268.1 mg (2 mmol) of 2-amino-4-methoxypyridine are then added. This mixture is stirred for 2 hours at room temperature, extracted with DCM, washed once with water and then with saturated NaCl solution, and the organic phase is dried over Na$_2$SO$_4$. The resulting phase is filtered and the filtrate is evaporated under reduced pressure. The residue is chromatographed on silica gel, eluting with a DCM/MeOH mixture from (100/0 v/v) up to (100/4 v/v). The solid obtained is then taken up in a DCM/MeOH/pentane mixture, filtered off and dried to give 85 mg of 1-(4-methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea.

LC/MS (method C): M+H$^+$=560; Tr=0.55 min $^1$H NMR (600 MHz, DMSO-d$_6$) δ ppm 9.42 (s, 1H); 8.11 (d, 1H); 7.50-7.54 (m, 4H); 7.10 (s, 1H); 6.64 (d, 1H); 4.41 (s, 2H); 4.10-4.40 (bs, 2H); 3.81 (s, 3H); 3.70 (s, 2H); 3.07-3.13 (m, 5H); 1.80-1.84 (m, 2H); 1.62-1.68 (m, 2H); 1.35 (s, 6H)

EXAMPLE 22

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(1-methylpiperidin-4-yloxy)pyridin-3-yl]urea

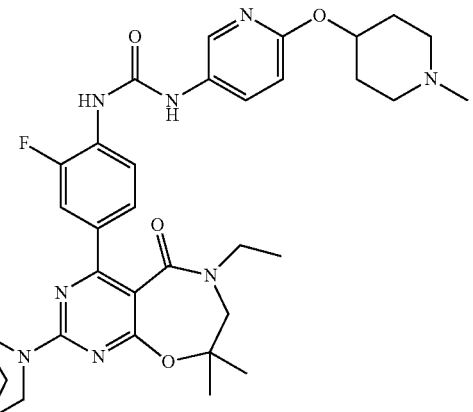

Step 22.1

2-(1-Methylpiperidin-4-yloxy)-5-nitropyridine

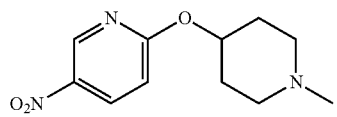 [SMILES: CN1CCC(Oc2ccc([N+](=O)[O-])cn2)CC1]

557 mg of NaH (14 mmol) suspended in 10 ml of THF are placed under nitrogen. The mixture is cooled to 0° C. and a solution of 1.5 g (9.3 mmol) of 2-chloro-5-nitropyridine and 1.28 g (11.1 mmol) of 4-hydroxy-1-methylpiperidine in 15 ml of THF is added dropwise. The reaction mixture is refluxed for 4 hours. After hydrolysing the excess NaH, the solvent is evaporated off under reduced pressure. The residue is taken up in ethyl acetate and washed with water and then with saturated NaCl solution. It is then dried over Na$_2$SO$_4$ and filtered, and the filtrate is evaporated under reduced pressure. The residue is chromatographed on silica gel, eluting with a DCM/MeOH mixture from (100/0 v/v) up to 100/4 v/v) to give 1.1 g of 2-(1-methylpiperidin-4-yloxy)-5-nitropyridine.

LC/MS (method E): M+H$^+$=238; Tr=0.79 min

Step 22.2

6-(1-Methylpiperidin-4-yloxy)pyridin-3-ylamine

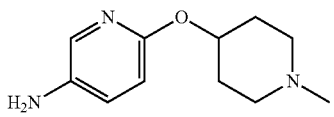

1.05 g of the compound obtained in step 20.1 are dissolved in 90 ml of MeOH and then hydrogenated at atmospheric pressure at 35° C. over 10% Pd/C. The medium is filtered and then evaporated under reduced pressure to give 860 mg of 6-(1-methylpiperidin-4-yloxy)pyridin-3-ylamine.

Step 22.3: (Which Corresponds to Step m) (Steps m1-1) and m1-2))

1-{4-[6-Ethyl-8,8-dimethyl-2-(8-oxa-3-azabicyclo [3.2.1]oct-3-yl)-5-oxo-5,6,7,8-tetrahydro-9-oxa-1,3, 6-triazabenzocyclohepten-4-yl]-2-fluorophenyl}-3-[6-(1-methylpiperidin-4-yloxy)pyridin-3-yl]urea

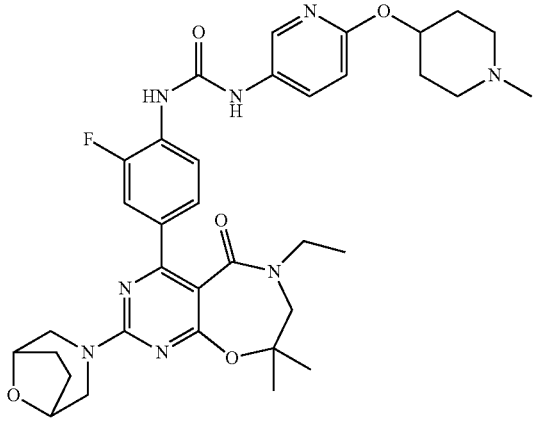 [SMILES: CCN1CC(C)(C)Oc2nc(N3CC4CCC(C3)O4)nc(-c3ccc(NC(=O)Nc4ccc(OC5CCN(C)CC5)nc4)c(F)c3)c2C1=O]

130 mg (0.29 mmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one and 180.6 mg (1.8 mmol) of triethylamine are placed in 3 ml of DCM. This mixture is then added under nitrogen to a solution containing 87.4 mg (0.29 mmol) of triphosgene in 3 ml of DCM. The resulting mixture is stirred at room temperature for 30 minutes, followed by addition of 244.1 mg (1.18 mmol) of the compound described in step 21.2. The resulting mixture is stirred for 2 hours at room temperature. This mixture is extracted with DCM, washed once with water and then with saturated NaCl solution, and the organic phase is dried over $Na_2SO_4$. The resulting phase is filtered and the filtrate is evaporated under reduced pressure. The residue is chromatographed on silica gel, eluting with a DCM/MeOH mixture from (100/0 v/v) up to (100/20 v/v). The solid obtained is then taken up in a DCM/pentane mixture, filtered off and dried to give 90 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(1-methylpiperidin-4-yloxy)pyridin-3-yl]urea.

LC/MS (method C): M+H$^+$=675; Tr=0.53 min $^1$H NMR (300 MHz, DMSO-d$_6$) δ ppm 9.03 (s, 1H); 8.80 (d, 1H); 8.15 (d, 1H); 8.13 (t, 1H); 7.84; (dd, 1H); 7.40 (dd, 1H); 7.29 (dd, 1H); 6.75 (d, 1H); 4.89 (m, 1H); 4.02-4.47 (m, 4H); 3.68 (s, 2H); 3.53 (bs, 2H); 3.08 (m, 2H); 2.63 (m, 2H); 2.17 (s, 3H); 2.12 (m, 2H); 1.93 (m, 2H); 1.81 (m, 2H); 1.65 (m, 4H); 1.34 (s, 6H); 1.14 (t, 3H)

EXAMPLE 23

(Which Corresponds to Step m) (Steps m1-1) and m1-2))

Synthesis of 1-[4-(4-dimethylaminopiperidine-1-carbonyl)phenyl]-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl] phenyl}urea

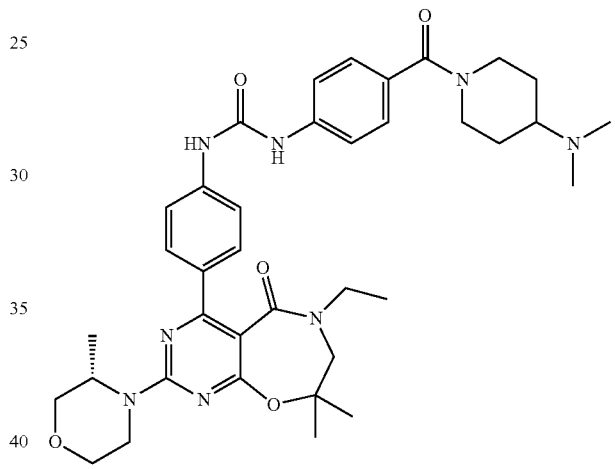

130 mg (316 μmol) of 4-(4-aminophenyl)-6-ethyl-8,8-dimethyl-2-((S)-3-methylmorpholin-4-yl)-7,8-dihydro-6H-9-oxa-1,3,6-triazabenzocyclohepten-5-one suspended in 3 ml of dioxane are heated at 50° C. for 30 minutes in the presence of 233 μl of a 1.9 M solution of phosgene in toluene (442.3 mmol) and 75 μl (442.3 mmol) of DIEA. 391 mg (1.58 mmol) of (4-aminophenyl)-(4-dimethylaminopiperidin-1-yl) methanone are then added. The medium is stirred for 16 hours at room temperature. The mixture is evaporated under reduced pressure and the residue is taken up in water and extracted with DCM. The organic phase is washed twice with water, dried over MgSO$_4$ and then filtered. The filtrate is evaporated under reduced pressure and the residue is then chromatographed on silica gel, eluting with a DCM/MeOH mixture from (100/0 v/v) up to (93/7 v/v). The product obtained is dissolved in a minimum amount of DCM and then reprecipitated from Et$_2$O to give 61 mg of 1-[4-(4-dimethylaminopiperidine-1-carbonyl)phenyl]-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl] phenyl}urea.

LC/MS (method C): M+H$^+$=685; Tr=0.52 min $^1$H NMR (600 MHz, DMSO-d$_6$) δ ppm 8.94 (s, 2H); 7.51 (d, 2H); 7.48 (m, 4H); 7.34 (d, 2H); 4.66 (m, 1H); 4.35 (m, 2H); 3.91 (m, 1H); 3.71 (m, 1H); 3.67 (m, 2H); 3.57 (m, 1H);

3.52 (m, 2H); 3.42 (m, 1H); 3.19 (m, 1H); 2.89 (bs, 2H); 2.32 (m, 1H); 2.18 (s, 6H); 1.75 (m, 2H); 1.33 (m, 8H); 1.22 (m, 3H); 1.16 (t, 3H)

EXAMPLE 24

(Which Corresponds to Step m) (Steps m1-1) and m1-2))

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-hydroxy-2-methylpropyl)urea

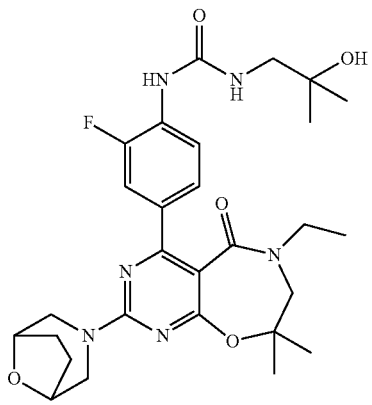 [SMILES: CCN1CC(C)(C)Oc2nc(N3CC4CCC(C3)O4)nc(-c3ccc(NC(=O)NCC(C)(C)O)c(F)c3)c2C1=O]

100 mg (226.5 µmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one suspended in 2 ml of dioxane are heated at 50° C. for 30 minutes in the presence of 179 µl of a 1.9 M solution of phosgene (339.75 µmol) in toluene and 58 µl (339.5 µmol) of DIEA. 101 mg (1.13 mmol) of 2-hydroxy-2-methylpropylamine dissolved in 1 ml of dioxane are then added. The reaction medium is stirred for 16 hours at room temperature and then diluted with water. The precipitate formed is filtered off and washed with water and then with ether. The solid obtained is dissolved in a minimum amount of DCM and then reprecipitated from ether to give 66 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-hydroxy-2-methylpropyl)urea.

LC/MS (method C): M+H⁺=557; Tr=0.62 min $^1$H NMR (600 MHz, DMSO-$d_6$) δ ppm 8.66 (s, 1H); 8.16 (t, 1H); 7.35 (d, 1H); 7.23 (d, 1H); 6.80 (t, 1H); 4.49 (m, 1H); 4.41 (m, 2H); 4.2 (bs, 2H); 3.66 (m, 2H); 3.52 (bs, 2H); 3.09 (m, 2H); 3.05 (m, 2H); 1.81 (m, 2H); 1.65 (m, 2H); 1.34 (s, 6H); 1.14 (t, 3H); 1.09 (s, 6H)

EXAMPLE 25

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-pyrrolidin-1-ylpyridin-2-yl)urea

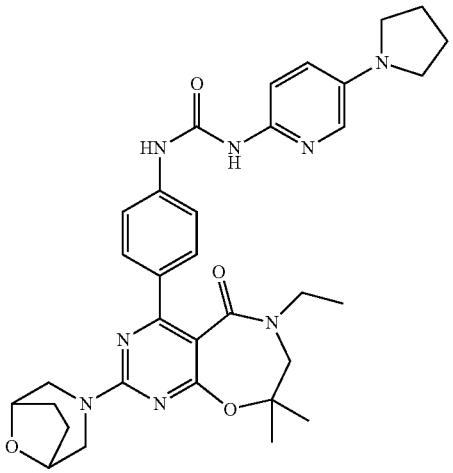 [SMILES: CCN1CC(C)(C)Oc2nc(N3CC4CCC(C3)O4)nc(-c3ccc(NC(=O)Nc4ccc(N5CCCC5)cn4)cc3)c2C1=O]

Step 25.1

2-Nitro-5-pyrrolidin-1-ylpyridine

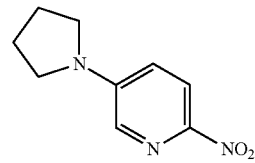 [SMILES: Nc1ccc(N2CCCC2)cn1]

A mixture of 600 mg (2.93 mmol) of 5-bromo-2-nitropyridine and 1.05 g (14.63 mmol) of pyrrolidine is heated in a Biotage microwave machine for 1 hour at 120° C. The reaction medium is diluted with water and then extracted with ethyl acetate. The organic phase is washed twice with water, dried over MgSO$_4$ and then filtered. The filtrate is evaporated under reduced pressure and then chromatographed on silica gel, eluting with a heptane/ethyl acetate mixture from (100/0 v/v) up to (50/50 v/v) to give 410 mg of 2-nitro-5-pyrrolidin-1-ylpyridine.

Step 25.2

5-Pyrrolidin-1-ylpyridin-2-ylamine

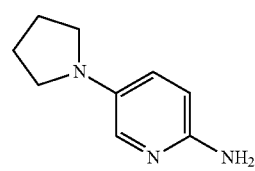

410 mg (2.12 mmol) of the product obtained in step 25.1 are hydrogenated in the presence of 10% Pd/C at atmospheric pressure at 35° C. The solution obtained is evaporated under reduced pressure to give 321 mg of 5-pyrrolidin-1-ylpyridin-2-ylamine.

Step 25.3: (Which Corresponds to Step m) (Steps m1-1) and m1-2))

1-{4-[6-Ethyl-8,8-dimethyl-2-(8-oxa-3-azabicyclo [3.2.1]oct-3-yl)-5-oxo-5,6,7,8-tetrahydro-9-oxa-1,3, 6-triazabenzocyclohepten-4-yl]phenyl}-3-(5-pyrrolidin-1-ylpyridin-2-yl)urea

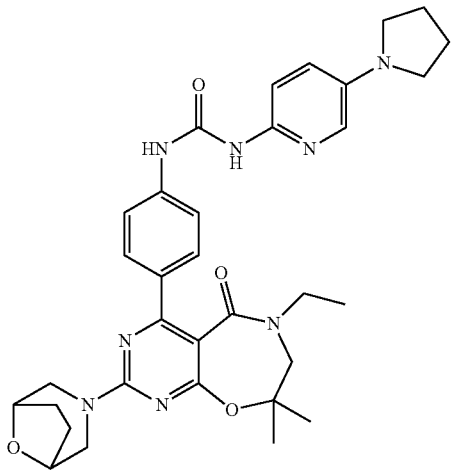 [SMILES: CCN1CC(C)(C)Oc2nc(N3CC4CCC(C3)O4)nc(-c3ccc(NC(=O)Nc4ccc(N5CCCC5)cn4)cc3)c2C1=O]

120 mg (223 μmol) of 4-(4-aminophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one 2,2,2-trifluoroacetic salt are extracted in carbonate medium with DCM and the free base obtained is then heated in dioxane at 50° C. for 30 minutes in the presence of 177 μl of a 1.9 M solution of phosgene (334.9 μmol) in toluene and 56 μl (893 μmol) of DIEA. 146 mg (893 μmol) of 5-pyrrolidin-1-ylpyridin-2-ylamine obtained in step 25.2 are then added and the reaction medium is stirred for 16 hours at room temperature. The medium is evaporated under reduced pressure and the residue is taken up in water and extracted with DCM. The organic phase is washed twice with water, dried over MgSO₄ and then filtered. The filtrate is evaporated under reduced pressure and the residue is then chromatographed on silica gel, eluting with a DCM/MeOH mixture from (100/0 v/v) up to (95/5 v/v) to give 68 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-pyrrolidin-1-ylpyridin-2-yl)urea.

LC/MS (method C): M+H⁺=613; Tr=0.63 min

¹H NMR (600 MHz, DMSO-d₆) δ ppm 10.42 (bs, 1H); 9.02 (bs, 1H); 7.64 (m, 1H); 7.44 (m, 4H); 7.39 (m, 1H); 7.05 (m, 1H); 4.30 (bs, 4H); 3.66 (s, 2H); 3.50 (bs, 2H); 3.22 (m, 4H); 3.10 (m, 2H); 1.95 (m, 4H); 1.82 (m, 2H); 1.66 (m, 2H); 1.35 (s, 6H); 1.16 (t, 3H)

EXAMPLE 26

Synthesis of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-methylphenyl}-3-isoxazol-3-ylurea

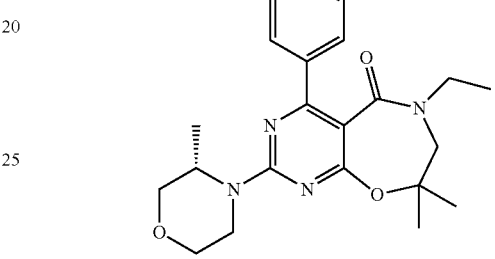

Step 26.1: (Which Corresponds to Step k))

{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-methylphenyl}carbamic acid tert-butyl ester

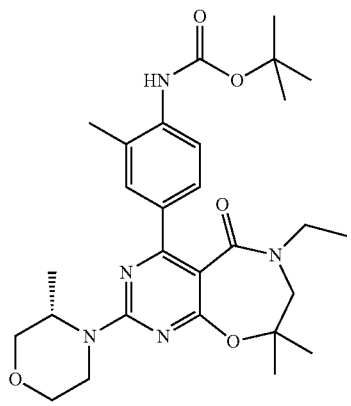 [SMILES: CCN1CC(C)(C)Oc2nc(N3CCOC[C@@H]3C)nc(-c3ccc(NC(=O)OC(C)(C)C)c(C)c3)c2C1=O]

A mixture of 1 g (2.13 mmol) of trifluoromethanesulfonic acid 6-ethyl-8,8-dimethyl-2-((S)-3-methylmorpholin-4-yl)-5-oxo-5,6,7,8-tetrahydro-9-oxa-1,3,6-triazabenzocyclohepten-4-yl ester, 711.35 mg (2.13 mmol) of [2-methyl-4-(4,4,5,5-tetramethyl-[1,3,2]dioxaborolan-2-yl)phenyl]carbamic acid tert-butyl ester, 906.25 mg (4.27 mmol) of tribasic potassium phosphate, 149.83 mg (213.47 μmol) of bis(triphenylphosphine)palladium(II) chloride in 10 ml of dioxane and 3 ml of water is heated in a Biotage microwave machine at 100° C. for 30 minutes. The reaction medium is diluted in 250 ml of ethyl acetate and filtered through Celite. The organic phase is dried over MgSO₄. The filtrate is evaporated under reduced pressure. The residue is taken up in 30 ml of heptane, brought to reflux and filtered while hot to give 1.24 g of {4-[6-ethyl-8,8-dimethyl-2-((S)-3-methylmorpholin-4-yl)-5-oxo-5,6,7,8-tetrahydro-9-oxa-1,3,6-triaza benzocyclohepten-4-yl]-2-methylphenyl}carbamic acid tert-butyl ester.

Step 26.2: (Which Corresponds to Step l))

4-(4-Amino-3-methylphenyl)-6-ethyl-8,8-dimethyl-2-((S)-3-methylmorpholin-4-yl)-7,8-dihydro-6H-9-oxa-1,3,6-triazabenzocyclohepten-5-one

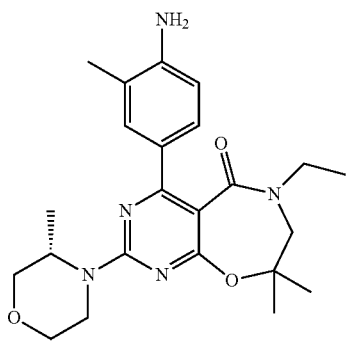 [SMILES: CCN1CC(C)(C)Oc2nc(N3CCOC[C@@H]3C)nc(-c3ccc(N)c(C)c3)c2C1=O]

A mixture of 1.24 g (2.36 mmol) of the compound described in step 26.1 and 5 ml (64.90 mmol) of TFA in 15 ml of DCM is stirred for 45 minutes at room temperature. The reaction medium is evaporated under reduced pressure, taken up in 10% and Na₂CO₃ solution and filtered. The precipitate is purified by chromatography on silica gel, eluting with a DCM/ethyl acetate mixture from (100/0 v/v) up to (95/5 v/v) to give 720 mg of 4-(4-amino-3-methylphenyl)-6-ethyl-8,8-dimethyl-2-((S)-3-methylmorpholin-4-yl)-7,8-dihydro-6H-9-oxa-1,3,6-triazabenzocyclohepten-5-one.

Step 26.3: (Which Corresponds to Step m) (Steps m1-1) and m1-2))

1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-methylphenyl}-3-isoxazol-3-ylurea

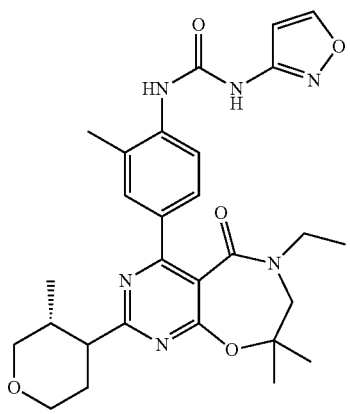 [SMILES: CCN1CC(C)(C)Oc2nc(C3CCOC[C@@H]3C)nc(-c3ccc(NC(=O)Nc4ccon4)c(C)c3)c2C1=O]

160.40 mg (540.51 μmol) of triphosgene are added to a mixture of 230 mg (540.51 μmol) of the compound described in step 26.2 and 452.02 μl (3.24 mmol) of triethylamine in 10 ml of DCM, under argon. The mixture is stirred for 45 minutes at room temperature, and 199.67 μl (2.70 mmol) of isoxazol-3-ylamine are then added. This mixture is stirred overnight at room temperature and the reaction medium is then poured into water. The resulting mixture is extracted with DCM and washed with saturated NaCl solution. The organic phase is dried over MgSO₄, filtered and evaporated under reduced pressure. The residue is purified by chromatography on silica gel, eluting with a DCM/EtOAc mixture from (100/0 v/v) up to 95/5 v/v) to give 39 mg of 1-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-methylphenyl}-3-isoxazol-3-ylurea.

LC/MS (method C): M+H⁺=536; Tr=0.70 min

¹H NMR (600 MHz, DMSO-d₆) δ ppm 10.03 (s, 1H); 9.34 (s, 1H); 9.35 (s, 1H); 7.94 (m, 1H); 7.34-7.39 (m, 2H); 6.83 (d, 1H); 4.65 (s, 1H); 4.30-4.35 (m, 1H); 3.92 (dd, 1H); 3.65-3.73 (m, 3H); 3.58 (dd, 1H); 3.52 (m, 2H); 3.40-3.44 (m, 1H); 3.16-3.22 (m, 1H); 2.26 (s, 3H); 1.36 (s, 6H); 1.22 (d, 3H); 1.16 (t, 3H)

EXAMPLE 27

(Which Corresponds to Step m) (Steps m1-1) and m1-2))

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-((R)-2-hydroxy-1-methylethyl)urea

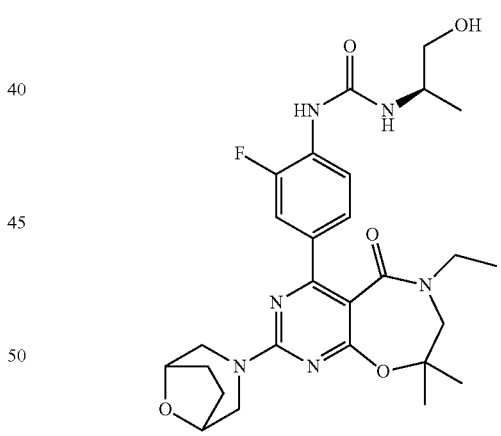

A mixture of 134.43 mg (0.45 mmol) of triphosgene, 200 mg (0.45 mmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one and 275.04 mg (2.72 mmol) of triethylamine in 50 ml of DCM is stirred at room temperature for 30 minutes. 138.88 mg (1.81 mmol) of (R)-2-aminopropan-1-ol are then added and the mixture is stirred at room temperature for 2 hours. The resulting mixture is hydrolysed with 5 ml of water and the solvent is then evaporated off under reduced pressure. The product is precipitated by addition of ethyl acetate/water. The product is filtered off and solvents are evaporated off under reduced pressure to give 68 mg of 1-{4-[6-ethyl-8,8-dimethyl-2-(8- oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-((R)-2-hydroxy-1-methylethyl)urea.

LC/MS (method C): M+H⁺=544; Tr=0.64 min

¹H NMR (600 MHz, DMSO-d₆) δ ppm 8.49 (bs, 1H); 8.16 (t, 1H); 7.35 (d, 1H); 7.24 (d, 1H); 6.70 (d, 1H); 3.78 (t, 1H); 4.42 (bs, 4H); 3.70 (m, 1H); 3.68 (s, 2H); 3.5 (bs, 2H); 3.37 (m, 2H); 3.1 (bs, 2H); 1.72 (bs, 2H); 1.66 (bs, 2H); 1.35 (bs, 6H); 1.15 (t, 3H); 1.08 (d, 3H)

EXAMPLE 28

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyrazin-2-yl)urea

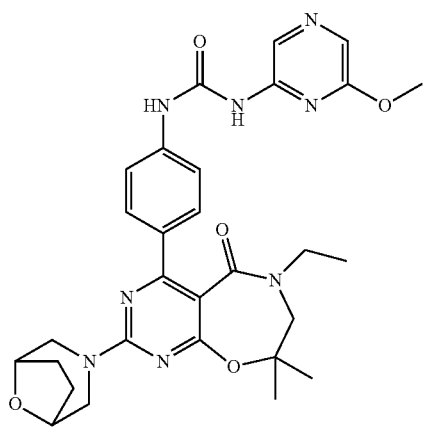 [SMILES: CCN1CC(C)(C)Oc2nc(N3CC4CCC(C3)O4)nc(-c3ccc(NC(=O)Nc4cncc(OC)n4)cc3)c2C1=O]

Step 28.1: (Preparation of a Compound of Formula (CIII))

1-(6-Methoxypyrazin-2-yl)-3-[4-(4,4,5,5-tetramethyl-[1,3,2]dioxaborolan-2-yl)phenyl]urea

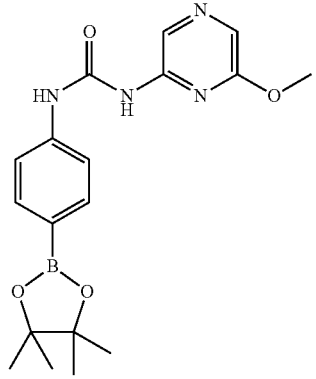

A mixture of 350 mg (1.60 mmol) of 4-(4,4,5,5-tetramethyl-[1,3,2]dioxaborolan-2-yl)phenylamine and 1.35 ml (9.59 mmol) of triethylamine in 10 ml of DCM is added, under nitrogen, to a solution of 474.07 mg (1.60 mmol) of triphosgene in 30 ml of DCM. The mixture is stirred for 30 minutes at room temperature, followed by addition of 1 g (7.99 mmol) of 6-methoxypyrazin-2-amine. The resulting mixture is stirred for 2 hours at room temperature. Water is added and the product is extracted with DCM. The solution is dried over MgSO₄ and then filtered. The filtrate is evaporated under reduced pressure and the residue is then chromatographed on silica gel, eluting with a DCM/MeOH mixture from (100/0 v/v) up to (96/4 v/v). The solvent is evaporated off under reduced pressure. The residue is taken up in ethyl acetate and washed three times with 1N hydrochloric acid solution and then with saturated NaCl solution. The resulting solution is dried over MgSO₄. 167 mg of 1-(6-methoxypyrazin-2-yl)-3-[4-(4,4,5,5-tetramethyl-[1,3,2]dioxaborolan-2-yl)phenyl]urea are obtained.

LC/MS (method E): M+H⁺=371; Tr=2.46 min

Step 28.2: (Which Corresponds to Step n))

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyrazin-2-yl)urea

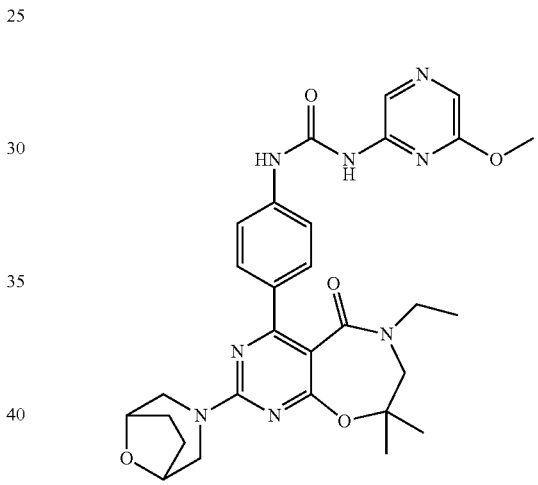

A mixture of 167 mg (0.451 mmol) of the compound described in step 28.1, 216 mg (0.451 mmol) of trifluoromethanesulfonic acid 6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl ester, 197 mg (0.902 mmol) of tripotassium phosphate and 32 mg (0.045 mmol) of bis(triphenylphosphine)palladium (II) chloride in 5 ml of water and 15 ml of dioxane is heated in a Biotage microwave machine at 100° C. for 20 minutes. The reaction mixture is evaporated under reduced pressure and the residue is then chromatographed on silica gel, eluting with a DCM/MeOH mixture from (100/0 v/v) up to (96/4 v/v). The product is taken up in EtOH and then filtered through a Millipore filter to give 85 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methoxypyrazin-2-yl)urea.

LC/MS (method C): M+H⁺=575; Tr=0.70 min

¹H NMR (600 MHz, DMSO-d₆) δ ppm 9.47 (s, 1H) 9.37 (s, 1H); 8.68 (s, 1H); 7.92 (s, 1H); 7.5 (m, 4H); 4.15-4.4 (bs, 4H);

3.95 (s, 3H); 3.65 (bs, 4H); 3.1 (d, 2H); 1.82 (bs, 2H); 1.65 (bs, 2H); 1.37 (s, 6H); 1.17 (t, 3H)

EXAMPLE 29

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((S)-3-methylmorpholin-4-yl)pyridin-3-yl]urea

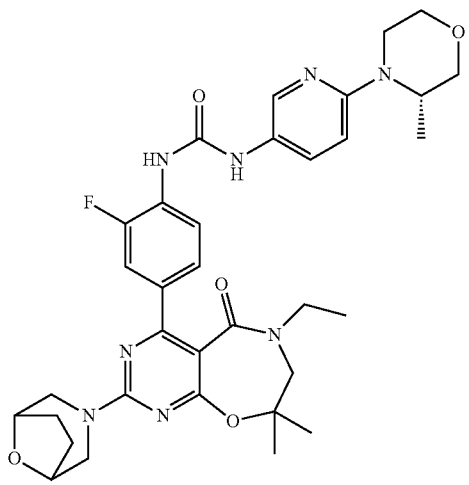 [SMILES: CCN1CC(C)(C)Oc2nc(N3CC4CCC(C3)O4)nc(-c3ccc(NC(=O)Nc4ccc(N5CCOC[C@@H]5C)nc4)c(F)c3)c2C1=O]

Step 29.1

(S)-3-Methyl-4-(5-nitropyridin-2-yl)morpholine

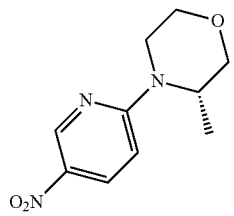 [SMILES: C[C@H]1COCCN1c1ccc([N+](=O)[O-])cn1]

A mixture of 1 g (6.18 mmol) of 2-chloro-5-nitropyridine and 1.31 g (12.36 mmol) of (S)-3-methylmorpholine is heated in a Biotage microwave machine for 1 hour at 150° C. The reaction medium is taken up in MeOH and then evaporated under reduced pressure. The residue is chromatographed on silica gel, eluting with a DCM/MeOH mixture from (100/0 v/v) up to (95/5 v/v) to give 1.35 g of (S)-3-methyl-4-(5-nitropyridin-2-yl)morpholine.

LC/MS (method E): M+H$^+$=224; Tr=1.72 min

Step 29.2

6-((S)-3-Methylmorpholin-4-yl)pyridin-3-ylamine

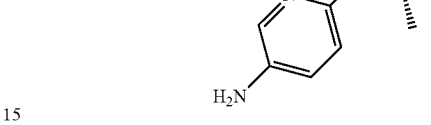

1.35 g (6 mmol) of the product obtained in step 29.1 are hydrogenated in the presence of 10% Pd/C at atmospheric pressure at 50° C. The solution obtained is evaporated under reduced pressure to give 1.17 g of 6-((S)-3-Methylmorpholin-4-yl)pyridin-3-ylamine.

LC/MS (method E): M+H$^+$=194; Tr=0.45 min

Step 29.3: (Which Corresponds to Step m) (Steps m1-1) and m1-2))

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((S)-3-methylmorpholin-4-yl)pyridin-3-yl]urea 150 mg (0.34 mmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one and 287.20 µl (2.04 mmol) of triethylamine are placed in 3 ml of DCM. This mixture is then added under nitrogen to a solution containing 100 mg (0.34 mmol) of triphosgene in 3 ml of DCM. The resulting mixture is stirred at room temperature for 30 minutes, followed by addition of 262.62 mg (1.36 mmol) of the compound described in step 29.2. This mixture is stirred for 2 hours at room temperature and is then extracted with DCM. The organic phase is washed once with water and with saturated NaCl solution. The organic phase is dried over Na$_2$SO$_4$, filtered and evaporated under reduced pressure. The residue is chromatographed on silica gel, eluting with a DCM/MeOH mixture from (100/0 v/v) up to (98/2 v/v). The solid obtained is then washed twice with EtOH and taken up in an ethyl acetate/pentane mixture (10/90), filtered and dried to give 72 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((S)-3-methylmorpholin-4-yl)pyridin-3-yl]urea.

LC/MS (method C): M+H$^+$=661; Tr=0.59 min $^1$H NMR (600 MHz, DMSO-d$_6$) δ ppm 8.9 (s, 1H); 8.73 (s, 1H); 8.15 (m, 2H); 7.72 (dd, 1H); 7.4 (d, 1H); 7.28 (d, 1H); 6.75 (d, 1H); 4.4 (bs, 4H); 4.25 (m, 1H); 3.92 (dd, 1H); 3.68 (m, 5H); 3.5 (dt, 3H); 3.1 (m, 2H); 3.02 (m, 1H); 1.82 (bs, 2H); 1.65 (bs, 2H); 1.35 (s, 6H); 1.15 (t, 4H); 1.08 (d, 3H)

EXAMPLE 30

Synthesis of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((R)-3-methylmorpholin-4-yl)pyridin-3-yl]urea

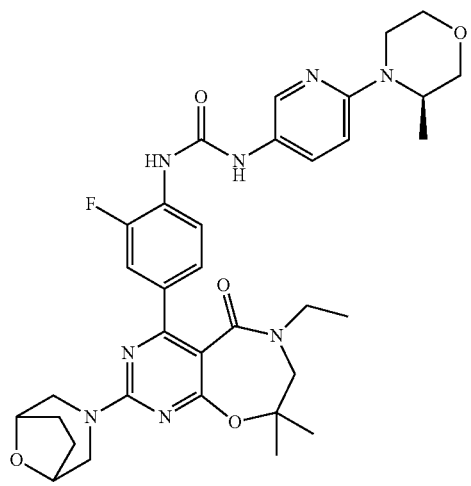 [SMILES: CCN1CC(C)(C)Oc2nc(N3CC4CCC(C3)O4)nc(-c3ccc(NC(=O)Nc4ccc(N5CCOC[C@H]5C)nc4)c(F)c3)c2C1=O]

Step 30.1

(R)-3-Methyl-4-(5-nitropyridin-2-yl)morpholine

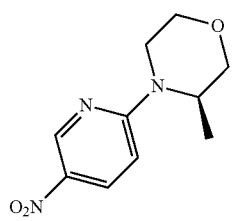

A mixture of 1 g (6.18 mmol) of 2-chloro-5-nitropyridine and 1.31 g (12.36 mmol) of (R)-3-methylmorpholine is heated in a Biotage microwave machine for 1 hour at 150° C. The reaction medium is taken up in MeOH and then evaporated under reduced pressure. The residue is chromatographed on silica gel, eluting with a DCM/MeOH mixture from (100/0 v/v) up to (95/5 v/v) to give 1.07 g of (R)-3-methyl-4-(5-nitro-pyridin-2-yl)-morpholine.

LC/MS (method E): M+H$^+$=224; Tr=1.72 min

Step 30.2

6-((R)-3-Methylmorpholin-4-yl)pyridin-3-ylamine

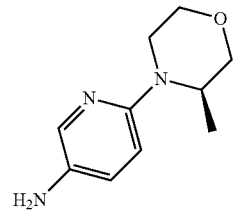 [SMILES: C[C@@H]1COCCN1c1ccc([N+](=O)[O-])cn1]

1.07 g (4.79 mmol) of the product obtained in step 30.1 are hydrogenated in the presence of 10% Pd/C at atmospheric pressure at 45° C. The solution obtained is evaporated under reduced pressure to give 840 mg of 6-((R)-3-methylmorpholin-4-yl)pyridin-3-ylamine.

LC/MS (method E): M+H$^+$=194; Tr=0.45 min

Step 30.3: (Which Corresponds to Step m) (Steps m1-1) and m1-2))

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((R)-3-methylmorpholin-4-yl)pyridin-3-yl]urea

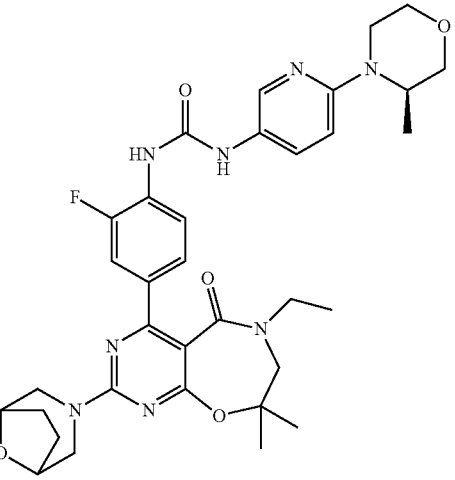

200 mg (453 μmol) of 4-(4-amino-3-fluorophenyl)-6-ethyl-8,8-dimethyl-2-(8-oxa-3-azabicyclo[3.2.1]oct-3-yl)-7,8-dihydro-6H-9-oxa-1,3,6-triazabenzocyclohepten-5-one and 287.20 μl (2.72 mmol) of triethylamine are placed in 3 ml of DCM. This mixture is then added under nitrogen to a solution containing 134 mg (453 μmol) of triphosgene in 3 ml of DCM. The resulting mixture is stirred at room temperature for 30 minutes, followed by addition of 350.16 mg (1.81 mmol) of the compound obtained in step 30.2. The resulting mixture is stirred for 2 hours at room temperature. The product is taken up in DCM and washed once with water and then with saturated NaCl solution. The organic phase is dried over Na$_2$SO$_4$. The resulting phase is filtered and the filtrate is evaporated under reduced pressure. The residue is chromatographed on silica gel, eluting with a DCM/MeOH mixture from (100/0 v/v) up to (98/2 v/v). The solid obtained is then washed twice with EtOH and taken up in an ethyl acetate/pentane mixture (10/90), filtered and dried over MgSO$_4$ to give 40 mg of 1-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((R)-3-methylmorpholin-4-yl)pyridin-3-yl]urea.

LC/MS (method C): M+H$^+$=661; Tr=0.59 min $^1$H NMR (600 MHz, DMSO-d$_6$) δ ppm 8.9 (s, 1H); 8.73 (s, 1H); 8.15 (m, 2H); 7.72 (dd, 1H); 7.4 (d, 1H); 7.28 (d, 1H); 6.75 (d, 1H); 4.4 (bs, 4H); 4.25 (m, 1H); 3.92 (dd, 1H); 3.68 (m, 5H); 3.5 (dt, 3H); 3.1 (m, 2H); 3.02 (m, 1H); 1.82 (bs, 2H); 1.65 (bs, 2H); 1.35 (s, 6H); 1.15 (t, 4H); 1.08 (d, 3H)

Table 3 below illustrates the chemical structures and physical properties of a number of examples of compounds according to the invention.

TABLE 3

Chemical structures and physical properties of a number of examples of compounds according to the invention.

| Expl | Structure | Mass | Tr (min) | LC/MS method |
|---|---|---|---|---|
| 1 | 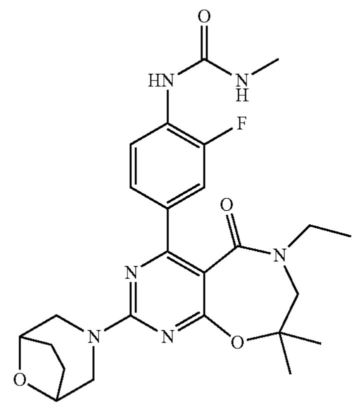 [SMILES: CCN1CC(C)(C)Oc2nc(N3CC4CCC(C3)O4)nc(-c3ccc(NC(=O)NC)c(F)c3)c2C1=O] | 499 | 0.9 | A |
| 2 | 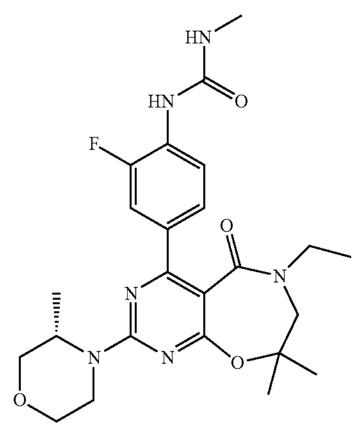 [SMILES: CCN1CC(C)(C)Oc2nc(N3CCOC[C@@H]3C)nc(-c3ccc(NC(=O)NC)c(F)c3)c2C1=O] | 487 | 0.91 | A |
| 3 | 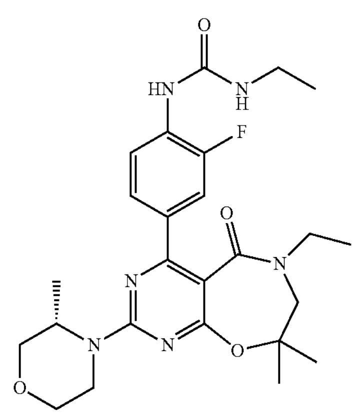 [SMILES: CCNC(=O)Nc1ccc(-c2nc(N3CCOC[C@@H]3C)nc3c2C(=O)N(CC)CC(C)(C)O3)cc1F] | 501 | 1.02 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 4 | 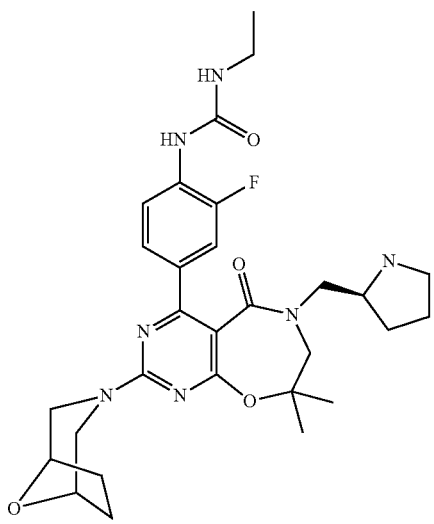 [SMILES: CCNC(=O)Nc1ccc(-c2nc(N3CC4CCC(C3)O4)nc3c2C(=O)N(C[C@@H]2CCCN2)CC(C)(C)O3)cc1F] | 568 | 0.76 | F |
| 5 | 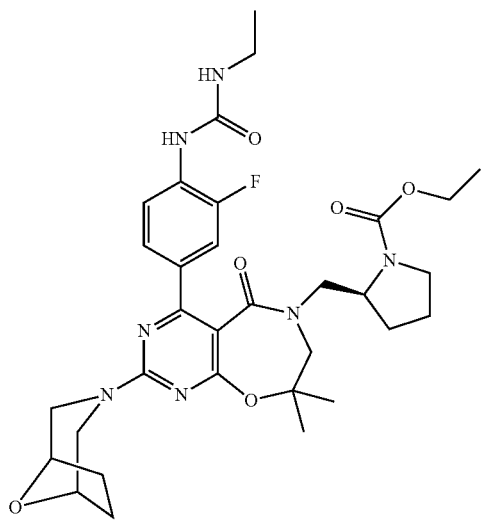 [SMILES: CCNC(=O)Nc1ccc(-c2nc(N3CC4CCC(C3)O4)nc3c2C(=O)N(C[C@@H]2CCCN2C(=O)OCC)CC(C)(C)O3)cc1F] | 640 | 1.08 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 6 | 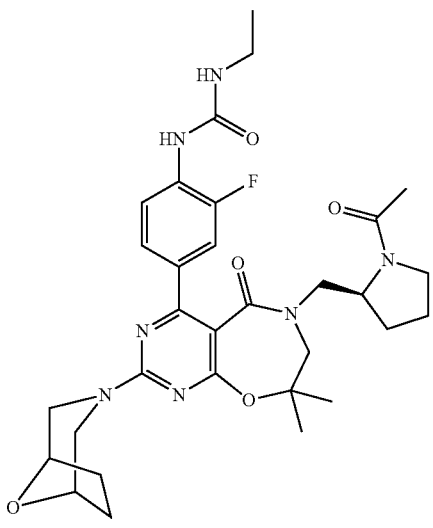 [SMILES: CCNC(=O)Nc1ccc(-c2nc(N3CC4CCC(C3)O4)nc3c2C(=O)N(C[C@@H]2CCCN2C(C)=O)CC(C)(C)O3)cc1F] | 610 | 0.91 | A |
| 7 | 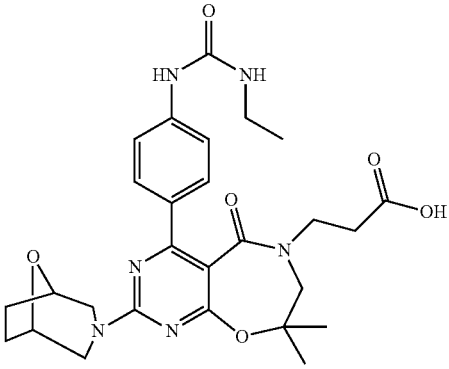 [SMILES: CCNC(=O)Nc1ccc(-c2nc(N3CC4CCC(C3)O4)nc3c2C(=O)N(CCC(=O)O)CC(C)(C)O3)cc1] | 539 | 0.86 | A |
| 8 | 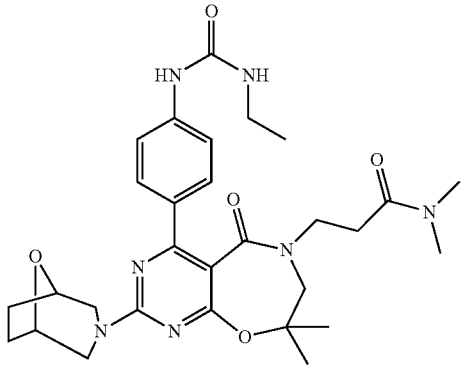 [SMILES: CCNC(=O)Nc1ccc(-c2nc(N3CC4CCC(C3)O4)nc3c2C(=O)N(CCC(=O)N(C)C)CC(C)(C)O3)cc1] | 566 | 0.86 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 9 | 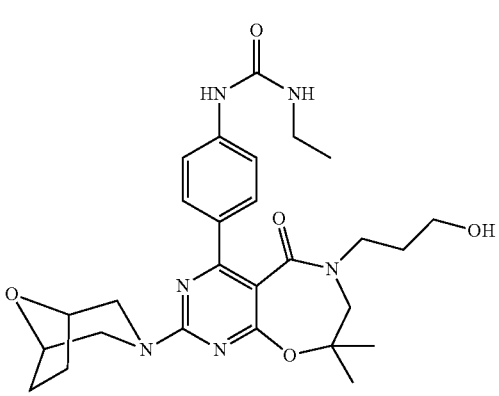 [SMILES: CCNC(=O)Nc1ccc(-c2nc(N3CC4CCC(C3)O4)nc3c2C(=O)N(CCCO)CC(C)(C)O3)cc1] | 525 | 0.82 | A |
| 10 | 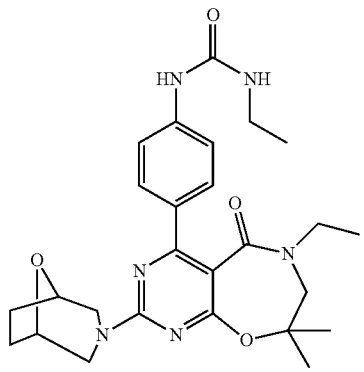 [SMILES: CCNC(=O)Nc1ccc(-c2nc(N3CC4CCC(C3)O4)nc3c2C(=O)N(CC)CC(C)(C)O3)cc1] | 509 | 0.96 | A |
| 11 | 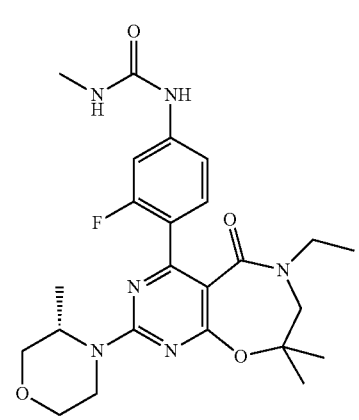 [SMILES: CCN1CC(C)(C)Oc2nc(N3CCOC[C@@H]3C)nc(-c3ccc(NC(=O)NC)cc3F)c2C1=O] | 487 | 0.64 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 12 | 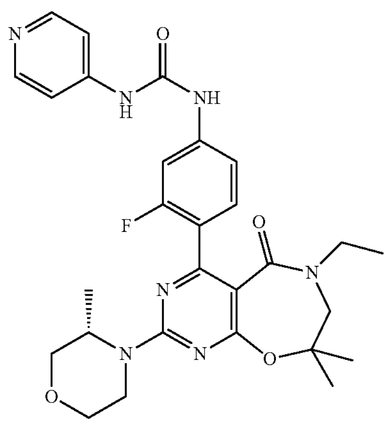 [SMILES: CCN1CC(C)(C)Oc2nc(N3CCOC[C@@H]3C)nc(-c3ccc(NC(=O)Nc4ccncc4)cc3F)c2C1=O] | 550 | 0.57 | C |
| 13 | 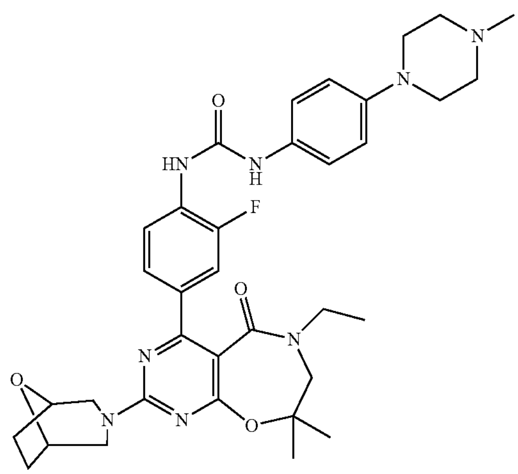 [SMILES: CCN1CC(C)(C)Oc2nc(N3CC4CCC(C3)O4)nc(-c3ccc(NC(=O)Nc4ccc(N5CCN(C)CC5)cc4)c(F)c3)c2C1=O] | 659 | 0.53 | C |
| 14 | 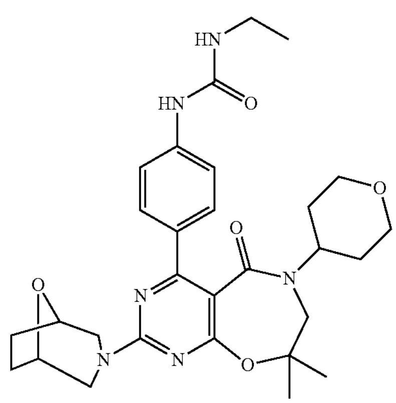 [SMILES: CCNC(=O)Nc1ccc(-c2nc(N3CC4CCC(C3)O4)nc3c2C(=O)N(C2CCOCC2)CC(C)(C)O3)cc1] | 551 | 0.61 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 15 | 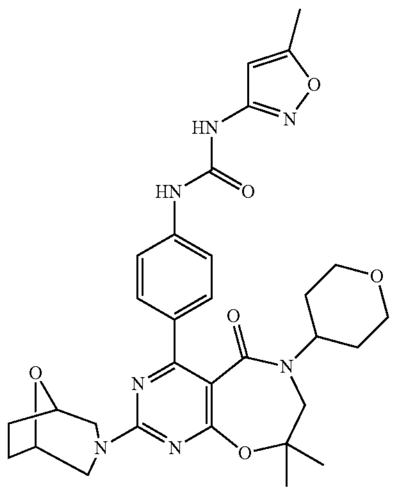 [SMILES: Cc1cc(NC(=O)Nc2ccc(-c3nc(N4CC5CCC(C4)O5)nc4c3C(=O)N(C3CCOCC3)CC(C)(C)O4)cc2)no1] | 604 | 0.68 | C |
| 16 | 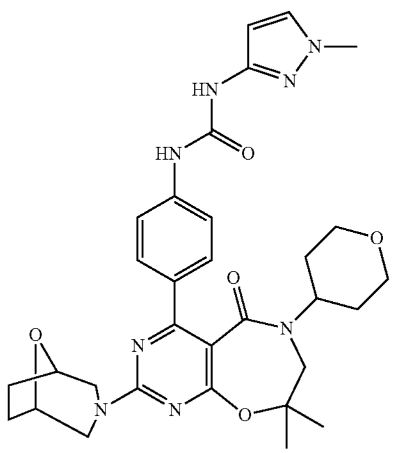 [SMILES: Cn1ccc(NC(=O)Nc2ccc(-c3nc(N4CC5CCC(C4)O5)nc4c3C(=O)N(C3CCOCC3)CC(C)(C)O4)cc2)n1] | 603 | 0.63 | C |
| 17 | 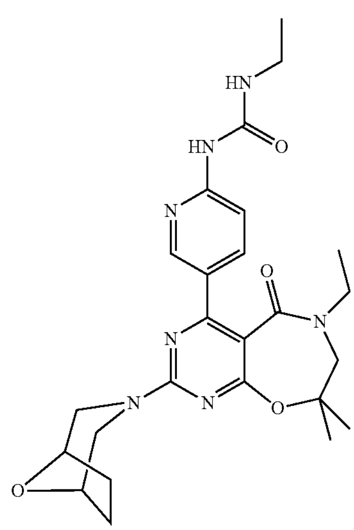 [SMILES: CCNC(=O)Nc1ccc(-c2nc(N3CC4CCC(C3)O4)nc3c2C(=O)N(CC)CC(C)(C)O3)cn1] | 496 | 0.59 | C |

TABLE 3-continued
Chemical structures and physical properties of a number of examples of compounds according to the invention.
| Expl | Structure | Mass | Tr (min) | LC/MS method |
|------|-----------|------|----------|--------------|
| 18 | 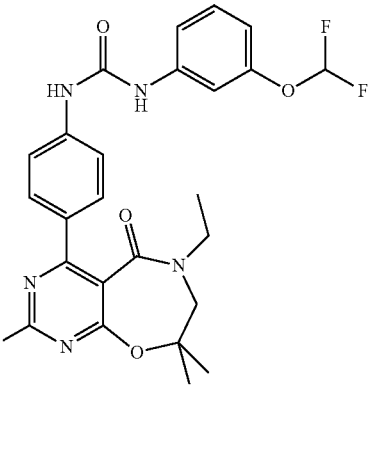 | 609 | 0.81 | C |
| 19 | 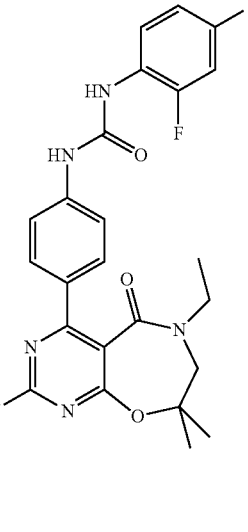 | 579 | 0.8 | C |
| 20 | 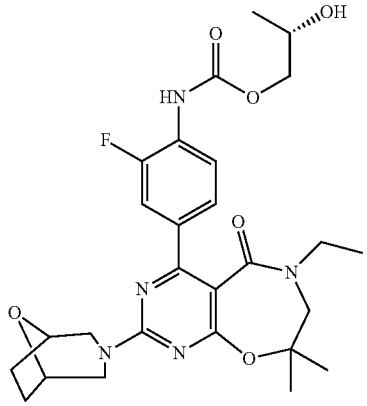 [SMILES: CCN1CC(C)(C)Oc2nc(N3CC4CCC(C3)O4)nc(-c3ccc(NC(=O)OC[C@H](C)O)c(F)c3)c2C1=O] | 544 | 0.64 | C |

TABLE 3-continued
Chemical structures and physical properties of a number of examples of compounds according to the invention.
| Expl | Structure | Mass | Tr (min) | LC/MS method |
|------|-----------|------|----------|--------------|
| 21 | 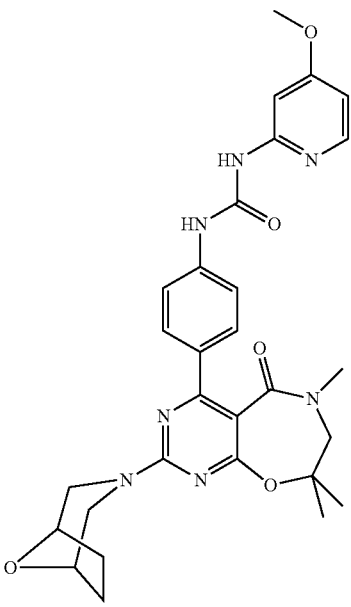 [SMILES: COc1ccnc(NC(=O)Nc2ccc(-c3nc(N4CC5CCC(C4)O5)nc4c3C(=O)N(C)CC(C)(C)O4)cc2)c1] | 560 | 0.55 | C |
| 22 | 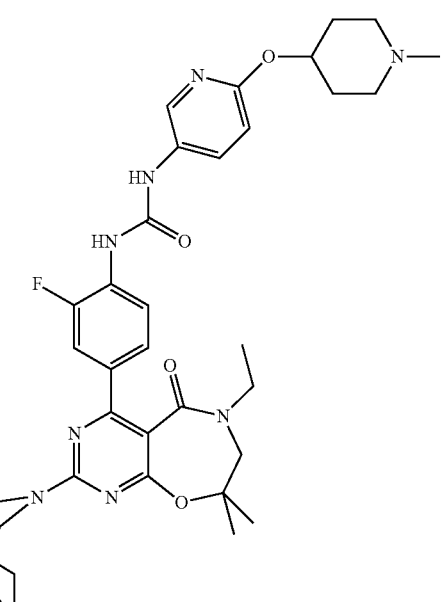 | 675 | 0.53 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 23 | 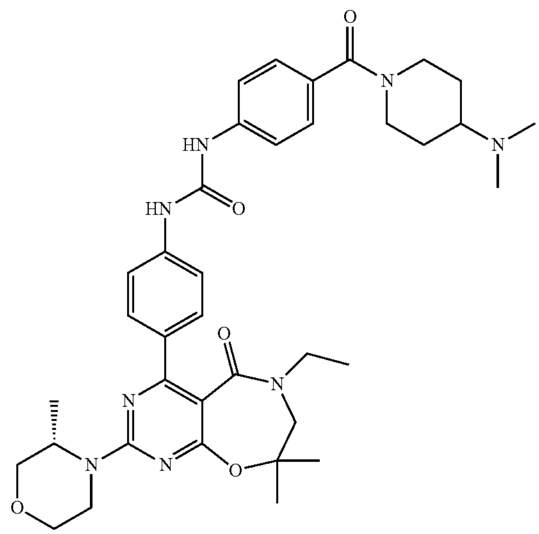 [SMILES: CCN1CC(C)(C)Oc2nc(N3CCOC[C@@H]3C)nc(-c3ccc(NC(=O)Nc4ccc(C(=O)N5CCC(N(C)C)CC5)cc4)cc3)c2C1=O] | 685 | 0.52 | C |
| 24 | 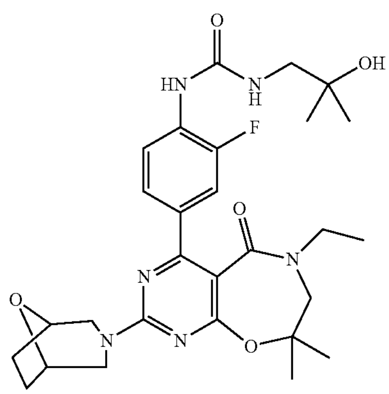 [SMILES: CCN1CC(C)(C)Oc2nc(N3CC4CCC(C3)O4)nc(-c3ccc(NC(=O)NCC(C)(C)O)c(F)c3)c2C1=O] | 557 | 0.62 | C |
| 25 | 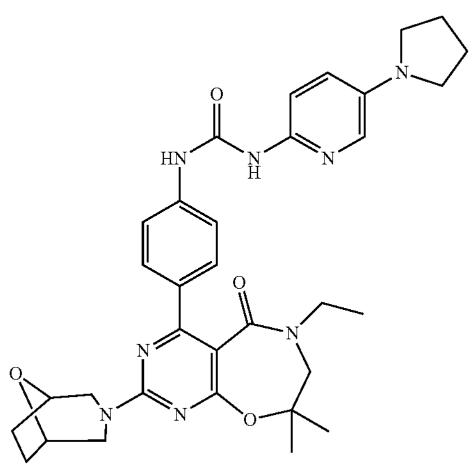 [SMILES: CCN1CC(C)(C)Oc2nc(N3CC4CCC(C3)O4)nc(-c3ccc(NC(=O)Nc4ccc(N5CCCC5)cn4)cc3)c2C1=O] | 613 | 0.63 | C |

TABLE 3-continued
Chemical structures and physical properties of a number of examples of compounds according to the invention.
| Expl | Structure | Mass | Tr (min) | LC/MS method |
|------|-----------|------|----------|--------------|
| 26 | 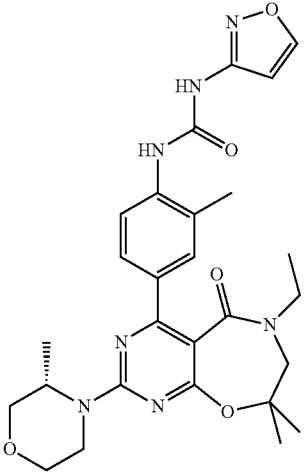 [SMILES: CCN1CC(C)(C)Oc2nc(N3CCOC[C@@H]3C)nc(-c3ccc(NC(=O)Nc4ccon4)c(C)c3)c2C1=O] | 536 | 0.7 | C |
| 27 | 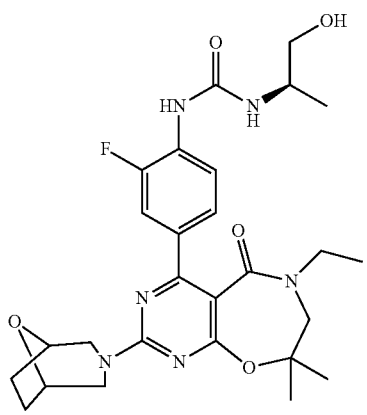 [SMILES: CCN1CC(C)(C)Oc2nc(N3CC4CCC(C3)O4)nc(-c3ccc(NC(=O)N[C@H](C)CO)c(F)c3)c2C1=O] | 543 | 0.6 | C |
| 28 | 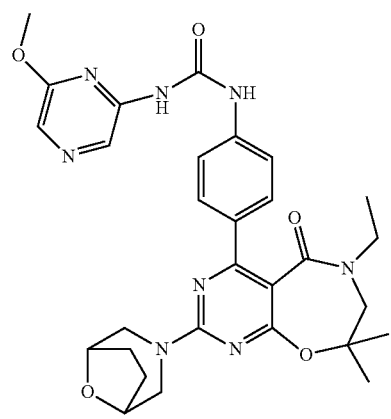 [SMILES: CCN1CC(C)(C)Oc2nc(N3CC4CCC(C3)O4)nc(-c3ccc(NC(=O)Nc4cncc(OC)n4)cc3)c2C1=O] | 575 | 0.7 | C |

TABLE 3-continued
Chemical structures and physical properties of a number of examples of compounds according to the invention.
| Expl | Structure | Mass | Tr (min) | LC/MS method |
|---|---|---|---|---|
| 29 | 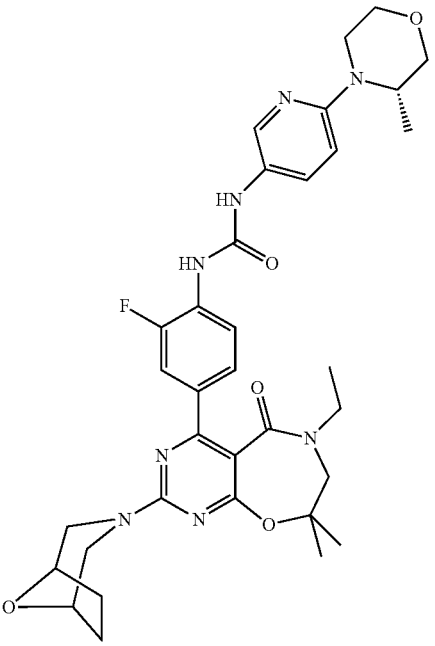 [SMILES: CCN1CC(C)(C)Oc2nc(N3CC4CCC(C3)O4)nc(-c3ccc(NC(=O)Nc4ccc(N5CCOC[C@@H]5C)nc4)c(F)c3)c2C1=O] | 661 | 0.59 | C |
| 30 | 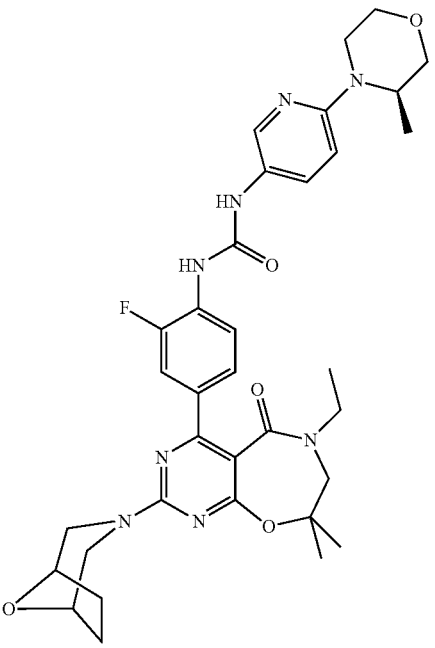 [SMILES: CCN1CC(C)(C)Oc2nc(N3CC4CCC(C3)O4)nc(-c3ccc(NC(=O)Nc4ccc(N5CCOC[C@H]5C)nc4)c(F)c3)c2C1=O] | 661 | 0.59 | C |

TABLE 3-continued
Chemical structures and physical properties of a number of examples of compounds according to the invention.
| Expl | Structure | Mass | Tr (min) | LC/MS method |
|---|---|---|---|---|
| 31 | 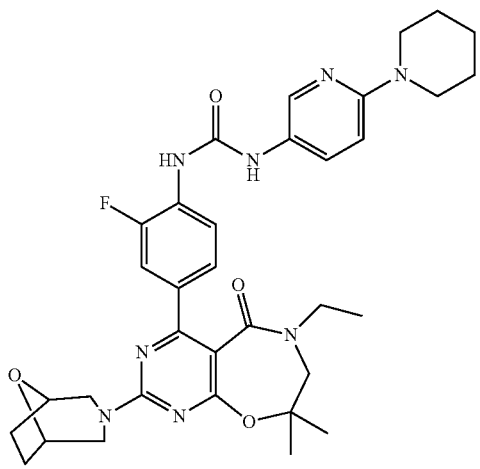 [SMILES: CCN1CC(C)(C)Oc2nc(N3CC4CCC(C3)O4)nc(-c3ccc(NC(=O)Nc4ccc(N5CCCCC5)nc4)c(F)c3)c2C1=O] | 645 | 0.57 | C |
| 32 | 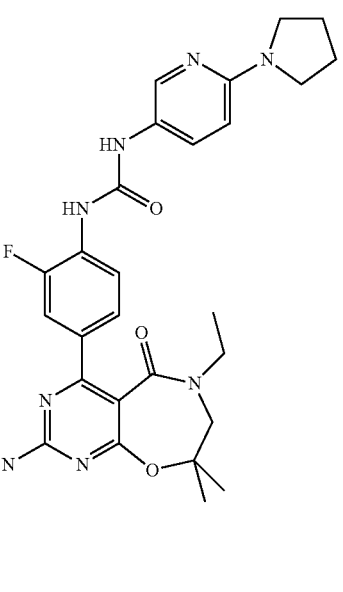 | 631 | 0.54 | C |

TABLE 3-continued
Chemical structures and physical properties of a number of examples of compounds according to the invention.
| Expl | Structure | Mass | Tr (min) | LC/MS method |
|---|---|---|---|---|
| 33 | 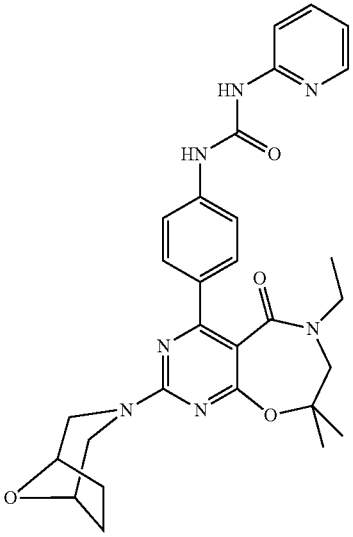 [SMILES: CCN1CC(C)(C)Oc2nc(N3CC4CCC(C3)O4)nc(-c3ccc(NC(=O)Nc4ccccn4)cc3)c2C1=O] | 544 | 0.61 | C |
| 34 | 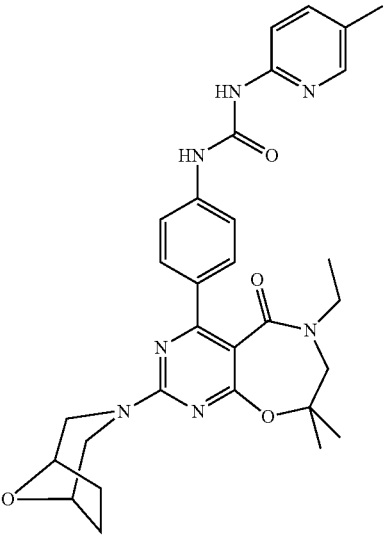 [SMILES: CCN1CC(C)(C)Oc2nc(N3CC4CCC(C3)O4)nc(-c3ccc(NC(=O)Nc4ccc(C)cn4)cc3)c2C1=O] | 558 | 0.62 | C |

TABLE 3-continued

Chemical structures and physical properties of a number of examples of compounds according to the invention.

| Expl | Structure | Mass | Tr (min) | LC/MS method |
|---|---|---|---|---|
| 35 | 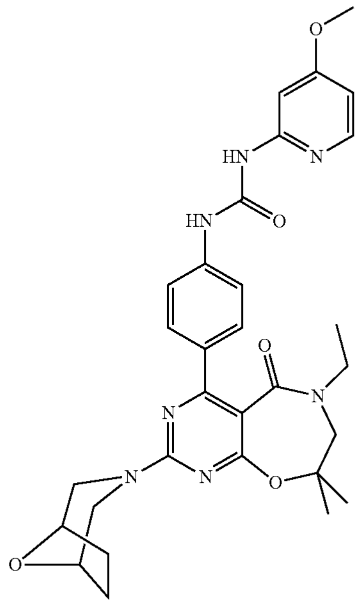 [SMILES: CCN1CC(C)(C)Oc2nc(N3CC4CCC(C3)O4)nc(-c3ccc(NC(=O)Nc4cc(OC)ccn4)cc3)c2C1=O] | 574 | 0.55 | C |
| 36 | 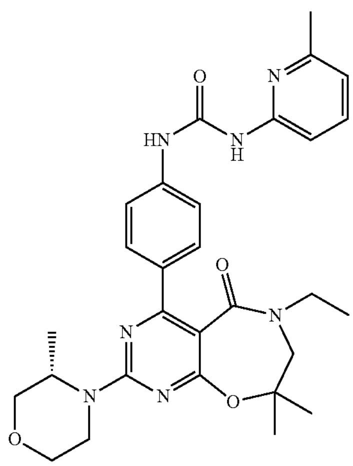 [SMILES: CCN1CC(C)(C)Oc2nc(N3CCOC[C@@H]3C)nc(-c3ccc(NC(=O)Nc4cccc(C)n4)cc3)c2C1=O] | 546 | 0.93 | A |
| 37 | 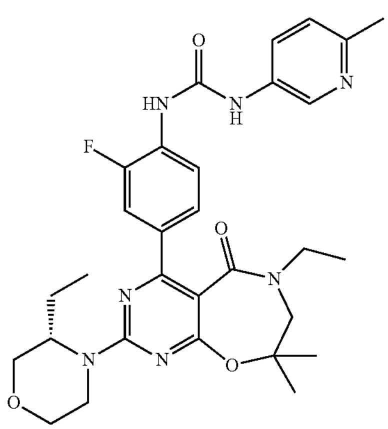 [SMILES: CC[C@H]1COCCN1c1nc2c(c(-c3ccc(NC(=O)Nc4ccc(C)nc4)c(F)c3)n1)C(=O)N(CC)CC(C)(C)O2] | 578 | 0.91 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 38 | 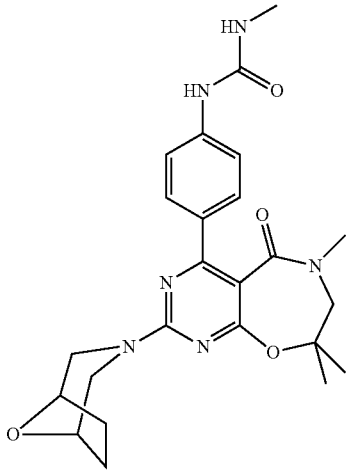 [SMILES: CNC(=O)Nc1ccc(-c2nc(N3CC4CCC(C3)O4)nc3c2C(=O)N(C)CC(C)(C)O3)cc1] | 467 | 0.54 | C |
| 39 | 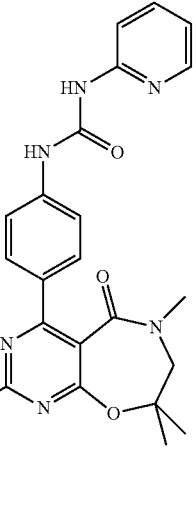 | 530 | 0.57 | C |
| 40 | 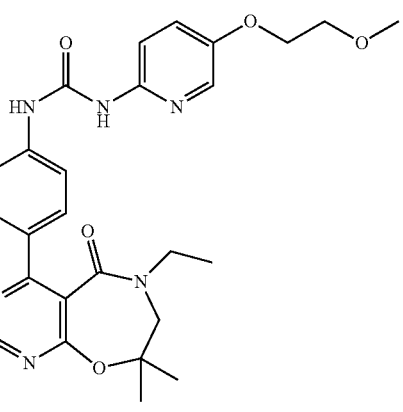 | 618 | 0.68 | C |

TABLE 3-continued

Chemical structures and physical properties of a number of examples of compounds according to the invention.

| Expl | Structure | Mass | Tr (min) | LC/MS method |
|---|---|---|---|---|
| 41 | 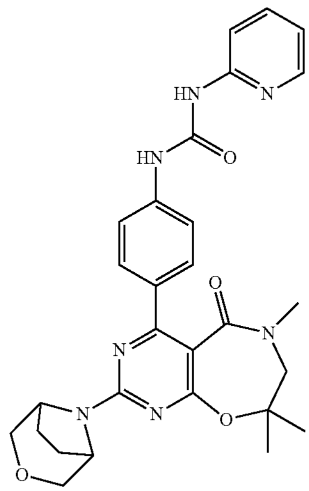 [SMILES: CN1CC(C)(C)Oc2nc(N3C4CCC3COC4)nc(-c3ccc(NC(=O)Nc4ccccn4)cc3)c2C1=O] | 530 | 0.58 | C |
| 42 | 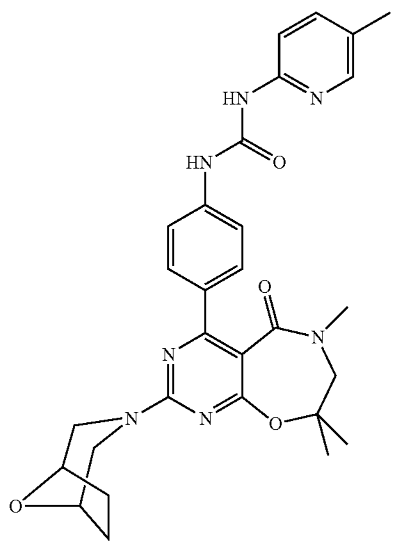 [SMILES: Cc1ccc(NC(=O)Nc2ccc(-c3nc(N4CC5CCC(C4)O5)nc4c3C(=O)N(C)CC(C)(C)O4)cc2)nc1] | 544 | 0.58 | C |
| 43 | 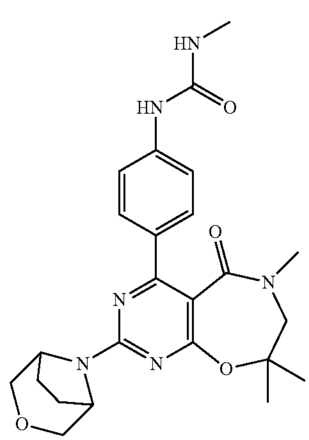 [SMILES: CNC(=O)Nc1ccc(-c2nc(N3C4CCC3COC4)nc3c2C(=O)N(C)CC(C)(C)O3)cc1] | 467 | 0.54 | C |

TABLE 3-continued
Chemical structures and physical properties of a number of examples of compounds according to the invention.
| Expl | Structure | Mass | Tr (min) | LC/MS method |
|---|---|---|---|---|
| 44 | 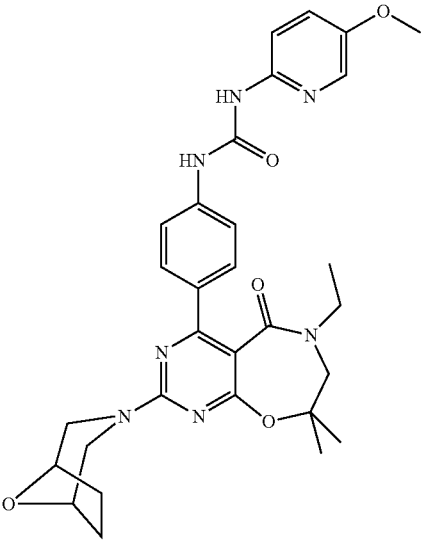 [SMILES: CCN1CC(C)(C)Oc2nc(N3CC4CCC(C3)O4)nc(-c3ccc(NC(=O)Nc4ccc(OC)cn4)cc3)c2C1=O] | 574 | 0.68 | C |
| 45 | 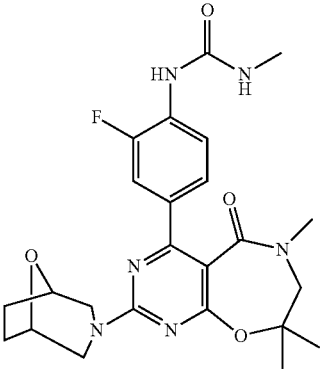 [SMILES: CNC(=O)Nc1ccc(-c2nc(N3CC4CCC(C3)O4)nc3c2C(=O)N(C)CC(C)(C)O3)cc1F] | 485 | 0.57 | C |
| 46 | 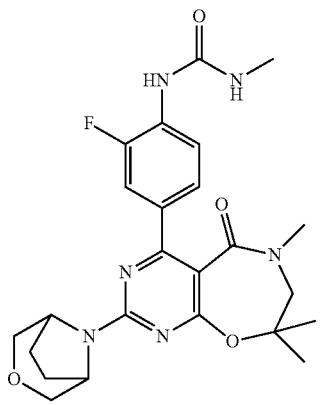 [SMILES: CNC(=O)Nc1ccc(-c2nc(N3C4CCC3COC4)nc3c2C(=O)N(C)CC(C)(C)O3)cc1F] | 485 | 0.58 | C |

TABLE 3-continued

Chemical structures and physical properties of a number of examples of compounds according to the invention.

| Expl | Structure | Mass | Tr (min) | LC/MS method |
|---|---|---|---|---|
| 47 | 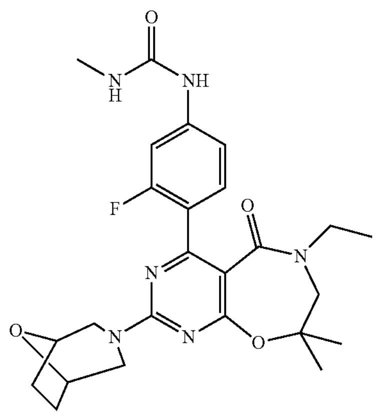 [SMILES: CCN1CC(C)(C)Oc2nc(N3CC4CCC(C3)O4)nc(-c3ccc(NC(=O)NC)cc3F)c2C1=O] | 499 | 0.62 | C |
| 48 | 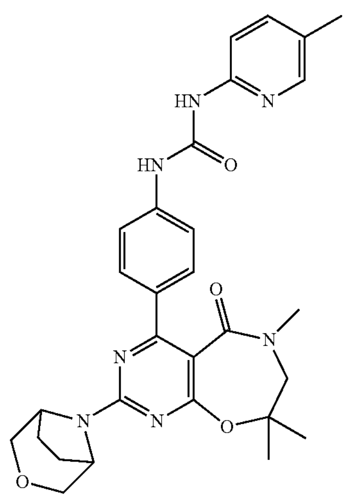 [SMILES: Cc1ccc(NC(=O)Nc2ccc(-c3nc(N4C5CCC4COC5)nc4c3C(=O)N(C)CC(C)(C)O4)cc2)nc1] | 544 | 0.59 | C |
| 49 | 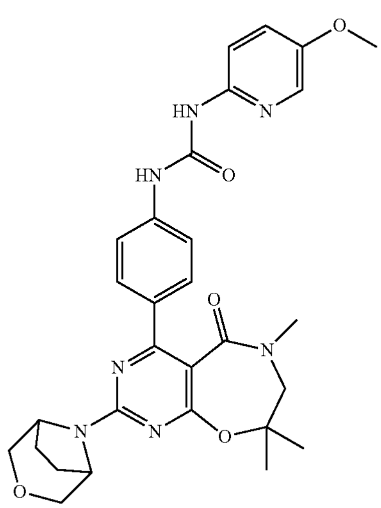 [SMILES: COc1ccc(NC(=O)Nc2ccc(-c3nc(N4C5CCC4COC5)nc4c3C(=O)N(C)CC(C)(C)O4)cc2)nc1] | 560 | 0.64 | C |

TABLE 3-continued
Chemical structures and physical properties of a number of examples of compounds according to the invention.
| Expl | Structure | Mass | Tr (min) | LC/MS method |
|---|---|---|---|---|
| 50 | 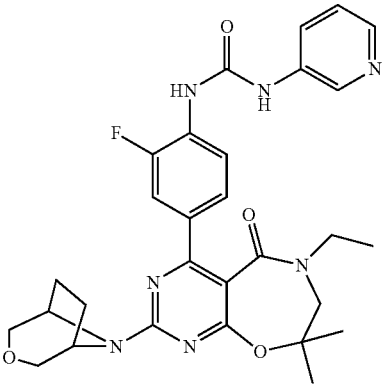 [SMILES: CCN1CC(C)(C)Oc2nc(N3C4CCC3COC4)nc(-c3ccc(NC(=O)Nc4cccnc4)c(F)c3)c2C1=O] | 562 | 0.81 | A |
| 51 | 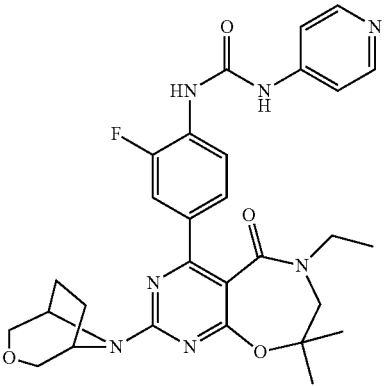 [SMILES: CCN1CC(C)(C)Oc2nc(N3C4CCC3COC4)nc(-c3ccc(NC(=O)Nc4ccncc4)c(F)c3)c2C1=O] | 562 | 0.82 | A |
| 52 | 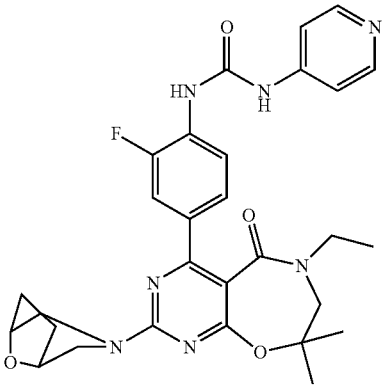 [SMILES: CCN1CC(C)(C)Oc2nc(N3CC4CC35CC5O4)nc(-c3ccc(NC(=O)Nc4ccncc4)c(F)c3)c2C1=O] | 562 | 0.82 | A |

TABLE 3-continued

Chemical structures and physical properties of a number of examples of compounds according to the invention.

| Expl | Structure | Mass | Tr (min) | LC/MS method |
|---|---|---|---|---|
| 53 | 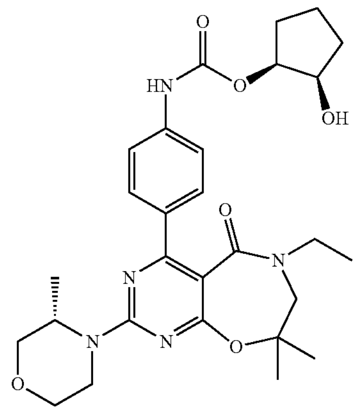 [SMILES: CCN1CC(C)(C)Oc2nc(N3CCOC[C@@H]3C)nc(-c3ccc(NC(=O)O[C@H]4CCC[C@H]4O)cc3)c2C1=O] | 540 | 1.03 | A |
| 54 | 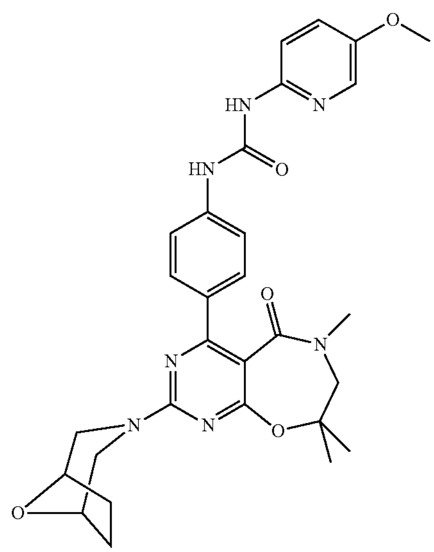 [SMILES: COc1ccc(NC(=O)Nc2ccc(-c3nc(N4CC5CCC(C4)O5)nc4c3C(=O)N(C)CC(C)(C)O4)cc2)nc1] | 560 | 0.64 | C |
| 55 | 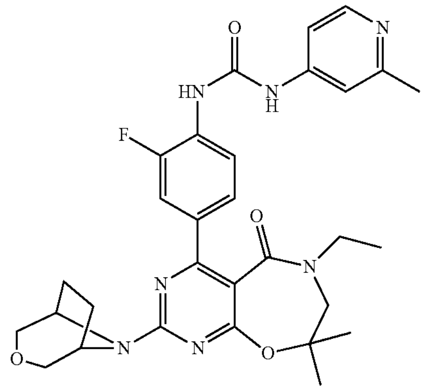 [SMILES: CCN1CC(C)(C)Oc2nc(N3C4CCC3COC4)nc(-c3ccc(NC(=O)Nc4ccnc(C)c4)c(F)c3)c2C1=O] | 576 | 0.85 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 56 | 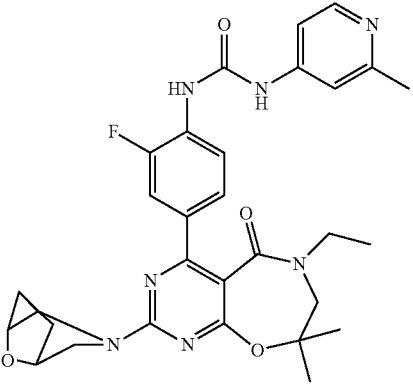 [SMILES: CCN1CC(C)(C)Oc2nc(N3CC4CC35CC5O4)nc(-c3ccc(NC(=O)Nc4ccnc(C)c4)c(F)c3)c2C1=O] | 576 | 0.84 | A |
| 57 | 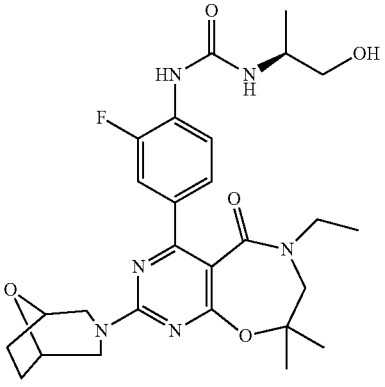 [SMILES: CCN1CC(C)(C)Oc2nc(N3CC4CCC(C3)O4)nc(-c3ccc(NC(=O)N[C@@H](C)CO)c(F)c3)c2C1=O] | 542 | 0.6 | C |
| 58 | 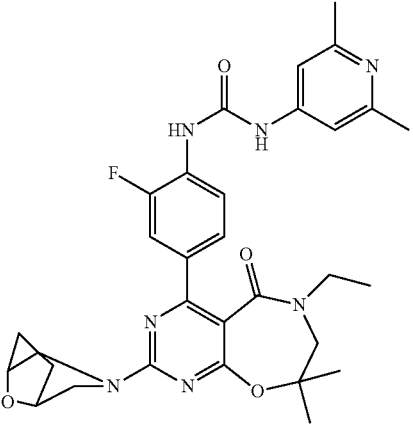 [SMILES: CCN1CC(C)(C)Oc2nc(N3CC4CC35CC5O4)nc(-c3ccc(NC(=O)Nc4cc(C)nc(C)c4)c(F)c3)c2C1=O] | 590 | 0.81 | A |

TABLE 3-continued

Chemical structures and physical properties of a number of examples of compounds according to the invention.

| Expl | Structure | Mass | Tr (min) | LC/MS method |
|---|---|---|---|---|
| 59 | 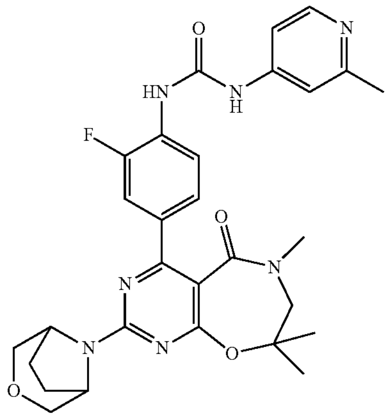 [SMILES: Cc1cc(NC(=O)Nc2ccc(-c3nc(N4C5CCC4COC5)nc4c3C(=O)N(C)CC(C)(C)O4)cc2F)ccn1] | 562 | 0.5 | C |
| 60 | 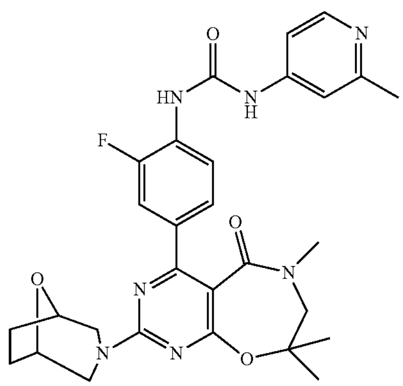 [SMILES: Cc1cc(NC(=O)Nc2ccc(-c3nc(N4CC5CCC(C4)O5)nc4c3C(=O)N(C)CC(C)(C)O4)cc2F)ccn1] | 562 | 0.5 | C |
| 61 | 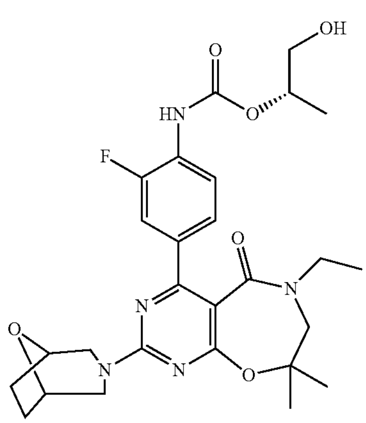 [SMILES: CCN1CC(C)(C)Oc2nc(N3CC4CCC(C3)O4)nc(-c3ccc(NC(=O)O[C@@H](C)CO)c(F)c3)c2C1=O] | 544 | 0.65 | C |

TABLE 3-continued
Chemical structures and physical properties of a number of examples of compounds according to the invention.
| Expl | Structure | Mass | Tr (min) | LC/MS method |
|---|---|---|---|---|
| 62 | 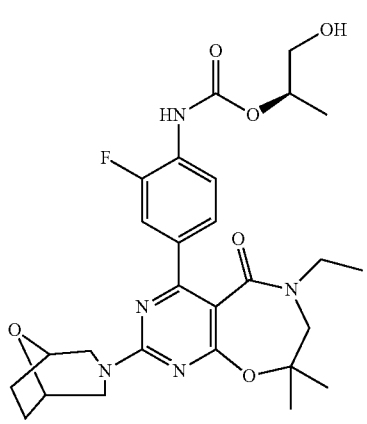 [SMILES: CCN1CC(C)(C)Oc2nc(N3CC4CCC(C3)O4)nc(-c3ccc(NC(=O)O[C@H](C)CO)c(F)c3)c2C1=O] | 544 | 0.65 | C |
| 63 | 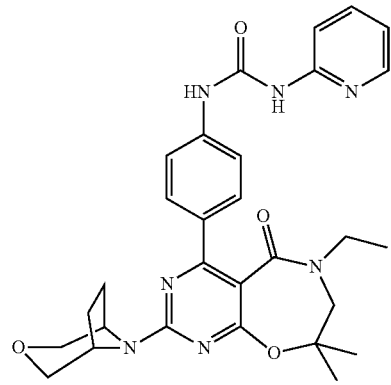 [SMILES: CCN1CC(C)(C)Oc2nc(N3C4CCC3COC4)nc(-c3ccc(NC(=O)Nc4ccccn4)cc3)c2C1=O] | 544 | 0.88 | A |
| 64 | 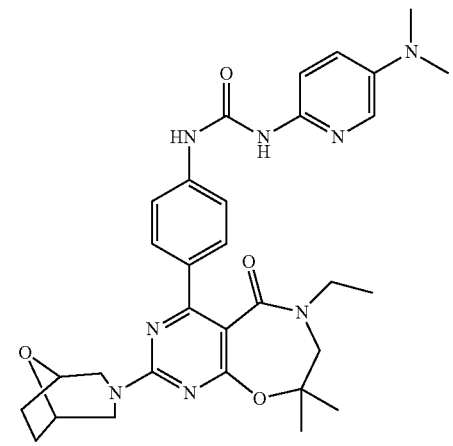 [SMILES: CCN1CC(C)(C)Oc2nc(N3CC4CCC(C3)O4)nc(-c3ccc(NC(=O)Nc4ccc(N(C)C)cn4)cc3)c2C1=O] | 587 | 0.58 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 65 | 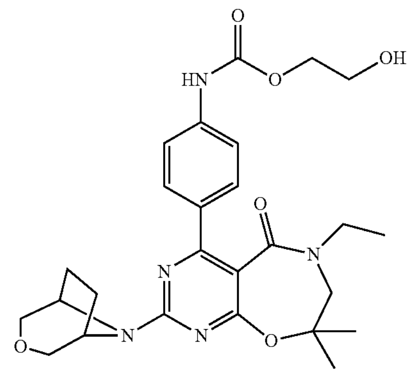 [SMILES: CCN1CC(C)(C)Oc2nc(N3C4CCC3COC4)nc(-c3ccc(NC(=O)OCCO)cc3)c2C1=O] | 512 | 0.88 | A |
| 66 | 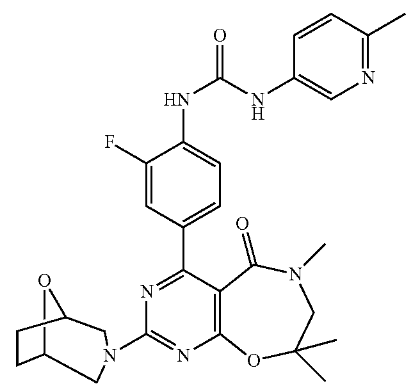 [SMILES: Cc1ccc(NC(=O)Nc2ccc(-c3nc(N4CC5CCC(C4)O5)nc4c3C(=O)N(C)CC(C)(C)O4)cc2F)cn1] | 562 | 0.53 | C |
| 67 | 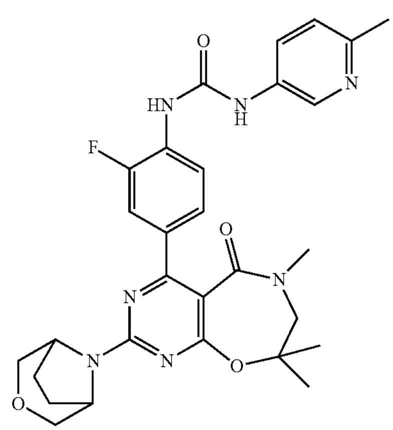 [SMILES: Cc1ccc(NC(=O)Nc2ccc(-c3nc(N4C5CCC4COC5)nc4c3C(=O)N(C)CC(C)(C)O4)cc2F)cn1] | 562 | 0.53 | C |

TABLE 3-continued
Chemical structures and physical properties of a number of examples of compounds according to the invention.
| Expl | Structure | Mass | Tr (min) | LC/MS method |
|------|-----------|------|----------|--------------|
| 68 | 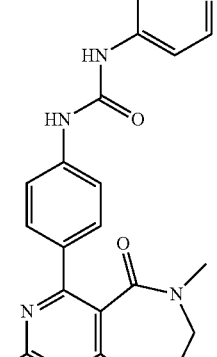 | 530 | 0.47 | C |
| 69 | 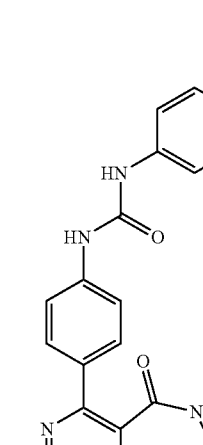 | 530 | 0.74 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 70 | 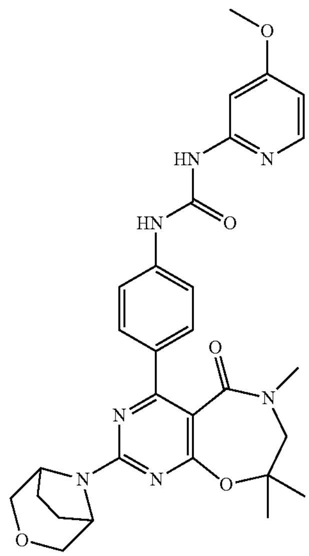 [SMILES: COc1ccnc(NC(=O)Nc2ccc(-c3nc(N4C5CCC4COC5)nc4c3C(=O)N(C)CC(C)(C)O4)cc2)c1] | 560 | 0.56 | C |
| 71 | 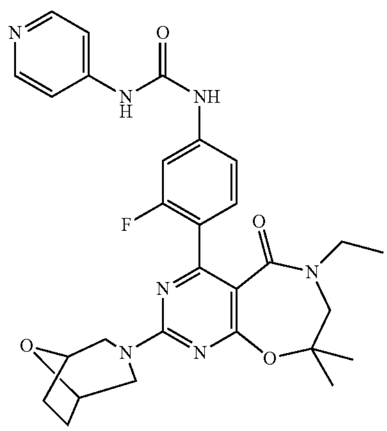 [SMILES: CCN1CC(C)(C)Oc2nc(N3CC4CCC(C3)O4)nc(-c3ccc(NC(=O)Nc4ccncc4)cc3F)c2C1=O] | 562 | 0.57 | C |
| 72 | 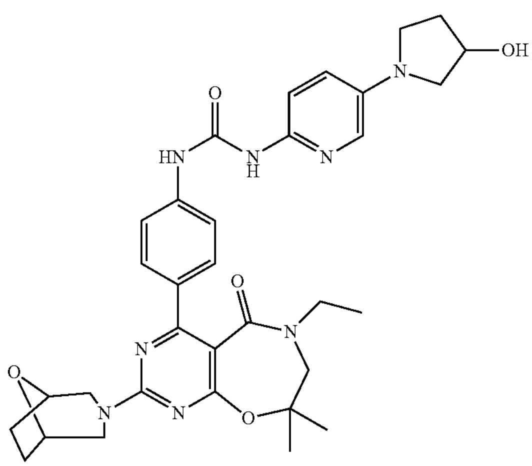 [SMILES: CCN1CC(C)(C)Oc2nc(N3CC4CCC(C3)O4)nc(-c3ccc(NC(=O)Nc4ccc(N5CCC(O)C5)cn4)cc3)c2C1=O] | 629 | 0.56 | C |

TABLE 3-continued
Chemical structures and physical properties of a number of examples of compounds according to the invention.
| Expl | Structure | Mass | Tr (min) | LC/MS method |
|---|---|---|---|---|
| 73 | 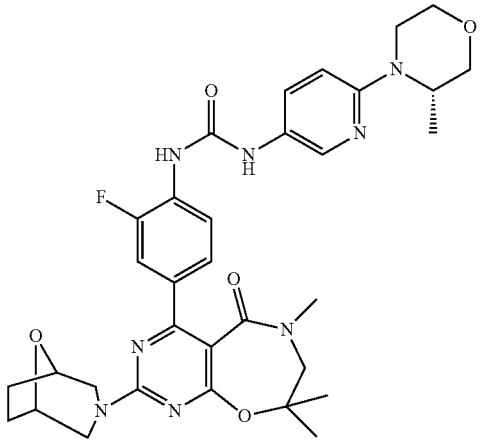 [SMILES: C[C@H]1COCCN1c1ccc(NC(=O)Nc2ccc(-c3nc(N4CC5CCC(C4)O5)nc4c3C(=O)N(C)CC(C)(C)O4)cc2F)cn1] | 647 | 0.57 | C |
| 74 | 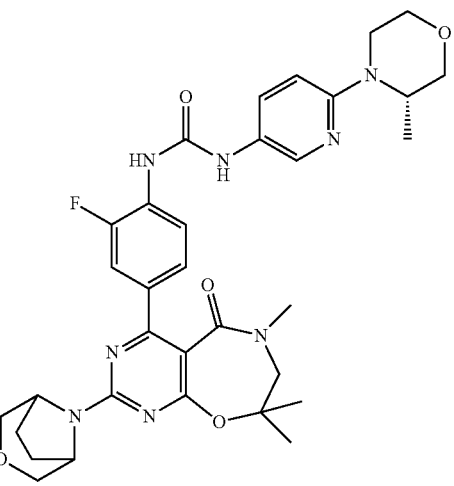 | 647 | 0.57 | C |
| 75 | 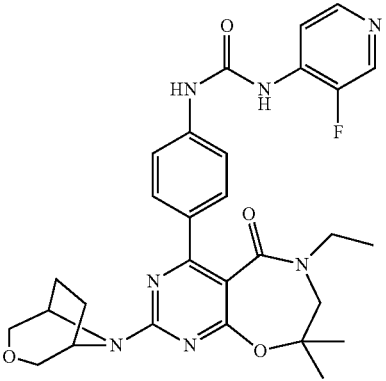 [SMILES: CCN1CC(C)(C)Oc2nc(N3C4CCC3COC4)nc(-c3ccc(NC(=O)Nc4ccncc4F)cc3)c2C1=O] | 562 | 0.81 | A |

TABLE 3-continued

Chemical structures and physical properties of a number of examples of compounds according to the invention.

| Expl | Structure | Mass | Tr (min) | LC/MS method |
|---|---|---|---|---|
| 76 | 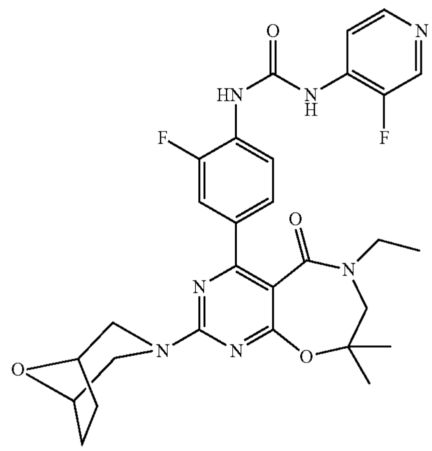 [SMILES: CCN1CC(C)(C)Oc2nc(N3CC4CCC(C3)O4)nc(-c3ccc(NC(=O)Nc4ccncc4F)c(F)c3)c2C1=O] | 580 | 0.86 | A |
| 77 | 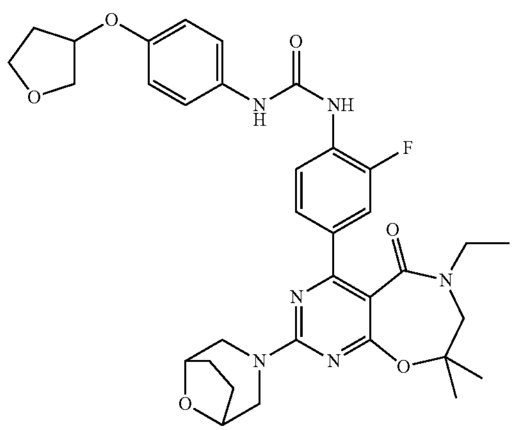 [SMILES: CCN1CC(C)(C)Oc2nc(N3CC4CCC(C3)O4)nc(-c3ccc(NC(=O)Nc4ccc(OC5CCOC5)cc4)c(F)c3)c2C1=O] | 647 | 1.08 | A |
| 78 | 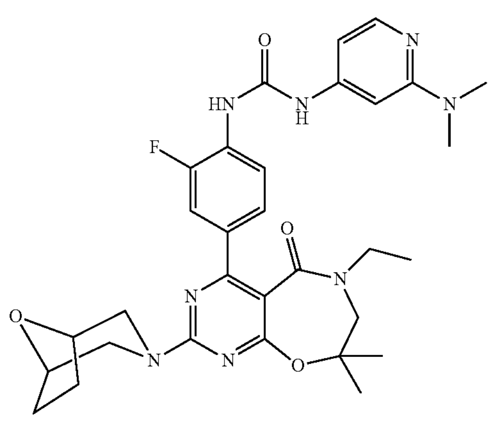 [SMILES: CCN1CC(C)(C)Oc2nc(N3CC4CCC(C3)O4)nc(-c3ccc(NC(=O)Nc4ccnc(N(C)C)c4)c(F)c3)c2C1=O] | 605 | 0.81 | A |

TABLE 3-continued
Chemical structures and physical properties of a number of examples of compounds according to the invention.
| Expl | Structure | Mass | Tr (min) | LC/MS method |
|---|---|---|---|---|
| 79 | 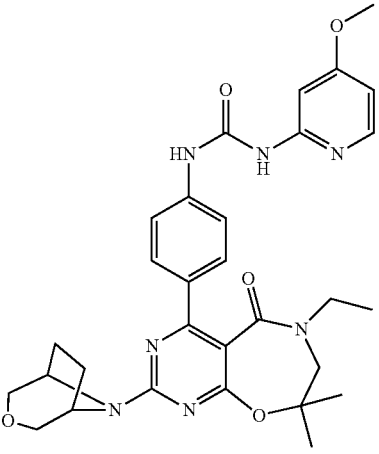 [SMILES: CCN1CC(C)(C)Oc2nc(N3C4CCC3COC4)nc(-c3ccc(NC(=O)Nc4cc(OC)ccn4)cc3)c2C1=O] | 574 | 0.84 | A |
| 80 | 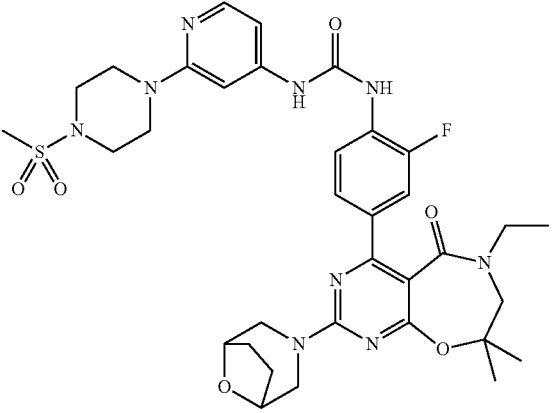 [SMILES: CCN1CC(C)(C)Oc2nc(N3CC4CCC(C3)O4)nc(-c3ccc(NC(=O)Nc4ccnc(N5CCN(S(C)(=O)=O)CC5)c4)c(F)c3)c2C1=O] | 724 | 0.82 | A |
| 81 | 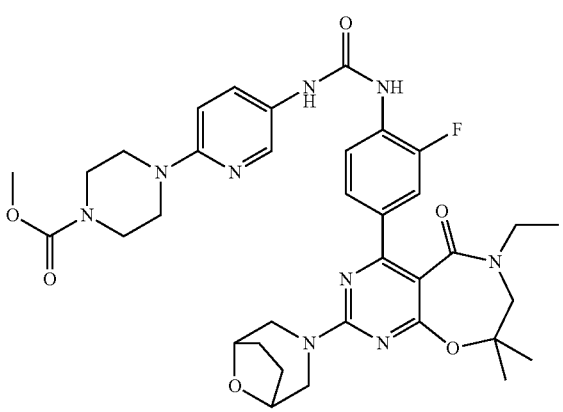 [SMILES: CCN1CC(C)(C)Oc2nc(N3CC4CCC(C3)O4)nc(-c3ccc(NC(=O)Nc4ccc(N5CCN(C(=O)OC)CC5)nc4)c(F)c3)c2C1=O] | 704 | 0.86 | A |

TABLE 3-continued

Chemical structures and physical properties of a number of examples of compounds according to the invention.

| Expl | Structure | Mass | Tr (min) | LC/MS method |
|---|---|---|---|---|
| 82 | 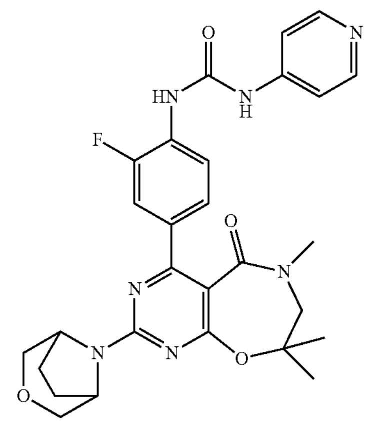 [SMILES: CN1CC(C)(C)Oc2nc(N3C4CCC3COC4)nc(-c3ccc(NC(=O)Nc4ccncc4)c(F)c3)c2C1=O] | 548 | 0.52 | C |
| 83 | 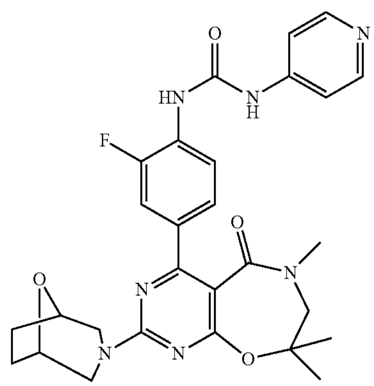 [SMILES: CN1CC(C)(C)Oc2nc(N3CC4CCC(C3)O4)nc(-c3ccc(NC(=O)Nc4ccncc4)c(F)c3)c2C1=O] | 548 | 0.52 | C |
| 84 | 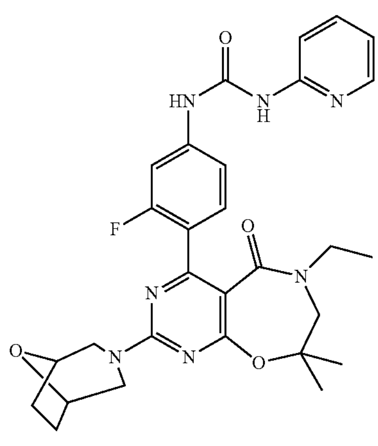 [SMILES: CCN1CC(C)(C)Oc2nc(N3CC4CCC(C3)O4)nc(-c3ccc(NC(=O)Nc4ccccn4)cc3F)c2C1=O] | 562 | 0.69 | C |

TABLE 3-continued

Chemical structures and physical properties of a number of examples of compounds according to the invention.

| Expl | Structure | Mass | Tr (min) | LC/MS method |
|---|---|---|---|---|
| 85 | 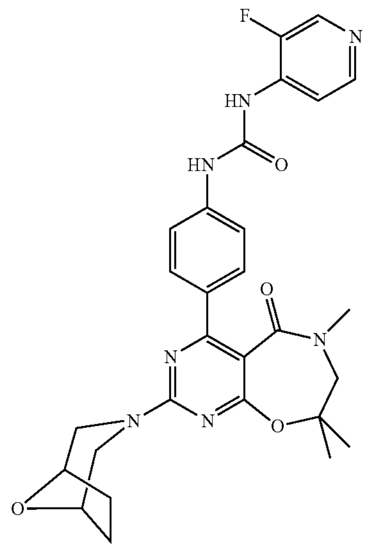 [SMILES: CN1CC(C)(C)Oc2nc(N3CC4CCC(C3)O4)nc(-c3ccc(NC(=O)Nc4ccncc4F)cc3)c2C1=O] | 548 | 0.53 | C |
| 86 | 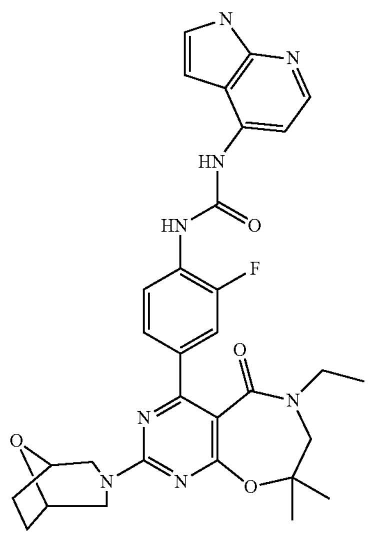 [SMILES: CCN1CC(C)(C)Oc2nc(N3CC4CCC(C3)O4)nc(-c3ccc(NC(=O)Nc4ccnc5[nH]ccc45)c(F)c3)c2C1=O] | 601 | 0.59 | C |
| 87 | 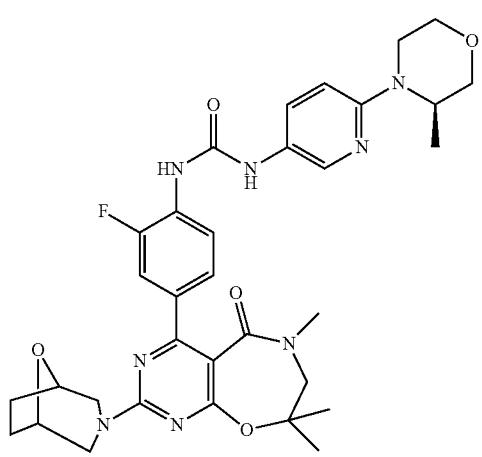 [SMILES: C[C@@H]1COCCN1c1ccc(NC(=O)Nc2ccc(-c3nc(N4CC5CCC(C4)O5)nc4c3C(=O)N(C)CC(C)(C)O4)cc2F)cn1] | 647 | 0.56 | C |

TABLE 3-continued

Chemical structures and physical properties of a number of examples of compounds according to the invention.

| Expl | Structure | Mass | Tr (min) | LC/MS method |
|---|---|---|---|---|
| 88 | 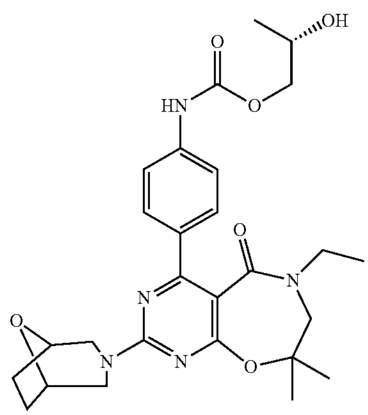 [SMILES: CCN1CC(C)(C)Oc2nc(N3CC4CCC(C3)O4)nc(-c3ccc(NC(=O)OC[C@H](C)O)cc3)c2C1=O] | 526 | 0.63 | C |
| 89 | 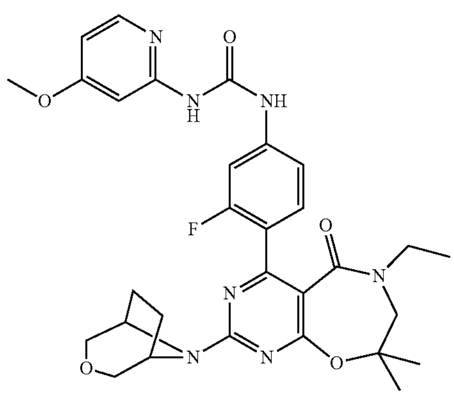 [SMILES: CCN1CC(C)(C)Oc2nc(N3C4CCC3COC4)nc(-c3ccc(NC(=O)Nc4cc(OC)ccn4)cc3F)c2C1=O] | 592 | 0.62 | C |
| 90 | 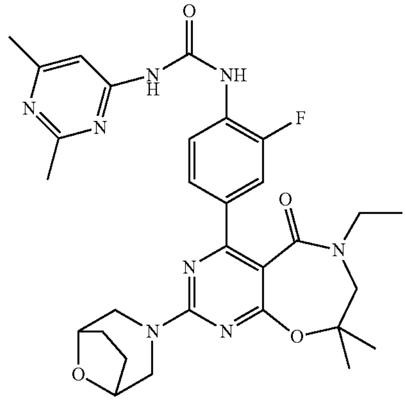 [SMILES: CCN1CC(C)(C)Oc2nc(N3CC4CCC(C3)O4)nc(-c3ccc(NC(=O)Nc4cc(C)nc(C)n4)c(F)c3)c2C1=O] | 591 | 0.9 | A |

TABLE 3-continued

Chemical structures and physical properties of a number of examples of compounds according to the invention.

| Expl | Structure | Mass | Tr (min) | LC/MS method |
|---|---|---|---|---|
| 91 | 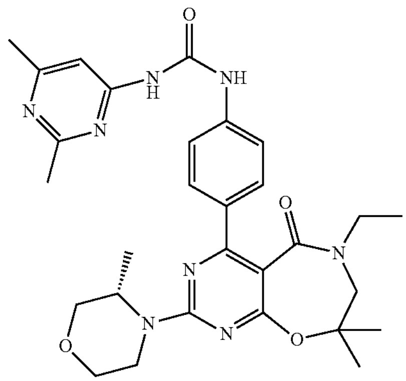 [SMILES: CCN1CC(C)(C)Oc2nc(N3CCOC[C@@H]3C)nc(-c3ccc(NC(=O)Nc4cc(C)nc(C)n4)cc3)c2C1=O] | 561 | 0.84 | A |
| 92 | 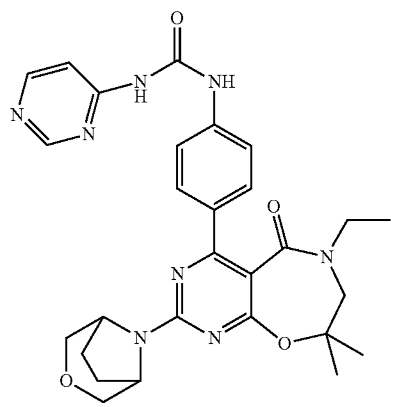 [SMILES: CCN1CC(C)(C)Oc2nc(N3C4CCC3COC4)nc(-c3ccc(NC(=O)Nc4ccncn4)cc3)c2C1=O] | 545 | 0.89 | A |
| 93 | 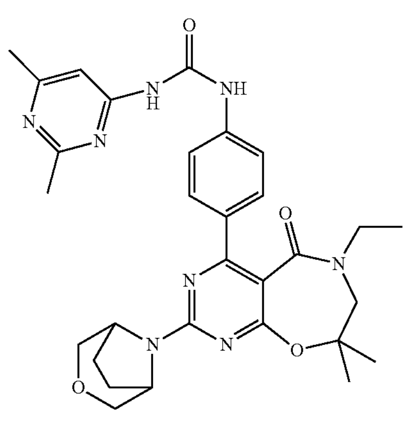 [SMILES: CCN1CC(C)(C)Oc2nc(N3C4CCC3COC4)nc(-c3ccc(NC(=O)Nc4cc(C)nc(C)n4)cc3)c2C1=O] | 573 | 0.82 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 94 | 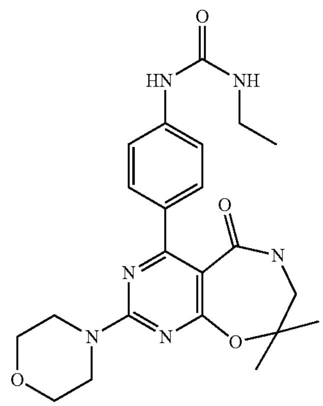 [SMILES: CCNC(=O)Nc1ccc(-c2nc(N3CCOCC3)nc3c2C(=O)NCC(C)(C)O3)cc1] | 441 | 3.8 | B |
| 95 | 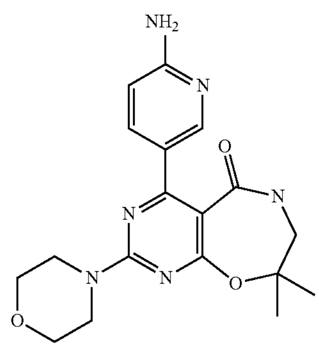 [SMILES: CC1(C)CNC(=O)c2c(nc(N3CCOCC3)nc2-c2ccc(N)nc2)O1] | 371 | 0.67 | A |
| 96 | 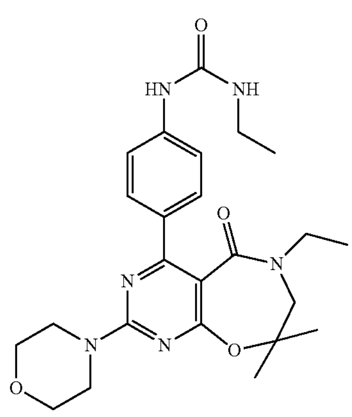 [SMILES: CCNC(=O)Nc1ccc(-c2nc(N3CCOCC3)nc3c2C(=O)N(CC)CC(C)(C)O3)cc1] | 469 | 3.27 | B |

TABLE 3-continued

Chemical structures and physical properties of a number of examples of compounds according to the invention.

| Expl | Structure | Mass | Tr (min) | LC/MS method |
|------|-----------|------|----------|--------------|
| 97   | 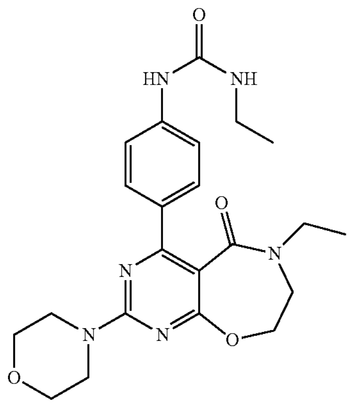 [SMILES: CCNC(=O)Nc1ccc(-c2nc(N3CCOCC3)nc3c2C(=O)N(CC)CCO3)cc1]          | 441  | 0.77     | A            |
| 98   | 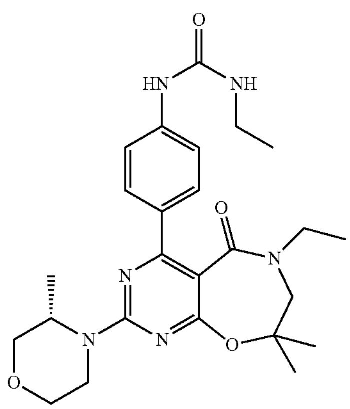 [SMILES: CCNC(=O)Nc1ccc(-c2nc(N3CCOC[C@@H]3C)nc3c2C(=O)N(CC)CC(C)(C)O3)cc1]          | 483  | 0.96     | A            |
| 99   | 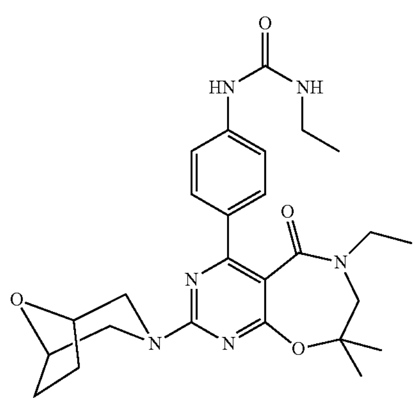 [SMILES: CCNC(=O)Nc1ccc(-c2nc(N3CC4CCC(C3)O4)nc3c2C(=O)N(CC)CC(C)(C)O3)cc1]          | 495  | 0.88     | A            |

TABLE 3-continued

Chemical structures and physical properties of a number of examples of compounds according to the invention.

| Expl | Structure | Mass | Tr (min) | LC/MS method |
|---|---|---|---|---|
| 100 | 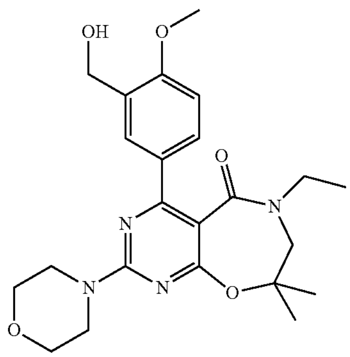 [SMILES: CCN1CC(C)(C)Oc2nc(N3CCOCC3)nc(-c3ccc(OC)c(CO)c3)c2C1=O] | 443 | 0.88 | A |
| 101 | 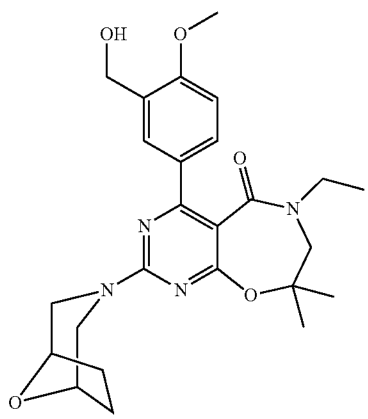 [SMILES: CCN1CC(C)(C)Oc2nc(N3CC4CCC(C3)O4)nc(-c3ccc(OC)c(CO)c3)c2C1=O] | 469 | 0.88 | A |
| 102 | 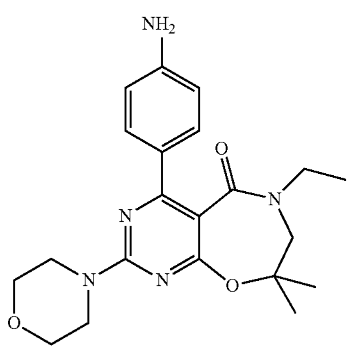 [SMILES: CCN1CC(C)(C)Oc2nc(N3CCOCC3)nc(-c3ccc(N)cc3)c2C1=O] | 398 | 0.67 | A |
| 103 | 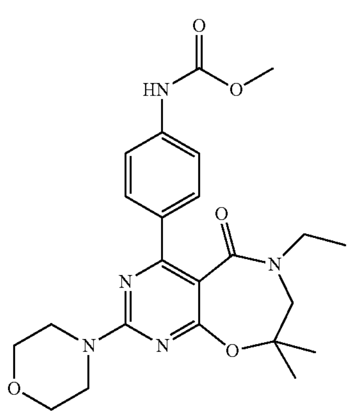 [SMILES: CCN1CC(C)(C)Oc2nc(N3CCOCC3)nc(-c3ccc(NC(=O)OC)cc3)c2C1=O] | 456 | 0.93 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 104 | 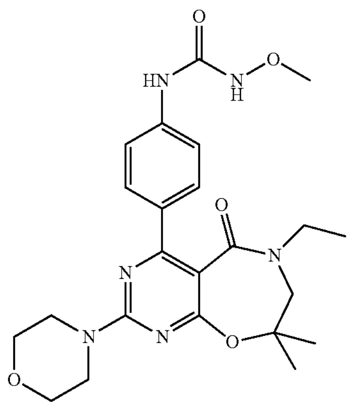 [SMILES: CCN1CC(C)(C)Oc2nc(N3CCOCC3)nc(-c3ccc(NC(=O)NOC)cc3)c2C1=O] | 471 | 0.88 | A |
| 105 | 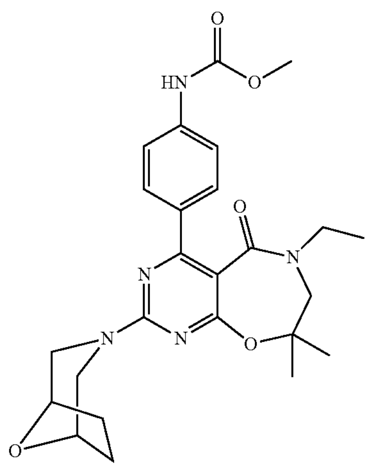 [SMILES: CCN1CC(C)(C)Oc2nc(N3CC4CCC(C3)O4)nc(-c3ccc(NC(=O)OC)cc3)c2C1=O] | 482 | 1.01 | A |
| 106 | 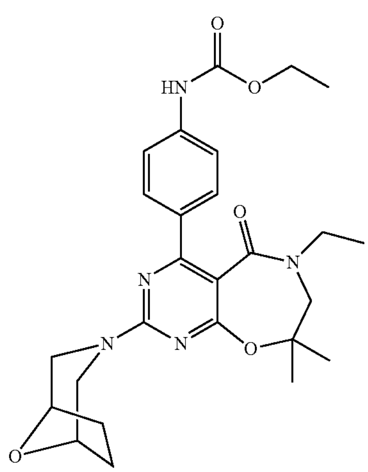 [SMILES: CCOC(=O)Nc1ccc(-c2nc(N3CC4CCC(C3)O4)nc3c2C(=O)N(CC)CC(C)(C)O3)cc1] | 496 | 1.08 | A |

TABLE 3-continued
Chemical structures and physical properties of a number of examples of compounds according to the invention.
| Expl | Structure | Mass | Tr (min) | LC/MS method |
|---|---|---|---|---|
| 107 | 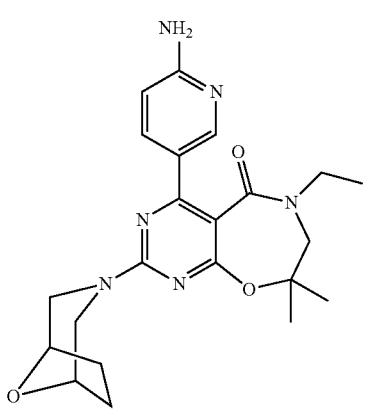 [SMILES: CCN1CC(C)(C)Oc2nc(N3CC4CCC(C3)O4)nc(-c3ccc(N)nc3)c2C1=O] | 425 | 0.72 | A |
| 108 | 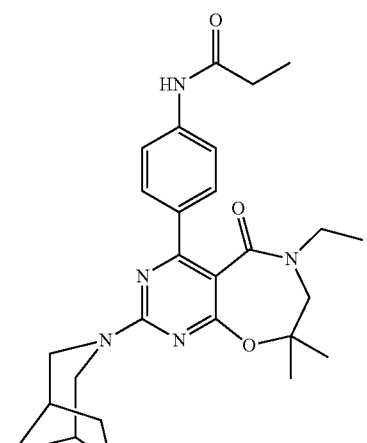 | 480 | 0.97 | A |
| 109 | 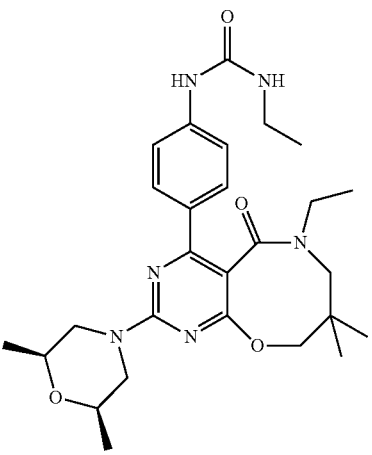 | 511 | 1.07 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 110  | 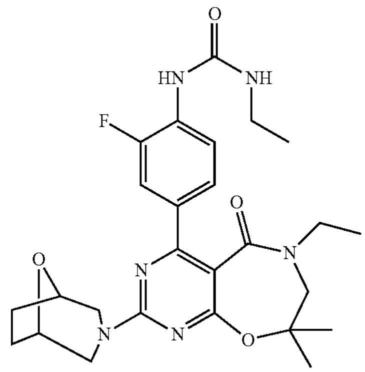 [SMILES: CCNC(=O)Nc1ccc(-c2nc(N3CC4CCC(C3)O4)nc3c2C(=O)N(CC)CC(C)(C)O3)cc1F]          | 513  | 1        | A            |
| 111  | 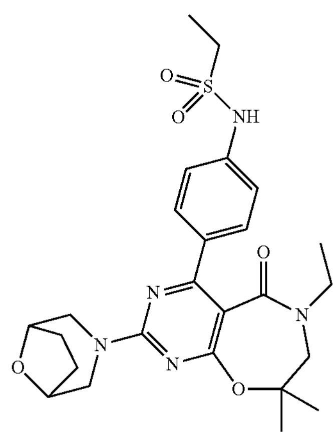 [SMILES: CCN1CC(C)(C)Oc2nc(N3CC4CCC(C3)O4)nc(-c3ccc(NS(=O)(=O)CC)cc3)c2C1=O]          | 516  | 0.99     | A            |
| 112  | 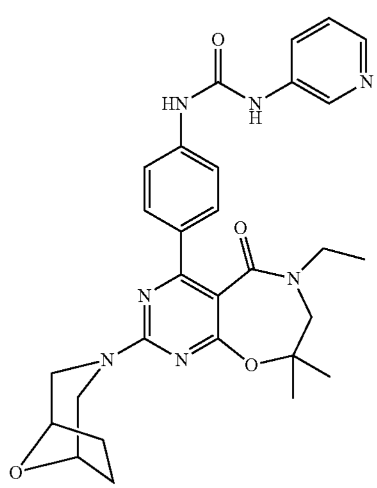 [SMILES: CCN1CC(C)(C)Oc2nc(N3CC4CCC(C3)O4)nc(-c3ccc(NC(=O)Nc4cccnc4)cc3)c2C1=O]          | 544  | 0.81     | A            |

TABLE 3-continued

Chemical structures and physical properties of a number of examples of compounds according to the invention.

| Expl | Structure | Mass | Tr (min) | LC/MS method |
|------|-----------|------|----------|--------------|
| 113 | 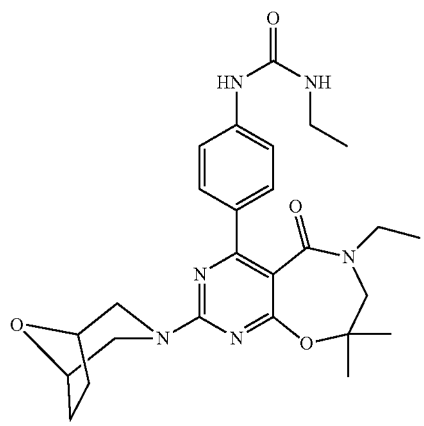 [SMILES: CCNC(=O)Nc1ccc(-c2nc(N3CC4CCC(C3)O4)nc3c2C(=O)N(CC)CC(C)(C)O3)cc1] | 481 | 0.75 | A |
| 114 | 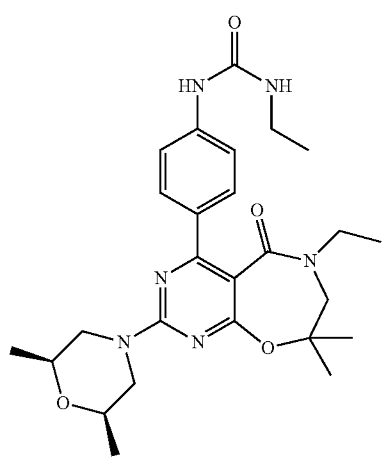 [SMILES: CCNC(=O)Nc1ccc(-c2nc(N3C[C@@H](C)O[C@@H](C)C3)nc3c2C(=O)N(CC)CC(C)(C)O3)cc1] | 497 | 1.03 | A |
| 115 | 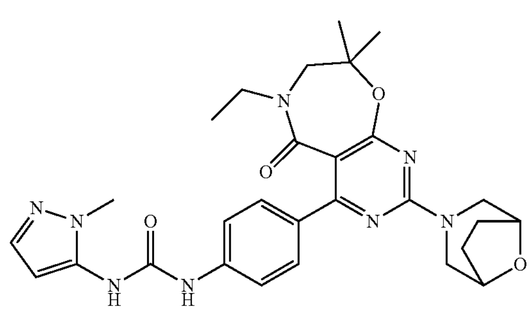 [SMILES: CCN1CC(C)(C)Oc2nc(N3CC4CCC(C3)O4)nc(-c3ccc(NC(=O)Nc4ccnn4C)cc3)c2C1=O] | 547 | 0.91 | A |

TABLE 3-continued
Chemical structures and physical properties of a number of examples of compounds according to the invention.
| Expl | Structure | Mass | Tr (min) | LC/MS method |
|---|---|---|---|---|
| 116 | 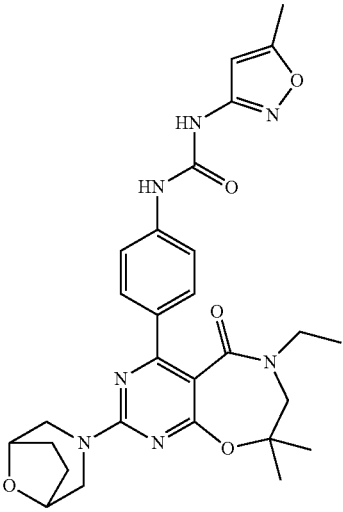 [SMILES: CCN1CC(C)(C)Oc2nc(N3CC4CCC(C3)O4)nc(-c3ccc(NC(=O)Nc4cc(C)on4)cc3)c2C1=O] | 548 | 1.06 | A |
| 117 | 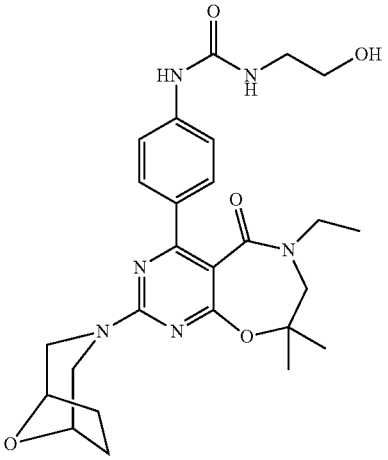 [SMILES: CCN1CC(C)(C)Oc2nc(N3CC4CCC(C3)O4)nc(-c3ccc(NC(=O)NCCO)cc3)c2C1=O] | 511 | 0.82 | A |
| 118 | 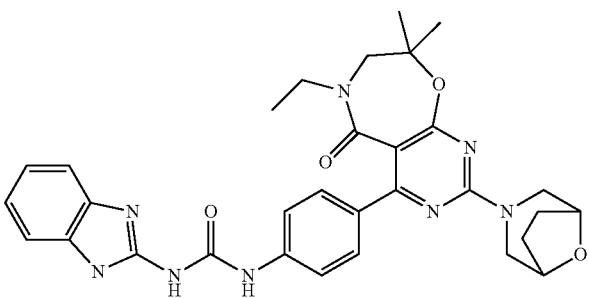 [SMILES: CCN1CC(C)(C)Oc2nc(N3CC4CCC(C3)O4)nc(-c3ccc(NC(=O)Nc4nc5ccccc5[nH]4)cc3)c2C1=O] | 540 | 0.91 | A |

TABLE 3-continued
Chemical structures and physical properties of a number of examples of compounds according to the invention.
| Expl | Structure | Mass | Tr (min) | LC/MS method |
|---|---|---|---|---|
| 119 | 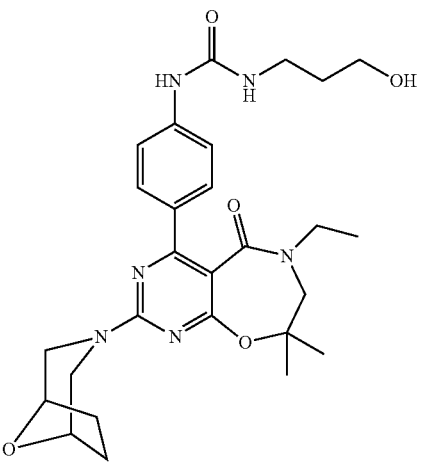 [SMILES: CCN1CC(C)(C)Oc2nc(N3CC4CCC(C3)O4)nc(-c3ccc(NC(=O)NCCCO)cc3)c2C1=O] | 525 | 0.85 | A |
| 120 | 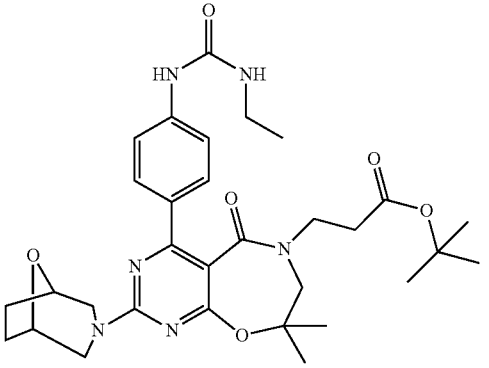 [SMILES: CCNC(=O)Nc1ccc(-c2nc(N3CC4CCC(C3)O4)nc3c2C(=O)N(CCC(=O)OC(C)(C)C)CC(C)(C)O3)cc1] | 595 | 1.14 | A |
| 121 | 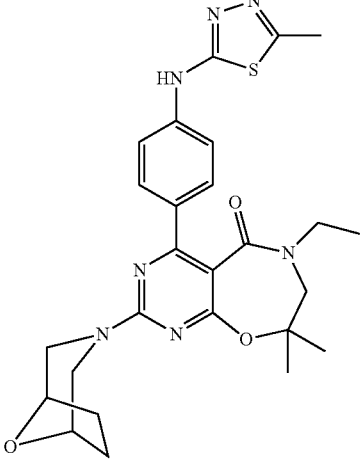 | 522 | 0.96 | A |

TABLE 3-continued
Chemical structures and physical properties of a number of examples of compounds according to the invention.
| Expl | Structure | Mass | Tr (min) | LC/MS method |
|---|---|---|---|---|
| 122 | 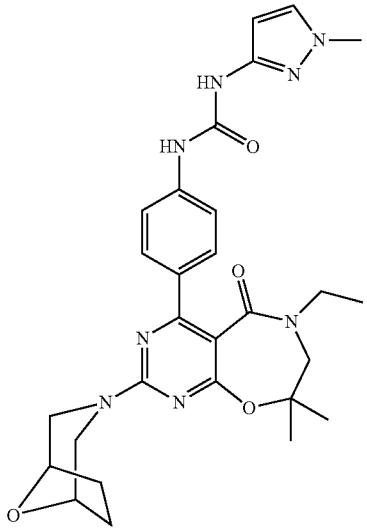 [SMILES: CCN1CC(C)(C)Oc2nc(N3CC4CCC(C3)O4)nc(-c3ccc(NC(=O)Nc4ccn(C)n4)cc3)c2C1=O] | 526 | 0.97 | A |
| 123 | 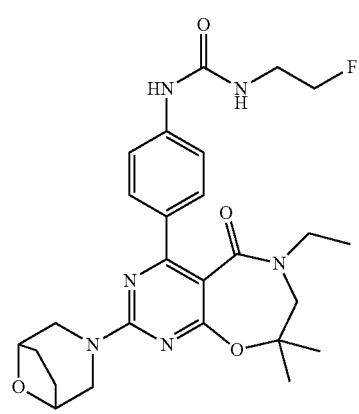 [SMILES: CCN1CC(C)(C)Oc2nc(N3CC4CCC(C3)O4)nc(-c3ccc(NC(=O)NCCF)cc3)c2C1=O] | 513 | 0.93 | A |
| 124 | 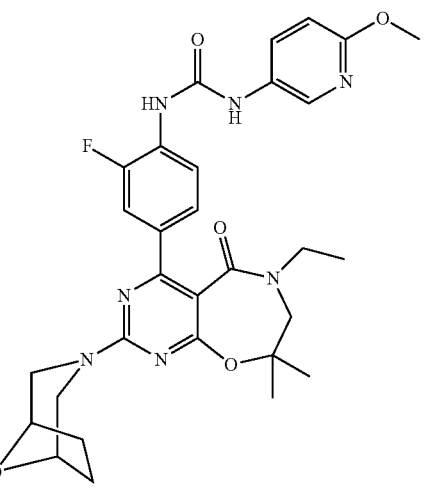 | 592 | 1.2 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 125 | 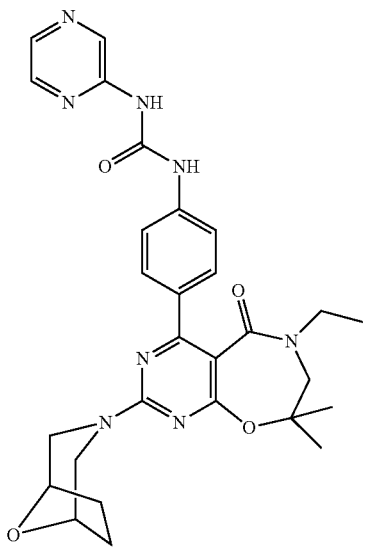 [SMILES: CCN1CC(C)(C)Oc2nc(N3CC4CCC(C3)O4)nc(-c3ccc(NC(=O)Nc4cnccn4)cc3)c2C1=O] | 547 | 1.07 | A |
| 126 | 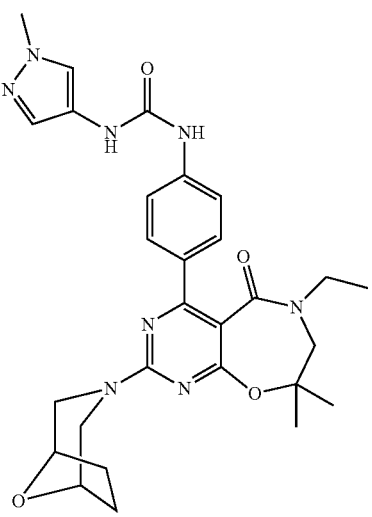 [SMILES: CCN1CC(C)(C)Oc2nc(N3CC4CCC(C3)O4)nc(-c3ccc(NC(=O)Nc4cnn(C)c4)cc3)c2C1=O] | 547 | 0.89 | A |

TABLE 3-continued
Chemical structures and physical properties of a number of examples of compounds according to the invention.
| Expl | Structure | Mass | Tr (min) | LC/MS method |
|---|---|---|---|---|
| 127 | 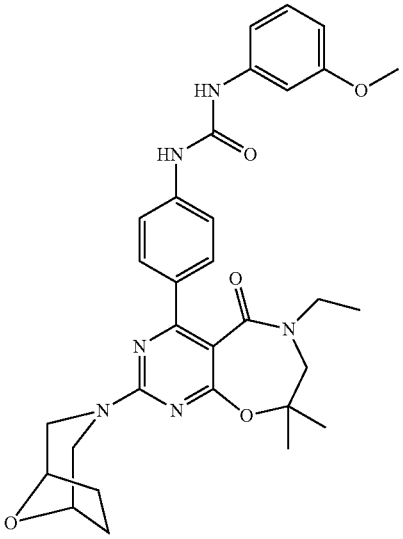 [SMILES: CCN1CC(C)(C)Oc2nc(N3CC4CCC(C3)O4)nc(-c3ccc(NC(=O)Nc4cccc(OC)c4)cc3)c2C1=O] | 573 | 1.26 | A |
| 128 | 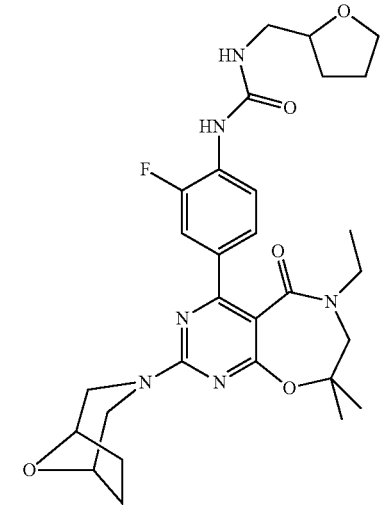 [SMILES: CCN1CC(C)(C)Oc2nc(N3CC4CCC(C3)O4)nc(-c3ccc(NC(=O)NCC4CCCO4)c(F)c3)c2C1=O] | 569 | 0.68 | C |
| 129 | 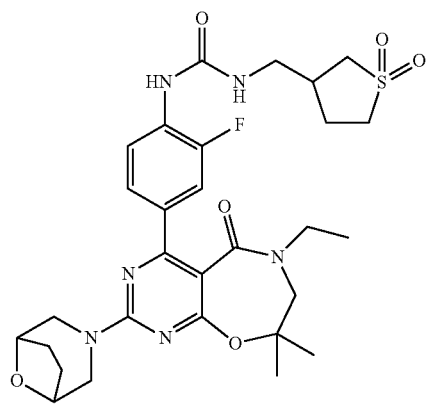 [SMILES: CCN1CC(C)(C)Oc2nc(N3CC4CCC(C3)O4)nc(-c3ccc(NC(=O)NCC4CCS(=O)(=O)C4)c(F)c3)c2C1=O] | 617 | 0.93 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 130  | 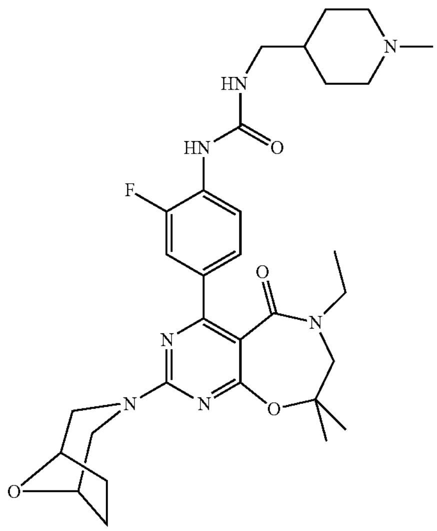 [SMILES: CCN1CC(C)(C)Oc2nc(N3CC4CCC(C3)O4)nc(-c3ccc(NC(=O)NCC4CCN(C)CC4)c(F)c3)c2C1=O]          | 596  | 0.49     | C            |
| 131  | 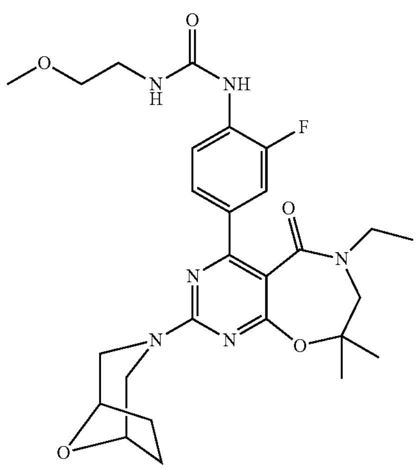 [SMILES: CCN1CC(C)(C)Oc2nc(N3CC4CCC(C3)O4)nc(-c3ccc(NC(=O)NCCOC)c(F)c3)c2C1=O]          | 543  | 0.96     | A            |
| 132  | 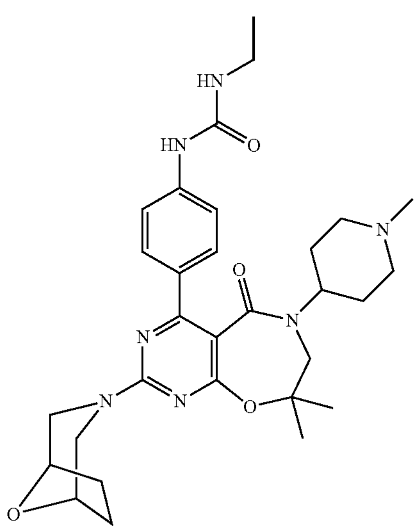 [SMILES: CCNC(=O)Nc1ccc(-c2nc(N3CC4CCC(C3)O4)nc3c2C(=O)N(C2CCN(C)CC2)CC(C)(C)O3)cc1]          | 564  | 3.23     | B            |

TABLE 3-continued
Chemical structures and physical properties of a number of examples of compounds according to the invention.
| Expl | Structure | Mass | Tr (min) | LC/MS method |
|------|-----------|------|----------|--------------|
| 133 | 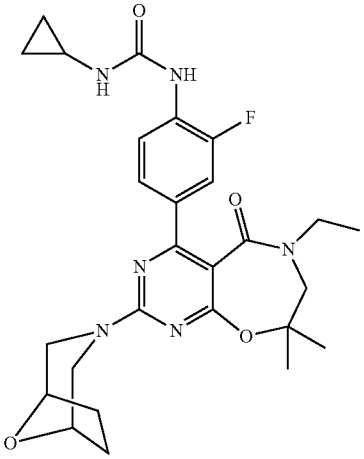 [SMILES: CCN1CC(C)(C)Oc2nc(N3CC4CCC(C3)O4)nc(-c3ccc(NC(=O)NC4CC4)c(F)c3)c2C1=O] | 525 | 1.01 | A |
| 134 | 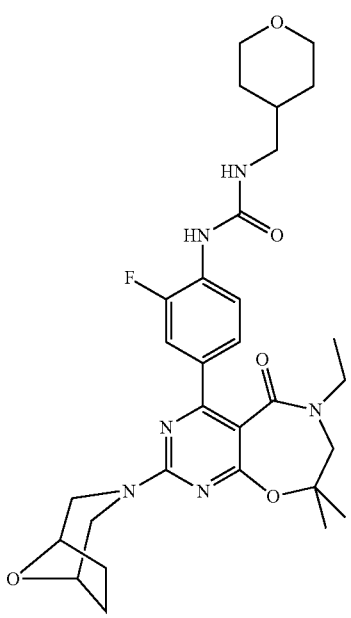 [SMILES: CCN1CC(C)(C)Oc2nc(N3CC4CCC(C3)O4)nc(-c3ccc(NC(=O)NCC4CCOCC4)c(F)c3)c2C1=O] | 583 | 0.67 | C |
| 135 | 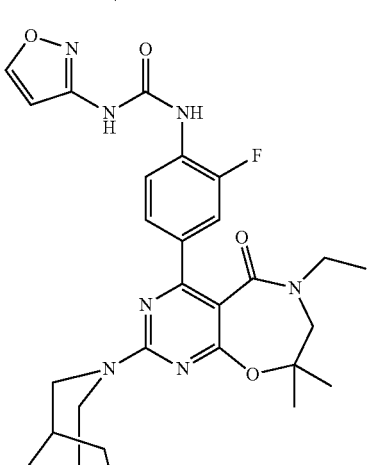 | 552 | 1.04 | A |

TABLE 3-continued

Chemical structures and physical properties of a number of examples of compounds according to the invention.

| Expl | Structure | Mass | Tr (min) | LC/MS method |
|---|---|---|---|---|
| 136 | 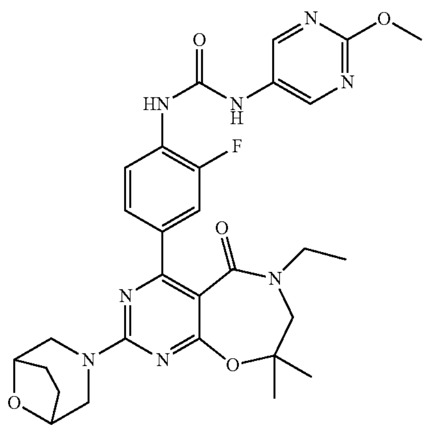 [SMILES: CCN1CC(C)(C)Oc2nc(N3CC4CCC(C3)O4)nc(-c3ccc(NC(=O)Nc4cnc(OC)nc4)c(F)c3)c2C1=O] | 593 | 0.98 | A |
| 137 | 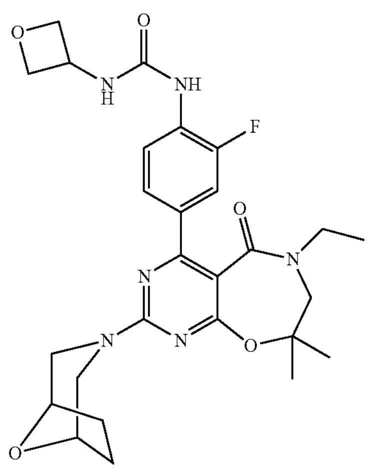 [SMILES: CCN1CC(C)(C)Oc2nc(N3CC4CCC(C3)O4)nc(-c3ccc(NC(=O)NC4COC4)c(F)c3)c2C1=O] | 541 | 3.4 | B |
| 138 | 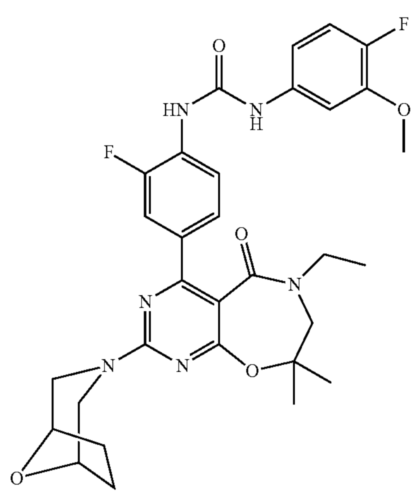 [SMILES: CCN1CC(C)(C)Oc2nc(N3CC4CCC(C3)O4)nc(-c3ccc(NC(=O)Nc4ccc(F)c(OC)c4)c(F)c3)c2C1=O] | 609 | 1.19 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 139 | 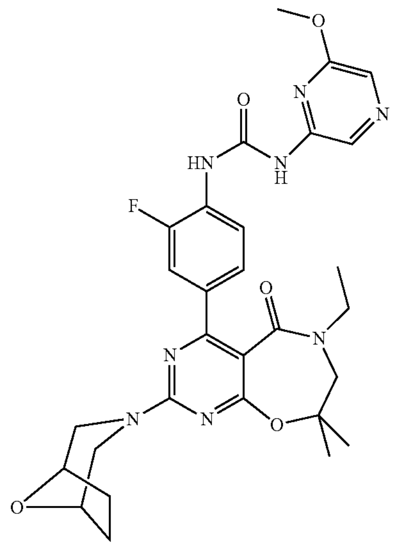 [SMILES: CCN1CC(C)(C)Oc2nc(N3CC4CCC(C3)O4)nc(-c3ccc(NC(=O)Nc4cncc(OC)n4)c(F)c3)c2C1=O] | 593 | 0.75 | C |
| 140 | 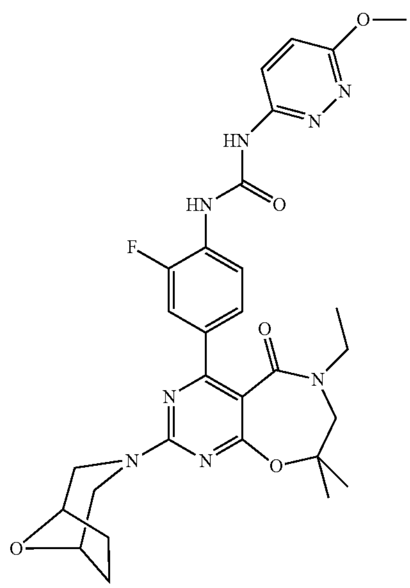 [SMILES: CCN1CC(C)(C)Oc2nc(N3CC4CCC(C3)O4)nc(-c3ccc(NC(=O)Nc4ccc(OC)nn4)c(F)c3)c2C1=O] | 593 | 0.72 | C |
| 141 | 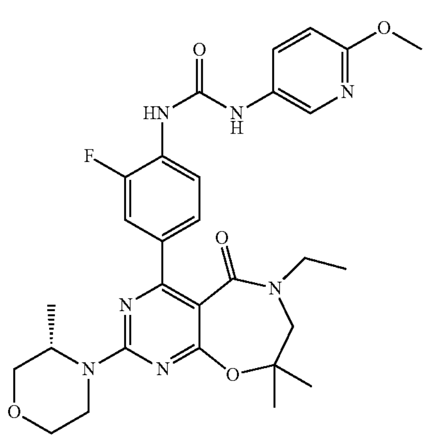 [SMILES: CCN1CC(C)(C)Oc2nc(N3CCOC[C@@H]3C)nc(-c3ccc(NC(=O)Nc4ccc(OC)nc4)c(F)c3)c2C1=O] | 580 | 1.08 | A |

TABLE 3-continued
Chemical structures and physical properties of a number of examples of compounds according to the invention.
| Expl | Structure | Mass | Tr (min) | LC/MS method |
|---|---|---|---|---|
| 142 | 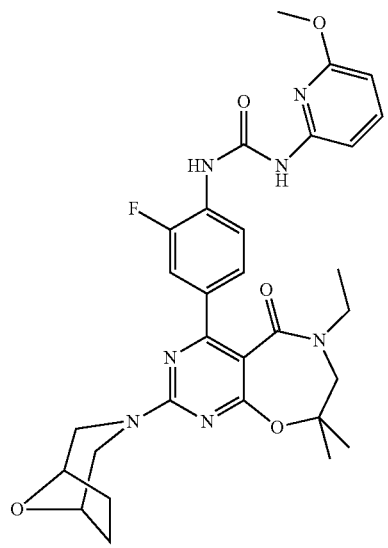 [SMILES: CCN1CC(C)(C)Oc2nc(N3CC4CCC(C3)O4)nc(-c3ccc(NC(=O)Nc4cccc(OC)n4)c(F)c3)c2C1=O] | 592 | 0.81 | C |
| 143 | 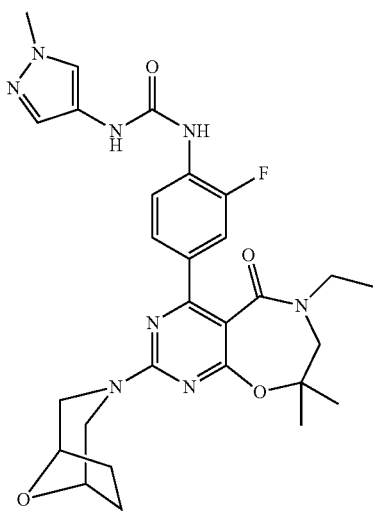 [SMILES: CCN1CC(C)(C)Oc2nc(N3CC4CCC(C3)O4)nc(-c3ccc(NC(=O)Nc4cnn(C)c4)c(F)c3)c2C1=O] | 565 | 0.93 | A |

TABLE 3-continued
Chemical structures and physical properties of a number of examples of compounds according to the invention.
| Expl | Structure | Mass | Tr (min) | LC/MS method |
|---|---|---|---|---|
| 144 | 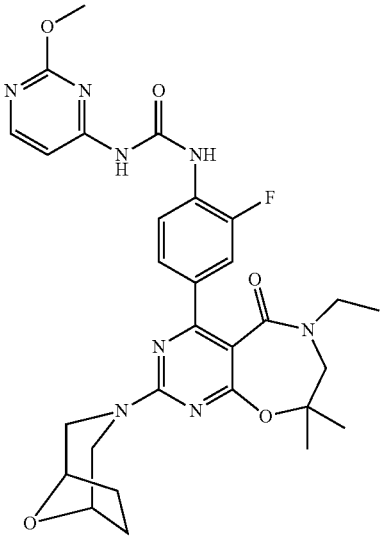 [SMILES: CCN1CC(C)(C)Oc2nc(N3CC4CCC(C3)O4)nc(-c3ccc(NC(=O)Nc4ccnc(OC)n4)c(F)c3)c2C1=O] | 593 | 1.05 | A |
| 145 | 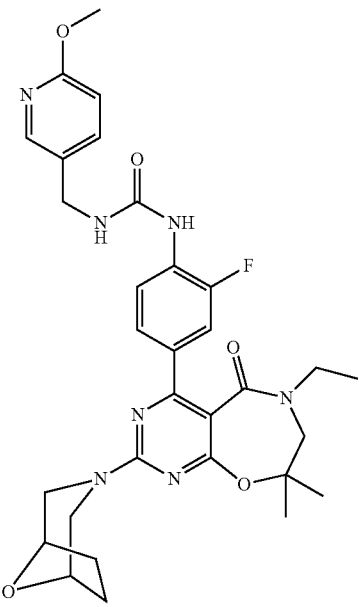 [SMILES: CCN1CC(C)(C)Oc2nc(N3CC4CCC(C3)O4)nc(-c3ccc(NC(=O)NCc4ccc(OC)nc4)c(F)c3)c2C1=O] | 606 | 1.02 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 146 | 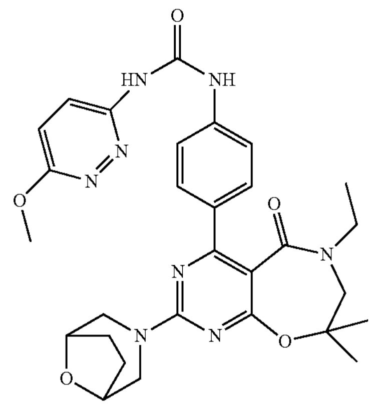 [SMILES: CCN1CC(C)(C)Oc2nc(N3CC4CCC(C3)O4)nc(-c3ccc(NC(=O)Nc4ccc(OC)nn4)cc3)c2C1=O] | 575 | 0.67 | C |
| 147 | 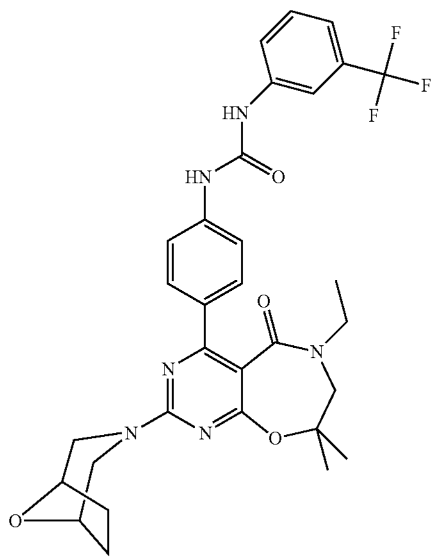 [SMILES: CCN1CC(C)(C)Oc2nc(N3CC4CCC(C3)O4)nc(-c3ccc(NC(=O)Nc4cccc(C(F)(F)F)c4)cc3)c2C1=O] | 611 | 0.86 | C |
| 148 | 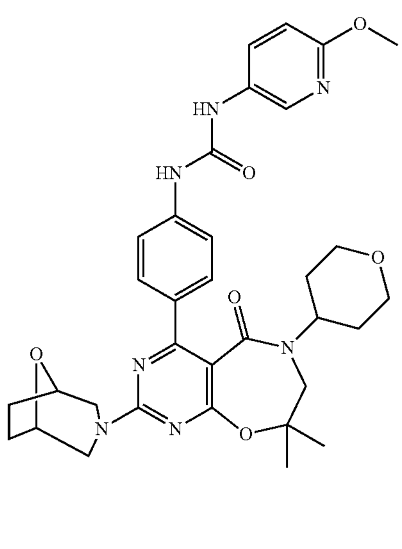 [SMILES: COc1ccc(NC(=O)Nc2ccc(-c3nc(N4CC5CCC(C4)O5)nc4c3C(=O)N(C3CCOCC3)CC(C)(C)O4)cc2)cn1] | 630 | 0.66 | C |

TABLE 3-continued
Chemical structures and physical properties of a number of examples of compounds according to the invention.
| Expl | Structure | Mass | Tr (min) | LC/MS method |
|---|---|---|---|---|
| 149 | 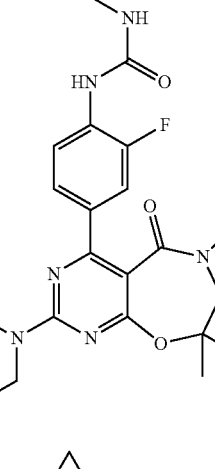 | 555 | 1.1 | A |
| 150 | 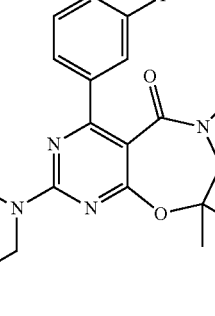 | 513 | 1.01 | A |
| 151 | 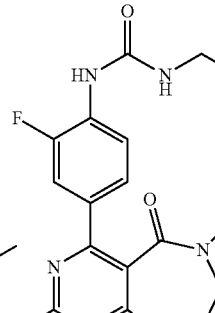 | 515 | 1.07 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 152 | 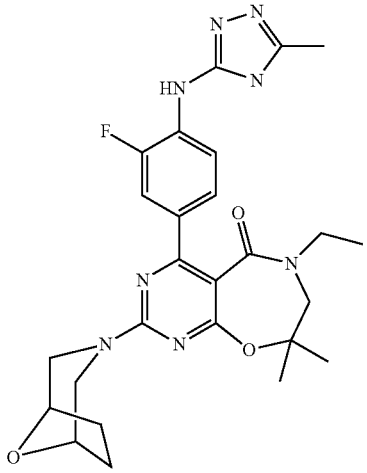 [SMILES: CCN1CC(C)(C)Oc2nc(N3CC4CCC(C3)O4)nc(-c3ccc(Nc4nnc(C)[nH]4)c(F)c3)c2C1=O] | 523 | 0.84 | A |
| 153 | 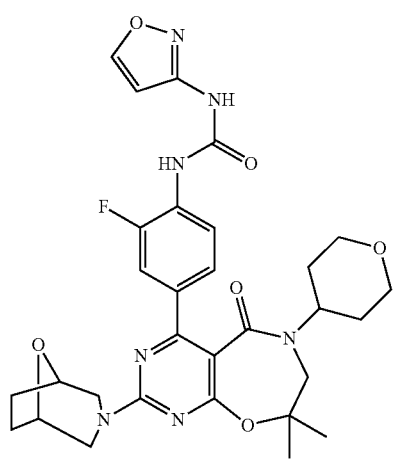 [SMILES: CC1(C)CN(C2CCOCC2)C(=O)c2c(nc(N3CC4CCC(C3)O4)nc2-c2ccc(NC(=O)Nc3ccon3)c(F)c2)O1] | 608 | 0.69 | C |

TABLE 3-continued
Chemical structures and physical properties of a number of examples of compounds according to the invention.
| Expl | Structure | Mass | Tr (min) | LC/MS method |
|---|---|---|---|---|
| 154 | 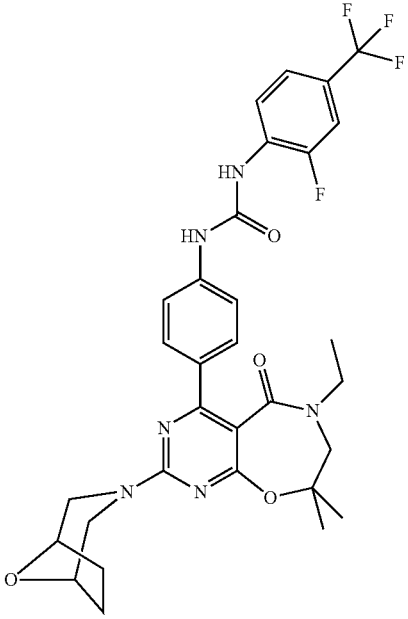 [SMILES: CCN1CC(C)(C)Oc2nc(N3CC4CCC(C3)O4)nc(-c3ccc(NC(=O)Nc4ccc(C(F)(F)F)cc4F)cc3)c2C1=O] | 629 | 0.9 | C |
| 155 | 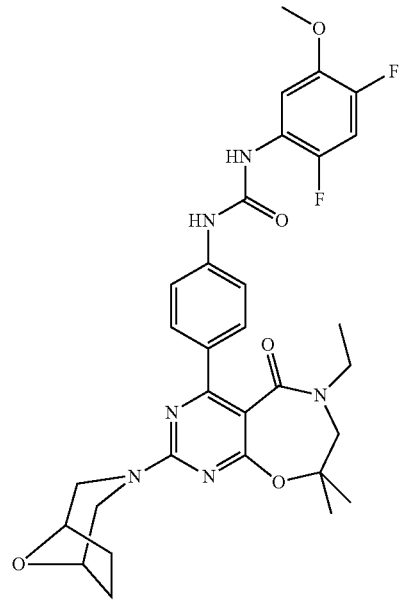 [SMILES: CCN1CC(C)(C)Oc2nc(N3CC4CCC(C3)O4)nc(-c3ccc(NC(=O)Nc4cc(OC)c(F)cc4F)cc3)c2C1=O] | 609 | 0.8 | C |

TABLE 3-continued

Chemical structures and physical properties of a number of examples of compounds according to the invention.

| Expl | Structure | Mass | Tr (min) | LC/MS method |
|---|---|---|---|---|
| 156 | 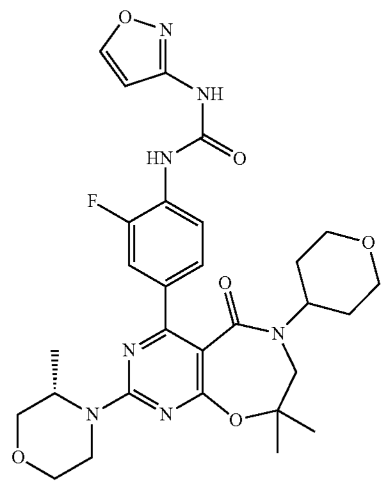 [SMILES: C[C@H]1COCCN1c1nc2c(c(-c3ccc(NC(=O)Nc4ccon4)c(F)c3)n1)C(=O)N(C1CCOCC1)CC(C)(C)O2] | 596 | 0.7 | C |
| 157 | 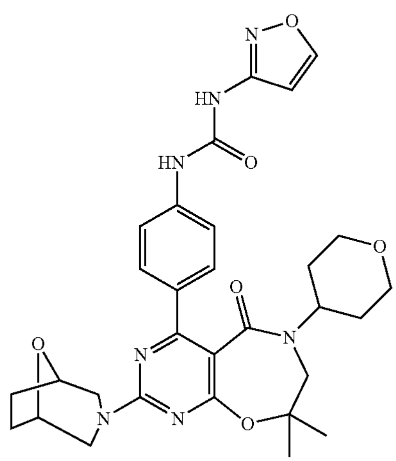 [SMILES: CC1(C)CN(C2CCOCC2)C(=O)c2c(nc(N3CC4CCC(C3)O4)nc2-c2ccc(NC(=O)Nc3ccon3)cc2)O1] | 590 | 0.65 | C |
| 158 | 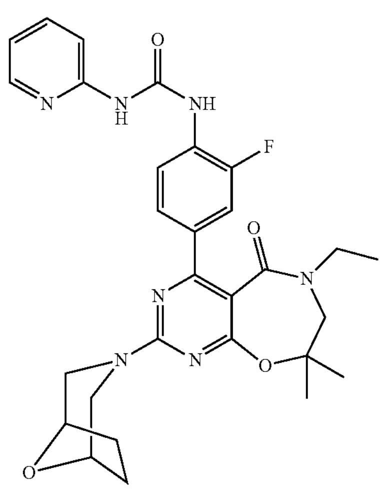 [SMILES: CCN1CC(C)(C)Oc2nc(N3CC4CCC(C3)O4)nc(-c3ccc(NC(=O)Nc4ccccn4)c(F)c3)c2C1=O] | 562 | 1.09 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 159  | 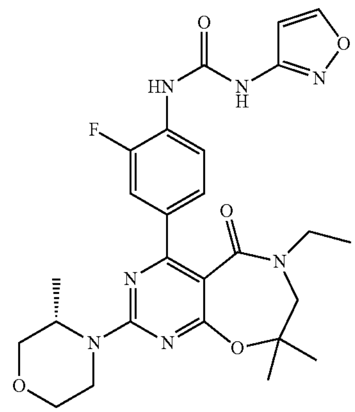 [SMILES: CCN1CC(C)(C)Oc2nc(N3CCOC[C@@H]3C)nc(-c3ccc(NC(=O)Nc4ccon4)c(F)c3)c2C1=O]          | 540  | 1.03     | A            |
| 160  | 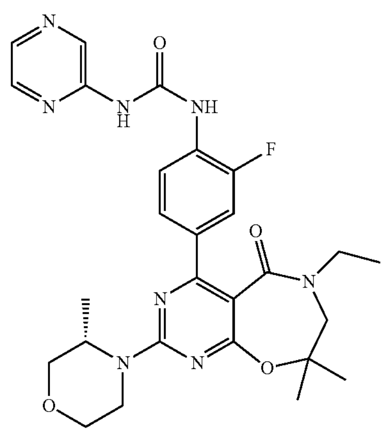 [SMILES: CCN1CC(C)(C)Oc2nc(N3CCOC[C@@H]3C)nc(-c3ccc(NC(=O)Nc4cnccn4)c(F)c3)c2C1=O]          | 551  | 1.04     | A            |
| 161  | 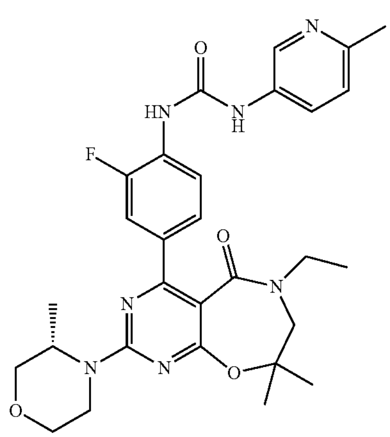 [SMILES: CCN1CC(C)(C)Oc2nc(N3CCOC[C@@H]3C)nc(-c3ccc(NC(=O)Nc4ccc(C)nc4)c(F)c3)c2C1=O]          | 564  | 0.79     | A            |

TABLE 3-continued

Chemical structures and physical properties of a number of examples of compounds according to the invention.

| Expl | Structure | Mass | Tr (min) | LC/MS method |
|---|---|---|---|---|
| 162 | 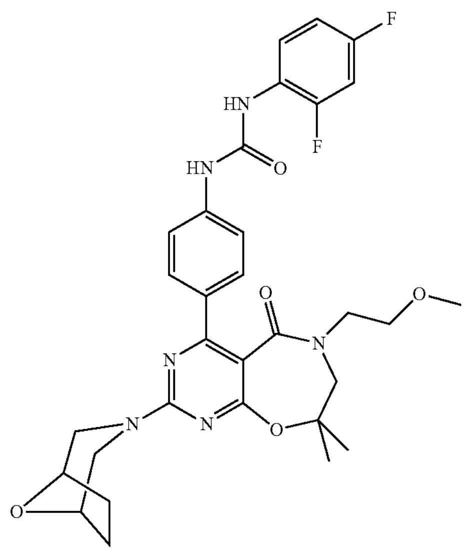 [SMILES: COCCN1CC(C)(C)Oc2nc(N3CC4CCC(C3)O4)nc(-c3ccc(NC(=O)Nc4ccc(F)cc4F)cc3)c2C1=O] | 609 | 0.79 | C |
| 163 | 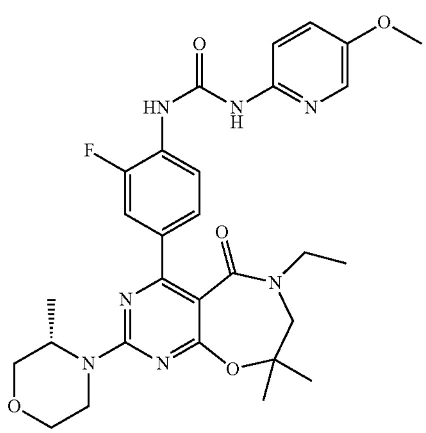 [SMILES: CCN1CC(C)(C)Oc2nc(N3CCOC[C@@H]3C)nc(-c3ccc(NC(=O)Nc4ccc(OC)cn4)c(F)c3)c2C1=O] | 580 | 1.15 | A |
| 164 | 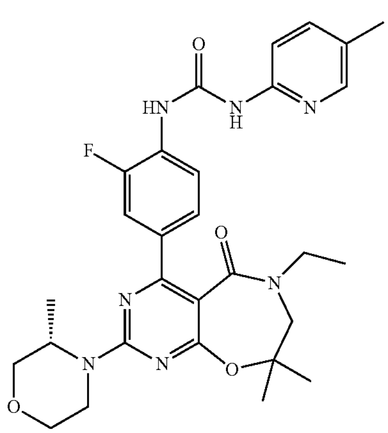 [SMILES: CCN1CC(C)(C)Oc2nc(N3CCOC[C@@H]3C)nc(-c3ccc(NC(=O)Nc4ccc(C)cn4)c(F)c3)c2C1=O] | 564 | 1.15 | A |

TABLE 3-continued
Chemical structures and physical properties of a number of examples of compounds according to the invention.
| Expl | Structure | Mass | Tr (min) | LC/MS method |
|---|---|---|---|---|
| 165 | 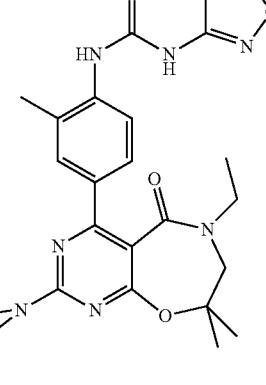 | 548 | 0.68 | C |
| 166 | 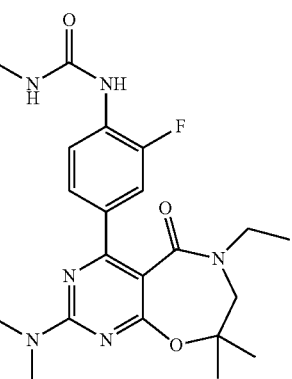 | 553 | 1.01 | A |
| 167 | 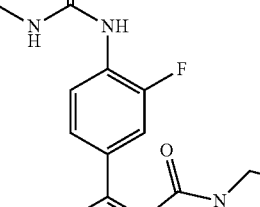 | 565 | 1.07 | A |

TABLE 3-continued

Chemical structures and physical properties of a number of examples of compounds according to the invention.

| Expl | Structure | Mass | Tr (min) | LC/MS method |
|---|---|---|---|---|
| 168 | 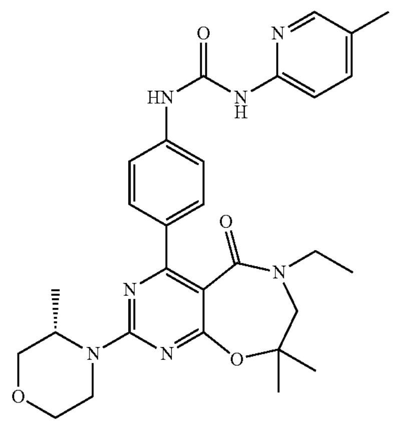 [SMILES: CCN1CC(C)(C)Oc2nc(N3CCOC[C@@H]3C)nc(-c3ccc(NC(=O)Nc4ccc(C)cn4)cc3)c2C1=O] | 546 | 0.9 | A |
| 169 | 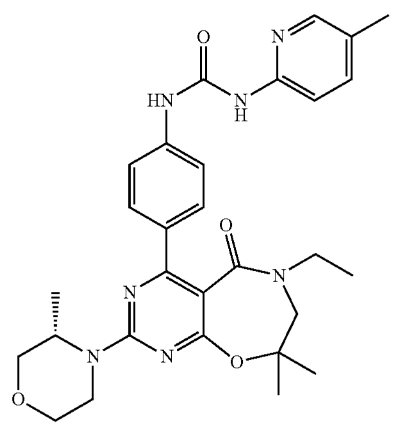 [SMILES: CCN1CC(C)(C)Oc2nc(N3CCOC[C@@H]3C)nc(-c3ccc(NC(=O)Nc4ccc(C)cn4)cc3)c2C1=O] | 546 | 1.01 | A |
| 170 | 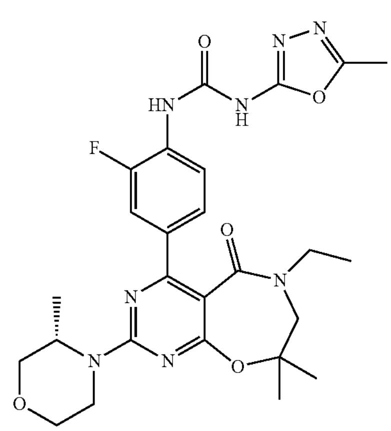 [SMILES: CCN1CC(C)(C)Oc2nc(N3CCOC[C@@H]3C)nc(-c3ccc(NC(=O)Nc4nnc(C)o4)c(F)c3)c2C1=O] | 555 | 0.95 | A |

TABLE 3-continued

Chemical structures and physical properties of a number of examples of compounds according to the invention.

| Expl | Structure | Mass | Tr (min) | LC/MS method |
|---|---|---|---|---|
| 171 | 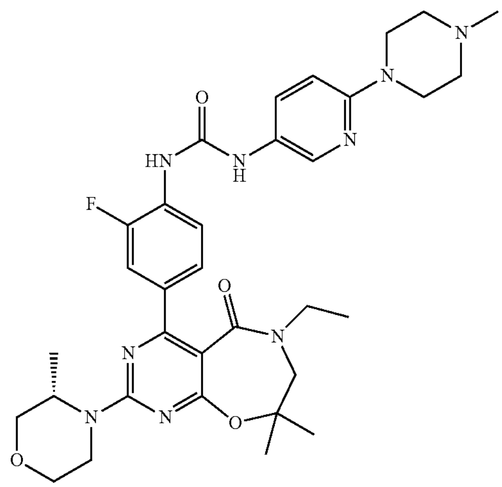 [SMILES: CCN1CC(C)(C)Oc2nc(N3CCOC[C@@H]3C)nc(-c3ccc(NC(=O)Nc4ccc(N5CCN(C)CC5)nc4)c(F)c3)c2C1=O] | 648 | 0.81 | A |
| 172 | 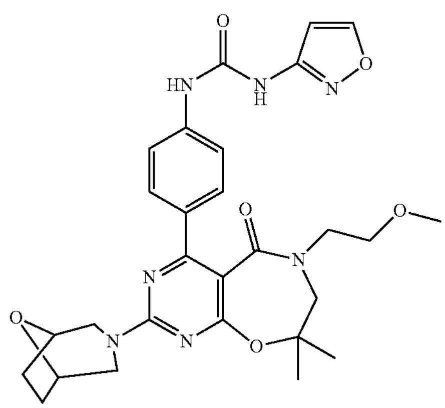 [SMILES: COCCN1CC(C)(C)Oc2nc(N3CC4CCC(C3)O4)nc(-c3ccc(NC(=O)Nc4ccon4)cc3)c2C1=O] | 564 | 0.66 | C |
| 173 | 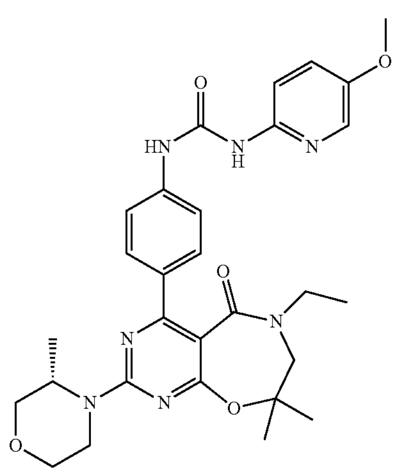 [SMILES: CCN1CC(C)(C)Oc2nc(N3CCOC[C@@H]3C)nc(-c3ccc(NC(=O)Nc4ccc(OC)cn4)cc3)c2C1=O] | 562 | 1.06 | A |

TABLE 3-continued
Chemical structures and physical properties of a number of examples of compounds according to the invention.
| Expl | Structure | Mass | Tr (min) | LC/MS method |
|---|---|---|---|---|
| 174 | 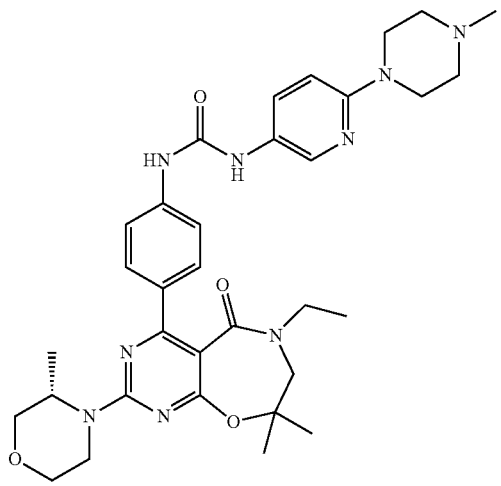 [SMILES: CCN1CC(C)(C)Oc2nc(N3CCOC[C@@H]3C)nc(-c3ccc(NC(=O)Nc4ccc(N5CCN(C)CC5)nc4)cc3)c2C1=O] | 630 | 0.76 | A |
| 175 | 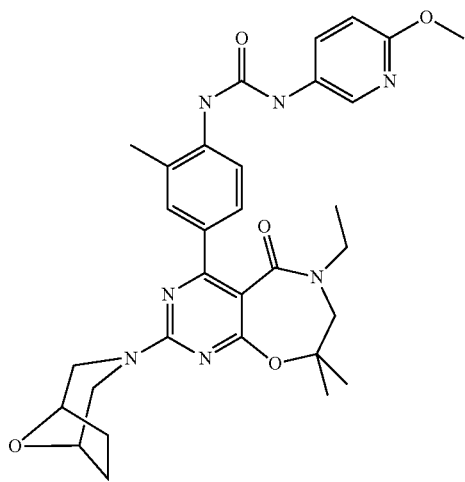 [SMILES: CCN1CC(C)(C)Oc2nc(N3CC4CCC(C3)O4)nc(-c3ccc(NC(=O)Nc4ccc(OC)nc4)c(C)c3)c2C1=O] | 588 | 0.69 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 176  | 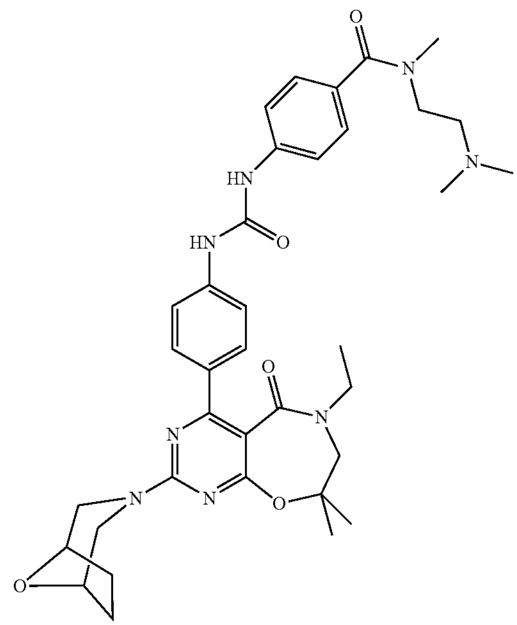 [SMILES: CCN1CC(C)(C)Oc2nc(N3CC4CCC(C3)O4)nc(-c3ccc(NC(=O)Nc4ccc(C(=O)N(C)CCN(C)C)cc4)cc3)c2C1=O]          | 671  | 0.51     | C            |
| 177  | 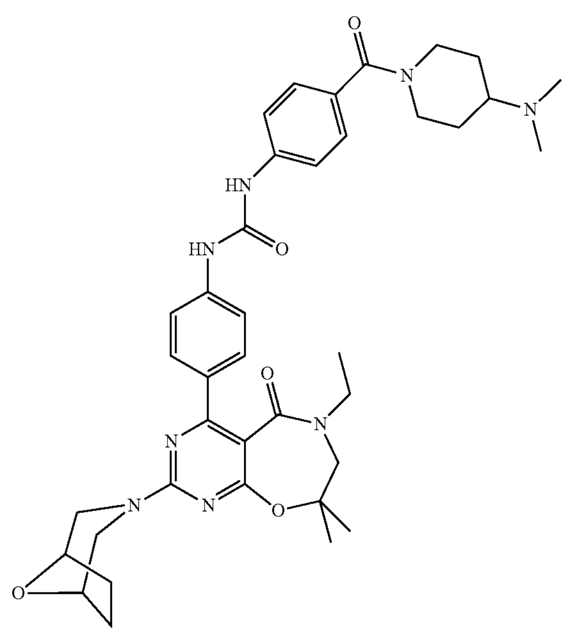 [SMILES: CCN1CC(C)(C)Oc2nc(N3CC4CCC(C3)O4)nc(-c3ccc(NC(=O)Nc4ccc(C(=O)N5CCC(N(C)C)CC5)cc4)cc3)c2C1=O]          | 697  | 0.5      | C            |

TABLE 3-continued
Chemical structures and physical properties of a number of examples of compounds according to the invention.
| Expl | Structure | Mass | Tr (min) | LC/MS method |
|---|---|---|---|---|
| 178 | 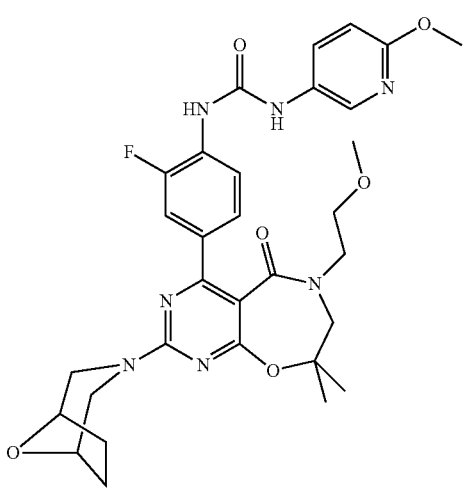 [SMILES: COCCN1CC(C)(C)Oc2nc(N3CC4CCC(C3)O4)nc(-c3ccc(NC(=O)Nc4ccc(OC)nc4)c(F)c3)c2C1=O] | 622 | 0.76 | C |
| 179 | 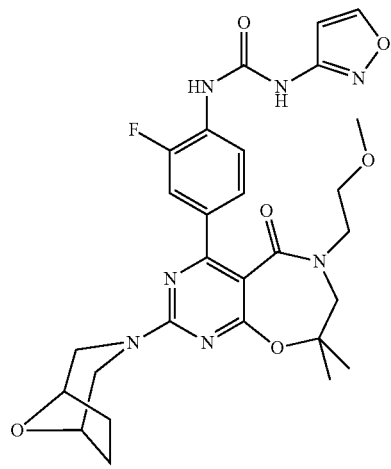 [SMILES: COCCN1CC(C)(C)Oc2nc(N3CC4CCC(C3)O4)nc(-c3ccc(NC(=O)Nc4ccon4)c(F)c3)c2C1=O] | 582 | 0.7 | C |
| 180 | 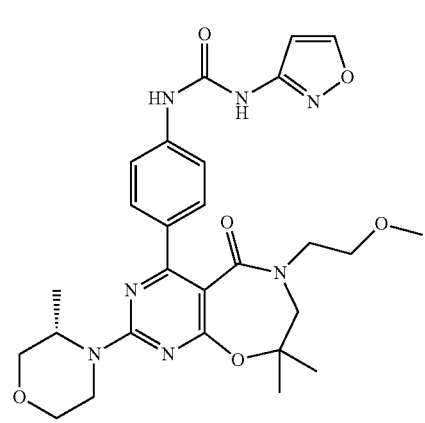 [SMILES: COCCN1CC(C)(C)Oc2nc(N3CCOC[C@@H]3C)nc(-c3ccc(NC(=O)Nc4ccon4)cc3)c2C1=O] | 552 | 0.67 | C |

TABLE 3-continued

Chemical structures and physical properties of a number of examples of compounds according to the invention.

| Expl | Structure | Mass | Tr (min) | LC/MS method |
|---|---|---|---|---|
| 181 | 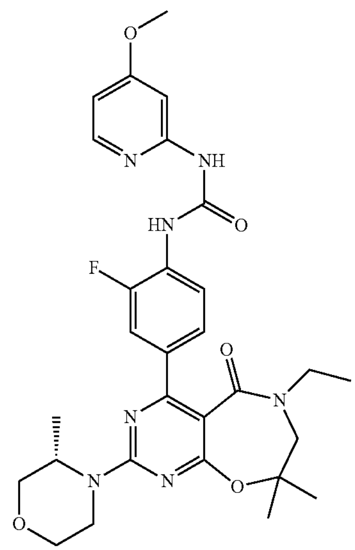 [SMILES: CCN1CC(C)(C)Oc2nc(N3CCOC[C@@H]3C)nc(-c3ccc(NC(=O)Nc4cc(OC)ccn4)c(F)c3)c2C1=O] | 580 | 0.99 | A |
| 182 | 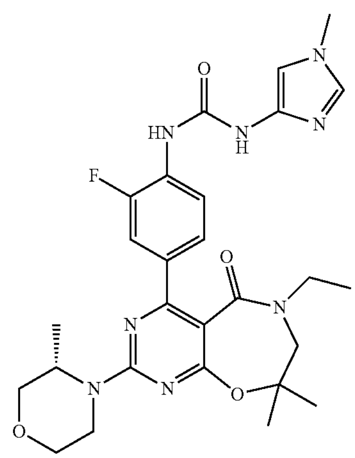 [SMILES: CCN1CC(C)(C)Oc2nc(N3CCOC[C@@H]3C)nc(-c3ccc(NC(=O)Nc4cn(C)cn4)c(F)c3)c2C1=O] | 553 | 0.8 | A |
| 183 | 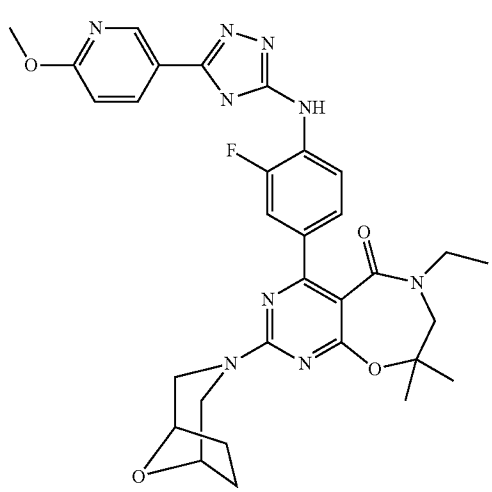 [SMILES: CCN1CC(C)(C)Oc2nc(N3CC4CCC(C3)O4)nc(-c3ccc(Nc4nnc(-c5ccc(OC)nc5)[nH]4)c(F)c3)c2C1=O] | 616 | 1.04 | A |

TABLE 3-continued

Chemical structures and physical properties of a number of examples of compounds according to the invention.

| Expl | Structure | Mass | Tr (min) | LC/MS method |
|---|---|---|---|---|
| 184 | 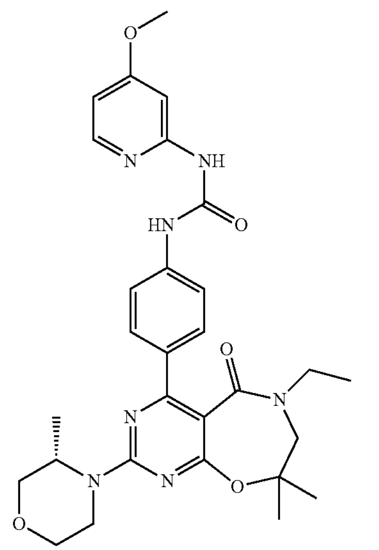 [SMILES: CCN1CC(C)(C)Oc2nc(N3CCOC[C@@H]3C)nc(-c3ccc(NC(=O)Nc4cc(OC)ccn4)cc3)c2C1=O] | 562 | 0.87 | A |
| 185 | 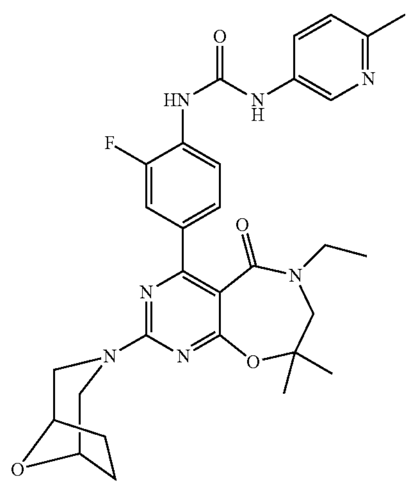 [SMILES: CCN1CC(C)(C)Oc2nc(N3CC4CCC(C3)O4)nc(-c3ccc(NC(=O)Nc4ccc(C)nc4)c(F)c3)c2C1=O] | 576 | 0.78 | A |
| 186 | 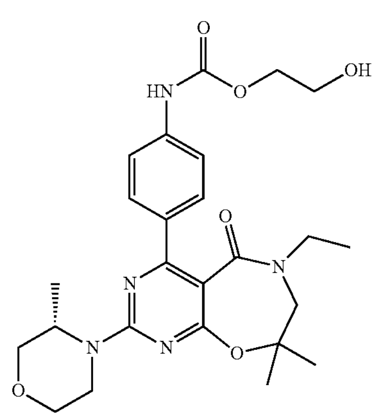 [SMILES: CCN1CC(C)(C)Oc2nc(N3CCOC[C@@H]3C)nc(-c3ccc(NC(=O)OCCO)cc3)c2C1=O] | 500 | 0.88 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 187 | 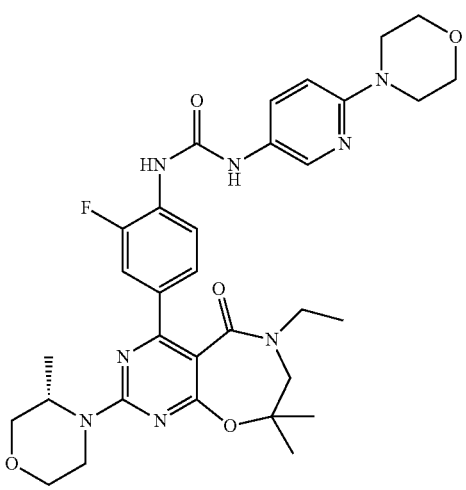 [SMILES: CCN1CC(C)(C)Oc2nc(N3CCOC[C@@H]3C)nc(-c3ccc(NC(=O)Nc4ccc(N5CCOCC5)nc4)c(F)c3)c2C1=O] | 635 | 0.86 | A |
| 188 | 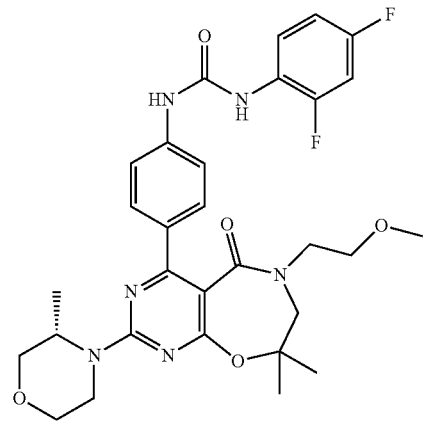 [SMILES: COCCN1CC(C)(C)Oc2nc(N3CCOC[C@@H]3C)nc(-c3ccc(NC(=O)Nc4ccc(F)cc4F)cc3)c2C1=O] | 597 | 3.13 | D |
| 189 | 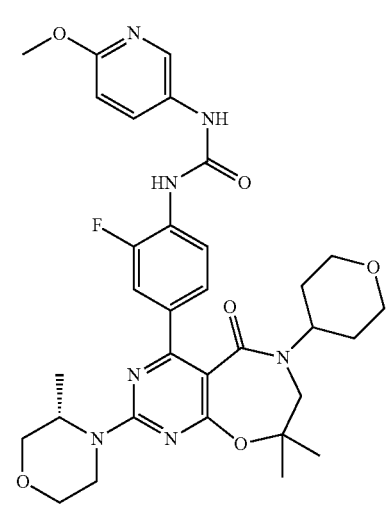 [SMILES: COc1ccc(NC(=O)Nc2ccc(-c3nc(N4CCOC[C@@H]4C)nc4c3C(=O)N(C3CCOCC3)CC(C)(C)O4)cc2F)cn1] | 636 | 4.38 | D |

TABLE 3-continued
Chemical structures and physical properties of a number of examples of compounds according to the invention.
| Expl | Structure | Mass | Tr (min) | LC/MS method |
|------|-----------|------|----------|--------------|
| 190 | 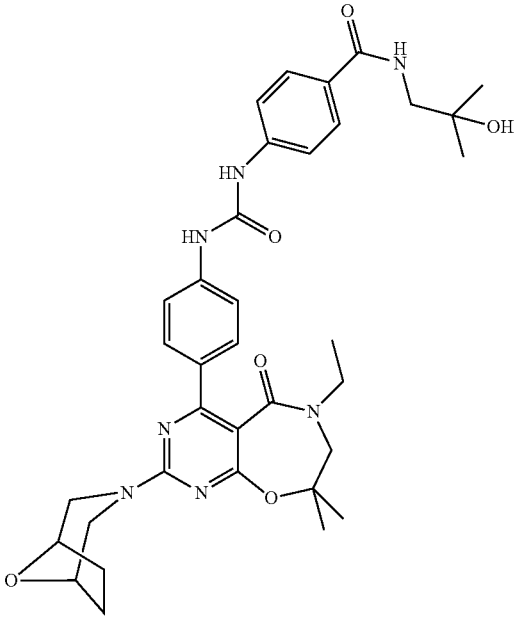 [SMILES: CCN1CC(C)(C)Oc2nc(N3CC4CCC(C3)O4)nc(-c3ccc(NC(=O)Nc4ccc(C(=O)NCC(C)(C)O)cc4)cc3)c2C1=O] | 658 | 2.49 | D |
| 191 | 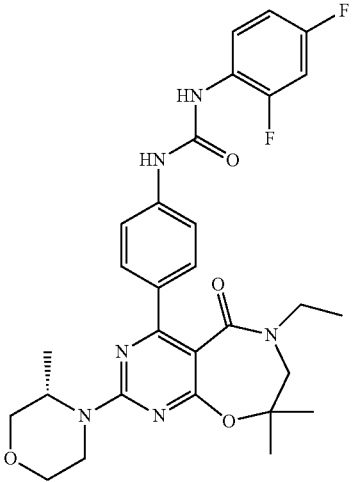 [SMILES: CCN1CC(C)(C)Oc2nc(N3CCOC[C@@H]3C)nc(-c3ccc(NC(=O)Nc4ccc(F)cc4F)cc3)c2C1=O] | 567 | 0.81 | C |
| 192 | 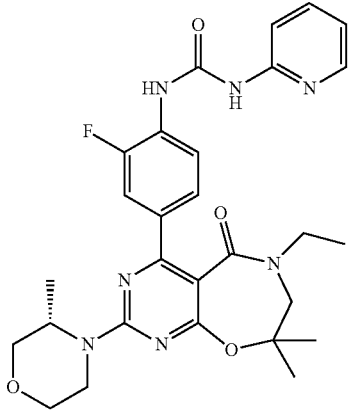 [SMILES: CCN1CC(C)(C)Oc2nc(N3CCOC[C@@H]3C)nc(-c3ccc(NC(=O)Nc4ccccn4)c(F)c3)c2C1=O] | 550 | 1.1 | A |

TABLE 3-continued
Chemical structures and physical properties of a number of examples of compounds according to the invention.
| Expl | Structure | Mass | Tr (min) | LC/MS method |
|---|---|---|---|---|
| 193 | 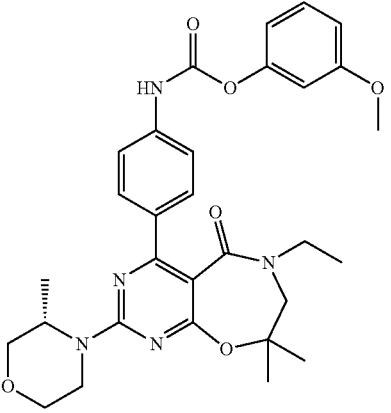 [SMILES: CCN1CC(C)(C)Oc2nc(N3CCOC[C@@H]3C)nc(-c3ccc(NC(=O)Oc4cccc(OC)c4)cc3)c2C1=O] | 562 | 1.19 | A |
| 194 | 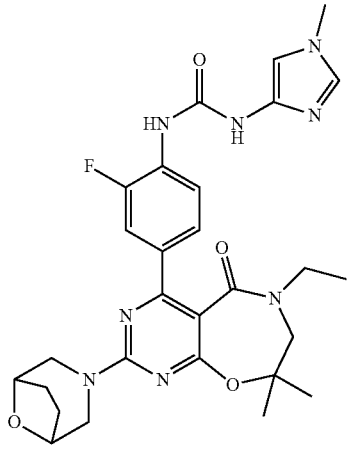 [SMILES: CCN1CC(C)(C)Oc2nc(N3CC4CCC(C3)O4)nc(-c3ccc(NC(=O)Nc4cn(C)cn4)c(F)c3)c2C1=O] | 565 | 0.75 | A |
| 195 | 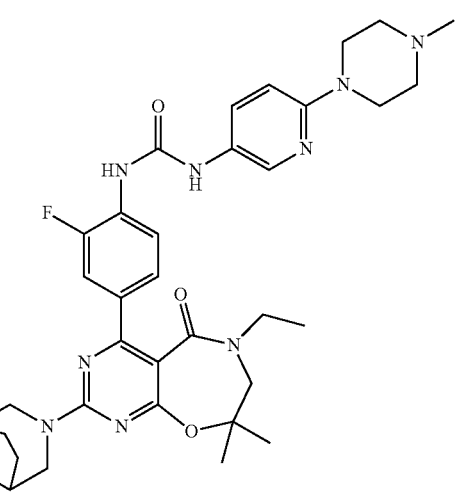 | 660 | 0.78 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 196 | 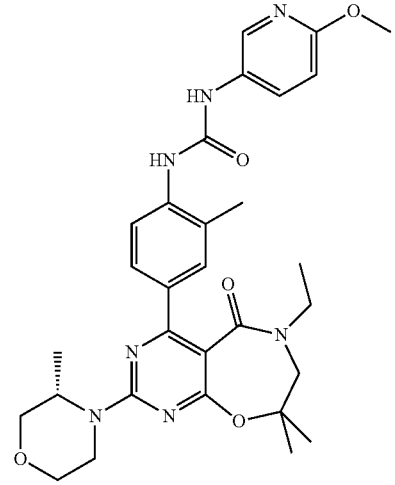 [SMILES: CCN1CC(C)(C)Oc2nc(N3CCOC[C@@H]3C)nc(-c3ccc(NC(=O)Nc4ccc(OC)nc4)c(C)c3)c2C1=O] | 576 | 0.71 | C |
| 197 | 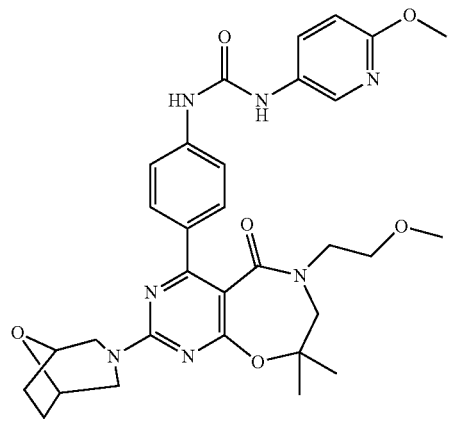 [SMILES: COCCN1CC(C)(C)Oc2nc(N3CC4CCC(C3)O4)nc(-c3ccc(NC(=O)Nc4ccc(OC)nc4)cc3)c2C1=O] | 604 | 0.67 | C |
| 198 | 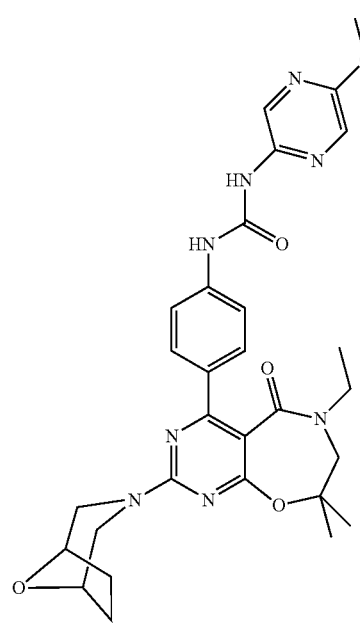 | 575 | 0.72 | C |

TABLE 3-continued

Chemical structures and physical properties of a number of examples of compounds according to the invention.

| Expl | Structure | Mass | Tr (min) | LC/MS method |
|---|---|---|---|---|
| 199 | 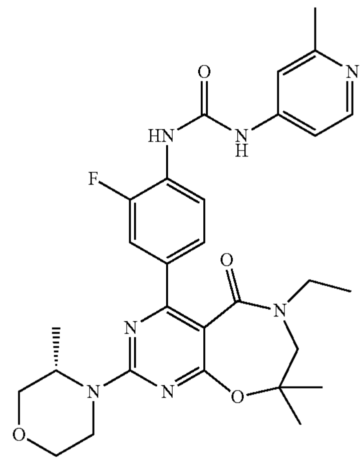 [SMILES: CCN1CC(C)(C)Oc2nc(N3CCOC[C@@H]3C)nc(-c3ccc(NC(=O)Nc4ccnc(C)c4)c(F)c3)c2C1=O] | 564 | 0.81 | A |
| 200 | 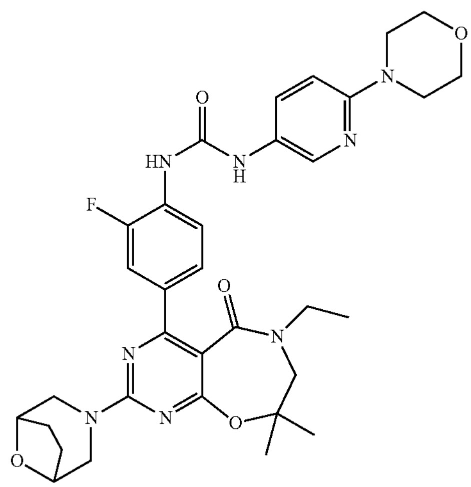 [SMILES: CCN1CC(C)(C)Oc2nc(N3CC4CCC(C3)O4)nc(-c3ccc(NC(=O)Nc4ccc(N5CCOCC5)nc4)c(F)c3)c2C1=O] | 647 | 0.85 | A |
| 201 | 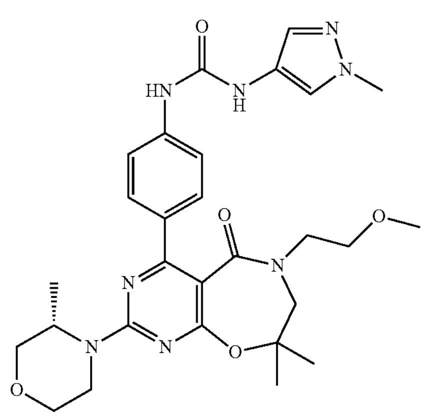 [SMILES: COCCN1CC(C)(C)Oc2nc(N3CCOC[C@@H]3C)nc(-c3ccc(NC(=O)Nc4cnn(C)c4)cc3)c2C1=O] | 565 | 0.6 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 202 | 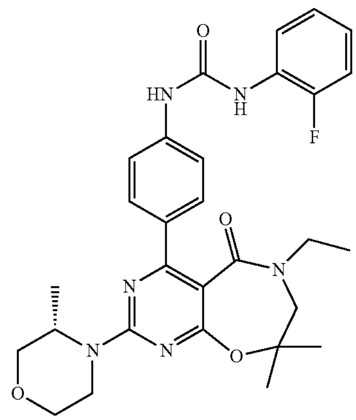 [SMILES: CCN1CC(C)(C)Oc2nc(N3CCOC[C@@H]3C)nc(-c3ccc(NC(=O)Nc4ccccc4F)cc3)c2C1=O] | 549 | 0.8 | C |
| 203 | 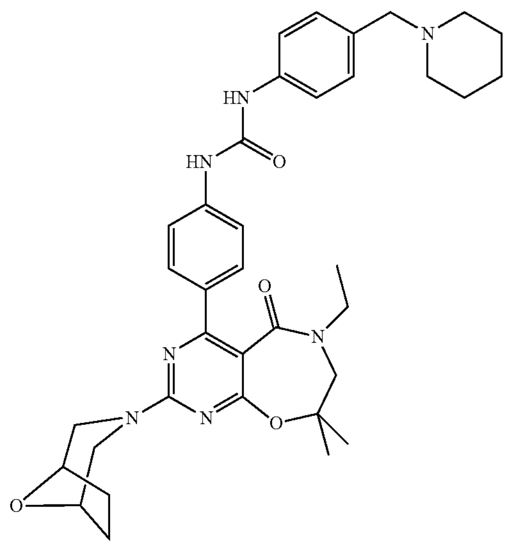 [SMILES: CCN1CC(C)(C)Oc2nc(N3CC4CCC(C3)O4)nc(-c3ccc(NC(=O)Nc4ccc(CN5CCCCC5)cc4)cc3)c2C1=O] | 640 | 0.54 | C |
| 204 | 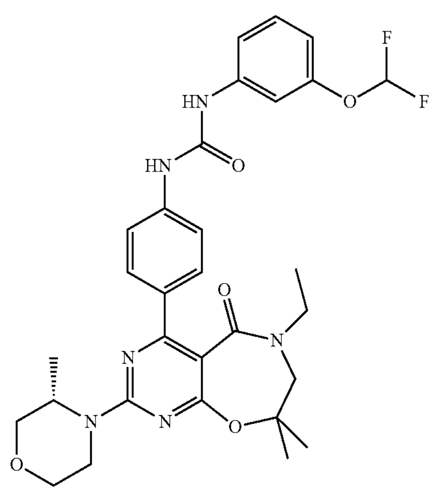 [SMILES: CCN1CC(C)(C)Oc2nc(N3CCOC[C@@H]3C)nc(-c3ccc(NC(=O)Nc4cccc(OC(F)F)c4)cc3)c2C1=O] | 597 | 0.82 | C |

TABLE 3-continued

Chemical structures and physical properties of a number of examples of compounds according to the invention.

| Expl | Structure | Mass | Tr (min) | LC/MS method |
|---|---|---|---|---|
| 205 | 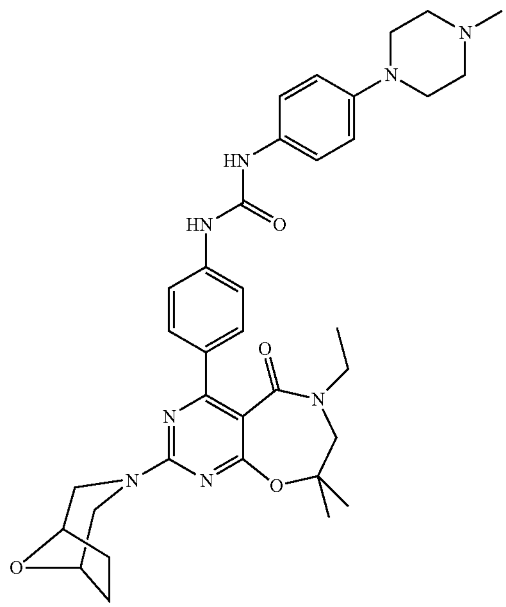 [SMILES: CCN1CC(C)(C)Oc2nc(N3CC4CCC(C3)O4)nc(-c3ccc(NC(=O)Nc4ccc(N5CCN(C)CC5)cc4)cc3)c2C1=O] | 641 | 0.51 | C |
| 206 | 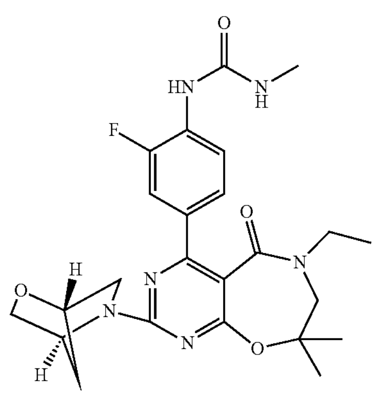 [SMILES: CCN1CC(C)(C)Oc2nc(N3C[C@@H]4C[C@H]3CO4)nc(-c3ccc(NC(=O)NC)c(F)c3)c2C1=O] | 485 | 0.77 | A |
| 207 | 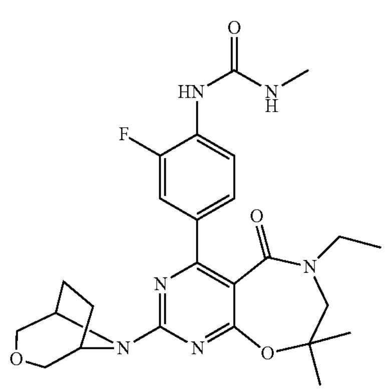 [SMILES: CCN1CC(C)(C)Oc2nc(N3C4CCC3COC4)nc(-c3ccc(NC(=O)NC)c(F)c3)c2C1=O] | 499 | 0.89 | A |

TABLE 3-continued

Chemical structures and physical properties of a number of examples of compounds according to the invention.

| Expl | Structure | Mass | Tr (min) | LC/MS method |
|---|---|---|---|---|
| 208 | 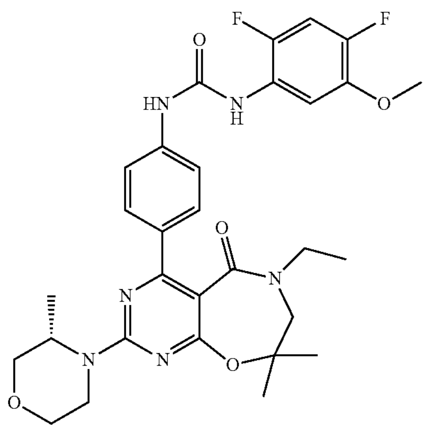 [SMILES: CCN1CC(C)(C)Oc2nc(N3CCOC[C@@H]3C)nc(-c3ccc(NC(=O)Nc4cc(OC)c(F)cc4F)cc3)c2C1=O] | 597 | 0.81 | C |
| 209 | 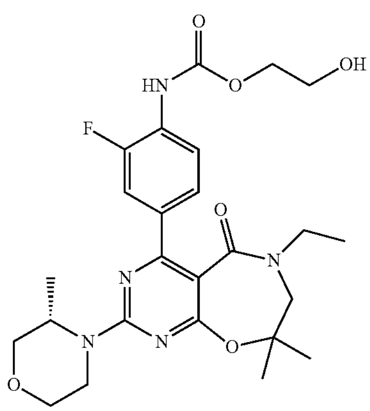 [SMILES: CCN1CC(C)(C)Oc2nc(N3CCOC[C@@H]3C)nc(-c3ccc(NC(=O)OCCO)c(F)c3)c2C1=O] | 518 | 0.92 | A |
| 210 | 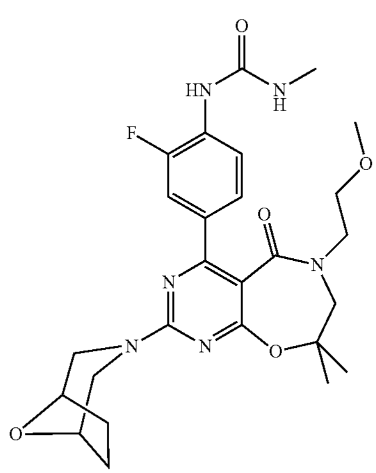 [SMILES: CNC(=O)Nc1ccc(-c2nc(N3CC4CCC(C3)O4)nc3c2C(=O)N(CCOC)CC(C)(C)O3)cc1F] | 529 | 0.61 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 211 | 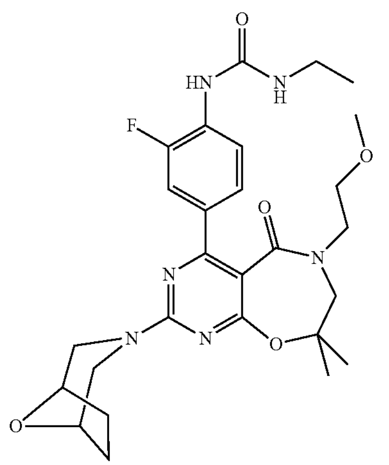 [SMILES: CCNC(=O)Nc1ccc(-c2nc(N3CC4CCC(C3)O4)nc3c2C(=O)N(CCOC)CC(C)(C)O3)cc1F] | 543 | 0.66 | C |
| 212 | 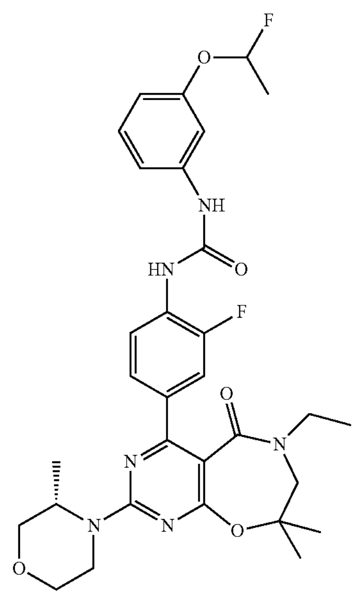 [SMILES: CCN1CC(C)(C)Oc2nc(N3CCOC[C@@H]3C)nc(-c3ccc(NC(=O)Nc4cccc(OC(C)F)c4)c(F)c3)c2C1=O] | 615 | 0.86 | C |
| 213 | 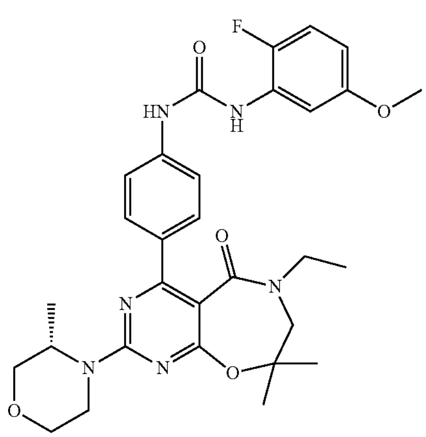 [SMILES: CCN1CC(C)(C)Oc2nc(N3CCOC[C@@H]3C)nc(-c3ccc(NC(=O)Nc4cc(OC)ccc4F)cc3)c2C1=O] | 579 | 0.81 | C |

TABLE 3-continued

Chemical structures and physical properties of a number of examples of compounds according to the invention.

| Expl | Structure | Mass | Tr (min) | LC/MS method |
|---|---|---|---|---|
| 214 | 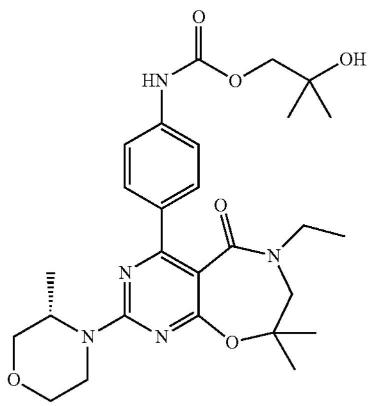 [SMILES: CCN1CC(C)(C)Oc2nc(N3CCOC[C@@H]3C)nc(-c3ccc(NC(=O)OCC(C)(C)O)cc3)c2C1=O] | 528 | 0.98 | A |
| 215 | 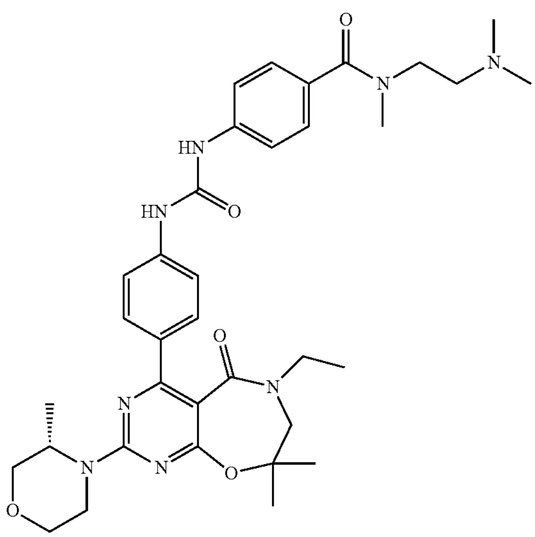 [SMILES: CCN1CC(C)(C)Oc2nc(N3CCOC[C@@H]3C)nc(-c3ccc(NC(=O)Nc4ccc(C(=O)N(C)CCN(C)C)cc4)cc3)c2C1=O] | 659 | 0.52 | C |
| 216 | 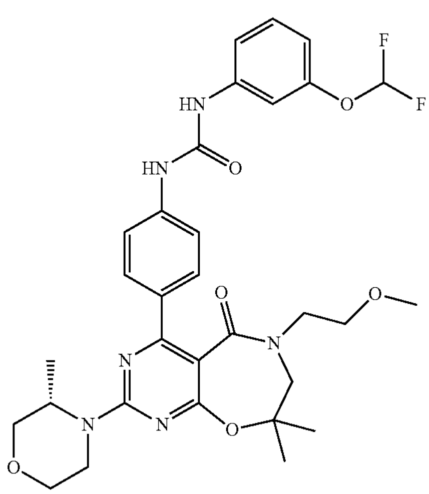 [SMILES: COCCN1CC(C)(C)Oc2nc(N3CCOC[C@@H]3C)nc(-c3ccc(NC(=O)Nc4cccc(OC(F)F)c4)cc3)c2C1=O] | 627 | 0.82 | C |

TABLE 3-continued

Chemical structures and physical properties of a number of examples of compounds according to the invention.

| Expl | Structure | Mass | Tr (min) | LC/MS method |
|---|---|---|---|---|
| 217 | 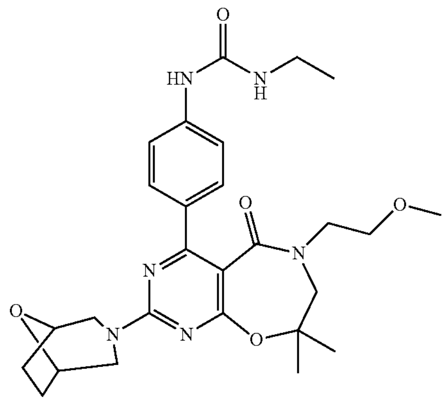 [SMILES: CCNC(=O)Nc1ccc(-c2nc(N3CC4CCC(C3)O4)nc3c2C(=O)N(CCOC)CC(C)(C)O3)cc1] | 525 | 0.62 | C |
| 218 | 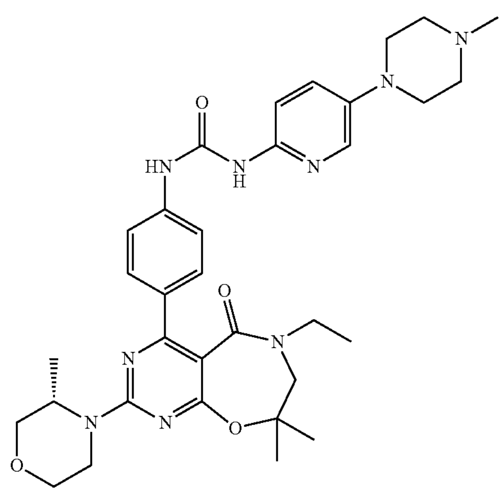 [SMILES: CCN1CC(C)(C)Oc2nc(N3CCOC[C@@H]3C)nc(-c3ccc(NC(=O)Nc4ccc(N5CCN(C)CC5)cn4)cc3)c2C1=O] | 630 | 0.75 | A |
| 219 | 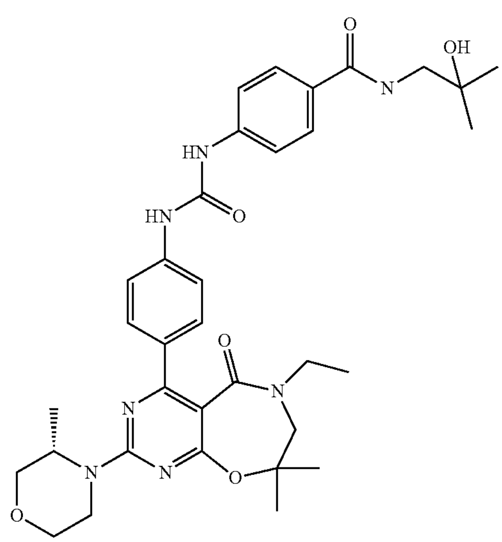 [SMILES: CCN1CC(C)(C)Oc2nc(N3CCOC[C@@H]3C)nc(-c3ccc(NC(=O)Nc4ccc(C(=O)NCC(C)(C)O)cc4)cc3)c2C1=O] | 646 | 0.64 | C |

TABLE 3-continued

Chemical structures and physical properties of a number of examples of compounds according to the invention.

| Expl | Structure | Mass | Tr (min) | LC/MS method |
|---|---|---|---|---|
| 220 | 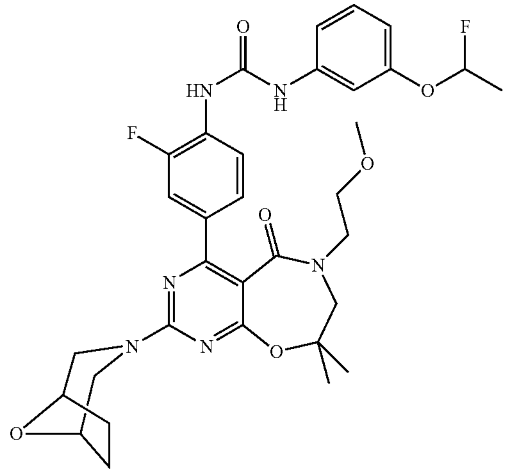 [SMILES: COCCN1CC(C)(C)Oc2nc(N3CC4CCC(C3)O4)nc(-c3ccc(NC(=O)Nc4cccc(OC(C)F)c4)c(F)c3)c2C1=O] | 657 | 0.84 | C |
| 221 | 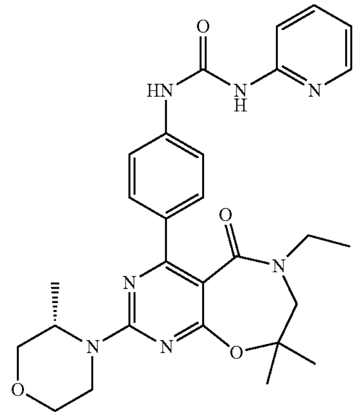 [SMILES: CCN1CC(C)(C)Oc2nc(N3CCOC[C@@H]3C)nc(-c3ccc(NC(=O)Nc4ccccn4)cc3)c2C1=O] | 532 | 1.01 | A |
| 222 | 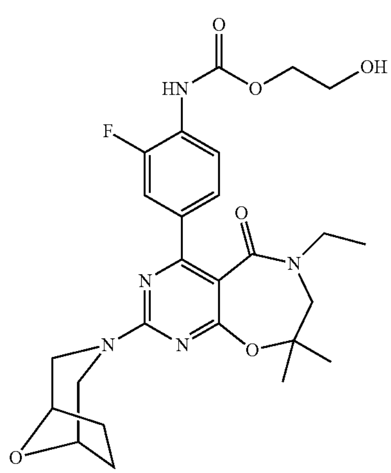 [SMILES: CCN1CC(C)(C)Oc2nc(N3CC4CCC(C3)O4)nc(-c3ccc(NC(=O)OCCO)c(F)c3)c2C1=O] | 530 | 0.88 | A |

TABLE 3-continued

Chemical structures and physical properties of a number of examples of compounds according to the invention.

| Expl | Structure | Mass | Tr (min) | LC/MS method |
|---|---|---|---|---|
| 223 | 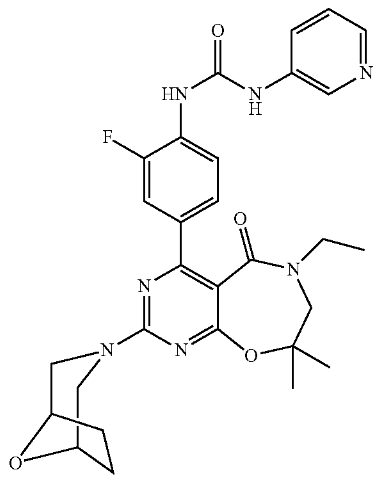 [SMILES: CCN1CC(C)(C)Oc2nc(N3CC4CCC(C3)O4)nc(-c3ccc(NC(=O)Nc4cccnc4)c(F)c3)c2C1=O] | 562 | 0.8 | A |
| 224 | 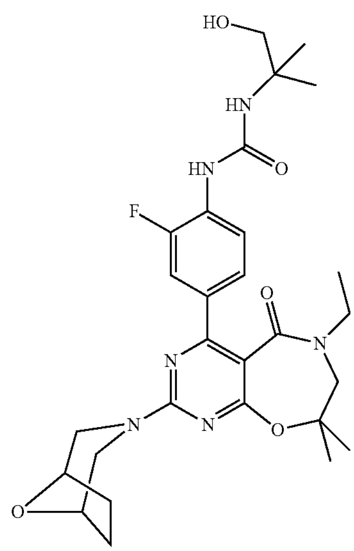 [SMILES: CCN1CC(C)(C)Oc2nc(N3CC4CCC(C3)O4)nc(-c3ccc(NC(=O)NC(C)(C)CO)c(F)c3)c2C1=O] | 557 | 0.66 | C |
| 225 | 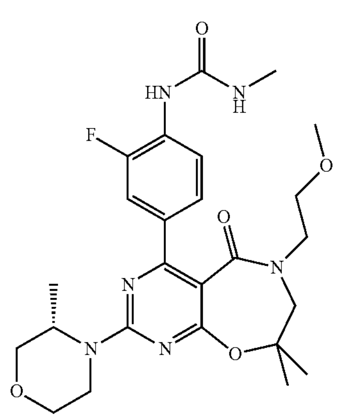 [SMILES: CNC(=O)Nc1ccc(-c2nc(N3CCOC[C@@H]3C)nc3c2C(=O)N(CCOC)CC(C)(C)O3)cc1F] | 517 | 0.63 | C |

TABLE 3-continued

Chemical structures and physical properties of a number of examples of compounds according to the invention.

| Expl | Structure | Mass | Tr (min) | LC/MS method |
|---|---|---|---|---|
| 226 | 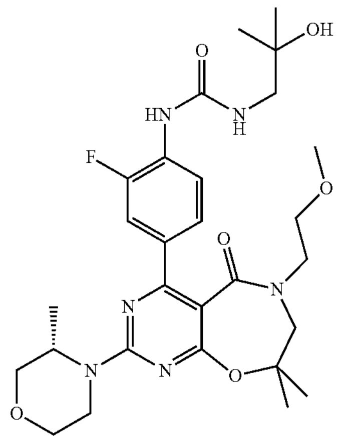 [SMILES: COCCN1CC(C)(C)Oc2nc(N3CCOC[C@@H]3C)nc(-c3ccc(NC(=O)NCC(C)(C)O)c(F)c3)c2C1=O] | 575 | 0.64 | C |
| 227 | 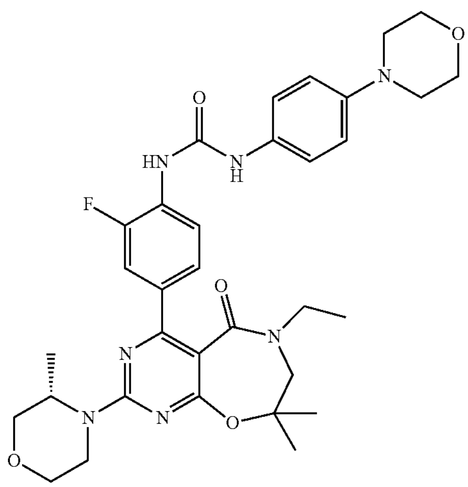 [SMILES: CCN1CC(C)(C)Oc2nc(N3CCOC[C@@H]3C)nc(-c3ccc(NC(=O)Nc4ccc(N5CCOCC5)cc4)c(F)c3)c2C1=O] | 634 | 0.97 | A |
| 228 | 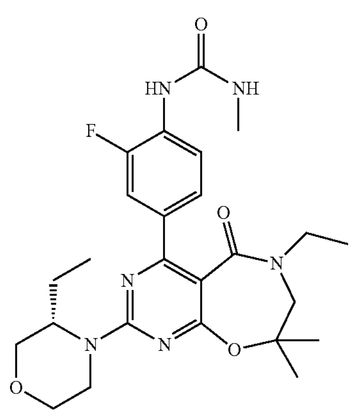 [SMILES: CC[C@H]1COCCN1c1nc2c(c(-c3ccc(NC(=O)NC)c(F)c3)n1)C(=O)N(CC)CC(C)(C)O2] | 501 | 0.98 | A |

TABLE 3-continued
Chemical structures and physical properties of a number of examples of compounds according to the invention.
| Expl | Structure | Mass | Tr (min) | LC/MS method |
|---|---|---|---|---|
| 229 | 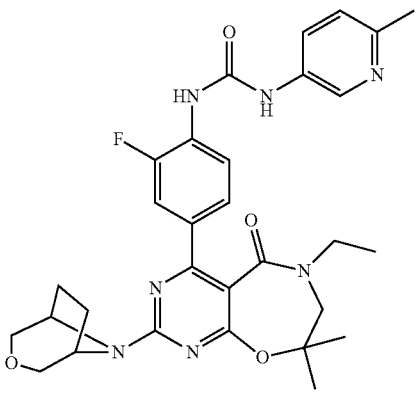 [SMILES: CCN1CC(C)(C)Oc2nc(N3C4CCC3COC4)nc(-c3ccc(NC(=O)Nc4ccc(C)nc4)c(F)c3)c2C1=O] | 576 | 0.84 | A |
| 230 | 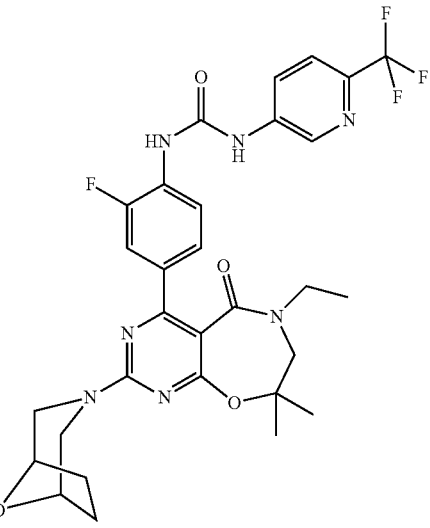 | 630 | 1.2 | A |
| 231 | 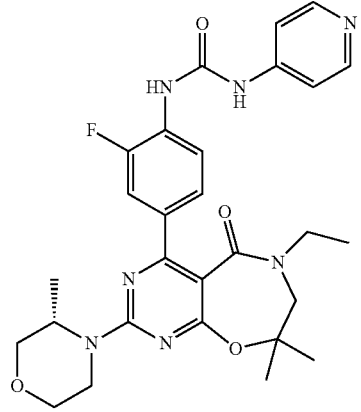 [SMILES: CCN1CC(C)(C)Oc2nc(N3CCOC[C@@H]3C)nc(-c3ccc(NC(=O)Nc4ccncc4)c(F)c3)c2C1=O] | 550 | 0.82 | A |

TABLE 3-continued
Chemical structures and physical properties of a number of examples of compounds according to the invention.
| Expl | Structure | Mass | Tr (min) | LC/MS method |
|------|-----------|------|----------|--------------|
| 232 | 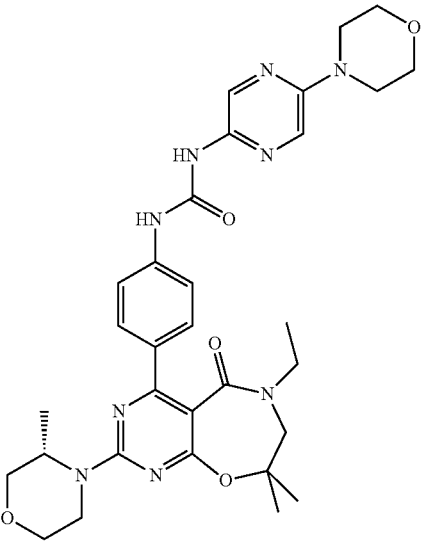 [SMILES: CCN1CC(C)(C)Oc2nc(N3CCOC[C@@H]3C)nc(-c3ccc(NC(=O)Nc4cnc(N5CCOCC5)cn4)cc3)c2C1=O] | 618 | 0.71 | C |
| 233 | 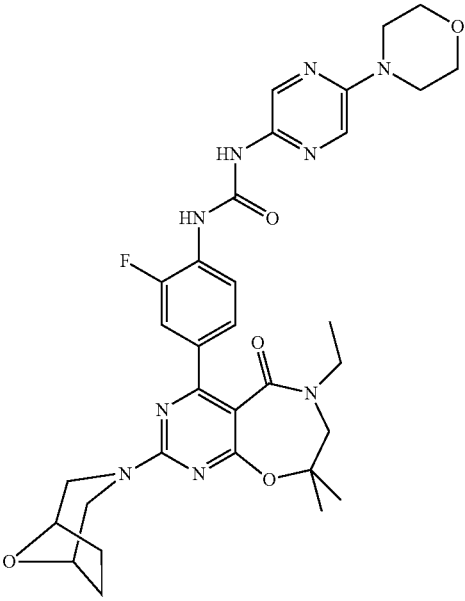 [SMILES: CCN1CC(C)(C)Oc2nc(N3CC4CCC(C3)O4)nc(-c3ccc(NC(=O)Nc4cnc(N5CCOCC5)cn4)c(F)c3)c2C1=O] | 648 | 0.74 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 234 | 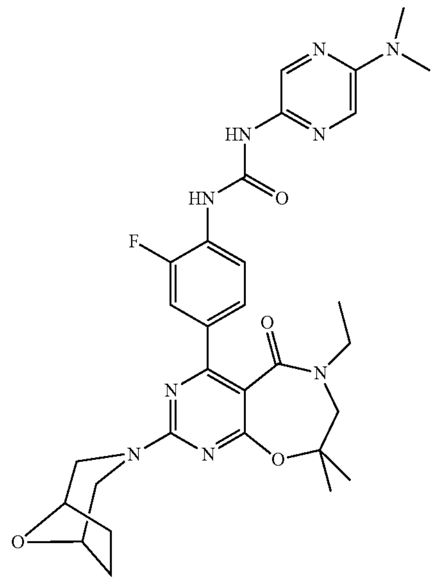 [SMILES: CCN1CC(C)(C)Oc2nc(N3CC4CCC(C3)O4)nc(-c3ccc(NC(=O)Nc4cnc(N(C)C)cn4)c(F)c3)c2C1=O] | 606 | 0.76 | C |
| 235 | 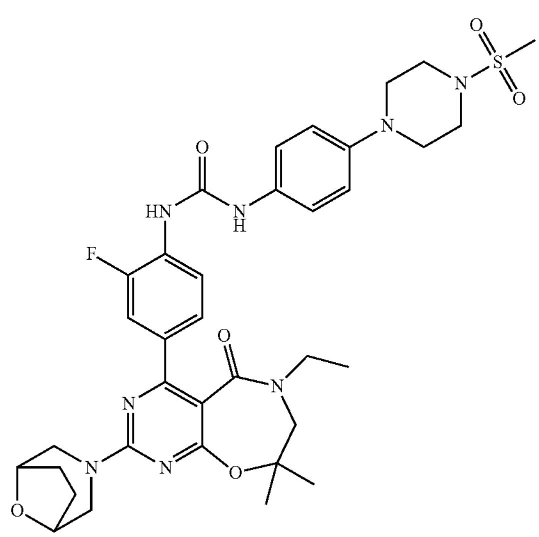 [SMILES: CCN1CC(C)(C)Oc2nc(N3CC4CCC(C3)O4)nc(-c3ccc(NC(=O)Nc4ccc(N5CCN(S(C)(=O)=O)CC5)cc4)c(F)c3)c2C1=O] | 723 | 1.04 | A |

TABLE 3-continued
Chemical structures and physical properties of a number of examples of compounds according to the invention.
| Expl | Structure | Mass | Tr (min) | LC/MS method |
|---|---|---|---|---|
| 236 | 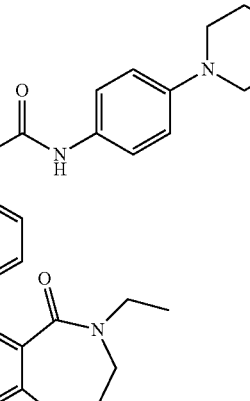 | 703 | 0.97 | A |
| 237 | 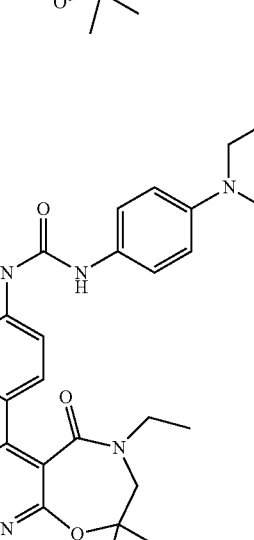 | 694 | 1.01 | A |
| 238 | 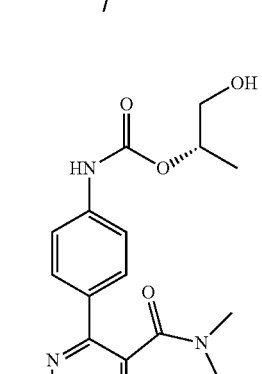 | 512 | 0.6 | C |

TABLE 3-continued
Chemical structures and physical properties of a number of examples of compounds according to the invention.
| Expl | Structure | Mass | Tr (min) | LC/MS method |
|---|---|---|---|---|
| 239 | 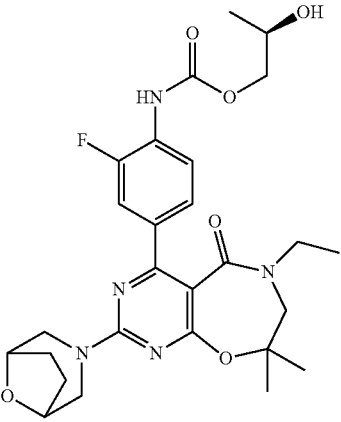 [SMILES: CCN1CC(C)(C)Oc2nc(N3CC4CCC(C3)O4)nc(-c3ccc(NC(=O)OC[C@@H](C)O)c(F)c3)c2C1=O] | 544 | 0.66 | C |
| 240 | 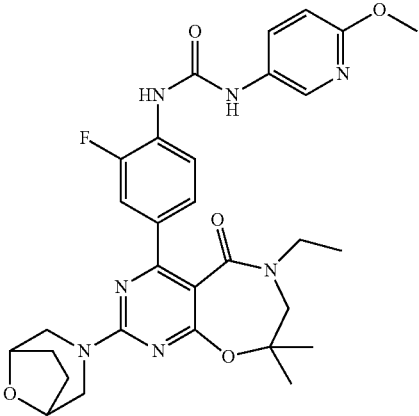 [SMILES: CCN1CC(C)(C)Oc2nc(N3CC4CCC(C3)O4)nc(-c3ccc(NC(=O)Nc4ccc(OC)nc4)c(F)c3)c2C1=O] | 592 | 1.03 | A |
| 241 | 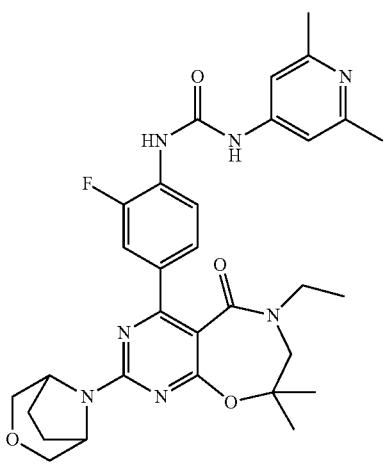 [SMILES: CCN1CC(C)(C)Oc2nc(N3C4CCC3COC4)nc(-c3ccc(NC(=O)Nc4cc(C)nc(C)c4)c(F)c3)c2C1=O] | 590 | 0.80 | A |

TABLE 3-continued
Chemical structures and physical properties of a number of examples of compounds according to the invention.
| Expl | Structure | Mass | Tr (min) | LC/MS method |
|---|---|---|---|---|
| 242 | 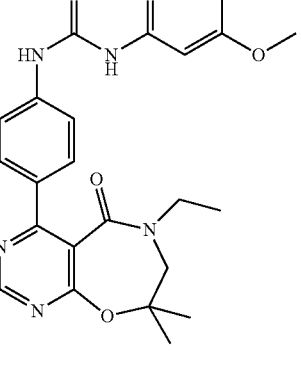 | 580 | 0.64 | C |
| 243 | 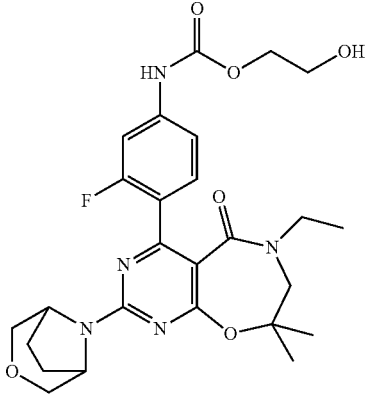 [SMILES: CCN1CC(C)(C)Oc2nc(N3C4CCC3COC4)nc(-c3ccc(NC(=O)OCCO)cc3F)c2C1=O] | 530 | 0.64 | C |
| 244 | 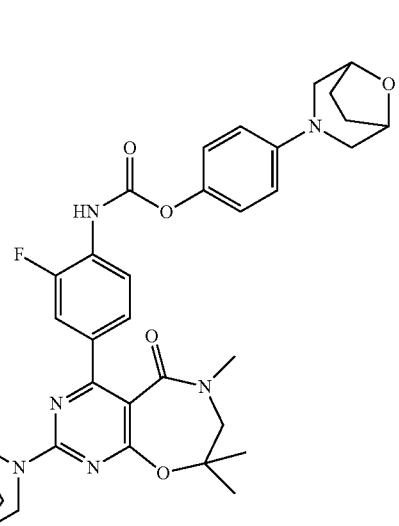 | 659 | 0.56 | C |

TABLE 3-continued
Chemical structures and physical properties of a number of examples of compounds according to the invention.
| Expl | Structure | Mass | Tr (min) | LC/MS method |
|------|-----------|------|----------|--------------|
| 245 | 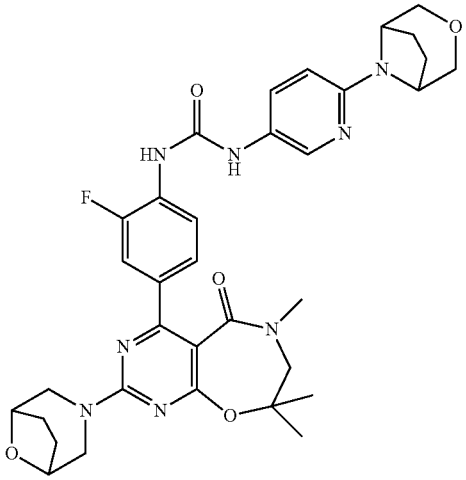 [SMILES: CN1CC(C)(C)Oc2nc(N3CC4CCC(C3)O4)nc(-c3ccc(NC(=O)Nc4ccc(N5C6CCC5COC6)nc4)c(F)c3)c2C1=O] | 659 | 0.56 | C |
| 246 | 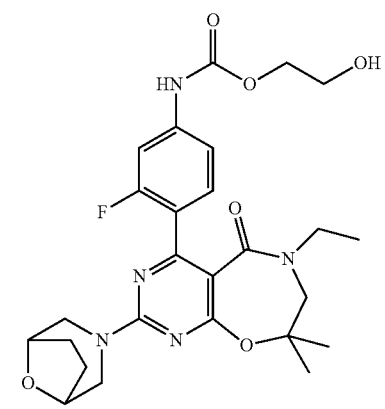 [SMILES: CCN1CC(C)(C)Oc2nc(N3CC4CCC(C3)O4)nc(-c3ccc(NC(=O)OCCO)cc3F)c2C1=O] | 530 | 0.64 | C |
| 247 | 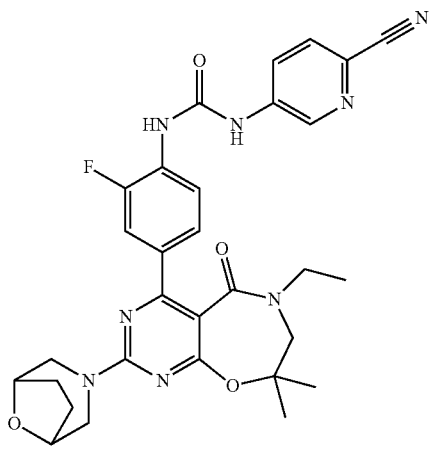 [SMILES: CCN1CC(C)(C)Oc2nc(N3CC4CCC(C3)O4)nc(-c3ccc(NC(=O)Nc4ccc(C#N)nc4)c(F)c3)c2C1=O] | 587 | 0.75 | C |

TABLE 3-continued

Chemical structures and physical properties of a number of examples of compounds according to the invention.

| Expl | Structure | Mass | Tr (min) | LC/MS method |
|------|-----------|------|----------|--------------|
| 248 | 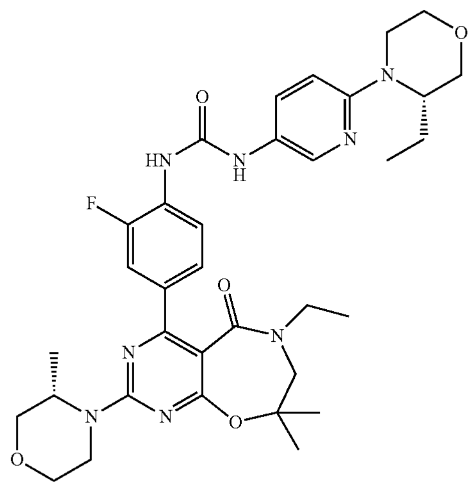 [SMILES: CC[C@H]1COCCN1c1ccc(NC(=O)Nc2ccc(-c3nc(N4CCOC[C@@H]4C)nc4c3C(=O)N(CC)CC(C)(C)O4)cc2F)cn1] | 663 | 1.28 | A |
| 249 | 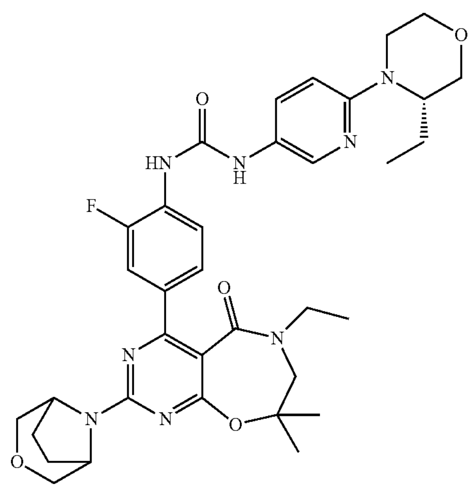 [SMILES: CC[C@H]1COCCN1c1ccc(NC(=O)Nc2ccc(-c3nc(N4C5CCC4COC5)nc4c3C(=O)N(CC)CC(C)(C)O4)cc2F)cn1] | 675 | 0.92 | A |
| 250 | 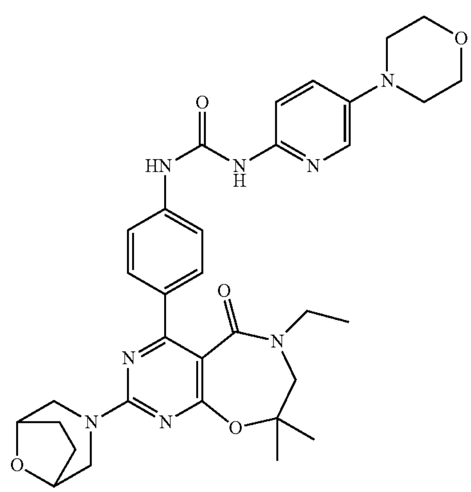 [SMILES: CCN1CC(C)(C)Oc2nc(N3CC4CCC(C3)O4)nc(-c3ccc(NC(=O)Nc4ccc(N5CCOCC5)cn4)cc3)c2C1=O] | 629 | 0.63 | C |

TABLE 3-continued
Chemical structures and physical properties of a number of examples of compounds according to the invention.
| Expl | Structure | Mass | Tr (min) | LC/MS method |
|---|---|---|---|---|
| 251 | 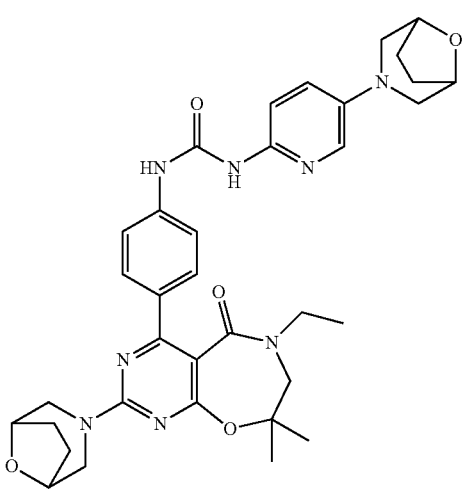 [SMILES: CCN1CC(C)(C)Oc2nc(N3CC4CCC(C3)O4)nc(-c3ccc(NC(=O)Nc4ccc(N5CC6CCC(C5)O6)cn4)cc3)c2C1=O] | 655 | 0.65 | C |
| 252 | 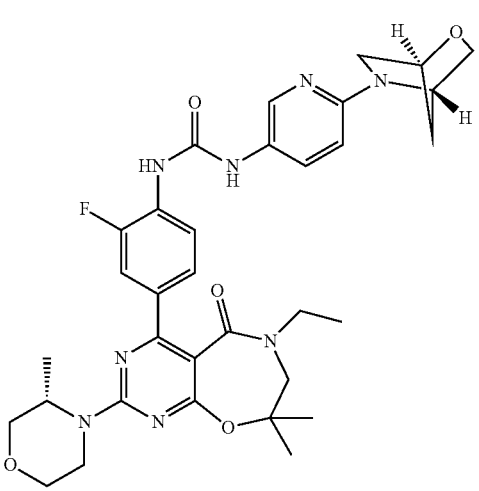 [SMILES: CCN1CC(C)(C)Oc2nc(N3CCOC[C@@H]3C)nc(-c3ccc(NC(=O)Nc4ccc(N5C[C@@H]6C[C@H]5CO6)nc4)c(F)c3)c2C1=O] | 647 | 0.84 | A |
| 253 | 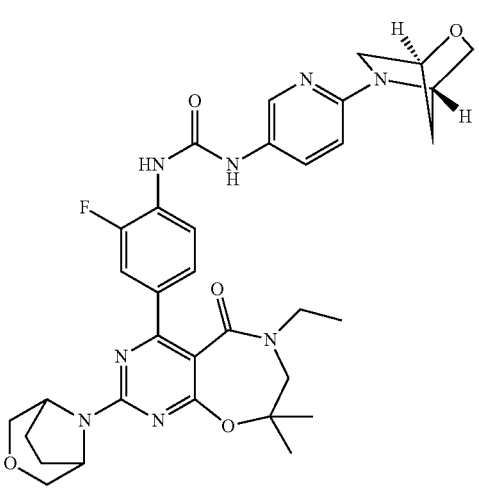 [SMILES: CCN1CC(C)(C)Oc2nc(N3C4CCC3COC4)nc(-c3ccc(NC(=O)Nc4ccc(N5C[C@@H]6C[C@H]5CO6)nc4)c(F)c3)c2C1=O] | 659 | 0.82 | A |

TABLE 3-continued

Chemical structures and physical properties of a number of examples of compounds according to the invention.

| Expl | Structure | Mass | Tr (min) | LC/MS method |
|------|-----------|------|----------|--------------|
| 254 | 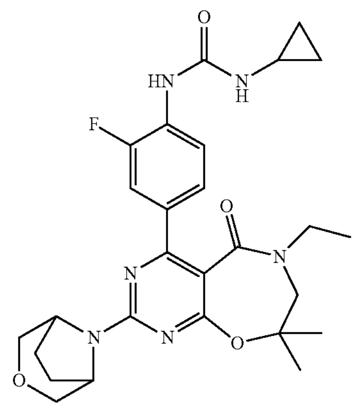 [SMILES: CCN1CC(C)(C)Oc2nc(N3C4CCC3COC4)nc(-c3ccc(NC(=O)NC4CC4)c(F)c3)c2C1=O] | 525 | 0.98 | A |
| 255 | 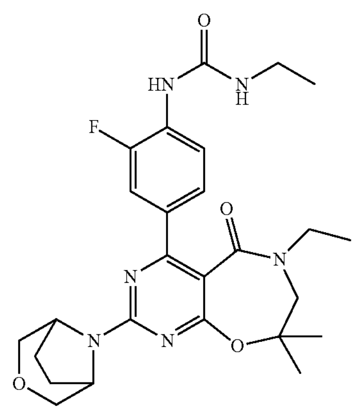 [SMILES: CCNC(=O)Nc1ccc(-c2nc(N3C4CCC3COC4)nc3c2C(=O)N(CC)CC(C)(C)O3)cc1F] | 513 | 0.97 | A |
| 256 | 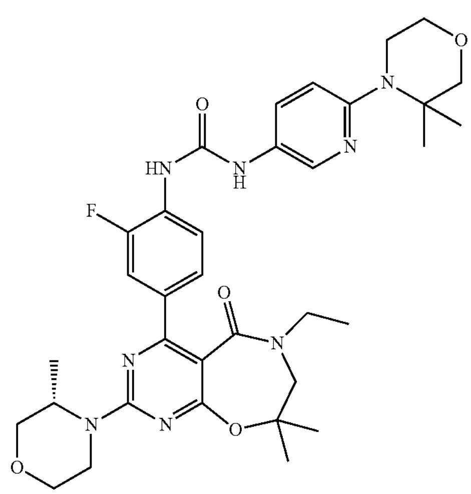 [SMILES: CCN1CC(C)(C)Oc2nc(N3CCOC[C@@H]3C)nc(-c3ccc(NC(=O)Nc4ccc(N5CCOCC5(C)C)nc4)c(F)c3)c2C1=O] | 663 | 0.96 | A |

TABLE 3-continued
Chemical structures and physical properties of a number of examples of compounds according to the invention.
| Expl | Structure | Mass | Tr (min) | LC/MS method |
|---|---|---|---|---|
| 257 | 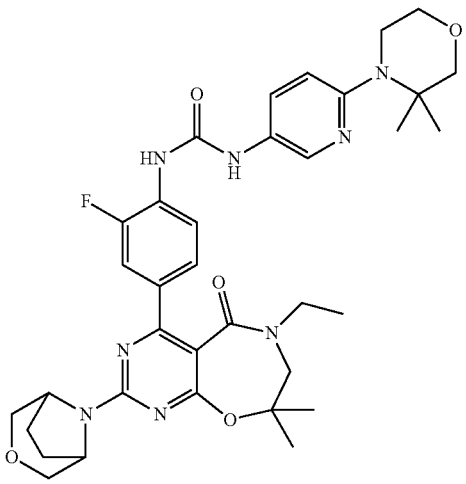 [SMILES: CCN1CC(C)(C)Oc2nc(N3C4CCC3COC4)nc(-c3ccc(NC(=O)Nc4ccc(N5CCOCC5(C)C)nc4)c(F)c3)c2C1=O] | 675 | 0.95 | A |
| 258 | 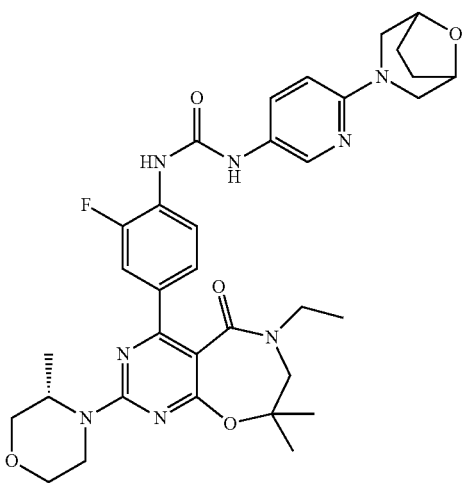 [SMILES: CCN1CC(C)(C)Oc2nc(N3CCOC[C@@H]3C)nc(-c3ccc(NC(=O)Nc4ccc(N5CC6CCC(C5)O6)nc4)c(F)c3)c2C1=O] | 661 | 0.87 | A |
| 259 | 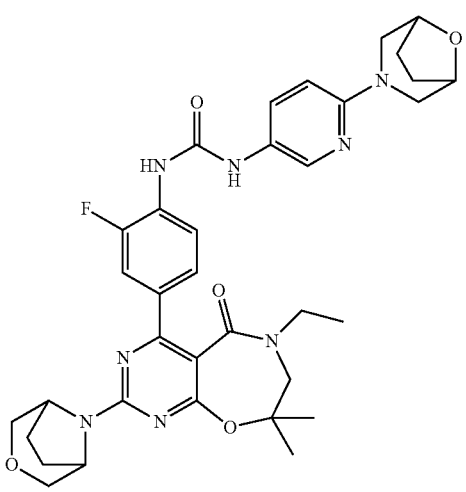 [SMILES: CCN1CC(C)(C)Oc2nc(N3C4CCC3COC4)nc(-c3ccc(NC(=O)Nc4ccc(N5CC6CCC(C5)O6)nc4)c(F)c3)c2C1=O] | 673 | 0.85 | A |

TABLE 3-continued

Chemical structures and physical properties of a number of examples of compounds according to the invention.

| Expl | Structure | Mass | Tr (min) | LC/MS method |
|---|---|---|---|---|
| 260 | 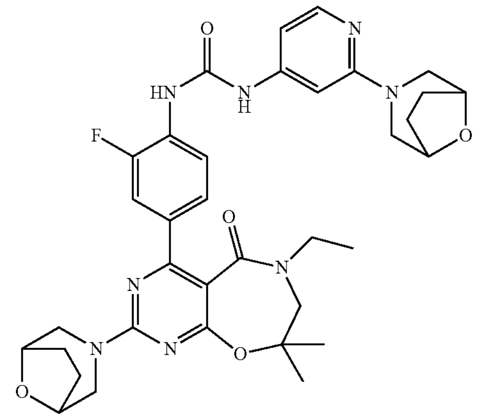 [SMILES: CCN1CC(C)(C)Oc2nc(N3CC4CCC(C3)O4)nc(-c3ccc(NC(=O)Nc4ccnc(N5CC6CCC(C5)O6)c4)c(F)c3)c2C1=O] | 673 | 0.84 | A |
| 261 | 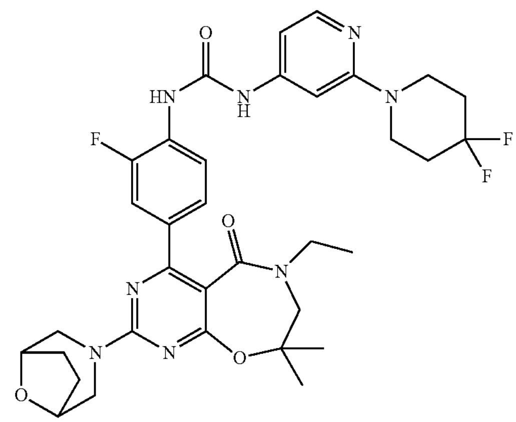 [SMILES: CCN1CC(C)(C)Oc2nc(N3CC4CCC(C3)O4)nc(-c3ccc(NC(=O)Nc4ccnc(N5CCC(F)(F)CC5)c4)c(F)c3)c2C1=O] | 680 | 0.90 | A |

[Therapeutic Application]

The compounds according to the invention underwent pharmacological trials to determine their inhibitory effect on mTOR and the effect of the two complexes mTORC1 and mTORC2.

The trials consisted in measuring the in vitro activity of the compounds of the invention on mTOR and also on PI3Kα, Akt-pS473 and on the proliferation of U87MG cells. The inhibitory activities are given by the concentration that inhibits 50% of the activity of mTOR, PI3Kα, Akt-pS473 or of the proliferation of U87MG cells.

Model 1: mTOR Enzymatic Test by TR-FRET (Time-resolved Fluorescence Resonance Energy Transfer).

The test detects the phosphorylation of the substrate GFP-4EBP1 using a terbium-labelled antibody that is specific for the phospho-Thr46 epitope. Binding of the Tb-antibody to the phosphorylated GFP peptide allows the transfer of energy from Tb, excited at 340 nm, to GFP with an increase in the fluorescence emission of the GFP at 520 nm. The test is performed in 96-well format (Corning/Costar 96 black flat-bottomed half-wells plate, ref. 3694) in a total volume of 30 μl. To 1 μl of inhibitor in 100% DMSO are added (final concentrations) 400 nM of GFP-4EBP1 (Invitrogen PV4759), 8 μM of ATP, 200 ng/ml of enzyme (human recombinant aa mTOR 1360-2549, Invitrogen PV4753) in a buffer of HEPES 50 mM pH 7.5, EGTA 1 mM, $MnCl_2$ 10 mM, BSA 0.1 mg/ml, glycerol 0.5%, NV-10 0.1 mg/ml, DTT 2 mM. The mixture is incubated for 30 minutes at room temperature. 10 μl of solution are taken up and the reaction is quenched by adding 10 μl of Tb-antibody solution (Invitrogen PV4757)/EDTA (2 nM Tb-Ac and 10 mM EDTA final). After 60 minutes at room temperature, the fluorescence at 490 nm, from the Tb emission, and at 520 nm, from the GFP emission, is measured in a BMG PHERAstar reader equipped with a Lanthascreen™ filter (excitation at 340 nm, emission at 490 and 520 nm). The results are given in the form of the 520/490 ratio.

The IC50 values are determined by the preparation of successive threefold dilutions on at least a scale of 10 000.

Model 2: PI3Kα Enzymatic Test by Measuring the Consumption of ATP.

The test uses a lucifeurerin/luciferase system to measure the concentration of ATP and its consumption during the enzymatic reaction. The test is performed in 96-well format (Corning/Costar 96 black flat-bottomed half-wells plate, ref. 3694) in a total volume of 30 μl.

To 1 μl of inhibitor in 100% DMSO are added (final concentrations) 50 μM of the substrate PIP2 ((L-α-phosphatidyl-D-myoinositol 4,5-bisphosphate, Echelon 117P-4516-0500), 2 μM of ATP and 1.7 μg/ml of PI3Kα, (p110α/p85α, Invitrogen PV4788) in a buffer of Tris/HCl 50 mM pH 7.5, EGTA 1 mM, $MgCl_2$ 10 mM, Chaps 0.03%, 1 mM DTT). After 90 minutes, the reaction is quenched by adding 20 µl/well of KinaseGlo reagent (Promega V6713). After 10 minutes in the dark, the luminescence is read on the PHERAStar microplate reader (reading at 0.8 sec/well).

The IC50 values are determined by the preparation of successive threefold dilutions on at least a scale of 10 000.

Model 3: Cellular Test of Phosphorylation of the Epitope S473 of the Akt Protein on the U87MG Line Via an ELISA Test Principle Starting with a cell lysate, the phosphorylation of Serine-473 of AKT kinase is measured via an ELISA sandwich test using an anti-AKT uptake antibody and an anti-AKT Phospho Serine-473 detection antibody. An electrochemiluminescence signal is generated by a ruthenium-labelled anti-rabbit antibody.

Cellular Test

The cells are seeded at $12 \times 10^4$ cells/well/100 µl of culture medium [90% of DMEM 4.5 g/l of glucose and L-glutamine (Gibco 41965), 10% of heat-inactivated foetal calf serum, 1 mM of sodium pyruvate (Gibco 11360-039), penicillin-streptomycin (10 000 IU-10 mg/ml, Gibco 15140-023, dil. 200×), and non-essential amino acids (Gibco 11140-035, dil. 100×)] in a type I collagen-coated 96-well culture plate (Becton Dickinson 356407). After culturing for 16-20 hours (the cells are at 100% of confluence) at 37° C. under 5% $CO_2$, 1 µl of the chemical compounds in 100% DMSO (1% DMSO final concentration on the cells) is added. The cells are incubated with the compounds for 3 hours at 37° C. under 5% $CO_2$.

After addition of 90 µl of lysis buffer [Hepes 50 mM (Sigma H-0887), NaCl 150 mM, Triton X-100 1%, protease inhibitor cocktail (Complete Mini: Roche 11836 153 001, extemporaneous addition), phosphatase inhibitor cocktail (Sigma P5726 and P0044, extemporaneous addition), AEBSF hydrochloride 2 µM (Calbiochem 101500), NaF 10 mM (Fluka 67414)], the mixture is incubated for 1 hour on ice with agitation.

Preparation of the ELISA Plates

Standard 96-well plates (MSD L11XA-6) are coated with an anti-goat Akt antibody (Santa Cruz sc1618g, without gelatin, without BSA, 2 mg/ml, diluted 30-40 fold in a buffer of HEPES 50 mM pH 7.2, 0.0075% Triton X-100) 2.5 µl/well overnight at room temperature. The free sites are blocked with 150 µl/well of a buffer of 50 mM Tris pH 7.5, 0.15 M NaCl, 0.02% Tween 20, 3% BSA with stirring at 450 rpm for 1 hour at room temperature, followed by a step of washing with 3×300 µl of a buffer of 50 mM Tris pH 7.5, 0.15 M NaCl, 0.02% Tween 20.

ELISA

15 µl of cell lysate are mixed with 15 µl of a 50 mM buffer of Tris pH 7.5, 0.15 M NaCl, 0.02% Tween 20, 1% BSA in a precoated ELISA plate (see above), and incubated for 1 hour at room temperature with stirring, followed by a step of washing with 3×300 µl of a buffer of 50 mM Tris pH 7.5, 0.15 M NaCl, 0.02% Tween 20. The pS473 epitope of Akt is detected with a rabbit polyclonal antibody (Cell Signaling, SC9271), diluted 100-fold in 50 mM Tris pH 7.5, 0.15 M NaCl, 0.02% Tween 20, 1% BSA, 25 µl/well (incubation for 1 hour at room temperature with stirring at 450 rpm).

After washing (see above), revelation is performed with a ruthenium-labelled anti-rabbit antibody (MSD R32AB1), diluted 3000-fold in a 50 mM buffer of Tris pH 7.5, 0.15 M NaCl, 0.02% Tween 20, 1% BSA, 25 µl/well, followed by incubation for 1 hour at room temperature with stirring at 450 rpm, and the plates are covered with aluminium.

After a further washing step, the plates are emptied and 150 µl of MSD Read Buffer T diluted fourfold with water are added. The electrochemiluminescence is measured on the MSD Sector Imager 6000.

Model 4: Test of in vitro Proliferation of U87MG Tumour Cells.

U87MG tumour cells are incubated with the chemical compounds for 72 hours at 37° C. under 5% $CO_2$. The cell growth is determined with the reagent CellTiter 96 AQueous One Solution Cell Proliferation Assay from Promega (Cat. No. G3581).

Seeding is performed at 2500 cells/well/100 µl of culture medium [90% DMEM 4.5 g/l of glucose and L-glutamine (Gibco 41965), 10% heat-inactivated foetal calf serum, 1 mM sodium pyruvate (Gibco 11360-039), penicillin-streptomycin (10 000 IU-10 mg/ml, Gibco 15140-023, diluted 200-fold), and non-essential amino acids (Gibco 11140-035, diluted 100-fold)], in a type I collagen-coated transparent 96-well culture plate (BD Biosciences Cat No. 356407).

After adhesion overnight, 1 µl of the chemical compounds in 100% DMSO (1% DMSO final concentration) is added. After 72 hours at 37° C. under 5% $CO_2$, 20 µl of the reagent CellTiter 96 AQueous One Solution Cell Proliferation Assay from Promega (Cat. No. G3581) are added per well. The mixture is incubated for 1 hour 30 minutes at 37° C. under 5% $CO_2$, and an absorbance reading at 490 nm is then taken (for example on the Victor reader from Wallac/Perkin-Elmer). A reading at T=0 (before the 72 hours of incubation) is taken, corresponding to 100% inhibition.

The pharmacological data are given in Table 4 below:

TABLE 4

Pharmacological data for a number of examples of compounds according to the invention (NT means not tested)

| Expl | mTOR IC50, nM | PI3Ka IC50, nM | U87 Akt-pS473 % Inhibition or IC50, nM | U87 Cell Proliferation IC50, nM |
|---|---|---|---|---|
| 1 | 23 | 8841 | 55 | 197 |
| 2 | 22 | 547 | 31 | 142 |
| 3 | 18 | 2110 | 48 | 242 |
| 4 | 721 | >10000 | >3000 | >10000 |
| 5 | 905 | >10000 | NT | >10000 |
| 6 | 1070 | >10000 | NT | 7150 |
| 7 | 17 | >10000 | >3000 | >10000 |
| 8 | 44 | >10000 | 537 | 3810 |
| 9 | 65 | >10000 | NT | 2500 |
| 10 | 344 | >10000 | 611 | 8770 |
| 11 | 13 | 2300 | 61 | 271 |
| 12 | 17 | 640 | 43 | 121 |
| 13 | 132 | 6470 | 13 | 32 |
| 14 | 41 | >10000 | 458 | 1420 |
| 15 | 12 | 5300 | 76 | 218 |
| 16 | 19 | >10000 | 269 | 527 |
| 17 | 2487 | >10000 | NT | >10000 |
| 18 | 25 | 7570 | 29 | 63 |
| 19 | 32 | 6219 | 28 | 122 |
| 20 | 286 | >10000 | >1000 | 7590 |
| 21 | 15 | >10000 | 51 | 549 |
| 22 | 76 | 3070 | 28 | 68 |
| 23 | 51 | 79 | 62 | 30 |
| 24 | 1072 | NT | >1000 | >10000 |
| 25 | 130 | >10000 | 124 | 196 |
| 26 | 112 | 3860 | >1000 | 3570 |
| 27 | 394 | NT | >1000 | 9150 |
| 28 | 59 | >10000 | 42 | 508 |
| 29 | 38 | >10000 | 32 | 165 |
| 30 | 21 | >10000 | 15 | 46 |
| 31 | 65 | >10000 | 17 | 35 |
| 32 | 84 | >10000 | 21 | 115 |
| 33 | 24 | 9240 | 42 | 226 |

TABLE 4-continued

Pharmacological data for a number of examples of compounds according to the invention (NT means not tested)

| Expl | mTOR IC50, nM | PI3Ka IC50, nM | U87 Akt-pS473 % Inhibition or IC50, nM | U87 Cell Proliferation IC50, nM |
|---|---|---|---|---|
| 34 | 43 | >10000 | 70 | 320 |
| 35 | 37 | >10000 | 75 | 336 |
| 36 | 55 | 4400 | 129 | 686 |
| 37 | 122 | 8630 | 54 | 869 |
| 38 | 22 | 3450 | 23 | 218 |
| 39 | 26 | 5870 | 34 | 207 |
| 40 | 56 | >10000 | 59 | 274 |
| 41 | 35 | >10000 | 31 | 122 |
| 42 | 43 | >10000 | 52 | 350 |
| 43 | 27 | 4730 | 20 | 82 |
| 44 | 34 | >10000 | 40 | 220 |
| 45 | 24 | 4000 | 32 | 85 |
| 46 | 26 | 8880 | 24 | 90 |
| 47 | 34 | >10000 | 151 | 564 |
| 48 | 47 | >10000 | 86 | 185 |
| 49 | 32 | >10000 | 21 | 155 |
| 50 | 39 | 2870 | 7 | 40 |
| 51 | 20 | 1900 | 14 | 12 |
| 52 | 18 | 1710 | 16 | 29 |
| 53 | 222 | >10000 | 555 | 2160 |
| 54 | 32 | 3000 | 41 | 161 |
| 55 | 66 | 4810 | 27 | 54 |
| 56 | 41 | 3230 | 26 | 57 |
| 57 | 239 | >10000 | >1000 | 7580 |
| 58 | 28 | 9470 | 20 | 71 |
| 59 | 67 | 4200 | 36 | 42 |
| 60 | 58 | NT | 17 | 46 |
| 61 | 993 | NT | >1000 | 4670 |
| 62 | 667 | >10000 | >1000 | >10000 |
| 63 | 31 | >10000 | 31 | 190 |
| 64 | 24 | >10000 | 37 | 270 |
| 65 | 27 | 22400 | 27 | 257 |
| 66 | 16 | 2950 | 21 | 71 |
| 67 | 15 | >10000 | 20 | 69 |
| 68 | 12 | 1360 | 16 | 82 |
| 69 | 6 | 472 | 35 | 79 |
| 70 | 27 | >10000 | 40 | 288 |
| 71 | 21 | >10000 | 59 | 209 |
| 72 | 23 | >10000 | 58 | 498 |
| 73 | 71 | 5910 | 48 | 119 |
| 74 | 64 | >10000 | 31 | 126 |
| 75 | 40 | 5570 | 8 | 47 |
| 76 | 28 | 2360 | 29 | 367 |
| 77 | 56 | 4490 | 16 | 53 |
| 78 | 90 | 6260 | 28 | 83 |
| 79 | 53 | >10000 | 41 | 383 |
| 80 | 72 | >10000 | 48 | 151 |
| 81 | 124 | 2100 | 17 | 108 |
| 82 | 21 | 2240 | 13 | 29 |
| 83 | 20 | 1460 | 16 | 41 |
| 84 | 23 | >10000 | 255 | 760 |
| 85 | 24 | 1950 | 28 | 77 |
| 86 | 377 | >10000 | 144 | 490 |
| 87 | 57 | >10000 | 20 | 59 |
| 88 | 198 | >10000 | 65% at 1000 nM | 1900 |
| 89 | 84 | >10000 | 260 | 221 |
| 90 | 450 | NT | 64% at 1000 nM | 2900 |
| 91 | 53 | 4640 | 47 | 410 |
| 92 | 40 | >10000 | 12 | 99 |
| 93 | 72 | >10000 | 65 | 410 |
| 94 | 112 | 7320 | >10000 | NT |
| 95 | 624 | >10000 | NT | NT |
| 96 | 72 | 1444 | 107 | 1469 |
| 97 | 800 | 2159 | NT | >10000 |
| 98 | 26 | 1138 | 20 | 184 |
| 99 | 31 | >10000 | 40 | 239 |
| 100 | 7285 | 7440 | NT | >10000 |
| 101 | 4045 | NoVal | NT | NT |
| 102 | 927 | 3610 | NT | 9830 |
| 103 | 194 | 6590 | 425 | 3510 |
| 104 | 1494 | 3750 | NT | >10000 |
| 105 | 180 | >10000 | 360 | 2690 |
| 106 | 442 | >10000 | 767 | 6560 |
| 107 | 2648 | 9380 | NT | >10000 |
| 108 | 472 | >10000 | NT | 4450 |
| 109 | 7770 | 2046 | NT | NT |
| 110 | 45 | >10000 | 89 | 506 |
| 111 | 6349 | >10000 | NT | NT |
| 112 | 20 | 2660 | 24 | 154 |
| 113 | 3960 | >10000 | NT | >10000 |
| 114 | 1220 | >10000 | NT | >10000 |
| 115 | 147 | >10000 | NT | 5000 |
| 116 | 42 | 4310 | 98 | 282 |
| 117 | 25 | 7410 | 812 | 1699 |
| 118 | 58 | 5040 | 32 | 233 |
| 119 | 104 | >10000 | 1060 | >3000 |
| 120 | 351 | >10000 | 1180 | 2258 |
| 121 | 66 | >10000 | 130 | 802 |
| 122 | 19 | 4200 | 140 | 340 |
| 123 | 22 | 3627 | 150 | 221 |
| 124 | 20 | >10000 | 61 | 115 |
| 125 | 16 | >10000 | 86 | 260 |
| 126 | 13 | 2963 | 68 | 225 |
| 127 | 16 | 3646 | 24 | 79 |
| 128 | 3475 | >10000 | NT | >10000 |
| 129 | 1384 | >10000 | >3000 | >10000 |
| 130 | 2120 | >10000 | >3000 | >10000 |
| 131 | 383 | >10000 | 1990 | 5900 |
| 132 | 245 | 4320 | >3000 | >10000 |
| 133 | 33 | >10000 | 92 | 219 |
| 134 | 3165 | >10000 | >3000 | >10000 |
| 135 | 11 | 6525 | 26 | 112 |
| 136 | 34 | >10000 | 37 | 239 |
| 137 | 29 | >10000 | 241 | 1330 |
| 138 | 299 | >10000 | 105 | 331 |
| 139 | 251 | >10000 | 721 | 3010 |
| 140 | 45 | >10000 | 507 | 472 |
| 141 | 34 | 598 | 19 | 94 |
| 142 | 495 | >10000 | NT | 3100 |
| 143 | 19 | 3180 | 62 | 295 |
| 144 | 105 | >10000 | 142 | 2570 |
| 145 | 2977 | >10000 | NT | >10000 |
| 146 | 35 | >10000 | 82 | 441 |
| 147 | 182 | >10000 | 28 | 297 |
| 148 | 68 | >10000 | 21 | 490 |
| 149 | 113 | >10000 | 154 | 854 |
| 150 | 40 | 5800 | 73 | 201 |
| 151 | 116 | >10000 | 82 | 531 |
| 152 | 348 | >10000 | 257 | 2680 |
| 153 | 31 | >10000 | 116 | 346 |
| 154 | 182 | >10000 | 54 | 97 |
| 155 | 79 | >10000 | 59 | 142 |
| 156 | 27 | 1140 | 92 | 395 |
| 157 | 27 | >10000 | 67 | 260 |
| 158 | 64 | >10000 | 1600 | 1700 |
| 159 | 18 | 561 | 21 | 98 |
| 160 | 41 | 4900 | 114 | 744 |
| 161 | 38 | 321 | 9 | 60 |
| 162 | 147 | >10000 | 110 | 486 |
| 163 | 55 | 3870 | 130 | 1020 |
| 164 | 85 | 3800 | 227 | 872 |
| 165 | 180 | >10000 | 1530 | 4200 |
| 166 | 86 | 2300 | 278 | 1270 |
| 167 | 62 | 3520 | 158 | 500 |
| 168 | 18 | 1385 | 48 | 231 |
| 169 | 31 | 1450 | 26 | 299 |
| 170 | 106 | 824 | 94 | 557 |
| 171 | 37 | 308 | 41 | 91 |
| 172 | 20 | <10000 | 98 | 198 |
| 173 | 12 | 1602 | 42 | 242 |
| 174 | 22 | 326 | 36 | 125 |
| 175 | 585 | >10000 | NT | 3050 |
| 176 | 69 | 100 | 314 | 83 |
| 177 | 84 | 87 | 435 | 57 |

TABLE 4-continued

Pharmacological data for a number of examples of compounds according to the invention (NT means not tested)

| Expl | mTOR IC50, nM | PI3Ka IC50, nM | U87 Akt-pS473 % Inhibition or IC50, nM | U87 Cell Proliferation IC50, nM |
|---|---|---|---|---|
| 178 | 45 | >10000 | 104 | 252 |
| 179 | 58 | >10000 | 331 | 1330 |
| 180 | 11 | 604 | 65 | 146 |
| 181 | 74 | 7650 | 285 | 1320 |
| 182 | 26 | 159 | 407 | 2930 |
| 183 | 128 | >10000 | 165 | 752 |
| 184 | 12 | 12978 | 65 | 368 |
| 185 | 24 | 5680 | 20 | 73 |
| 186 | 25 | 3940 | 60 | 266 |
| 187 | 37 | 472 | 22 | 67 |
| 188 | 63 | 2330 | 45 | 505 |
| 189 | 62 | 1890 | 56 | 451 |
| 190 | 40 | 927 | 69% at 3000 nM | 734 |
| 191 | 24 | 570 | 26 | 105 |
| 192 | 29 | 1310 | 82% at 3000 nM | 1770 |
| 193 | 970 | 9440 | >1000 | 4660 |
| 194 | 27 | 1230 | 62% at 3000 nM | 2130 |
| 195 | 61 | 6800 | 45 | 57 |
| 196 | 276 | 7470 | 60% at 3000 nM | 5050 |
| 197 | 117 | >10000 | 150 | 523 |
| 198 | 57 | >10000 | 44 | 318 |
| 199 | 39 | 174 | 10 | 32 |
| 200 | 52 | >10000 | 9 | 108 |
| 201 | 48 | 813 | 230 | 898 |
| 202 | 19 | 213 | 5 | 73 |
| 203 | 96 | 9610 | 111 | 43 |
| 204 | 61 | 468 | 18 | 74 |
| 205 | 63 | 3740 | 13 | 22 |
| 206 | 145 | >10000 | 87% at 1000 nM | 1340 |
| 207 | 18 | >10000 | 19 | 74 |
| 208 | 81 | 1240 | 26 | 181 |
| 209 | 155 | >10000 | 69 | 1050 |
| 210 | 41 | >10000 | 174 | 625 |
| 211 | 87 | >10000 | 270 | 894 |
| 212 | 141 | 1540 | 8 | 71 |
| 213 | 48 | 991 | 20 | 103 |
| 214 | 2448 | >10000 | >1000 | >10000 |
| 215 | 48 | 37 | 33 | 32 |
| 216 | 125 | 1830 | NT | 514 |
| 217 | 59 | >10000 | 80% at 3000 nM | 1760 |
| 218 | 58 | 1060 | 17 | 211 |
| 219 | 38 | 98 | 28 | 436 |
| 220 | 348 | 1860 | 30 | 285 |
| 221 | 13 | 372 | 11 | 137 |
| 222 | 123 | >10000 | 213 | 1680 |
| 223 | 20 | 2070 | 4 | 61 |
| 224 | 1120 | >10000 | NT | NT |
| 225 | 36 | 1360 | 91 | 365 |
| 226 | 1280 | >10000 | NT | NT |
| 227 | 76 | 484 | 7 | 29 |
| 228 | 70 | 6600 | 72 | 229 |
| 229 | 43 | >10000 | 19 | 86 |
| 230 | 77 | >10000 | 18 | 58 |
| 231 | 16 | 103 | 12 | 29 |
| 232 | 32 | 5630 | 26 | 95 |
| 233 | 68 | >10000 | 87 | 908 |
| 234 | 67 | >10000 | 118 | 2290 |
| 235 | 89 | >7200 | 10 | 29 |
| 236 | 112 | >7200 | 20 | 29 |
| 237 | 39 | >7200 | 80 | 49 |
| 238 | 678 | >10000 | >1000 | 1700 |
| 239 | 1070 | NT | 38% at 1000 nM | >10000 |
| 240 | 61 | >10000 | 29 | 75 |
| 241 | 165 | >10000 | 43 | 59 |
| 242 | 89 | >10000 | 770 | 2300 |
| 243 | 63 | 3870 | 160 | 610 |
| 244 | 60 | >10000 | 29 | 77 |
| 245 | 63 | >10000 | 67 | NT |
| 246 | 82 | >10000 | 240 | 1600 |
| 247 | 26 | 7200 | 8 | 62 |
| 248 | 68 | >10000 | 29 | 96 |
| 249 | 365 | >10000 | 27 | 29 |
| 250 | 36 | >10000 | 38 | 100 |
| 251 | 64 | >10000 | 80 | 340 |
| 252 | 68 | 1360 | 48 | 282 |
| 253 | 72 | >10000 | 68 | 167 |
| 254 | 68 | >10000 | 68 | 240 |
| 255 | 72 | >10000 | 68 | 210 |
| 256 | 196 | 199 | 42 | 83 |
| 257 | 142 | >10000 | 46 | 63 |
| 258 | 53 | 2940 | 20 | 125 |
| 259 | 87 | >10000 | 16 | 87 |
| 260 | 174 | >10000 | 24 | 95 |
| 261 | 387 | >10000 | 20 | 160 |

It thus appears that the compounds according to the invention have selective inhibitory activity on the kinase mTOR.

The compounds according to the invention may thus be used for the preparation of medicaments, in particular medicaments for inhibiting mTOR.

A subject of the present invention is also the use of a compound according to the invention in the treatment of diseases requiring inhibition of the kinase mTOR.

According to another of its aspects, a subject of the present invention is more particularly the use of a compound as defined above for the preparation of a medicament that is useful for treating or preventing:
  cancers, especially:
    malignant haematological tumours, such as leukaemia, multiple myeloma, lymphomas such as Hodgkin's disease, non-Hodgkin lymphomas (including mantle-cell lymphoma) and myelodysplastic syndromes,
    solid tumours and metastases thereof such as breast cancer and lung cancer (non-small cell lung cancer, NSCL; small cell lung cancer, SCLC), squamous cell carcinoma and cancer of the endometrium,
    central nervous system tumours, such as gliomas, neurodysembryoplastic tumours, glioblastoma multiforme, mixed gliomas, medulloblastoma, retinoblastoma, neuroblastoma, germinoma and teratoma,
    cancers of the gastrointestinal tract, such as stomach cancer, oesophageal cancer, hepatocellular carcinoma (liver), cholangiocarcinomas, bowel and rectal carcinomas, bowel cancer and pancreatic cancers,
    skin cancers such as melanomas (in particular metastatic melanoma), thyroid cancers, cancers of the head and neck, cancers of the salivary glands, of the prostate, of the testicles, of the ovaries, of the cervix, of the vulva, of the bladder, of the kidneys (including clear-cell renal carcinoma and renal oncocytoma), squamous cell carcinomas, sarcomas such as osteosarcoma, chondrosarcoma, leiomyosarcoma, soft-tissue sarcomas, Ewing's sarcomas, gastrointestinal stromal tumours (GIST), Kaposi's sarcoma, and paediatric cancers such as rhabdomyosarcomas and neuroblastomas,
  inflammatory and immune diseases, such as rheumatoid arthritis,
  diabetes,
  obesity,
  obstructive diseases of the respiratory pathways,
  fibroses (including lung, kidney and liver fibrosis), Pompe's disease (Cori's type II glycogenosis),
cardiovascular diseases, or
age-related diseases such as neurodegenerative diseases (including Alzheimer's disease, Huntington's diseases and Parkinson's disease), loss of hearing and ocular diseases, including age-related macular degeneration (ARMD),
epilepsy,
parasitic diseases.

Thus, according to another of its aspects, a subject of the invention is medicaments that comprise a compound of formula (I), or a pharmaceutically acceptable acid-addition salt thereof.

These medicaments find their use in therapeutics, especially in the treatment or prevention of:
cancers, especially:
malignant haematological tumours, such as leukaemia, multiple myeloma, lymphomas such as Hodgkin's disease, non-Hodgkin lymphomas (including mantle-cell lymphoma) and myelodysplastic syndromes,
solid tumours and metastases thereof such as breast cancer and lung cancer (non-small cell lung cancer, NSCL; small cell lung cancer, SCLC), squamous cell carcinoma and cancer of the endometrium,
central nervous system tumours, such as gliomas, neurodysembryoplastic tumours, glioblastoma multiforme, mixed gliomas, medulloblastoma, retinoblastoma, neuroblastoma, germinoma and teratoma,
cancers of the gastrointestinal tract, such as stomach cancer, oesophageal cancer, hepatocellular carcinoma (liver), cholangiocarcinomas, bowel and rectal carcinomas, bowel cancer and pancreatic cancers,
skin cancers such as melanomas (in particular metastatic melanoma), thyroid cancers, cancers of the head and neck, cancers of the salivary glands, of the prostate, of the testicles, of the ovaries, of the cervix, of the vulva, of the bladder, of the kidneys (including clear-cell renal carcinoma and renal oncocytoma), squamous cell carcinomas, sarcomas such as osteosarcoma, chondrosarcoma, leiomyosarcoma, soft-tissue sarcomas, Ewing's sarcomas, gastrointestinal stromal tumours (GIST), Kaposi's sarcoma, and paediatric cancers such as rhabdomyosarcomas and neuroblastomas,
inflammatory and immune diseases, such as rheumatoid arthritis,
diabetes,
obesity,
obstructive diseases of the respiratory pathways,
fibroses (including lung, kidney and liver fibrosis),
Pompe's disease (Cori's type II glycogenosis),
cardiovascular diseases, or
age-related diseases such as neurodegenerative diseases (including Alzheimer's disease, Huntington's diseases and Parkinson's disease), loss of hearing and ocular diseases, including age-related macular degeneration (ARMD),
epilepsy,
parasitic diseases.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the treatment or prevention of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical application, the compounds according to the invention may be used in creams, gels, pomades or lotions.

By way of example, a unit administration form of a compound according to the invention in tablet form may comprise the following constituents:

| Compound according to the invention | 50.0 mg |
|---|---|
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating or preventing the pathologies indicated above, which comprises the administration, to a patient, of an effective dose of a compound according to the invention, or a pharmaceutically acceptable salt thereof.

The invention claimed is:
1. A compound of formula (I):

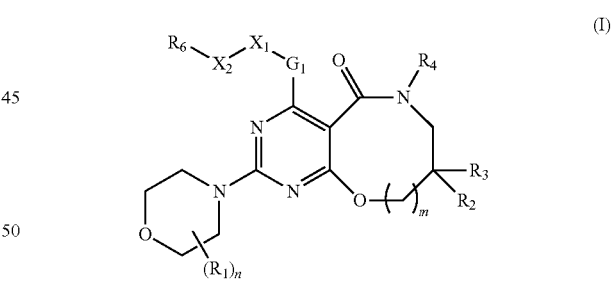

wherein:
each $R_1$ is independently $(C_1-C_6)$-alkyl, wherein two $R_1$ groups on different carbon atoms of the morpholinyl ring may be linked together to form, with the morpholinyl ring, a bicyclic heterocyclic structure;
$R_2$ and $R_3$ are independently hydrogen or $(C_1-C_6)$ alkyl;
$R_4$ is hydrogen, $(C_1-C_6)$ alkyl optionally substituted with a hydroxyl group, $(C_1-C_6)$-alkoxy or $-L_1-R_{10}$, wherein $L_1$ is $(C_1-C_6)$-alkylene, and
$R_{10}$ is $-COOR_{11}$, $-CO-R_{12}$, $-OR_{13}$, $-CONR_{14}R_{15}$, a 5- or 6-atom heterocycle optionally substituted with $-R_{16}$, $-COOR_{17}$, $-CO-R_{18}$, $-OR_{19}$ or $-NR_{20}R_{21}$, or a 5- or 6-atom heterocycle optionally substituted with $-R_{22}$, $-COOR_{23}$, —CO—R$_{24}$, —OR$_{25}$ or —CONR$_{26}$R$_{27}$, wherein each 5- or 6-atom heterocycle is saturated, partially unsaturated or aromatic, and includes one or more heteroatoms selected from O, N and S;

G$_1$ is phenylene or a 5- to 6-atom heteroarylene, optionally substituted with 1 to 4 R$_5$ groups, each R$_5$ group being independently chosen from halogen, —OR$_{30}$ and —(C$_1$-C$_6$)-alkyl optionally substituted with hydroxyl;

X$_1$ is —O— or —NR$_{40}$—;

X$_2$ is a single bond, —CONR$_{50}$—, —CONR$_{51}$—O—, —COO—, —CO— or —SO$_2$—;

R$_6$ is hydrogen or -L$_2$-R$_7$, wherein
-L$_2$- is (C$_1$-C$_6$)-alkylene or (C$_3$-C$_6$)-cycloalkylene;

R$_7$ is hydrogen, —OR$_{60}$, halogen, (C$_1$-C$_6$)-haloalkyl, a 5- to 6-atom heterocycle optionally substituted with one or more groups chosen from (C$_1$-C$_6$)-alkyl, (C$_1$-C$_6$)-alkoxy and =O, or -G$_2$-X$_3$-G$_3$, wherein:

X$_3$ is a single bond or —O—, —CO— or —CH$_2$—;

G$_2$ is a single bond or a 5- to 6-atom divalent cyclic radical optionally substituted with one or more R$_{80}$, G$_3$ is a 4- to 8-atom ring optionally substituted with one or more R$_{81}$, or -G$_2$-X$_3$-G$_3$ together form a 7- to 10-atom fused bicycle, wherein each R$_{80}$ and R$_{81}$ is independently halogen, —COOR$_{70}$, —CO—R$_{71}$, —OR$_{72}$, —NR$_{73}$R$_{74}$, —CONR$_{75}$R$_{76}$, —CN or —S(O)$_p$—R$_{77}$, (C$_1$-C$_6$)-alkyl optionally substituted with one or more R$_{100}$ groups, and/or optionally interrupted with one or more oxygen atoms, and (C$_1$-C$_6$)-alkoxy optionally substituted with one or more R$_{101}$ groups, and/or optionally interrupted with one or more oxygen atoms, n is 0, 1 or 2;
m is 0 or 1;
p is 0, 1 or 2;

R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{30}$, R$_{40}$, R$_{50}$, R$_{51}$, R$_{60}$, R$_{70}$, R$_{71}$, R$_{72}$, R$_{73}$, R$_{74}$, R$_{75}$, R$_{76}$ and R$_{77}$ are independently H or (C$_1$-C$_6$)-alkyl optionally substituted with a R$_{90}$ group, and/or optionally interrupted with one or more oxygen atoms;

R$_{90}$ is —OR$_{91}$ or —NR$_{92}$R$_{93}$;

R$_{91}$, R$_{92}$ and R$_{93}$ are independently hydrogen or (C$_1$-C$_6$)-alkyl; and R$_{100}$ and R$_{101}$ are independently halogen or hydroxyl;

or a pharmaceutically acceptable salt thereof.

2. The compound of claim 1, of formula (II):

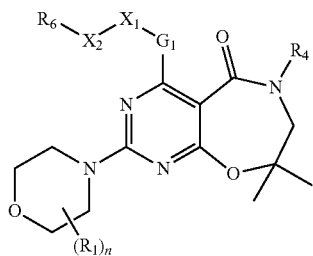

(II)

or a pharmaceutically acceptable salt thereof.

3. The compound of claim 1, wherein

R$_4$ is hydrogen, (C$_1$-C$_6$)-alkyl, optionally substituted with a hydroxyl group, or -L$_1$-R$_{10}$, wherein
L$_1$ is (C$_1$-C$_6$)-alkylene, and R$_{10}$ is —COOR$_{11}$, —OR$_{13}$, —CONR$_{14}$R$_{15}$, a 5- or 6-atom heterocycle optionally substituted with —COOR$_{17}$ or —CO—R$_{18}$, or a 5- or 6-atom heterocycle optionally substituted with —R$_{22}$.

4. The compound of claim 1, wherein G$_1$ is phenyl or pyridyl, each optionally substituted with an R$_5$ group, wherein R$_5$ is halogen.

5. The compound of claim 1, wherein X$_1$ is —NR$_{40}$—.

6. The compound of claim 1, wherein X$_2$ is —CONR$_{50}$— or —COO—.

7. The compound of claim 1, of formula (III):

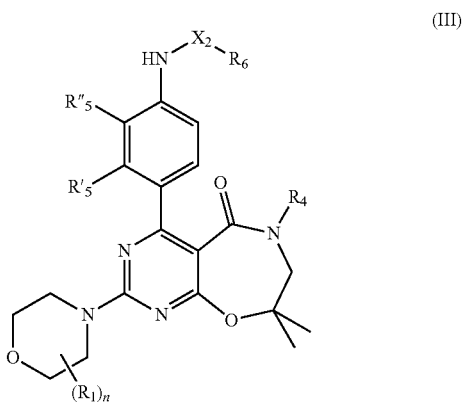

(III)

wherein

R$_4$ is (C$_1$-C$_6$)-alkyl;

R'$_5$ and R''$_5$ are independently hydrogen or fluoro, provided that when one of R'$_5$ or R''$_5$ is fluoro, the other is hydrogen;

X$_2$ is —CONR$_{50}$— or —COO—;

R$_6$ is -L$_2$-R$_7$, wherein
-L$_2$- is (C$_1$-C$_6$)-alkylene or (C$_3$-C$_6$)-cycloalkylene, and
R$_7$ is hydrogen, —OR$_{60}$, or -G$_2$-X$_3$-G$_3$, wherein
X$_3$ is a single bond or —O—,
G$_2$ is a single bond or a cyclic divalent radical of 6 atoms,
G$_3$ is a 4- to 8-atom ring optionally substituted with one or more R$_{81}$, or a pharmaceutically acceptable salt thereof.

8. The compound of claim 1, wherein R$_4$ is methyl or ethyl.

9. The compound of claim 1, wherein the compound is:

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-methylurea;

1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-methylurea;

1-Ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea;

1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-3-fluorophenyl}-3-pyridin-4-ylurea;

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methylpiperazin-1-yl)phenyl]urea;

1-(4-Methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea;

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(1-methylpiperidin-4-yloxy)pyridin-3-yl]urea;

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((S)-3-methylmorpholin-4-yl)pyridin-3-yl]urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-((R)-3-methylmorpholin-4-yl)pyridin-3-yl]urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(3,4,5,6-tetrahydro-2H-[1,2']bipyridinyl-5'-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-pyrrolidin-1-ylpyridin-3-yl)urea;
1-{4-[6-Ethyl-2-((S)-3-ethylmorpholin-4-yl)-8,8-dimethyl-5-oxo-5,6,7,8-tetrahydro-9-oxa-1,3,6-triazabenzocyclohepten-4-yl]-2-fluorophenyl}-3-(6-methylpyridin-3-yl)urea;
1-Methyl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(2-methoxyethoxy)pyridin-2-yl]urea;
1-Methyl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-methylurea;
1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-methylurea;
1-(5-Methoxypyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-pyridin-3-ylurea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-pyridin-4-ylurea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-4-ylurea;
1-(5-Methoxypyridin-2-yl)-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-(2-methylpyridin-4-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(2-methylpyridin-4-yl)urea;
1-(2,6-Dimethylpyridin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;
1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(2-methylpyridin-4-yl)urea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(2-methylpyridin-4-yl)urea;
1-(5-Dimethylaminopyridin-2-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(6-methylpyridin-3-yl)urea;
1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(6-methylpyridin-3-yl)urea;
1-Pyridin-4-yl-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea;
1-Pyridin-4-yl-3-{4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea;
1-(4-Methoxypyridin-2-yl)-3-{4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}urea;

1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-3-fluorophenyl}-3-pyridin-4-ylurea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-((S)-3-methylmorpholin-4-yl)pyridin-3-yl]urea;
1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-[6-((S)-3-methylmorpholin-4-yl)pyridin-3-yl]urea;
1-[4-(((1S,5R)-6-Ethyl-8,8-dimethyl-2-3-oxa-8-azabicyclo[3.2.1]oct-8-yl-5-oxo-5,6,7,8-tetrahydro-9-oxa-1,3,6-triazabenzocyclohepten-4-yl)phenyl]-3-(3-fluoropyridin-4-yl)urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(3-fluoropyridin-4-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(tetrahydrofuran-3-yloxy)phenyl]urea;
1-(2-Dimethylaminopyridin-4-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-(4-methoxypyridin-2-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[2-(4-methanesulfonylpiperazin-1-yl)pyridin-4-yl]urea;
4-[5-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}ureido)pyridin-2-yl]piperazine-1-carboxylic acid methyl ester;
1-{2-Fluoro-4-[6,8,8-trimethyl-2-(3-oxa-8-azabicyclo[3.2.1]oct-8-yl)-5-oxo-5,6,7,8-tetrahydro-9-oxa-1,3,6-triazabenzocyclohepten-4-yl]phenyl}-3-pyridin-4-ylurea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-4-ylurea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-((R)-3-methylmorpholin-4-yl)pyridin-3-yl]urea;
1-Ethyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}urea;
1-Ethyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}urea;
1-Ethyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-pyridin-3-ylurea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-methylisoxazol-3-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-yl)urea;
1-Cyclopropyl-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-isoxazol-3-ylurea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-methoxypyridin-3-yl)urea;
1-Cyclopropyl-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-isoxazol-3-ylurea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-methylpyridin-3-yl)urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(5-methylpyridin-2-yl)urea;

1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-(4-methylpiperazin-1-yl)pyridin-3-yl]urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-[6-(4-methylpiperazin-1-yl)pyridin-3-yl]urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(4-methoxypyridin-2-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methylpyridin-3-yl)urea;
{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}carbamic acid 2-hydroxyethyl ester;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(6-morpholin-4-ylpyridin-3-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[6-(4-methylpiperazin-1-yl)pyridin-3-yl]urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(2-methylpyridin-4-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-morpholin-4-ylpyridin-3-yl)urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-(2-fluorophenyl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[4-(4-methylpiperazin-1-yl)phenyl]urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-methylurea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-[5-(4-methylpiperazin-1-yl)pyridin-2-yl]urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]phenyl}-3-pyridin-2-ylurea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-pyridin-3-ylurea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-(4-morpholin-4-ylphenyl)urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-(6-methylpyridin-3-yl)urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-pyridin-4-ylurea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[4-(4-methanesulfonylpiperazin-1-yl)phenyl]urea;
4-[4-(3-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}ureido)phenyl]piperazine-1-carboxylic acid methyl ester;
1-[4-(1,1-Dioxo-1λ6-thiomorpholin-4-yl)phenyl]-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-(6-methoxypyridin-3-yl)urea;
1-(2,6-Dimethylpyridin-4-yl)-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea;
{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-3-fluorophenyl}carbamic acid 2-hydroxyethyl ester;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-(8-oxa-3-azabicyclo[3.2.1]oct-3-yl)pyridin-3-yl]urea;
1-{2-Fluoro-4-[6,8,8-trimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[6-(3-oxa-8-azabicyclo[3.2.1]oct-8-yl)pyridin-3-yl]urea;
1-(6-Cyanopyridin-3-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-((S)-3-ethylmorpholin-4-yl)pyridin-3-yl]urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[6-((S)-3-ethylmorpholin-4-yl)pyridin-3-yl]urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-(5-morpholin-4-ylpyridin-2-yl)urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]phenyl}-3-[5-(8-oxa-3-azabicyclo[3.2.1]oct-3-yl)pyridin-2-yl]urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[(1S,4S)-6-(2-oxa-5-azabicyclo[2.2.1]hept-5-yl)pyridin-3-yl]urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[(1S,4S)-6-(2-oxa-5-azabicyclo[2.2.1]hept-5-yl)pyridin-3-yl]urea;
1-Cyclopropyl-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea;
1-Ethyl-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea;
1-[6-(3,3-Dimethylmorpholin-4-yl)pyridin-3-yl]-3-{4-[6-ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}urea;
1-[6-(3,3-Dimethylmorpholin-4-yl)pyridin-3-yl]-3-{4-[6-ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}urea;
1-{4-[6-Ethyl-8,8-dimethyl-2-((S)-3-methylmorpholin-4-yl)-5-oxo-5,6,7,8-tetrahydro-9-oxa-1,3,6-triazabenzocyclohepten-4-yl]-2-fluorophenyl}-3-[6-(8-oxa-3-azabicyclo[3.2.1]oct-3-yl)pyridin-3-yl]urea;
1-{4-[6-Ethyl-8,8-dimethyl-2-(3-oxa-8-azabicyclo[3.2.1]oct-8-yl)-5-oxo-5,6,7,8-tetrahydro-9-oxa-1,3,6-triazabenzocyclohepten-4-yl]-2-fluorophenyl}-3-[6-(8-oxa-3-azabicyclo[3.2.1]oct-3-yl)pyridin-3-yl]urea;
1-{4-[6-Ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}-3-[2-(8-oxa-3-azabicyclo[3.2.1]oct-3-yl)pyridin-4-yl]urea;
1-(4,4-Difluoro-3,4,5,6-tetrahydro-2H-[1,2']bipyridinyl-4'-yl)-3-{4-[6-ethyl-8,8-dimethyl-2-(8-oxa-3-azabicyclo[3.2.1]oct-3-yl)-5-oxo-5,6,7,8-tetrahydro-9-oxa-1,3,6-triazabenzocyclohepten-4-yl]-2-fluorophenyl}urea;

or a pharmaceutically acceptable salt thereof.

10. A process for preparing a compound of formula (I) according to claim 1, the process comprising grafting a group —$X_2$—$R_6$ onto a compound of formula (XLII) below:

(XLII)

to obtain the compound of formula (I).

11. A process for preparing a compound of formula (I) according to claim 1, in which $X_1$ is —$NR_{40}$— and $X_2$ is —$CONR_{50}$—, the process comprising Suzuki reaction of the compound of formula (XXXV):

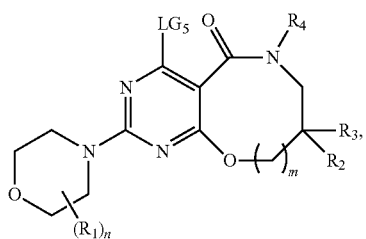

(XXXV)

in which $LG_5$ is a leaving group, with a compound of formula $R_6R_{50}N$—(C=O)—$NR_{40}$-$G_1$-$R_{300}$, in which $R_{300}$ is a boronic acid or boronic ester to obtain the compound of formula (I) wherein $X_1$ is —$NR_{40}$— and $X_2$ is —$CONR_{50}$—.

12. A process for preparing a compound of formula (I) according to claim 1, the process comprising nucleophilic attack of a compound of formula (CI):

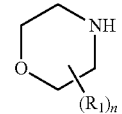

(CI)

on a compound of formula (LII):

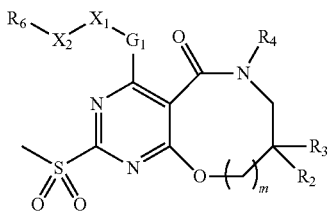

(LII)

to obtain the compound of formula (I).

13. A pharmaceutical composition, comprising a compound according to claim 1, or a pharmaceutically acceptable salt thereof, and at least one pharmaceutically acceptable excipient.

* * * * *